US007754712B2

(12) United States Patent
Bowers et al.

(10) Patent No.: US 7,754,712 B2
(45) Date of Patent: Jul. 13, 2010

(54) BRIDGED N-CYCLIC SULFONAMIDO INHIBITORS OF GAMMA SECRETASE

(75) Inventors: Simeon Bowers, Oakland, CA (US); Albert W. Garofalo, South San Francisco, CA (US); Roy K. Hom, San Francisco, CA (US); Andrei W. Konradi, Burlingame, CA (US); Matthew N. Mattson, Santa Clara, CA (US); Martin L. Neitzel, Pacifica, CA (US); Christopher M. Semko, Fremont, CA (US); Anh P. Truong, Burlingame, CA (US); Jing Wu, Redwood City, CA (US); Ying-zi Xu, Palo Alto, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 193 days.

(21) Appl. No.: 11/951,097

(22) Filed: Dec. 5, 2007

(65) Prior Publication Data
US 2008/0090817 A1    Apr. 17, 2008

Related U.S. Application Data

(62) Division of application No. 11/465,726, filed on Aug. 18, 2006, now Pat. No. 7,345,056.

(60) Provisional application No. 60/709,961, filed on Aug. 19, 2005.

(51) Int. Cl.
*A61K 31/5365* (2006.01)
*A61K 31/437* (2006.01)
*A61K 31/4985* (2006.01)
*A61P 25/28* (2006.01)
*C07D 497/04* (2006.01)
*C07D 497/14* (2006.01)
*C07D 471/14* (2006.01)

(52) U.S. Cl. ............... 514/230.2; 514/230.5; 514/250; 514/293; 544/101; 544/105; 544/346; 546/82

(58) Field of Classification Search ............ 514/230.2, 514/230.5, 250, 293; 546/82; 544/101, 105, 544/346
See application file for complete search history.

(56) References Cited

U.S. PATENT DOCUMENTS

| | | | |
|---|---|---|---|
| 4,232,158 A * | 11/1980 | Shepard et al. | ............... 546/72 |
| 6,414,149 B1 | 7/2002 | Chu-Moyer et al. | |
| 6,573,275 B1 | 6/2003 | Urch et al. | |
| 7,205,434 B2 | 4/2007 | Hannam et al. | |
| 7,368,457 B2 * | 5/2008 | Josien | ........................ 514/291 |
| 2004/0229902 A1 | 11/2004 | Josien | |
| 2006/0100228 A1 * | 5/2006 | Shankar et al. | ............. 514/278 |
| 2006/0148867 A1 * | 7/2006 | Brown et al. | ............... 514/373 |

FOREIGN PATENT DOCUMENTS

| | | | |
|---|---|---|---|
| EP | 1088819 | | 4/2001 |
| WO | 2003106456 | * | 12/2003 |

OTHER PUBLICATIONS

Tomita et al., Naunyn-Schmiedeberg's archives of pharmacology, (Jun. 2008) vol. 377, No. 4-6, pp. 295-300. Electronic Publication: Nov. 24, 2007. Ref: 45.*
Armstrong et al., Chinese Journal of Chemistry (2005), 23(9), 1270-1272.*
Armstrong et al., Organic Letters (2005), 7(7), 1335-1338.*
Pearson et al., Journal of Organic Chemistry (2004), 69(4), 1235-1247.*
Pearson et al., Organic Letters (2002), 4(18), 3099-3102.*
Wang et al., Shanghai Dier Yike Daxue Xuebao (1993), 13(4), 297-9.*
Kozikowski et al., Journal of Medicinal Chemistry (1994), 37(20), 3440-2.*
Furuya et al., Heterocycles (1988), 27(11), 2609-18.*
Baeckvall et al., Tetrahedron Letters (1987), 28(36), 4199-202.*
Brenner et al., Journal of Heterocyclic Chemistry (1986), 23(1), 145-8.*
Schneider et al., Archiv der Pharmazie (Weinheim, Germany) (1976), 309(6), 447-57.*

(Continued)

*Primary Examiner*—D. Margaret Seaman
*Assistant Examiner*—Niloofar Rahmani
(74) *Attorney, Agent, or Firm*—McDonnell Boehnen Hulbert & Berghoff LLP

(57) ABSTRACT

The invention provides N-cyclic sulfonamido compounds and salts of Formula I:

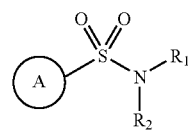

wherein A is as described in the specification and $R_1$ and $R_2$ combine to form a [3.3.1] or a [3.2.1] ring system, where the nitrogen is attached to the two bridgehead carbons, and the [3.3.1] or [3.2.1] ring systems are optionally fused with an heteroaryl or heterocycloalkyl ring. Compounds of Formula I are useful in treating or preventing cognitive disorders, such as Alzheimer's Disease. The invention also encompasses pharmaceutical compositions comprising compounds of Formula I, methods of treating cognitive disorders, such as Alzheimer's disease, and the intermediates useful in preparing the compounds of Formula I.

27 Claims, No Drawings

OTHER PUBLICATIONS

Schneider et al., Archiv der Pharmazie (Weinheim, Germany) (1975), 308(5), 365-75.*

Hamada et al., "Synthesis of New Chiral Amines, 2,6-Dimethyl-9-Azabicyclo[3.3.1]nonane and its derivatives," Heterocycles, 52(2):929-934 (2000).

Kirihara et al., "Hypervalent γn-Iodane-Mediated Fragmentation of Tertiary Cyclopropanol Systems II: Application to Asymmetric Syntheses of Piperdine and Indolizaidine Alkaloids," Tetrahedron, 55, 3911-2926 (1999).

Oh et al., "A Formal Total Synthesis of (±)-Anatoxin-a by an Intramolecular Pd-Catalyzed Aminocarbonylation Reaction," Tetrahedron Letters, 39:213-2136 (1998).

Muraoka et al., "Tandem Beckmann and Huisgen-WHite rearrangement of the 9-azabicyclo[3.3.1]nonan-3-one system. Part 2. The second mode of the rearrangement leading to 6-(prop-1-enyl)piperidin-2-ylacetic acid, a verssatile intermediate for the syntheses of piperidine alkaloids (+)-pinidine and (+)-monomorine I," Journal of the Chemical Society, 2, 113-119 (1997).

Momose et al., "Efficient Synthesis of an Enantiomeric Pair of Pinidine: An Illustration of Organochemical Carving on the Rigid Bridged System as the Stereochemical Tactics," Tetrahedron Letters, 27(28):4987-4990 (1996).

Muraoka et al., "Tandem Beckmann and Huisgen-White rearrangement as an alternative to the Baeyer-Villiger oxidation of the bicyclo[3.3.1]nonane system: first asymmetric synthesis of (−)-dihydropalustramic acid. X-Ray molecular structure of 2β-ethyl-9-phenylsulfonyl-9-azabicyclo[3.3.1]nonan-3-one," Journal of the Chemical Society, 13:1567-1575 (1996).

Nelson et al., "13C NMR Studies of 9-Methyl-9-azabicyclo[3.3.1]nonane and Related Compounds,"Journal of the American Chemical Society, 98:6893-6896 (1976).

International Search Report issued in International Application No. PCT/US06/32261 on Apr. 16, 2007.

Kozikowski et al., "Structure-Activity Relationship Studies of N-Sulfonyl Analogs of Cocaine: Role of Ionic Interaction in Cocaine Binding," J. Med. Chem., 37:340-3442 (1994).

Bonjoch et al., "A Stereoselective Synthesis of CIS-4-Acetonyl-1-Benzyl-3-Ethypiperidine," Heterocycles, 26 (8):2165-2174 (1987).

Mewshaw et al., "Bridged γ0Carbolines and Derivatives Possessing Selective and Combined Affinity for 5-HT2 and D2 Receptors," J. Med. Chem., 36(10):1488-1495 (1993).

Ferrer et al., "Photocycloaddition reactions of 2-acylcyclohex-2-enones," Chemical Communications, 5, 481-482 (2001).

Hasan et al., "Syntheses and CD Studies of 5α-Cholesteno [3,2-d]-, -[2,3-d]- [3,4-d]pyrimidines," Liebigs Ann., 5, 889-896 (1995).

Hajos et al., "Synthesis and Circular Dichroism of Cholestenopyrimidines," Liebigs Ann. Chem., (1), 31-33 (1989).

Patra et al., "A New Regiospecific Method for the Synthesis of Substituted Phenanthridines and Benzo[j] phenanthridines via Aromatic Annelation of 1-N-Benzenesulfonyl-3-[Bis(methylthio)methylene]-1,2,3,4- tetrahydroquinoline-4-one," Tetrahedron, 54(34):10167-10178 (1998).

Gonzalez Trigo et al., "Application del Metodo de Desmetilacion de von Braun Modificado: Sintesis de Norpseudopelletierina," Anales de Quimica, 782-783 (1979).

* cited by examiner

BRIDGED N-CYCLIC SULFONAMIDO INHIBITORS OF GAMMA SECRETASE

This application claims priority from U.S. Provisional application No. 60/709,961, filed Aug. 19, 2005, which is incorporated by reference, in its entirety.

CROSS-REFERENCE TO RELATED APPLICATIONS

This application is a divisional of U.S. application Ser. No. 11/465,726 filed Aug. 18, 2006, which claims the benefit under 35 U.S.C. 119(e) to provisional application U.S. Ser. No. 60/709,961 filed Aug. 19, 2005, both of which are incorporated herein by reference.

BACKGROUND OF THE INVENTION

1. Field of the Invention

The invention relates to bridged N-cyclic sulfonamido compounds fused with a heteroaryl or heterocycloalkyl ring, which inhibit gamma secretase and β-amyloid peptide release and/or its synthesis. Therefore, the N-cyclic sulfonamido compounds of the present invention are useful in the prevention of cognitive disorders in patients susceptible to cognitive disorders and/or in the treatment of patients with cognitive disorders in order to inhibit further deterioration in their condition.

2. State of the Art

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39-43 amino acids designated the β-amyloid peptide (βAP) or sometimes Aβ, AβP or β/A4. β-Amyloid peptide was first purified and a partial amino acid sequence was provided by Glenner et al., Biochem. Biophys. Res. Commun., 120:885-890 (1984) The isolation procedure and the sequence data for the first 28 amino acids are described in U.S. Pat. No. 4,666,829.

Molecular biological and protein chemical analyses have shown that the β-amyloid peptide is a small fragment of a much larger precursor protein termed the amyloid precursor protein (APP), that is normally produced by cells in many tissues of various animals, including humans. Knowledge of the structure of the gene encoding APP has demonstrated that β-amyloid peptide arises as a peptide fragment that is cleaved from APP by protease enzyme(s). Sequential processing of the precursor protein by the enzymes referred to generically as beta- and gamma-secretases, gives rise to the β-amyloid peptide fragment. Both enzymes have now been molecularly cloned, and characterized to differing levels.

Several lines of evidence indicate that progressive cerebral deposition of β-amyloid peptide plays a seminal role in the pathogenesis of AD and can precede cognitive symptoms by years or decades. See, for example, Selkoe, Neuron, 6:487-498 (1991). The most important line of evidence is the discovery that missense DNA mutations at amino acid 717 of the 770-amino acid isoform of APP can be found in affected members but not unaffected members of several families with a genetically determined (familial) form of AD (Goate et al., Nature, 349:704-706 (1990); Chartier Harlan et al., Nature, 353:844-846 (1989); and Murrell et al., Science, 254:97-99 (1991).) Another such mutation, known as the Swedish variant, is comprised of a double mutation changing lysine$^{595}$-methionine$^{596}$ to asparagine$^{595}$-leucine$^{596}$ (with reference to the 695 isoform was found in a Swedish family) was reported in 1992 (Mullan et al., Nature Genet., 1:345-347 (1992). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP metabolism, and subsequent deposition of its β-amyloid peptide fragment, can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs, which are capable of inhibiting β-amyloid peptide release and/or its synthesis in vivo.

One approach toward inhibiting amyloid peptide synthesis in vivo is by inhibiting gamma secretase, the enzyme responsible for the carboxy-terminal cleavage resulting in production of β-amyloid peptide fragments of 40 or 42 residues in length. The immediate substrates for gamma secretase are β-cleaved, as well as α-cleaved carboxy-terminal fragments (CTF) of APP. The gamma-secretase cleavage site on β- and α-CTF fragments occurs in the predicted transmembrane domain of APP. Inhibitors of gamma-secretase have been demonstrated to effect amyloid pathology in transgenic mouse models (Dovey, H. F., V. John, J. P. Anderson, L. Z. Chen, P. de Saint Andrieu, L. Y. Fang, S. B. Freedman, B. Folmer, E. Goldbach, E. J. Holsztynska et al. (2001). "Functional gamma-secretase inhibitors reduce beta-amyloid peptide levels in brain." J Neurochem 76(1): 173-81.)

Gamma secretase is recognized to be a multi-subunit complex comprised of the presenilins (PS1 or PS2), Nicastrin, Aph-1, and Pen 2 (De Strooper, B. (2003). "Aph-1, Pen-2, and Nicastrin with Presenilin generate an active gamma-Secretase complex." Neuron 38(1): 9-12; Edbauer, D., E. Winkler, J. T. Regula, B. Pesold, H. Steiner and C. Haass (2003). "Reconstitution of gamma-secretase activity." Nat Cell Biol 5(5): 486-8; Kimberly, W. T., M. J. LaVoie, B. L. Ostaszewski, W. Ye, M. S. Wolfe and D. J. Selkoe (2003). "Gamma-secretase is a membrane protein complex comprised of presenilin, nicastrin, Aph-1, and Pen-2." Proc Natl Aced Sci USA 100(11): 6382-7). Much evidence indicates that PS comprises the catalytic moiety of the complex, while the other identified subunits are necessary for proper maturation and sub-cellular localization of the active enzyme complex (reviewed in De Strooper, B. (2003). "Aph-1, Pen-2, and Nicastrin with Presenilin generate an active gamma-Secretase complex." Neuron 38(1): 9-12.) Consistent with this hypothesis: PS knock-out mice exhibit significant reductions in β-amyloid production (De Strooper, B., P. Saftig, K. Craessaerts, H. Vanderstichele, G. Guhde, W. Annaert, K. Von Figura and F. Van Leuven (1998). "Deficiency of presenilin-1 inhibits the normal cleavage of amyloid precursor protein." Nature 391(6665): 387-90; Haass, C. and D. J. Selkoe (1998). "Alzheimer's disease. A technical KO of amyloid-beta peptide." Nature 391(6665): 339-40; Herreman, A., L. Serneels, W. Annaert, D. Collen, L. Schoonjans and B. De Strooper (2000). "Total inactivation of gamma-secretase activity in presenilin-deficient embryonic stem cells." Nat Cell Biol 2(7): 461-2); point mutations of putative active site aspartate residues in PS trans-membrane domains inhibit β-amyloid production in cells in a dominant negative fashion (Wolfe, M. S., W. Xia, B. L. Ostaszewski, T. S. Diehl, W. T. Kimberly and D. J. Selkoe (1999). "Two transmembrane aspartates in presenilin-1 required for presenilin endoproteolysis and gamma-secretase activity." Nature 398(6727): 513-7; Kimberly, W. T., W. Xia, T. Rahmati, M. S. Wolfe and D. J. Selkoe (2000). "The transmembrane aspartates in presenilin 1 and 2 are obligatory for gamma-secretase activity and amyloid beta-protein generation." J Biol Chem 275(5): 3173-8); active site directed substrate-based transition state isosteres designed to inhibit gamma secretase directly conjugate to PS (Esler, W. P., W. T. Kimberly, B. L. Ostaszewski, T. S. Diehl, C. L. Moore, J. Y. Tsai, T. Rahmati, W. Xia, D. J. Selkoe and M. S. Wolfe (2000). "Transition-state analogue inhibitors of gamma-secretase bind directly to presenilin-1." Nat Cell Biol 2(7): 428-34; Li, Y. M., M. Xu, M. T. Lai, Q. Huang, J. L. Castro, J. DiMuzio-Mower, T. Harrison, C. Lellis, A. Nadin, J. G. Neduvelil et al. (2000). "Photoactivated gamma-secretase inhibitors directed to the active site covalently label presenilin 1." Nature 405(6787): 689-94); finally, allosteric gamma secretase inhibitors have likewise been demonstrated to bind directly to PS (Seiffert, D., J. D. Bradley, C. M. Rominger, D. H. Rominger, F. Yang, J. E. Meredith, Jr., Q. Wang, A. H. Roach, L. A. Thompson, S. M. Spitz et al. (2000). "Presenilin-1 and -2 are molecular targets for gamma-secretase inhibitors." J Biol Chem 275(44): 34086-91.)

Current evidence indicates that in addition to APP processing leading to β-amyloid synthesis, gamma-secretase also mediates the intra-membrane cleavage of other type I transmembrane proteins (reviewed in Fortini, M. E. (2002). "Gamma-secretase-mediated proteolysis in cell-surface-receptor signaling." Nat Rev Mol Cell Biol 3(9): 673-84, see also Struhl, G. and A. Adachi (2000). "Requirements for presenilin-dependent cleavage of notch and other transmembrane proteins." Mol Cell 6(3): 625-36.) Noteworthy among the known substrates of gamma-secretase is mammalian Notch 1. The Notch 1 protein is important for cell fate determination during development, and tissue homeostasis in the adult. Upon ligand engagement via the Notch ecto-domain, Notch undergoes sequential extra-cellular and intra-membrane processing analogous to APP. The intra-membrane processing of Notch mediated by gamma secretase leads to release of the Notch intracellular domain (NICD). The NICD fragment mediates Notch signaling via translocation to the nucleus, where it regulates expression of genes mediating cellular differentiation in many tissues during development, as well as in the adult.

Disruption of Notch signaling via genetic knock-out (KO) results in embryonic lethal phenotype in mice (Swiatek, P. J., C. E. Lindsell, F. F. del Amo, G. Weinmaster and T. Gridley (1994). "Notch1 is essential for postimplantation development in mice." Genes Dev 8(6): 707-19; Conlon, R. A., A. G. Reaume and J. Rossant (1995). "Notch1 is required for the coordinate segmentation of somites." Development 121(5): 1533-45.) The Notch KO phenotype is very similar to the phenotype observed PS1 KO mice, and precisely reproduced by PS1/PS2 double KO mice (De Strooper et al. (1998). "Deficiency of presenilin-1 inhibits the normal cleavage of amyloid precursor protein." Nature 391(6665): 387-90; Donoviel, D. B., A. K. Hadjantonakis, M. Ikeda, H. Zheng, P. S. Hyslop and A. Bernstein (1999). "Mice lacking both presenilin genes exhibit early embryonic patterning defects." Genes Dev 13(21): 2801-10; Herreman, A., L. Serneels, W. Annaert, D. Collen, L. Schoonjans and B. De Strooper (2000). "Total inactivation of gamma-secretase activity in presenilin-deficient embryonic stem cells." Nat Cell Biol 2(7): 461-2.) This convergence of phenotypes observed in knock-out mice of either the substrate (Notch) or the enzyme (PS) suggests that inhibitors of gamma secretase that also inhibit Notch function may be limited as therapeutic agents owing to the importance of Notch function in adult tissues (Fortini, M. E. (2002). "Gamma-secretase-mediated proteolysis in cell-surface-receptor signaling." Nat Rev Mol Cell Biol 3(9): 673-84.) As APP knock-out mice develop normally and without an overt phenotype Zheng, H., M. Jiang, M. E. Trumbauer, R. Hopkins, D. J. Sirinathsinghji, K. A. Stevens, M. W. Conner, H. H. Slunt, S. S. Sisodia, H. Y. Chen et al. (1996). "Mice deficient for the amyloid precursor protein gene." Ann N Y Acad Sci 777: 421-6; Zheng, H., M. Jiang, M. E. Trumbauer, D. J. Sirinathsinghji, R. Hopkins, D. W. Smith, R. P. Heavens, G. R. Dawson, S. Boyce, M. W. Conner et al. (1995). "beta-Amyloid precursor protein-deficient mice show reactive gliosis and decreased locomotor activity." Cell 81(4): 525-31, the cumulative evidence, therefore, suggests that preferred gamma secretase inhibitors would have selectivity for inhibiting gamma secretase processing of APP over gamma secretase processing of Notch.

SUMMARY OF THE INVENTION

In a broad aspect, the invention provides compounds of Formula I:

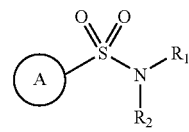

Formula I stereoisomers, tautomers, mixtures of stereoisomers and/or tautomers or pharmaceutically acceptable salts thereof, wherein, the A-ring is aryl, cycloalkyl, heteroaryl or heterocycloalkyl, where each ring is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, aryloxy, —S(O)$_{0-2}$—($C_1$-$C_6$ alkyl), —NR$_{10}$R$_{11}$, $C_1$-$C_6$ alkanoyl, $C_0$-$C_3$alkylCO$_2$R', heteroaryl, heterocycloalkyl, aryl, arylalkyl, or —SO$_2$NR$_{10}$R$_{11}$;

R$_1$ and R$_2$ combine to form a [3.3.1] or a [3.2.1] ring system, where the nitrogen is attached to the two bridgehead carbons, where 0 or 1 of the carbons in the ring system is optionally replaced with an —O—, —S(O)$_{0-2}$—, or —NR$_{15}$— group, and where the [3.3.1] or [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$;

two adjacent carbons (not including the bridgehead carbons) in the [3.3.1] or [3.2.1] ring system combine to form part of a fused heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or $C_0$-$C_1$alkylaryl (such as phenyl or naphthyl, where phenyl is preferred), where the aryl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, aryloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$, and additionally, two adjacent carbons in the [3.3.1] or the [3.2.1] ring system (not including the bridgehead carbons) may combine with one or more —C—, —CH—, and/or —CH$_2$— groups to form a cycloalkyl ring that may optionally be substituted with one or more groups that are independently halogen, $C_1$-$C_6$ alkyl or haloalkyl.

R$_{10}$ and R$_{11}$ at each occurrence are independently H or $C_1$-$C_6$ alkyl, where the alkyl is optionally substituted with an aryl (such as phenyl or naphthyl, where phenyl is preferred), where the aryl is optionally substituted with 1 to 5 groups that are independently halogen, hydroxyl, alkyl, alkoxy, haloalkyl, haloalkoxy, CN or NO$_2$; and R$_{10}$ and R$_{11}$ together may form a 3-8 membered ring optionally including an additional heteroatom such as N, O or S;

R$_{12}$ is H, $C_1$-$C_6$ alkyl or —SO$_2$-aryl (such as phenyl or naphthyl, where phenyl is preferred), where the aryl is optionally substituted with 1 to 5 groups that are independently halogen, hydroxyl, alkyl, alkoxy, haloalkyl, haloalkoxy, CN or NO$_2$;

R$_{13}$ is H or $C_1$-$C_6$ alkyl optionally substituted with aryl (such as phenyl or naphthyl, more preferably, phenyl), hydroxyl, or halogen, where the aryl is optionally substituted with 1 to 5 groups that are independently halogen, hydroxyl, alkyl, alkoxy, haloalkyl, haloalkoxy, CN or NO$_2$;

R$_{15}$ is H, aryl, heteroaryl, heterocycloalkyl, —SO$_2$R', —C(O)R'. —C(O)OR', or $C_1$-$C_6$ alkyl optionally substituted with aryl, hydroxyl, or halogen, where the aryl groups are optionally substituted with 1 to 5 groups that are independently halogen, hydroxyl, alkyl, alkoxy, haloalkyl, haloalkoxy, CN, amino, NH($C_1$-$C_6$ alkyl), N($C_1$-$C_6$ alkyl)($C_1$-$C_6$ alkyl) or NO$_2$, and R' and R" at each occurrence are independently hydrogen, $C_1$-$C_6$ alkyl, haloalkyl, $C_2$-$C_6$ alkenyl or phenyl optionally substituted with 1 to 5 groups that are independently halogen, $C_1$-$C_6$ alkyl, —C(O)OR', $C_1$-$C_6$ alkoxy, haloalkyl, haloalkoxy, hydroxyl, CN, aryloxy, —SO$_2$—($C_1$-$C_6$ alkyl), —NR$_{10}$R$_{11}$, $C_1$-$C_6$ alkanoyl, pyridyl, phenyl, NO$_2$, or —SO$_2$NR$_{10}$R$_{11}$.

The compounds of Formula I inhibit β-amyloid peptide release and/or its synthesis and, therefore, are useful in the prevention of Alzheimer's Disease (AD) in patients susceptible to AD and/or in the treatment of patients with AD in order to inhibit further deterioration in their condition. The invention also, encompasses pharmaceutical compositions containing the compounds of Formula I, and methods employing such compounds or compositions in the treatment of cognitive diseases, including Alzheimer's disease.

The invention also provides a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, age related macular degeneration or diffuse Lewy body type of Alzheimer's disease and who is in need of such treatment which comprises administration of a therapeutically effective amount of a compound of formula I.

In another aspect, the invention provides methods of preparing the compounds of interest, as well as intermediates useful in preparing the compounds of interest.

DETAILED DESCRIPTICN OF THE INVENTION

As described above, the invention provides for compounds according to Formula I.

In one aspect, the invention provides compounds of Formula Ia, Ib or Ic, i.e. compounds of Formula I having the following structures:

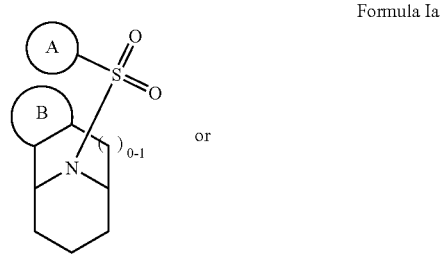

Formula Ia

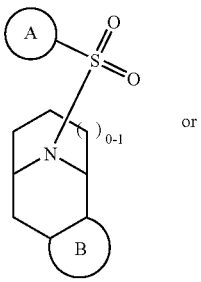

Formula Ib or

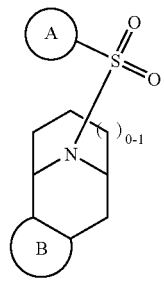

Formula Ic wherein, no carbons in the ring system are replaced with an —O—, —S(O)$_{0-2}$— or —NR$_{15}$— group;

B is a heteroaryl or heterocycloalkyl ring, where the heteroaryl and heterocycloalkyl groups are monocyclic or bicyclic, each of which is optionally substituted at a substitutable position with a group that is independently C$_1$-C$_6$ alkyl, C$_3$-C$_8$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$R', hydroxy, hydroxyalkyl, halo, C$_1$-C$_2$ haloalkyl, C$_1$-C$_2$ haloalkoxy, —NR'C(O)R'', —NR'SO$_2$R'', —C(O)R', —C(O)OR', —C(O)alkylOC(O)R'; —C(O)NR$_{10}$R$_{11}$, oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, aryloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$; and two adjacent carbons in the [3.3.1] or the [3.2.1] ring system (not including the bridgehead carbons) may combine with one or more —C—, —CH—, and/or —CH$_2$— groups to form a cycloalkyl ring that may optionally be substituted with one or more groups that are independently halogen, C$_1$-C$_6$ alkyl or haloalkyl.

In another aspect, the invention provides compounds of Formula Id and Ie, i.e., compounds of Formula I having the following structures:

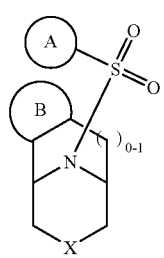

Formula Id

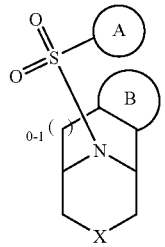

Formula Ie wherein
R$_1$ and R$_2$ combine to form a [3.3.1] or a [3.2.1] ring system where the ring system is optionally substituted with 1, 2, 3, or 4 groups that are independently oxo, halogen, C$_1$-C$_6$ alkyl, C$_2$-C$_6$ alkenyl, C$_1$-C$_6$ haloalkyl, C$_2$-C$_6$ alkynyl, hydroxy —C$_0$-C$_3$-alkyl, C$_1$-C$_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR'', —NR'S(O)$_2$R'', —OS(O)$_2$R'', —NR'C(O)R'', CN, =N—NR$_{12}$, or =N—O—R$_{13}$; and
X is —C—, —CH—, —CH$_2$—, —O—, —S(O)$_{0-2}$—, or —NR$_{15}$—.

In another aspect, the invention provides compounds according to any one of Formulas I, Ia, Ib, Ic, Id, or Ie, where the A-ring is phenyl, C$_3$-C$_8$ cycloalkyl, heteroaryl that is pyridyl, pyrimidyl, pyridazinyl, pyrazinyl, thienyl, furanyl, pyrrolyl, pyrazolyl, or imidazolyl, or heterocycloalkyl that is pyrrolidinyl, piperidinyl, piperazinyl, morpholinyl, thiomorpholinyl, or thiomorpholinyl-S,S-dioxide, where each of the above rings is optionally substituted at a substitutable position with C$_1$-C$_6$ alkyl, C$_2$-C$_6$ alkenyl, C$_2$-C$_6$ alkynyl, C$_1$-C$_6$ alkoxy, haloalkyl, haloalkoxy, hydroxyl, hydroxyalkyl, CN, phenyloxy, —S(O)$_{0-2}$—(C$_1$-C$_6$ alkyl), —NR$_{10}$R$_{11}$, C$_1$-C$_6$ alkanoyl, C$_0$-C$_3$alkylCO$_2$R', pyridyl, thienyl, furanyl, pyrrolyl, pyrrolidinyl, piperidinyl, piperazinyl, phenyl, phenyl C$_1$-C$_4$ alkyl, or —SO$_2$NR$_{10}$R$_{11}$.

In another aspect, the invention provides a compound of Formula II, i.e., a compound of Formula I with the structure:

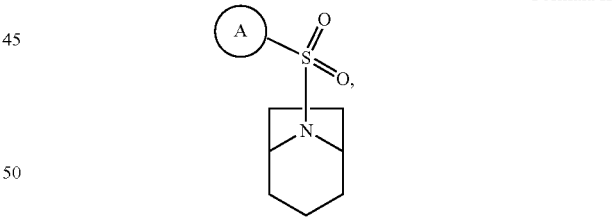

Formula II wherein
two adjacent carbons (not including the bridgehead carbons) in the [3.2.1] ring system combine to form part of a fused heteroaryl or heterocycloalkyl ring, each of which is optionally substituted at a substitutable position, as is described above for Formula I,
where two adjacent carbons (not including the bridgehead carbons) may combine to form part of a cycloalkyl ring that may optionally be substituted at a substitutable position with one or more groups that are independently halogen, C$_1$-C$_6$ alkyl or haloalkyl;
where 0 or 1 of the carbons in the [3.2.1] ring system is optionally replaced with an —O—, —S(O)$_{0-2}$—, or —NR$_{15}$— group;

the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$; and R$_{15}$ is H, phenyl, pyridyl, pyrimidinyl, oxazolyl, thiazolyl, imidazolyl, thienyl, furanyl, pyrrolyl, piperidinyl, piperazinyl, pyrrolidinyl, imidazolidinyl, indolyl, quinolinyl, —SO$_2$R', C(O)R', —C(O)OR', or $C_1$-$C_6$ alkyl optionally substituted with phenyl, hydroxyl, or halogen, where the above cyclic groups are optionally substituted with 1 to 5 groups that are independently halogen, hydroxyl, $C_1$-$C_6$ alkyl, $C_1$-$C_6$ alkoxy, $C_1$-$C_6$ haloalkyl (such as CF$_3$ or CH$_2$CF$_3$), $C_1$-$C_4$ haloalkoxy (such as OCF$_3$ or OCH$_2$CF$_3$), CN, amino, NH($C_1$-$C_6$ alkyl), N($C_1$-$C_6$ alkyl) ($C_1$-$C_6$ alkyl) or NO$_2$.

In still another aspect, the invention provides compounds of Formula II, i.e compounds of Formula II, wherein the A-ring is phenyl or naphthyl (preferably phenyl), which is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —S(O)$_{0-2}$—($C_1$-$C_6$ alkyl), —NR$_{10}$R$_{11}$, $C_1$-$C_6$ alkanoyl, $C_0$-$C_3$alkylCO$_2$R', pyridyl, thienyl, furanyl, pyrrolyl, pyrrolidinyl, piperidinyl, piperazinyl, phenyl, phenyl $C_1$-$C_4$ alkyl, or —SO$_2$NR$_{10}$R$_{11}$.

In another aspect, the invention provides compounds of Formulas IIIa, IIIb, and IIIc, i.e. compounds of Formula III wherein no carbons in the [3.2.1] ring system are replaced with an —O—, —S(O)$_{0-2}$—, or —NR$_{15}$— group, having the following structures:

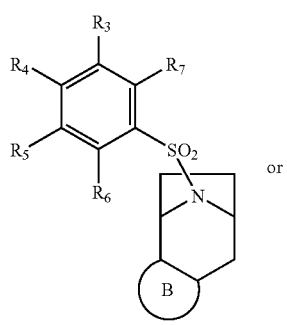

Formula IIIa

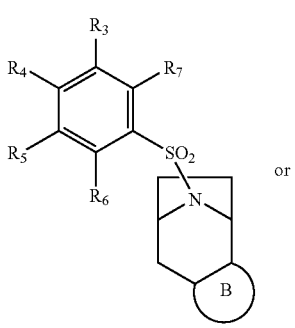

Formula IIIb

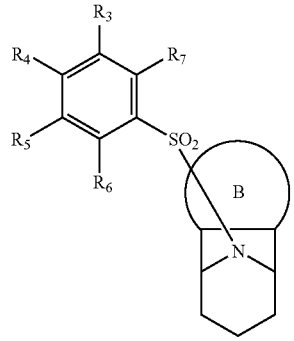

Formula IIIc wherein, the B-ring is a heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R', —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$;

the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{11}$, and additionally, two adjacent carbons (not including the bridgehead carbons) may combine to form a cycloalkyl ring that may optionally be substituted with halogen, $C_1$-$C_6$ alkyl or haloalkyl;

R$_3$, R$_4$, R$_5$, R$_6$, R$_7$ are independently of each other H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, —$C_1$-$C_3$ alkyl-OH, —$C_1$-$C_3$ alkyl-alkoxy, phenyloxy, —S(O$_2$)R', —NR$_{10}$R$_{11}$, $C_1$-$C_6$ alkanoyl, oxazolyl, pyrazolyl, thiazolyl, pyridyl, pyrimidinyl, imidazolyl, indolyl, furanyl, thienyl, phenyl, or phenyl $C_1$-$C_4$ alkyl, or R$_4$ and R$_5$, or R$_5$ and R$_6$ and the carbons to which they are attached form a heterocycloalkyl or a heteroaryl ring which is optionally substituted with 1, 2, 3, or 4 groups that are independently $C_1$-$C_4$ alkyl, $C_1$-$C_4$ alkoxy, halogen, or $C_1$-$C_4$ alkanoyl wherein the alkanoyl group is optionally substituted with up to 3 halogen atoms; or R$_4$ and R$_5$, or R$_5$ and R$_6$ and the carbons to which they are attached form a benzo ring which is optionally substituted with optionally substituted with 1 to 5 groups that are independently halogen, hydroxyl, alkyl, alkoxy, haloalkyl, haloalkoxy, CN or NO$_2$; and R' and R" are independently of each other hydrogen, $C_1$-$C_6$ alkyl, haloalkyl, $C_2$-$C_6$ alkenyl or phenyl optionally substituted with 1 to 5 groups that are independently halogen, $C_1$-$C_6$ alkyl, —C(O)OR', $C_1$-$C_6$ alkoxy, haloalkyl, haloalkoxy, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, NO$_2$, or —SO$_2$NR$_{10}$R$_{11}$.

In another aspect, the invention provides compounds of Formulas IIId, IIIe and IIIf, i.e., compounds of Formula III, having the structures:

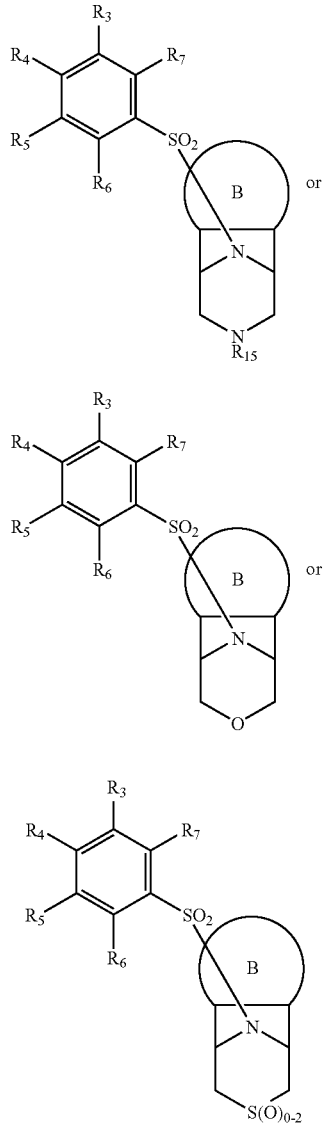

Formula IIId

Formula IIIe

Formula IIIf wherein, the B-ring is a heteroaryl or heterocycloalkyl ring, each of which is optionally substituted at a substitutable position with a group that is independently C$_1$-C$_6$ alkyl, C$_3$-C$_8$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$R', hydroxy, hydroxyalkyl, halo, C$_1$-C$_2$ haloalkyl, C$_1$-C$_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, phenyloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$;

the [3.2.1] ring system is optionally substituted with 1, 2, 3, or 4 groups that are independently oxo, halogen, C$_1$-C$_6$ alkyl, C$_2$-C$_6$ alkenyl, C$_1$-C$_6$ haloalkyl, C$_2$-C$_6$ alkynyl, hydroxy, hydroxyalkyl, C$_1$-C$_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, C$_1$-C$_6$ alkyl or haloalkyl;

R$_3$, R$_4$, R$_5$, R$_6$, R$_7$ are independently of each other H, halogen, C$_1$-C$_6$ alkyl, C$_1$-C$_6$ haloalkyl, C$_1$-C$_6$ haloalkoxy, CN, hydroxyl, C$_1$-C$_6$ alkoxy, —C$_1$-C$_3$ alkyl-OH, —C$_1$-C$_3$ alkyl-alkoxy, phenyloxy, —SO$_2$R', —NR$_{10}$R$_{11}$, C$_1$-C$_6$ alkanoyl, oxazolyl, pyrazolyl, thiazolyl, pyridyl, pyrimidinyl, imidazolyl, indolyl, furanyl, thienyl, phenyl, or phenyl C$_1$-C$_4$ alkyl, or R$_4$ and R$_5$, or R$_5$ and R$_6$ and the carbons to which they are attached form a heterocycloalkyl or a heteroaryl ring which is optionally substituted with 1, 2, 3, or 4 groups that are independently C$_1$-C$_4$ alkyl, C$_1$-C$_4$ alkoxy, halogen, or C$_1$-C$_4$ alkanoyl wherein the alkanoyl group is optionally substituted with up to 3 halogen atoms; or R$_4$ and R$_5$, or R$_5$ and R$_6$ and the carbons to which they are attached form a benzo ring which is optionally substituted with 1 to 5 groups that are independently halogen, hydroxyl, alkyl, alkoxy, haloalkyl, haloalkoxy, CN or NO$_2$;

R' and R" are independently of each other hydrogen, C$_1$-C$_6$ alkyl, haloalkyl, C$_2$-C$_6$ alkenyl or phenyl optionally substituted with 1 to 5 groups that are independently halogen, C$_1$-C$_6$ alkyl, —C(O)OR', C$_1$-C$_6$ alkoxy, haloalkyl (such as CF$_3$), haloalkoxy (such as OCF$_3$), hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, NO$_2$, or —SO$_2$NR$_{10}$R$_{11}$; and R$_{15}$ is H, phenyl, pyridyl, pyrimidinyl, oxazolyl, thienyl, furanyl, pyrrolyl, piperidinyl, piperazinyl, pyrrolidinyl, imidazolidinyl, indolyl, —SO$_2$R', —C(O)R'. —C(O)OR', or C$_1$-C$_6$ alkyl optionally substituted with phenyl, hydroxyl, or halogen, where the above cyclic groups are optionally substituted with 1 to 5 groups that are independently halogen, hydroxyl, C$_1$-C$_4$ alkyl, C$_1$-C$_4$ alkoxy, C$_1$-C$_4$ haloalkyl (such as CF$_3$), C$_1$-C$_4$ haloalkoxy (such as OCF$_3$), amino, NH(C$_1$-C$_4$ alkyl), N(C$_1$-C$_4$ alkyl) (C$_1$-C$_4$ alkyl), CN or NO$_2$.

In some aspects, the invention provides compounds of Formulas IIIa, IIIb, IIIc, IIId, IIIe or IIIf wherein the B-ring is pyrazolyl, imidazolyl, pyrrolyl, triazolyl, pyrrolidinyl, pyrazolidinyl, imidazolidinyl, triazolopyrimidinyl, imidazopyrimidinyl, pyrazolopyrimidinyl, indolyl or pyridyl, each of which is optionally substituted at a substitutable position with a group that is independently C$_1$-C$_6$ alkyl, C$_3$-C$_8$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$R', hydroxy, hydroxyalkyl, halo, C$_1$-C$_2$ haloalkyl, C$_1$-C$_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, phenyloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$.

In some other aspects, the invention provides compounds of Formulas IIIa, IIIb, IIIc, IIId, IIIe or IIIf wherein the B-ring is pyrazolyl, imidazolyl, pyrrolyl, triazolyl, pyrrolidinyl, pyrazolidinyl, imidazolidinyl or pyridyl, each of which is optionally substituted at a substitutable position with a group that is independently $C_1$-$C_4$ alkyl, $C_3$-$C_6$ cycloalkyl, $C_2$-$C_6$ alkenyl, $C_2$-$C_6$ alkynyl, $C_1$-$C_4$ alkoxy, amino, $C_1$-$C_4$ alkylamino, $C_1$-$C_4$ dialkylamino, —S(O)$_{0-2}$R', hydroxy, hydroxy $C_1$-$C_4$ alkyl, halo, $C_1$-$C_2$ haloalkyl (such as $CF_3$), $C_1$-$C_2$ haloalkoxy (such as $OCF_3$), —NR'C(O)R", —NR'SO$_2$R", —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-5 groups independently selected from halogen, $C_1$-$C_4$ alkyl, —CO$_2$R', $C_1$-$C_4$ alkoxy, $C_1$-$C_2$ haloalkyl (such as $CF_3$), $C_1$-$C_2$ haloalkoxy (such as $OCF_3$), hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$.

In some other aspects, the invention provides compounds of Formulas IIIa, IIIb, IIIc, IIId, IIIe or IIIf wherein the B-ring is pyrazolyl, imidazolyl, pyrrolyl, triazolyl, pyrrolidinyl, pyrazolidinyl, imidazolidinyl or pyridyl, each of which is unsubstituted.

In some other aspects, the invention provides compounds of Formulas IIIa, IIIb, IIIc, IIId, IIIe or IIIf wherein the B-ring is pyrazolyl, imidazolyl, pyrrolyl, triazolyl, pyrrolidinyl, pyrazolidinyl, imidazolidinyl or pyridyl, each of which is substituted at a substitutable position with a group that is independently $C_1$-$C_4$ alkyl, $C_3$-$C_6$ cycloalkyl, $C_2$-$C_6$ alkenyl, $C_1$-$C_4$ alkoxy, amino, $C_1$-$C_4$ alkylamino, $C_1$-$C_4$ dialkylamino, —S(O)$_{0-2}$R', hydroxy, hydroxy $C_1$-$C_4$ alkyl, halo, $C_1$-$C_2$ haloalkyl (such as $CF_3$), $C_1$-$C_2$ haloalkoxy (such as $OCF_3$), —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-3 groups independently selected from halogen, $C_1$-$C_4$ alkyl, —CO$_2$R', $C_1$-$C_4$ alkoxy, $C_1$-$C_2$ haloalkyl (such as $CF_3$), $C_1$-$C_2$ haloalkoxy (such as $OCF_3$), hydroxyl, —NR$_{10}$R$_{11}$, and $C_1$-$C_6$ alkanoyl.

In some aspects, the invention provides compounds of Formulas IIIa, IIIb, IIIc, IIId, IIIe or IIIf wherein the B-ring is triazolopyrimidinyl, imidazopyrimidinyl, pyrazolopyrimidinyl, or indolyl, each of which is optionally substituted at a substitutable position with a group that is independently $C_1$-$C_4$ alkyl, $C_3$-$C_6$ cycloalkyl, $C_2$-$C_6$ alkenyl, $C_2$-$C_6$ alkynyl, $C_1$-$C_4$ alkoxy, amino, $C_1$-$C_4$ alkylamino, $C_1$-$C_4$ dialkylamino, —S(O)$_{0-2}$R', hydroxy, hydroxy $C_1$-$C_4$ alkyl, halo, $C_1$-$C_2$ haloalkyl (such as $CF_3$), $C_1$-$C_2$ haloalkoxy (such as $OCF_3$), —NR'C(O)R", —NR'SO$_2$R', —C(O)R', —C(O)OR', —C(O)alkylOC(O)R'; —C(O)NR$_{10}$R$_{11}$, oxo, CN, or CO—$C_1$alkylphenyl, where the phenyl is optionally substituted with 1-5 groups independently selected from halogen, $C_1$-$C_4$ alkyl, —CO$_2$R', $C_1$-$C_4$ alkoxy, $C_1$-$C_2$ haloalkyl (such as $CF_3$), $C_1$-$C_2$ haloalkoxy (such as $OCF_3$), hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$.

In some other aspects, the invention provides compounds of Formulas IIIa, IIIb, IIIc, IIId, IIIe or IIIf wherein the B-ring is triazolopyrimidinyl, imidazopyrimidinyl, pyrazolopyrimidinyl, or indolyl, each of which is unsubstituted.

In some other aspects, the invention provides compounds of Formulas IIIa, IIIb, IIIc, IIId, IIIe or IIIf wherein the B-ring is triazolopyrimidinyl, imidazopyrimidinyl, pyrazolopyrimidinyl, or indolyl, each of which is substituted at a substitutable position with a group that is independently $C_1$-$C_4$ alkyl, $C_3$-$C_6$ cycloalkyl, $C_2$-$C_6$ alkenyl, $C_1$-$C_4$ alkoxy, amino, $C_1$-$C_4$ alkylamino, $C_1$-$C_4$ dialkylamino, —S(O)$_{0-2}$R', hydroxy, hydroxy $C_1$-$C_4$ alkyl, halo, $C_1$-$C_2$ haloalkyl (such as $CF_3$), $C_1$-$C_2$ haloalkoxy (such as $OCF_3$), —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-3 groups independently selected from halogen, $C_1$-$C_4$ alkyl, —CO$_2$R', $C_1$-$C_4$ alkoxy, $C_1$-$C_2$ haloalkyl (such as $CF_3$), $C_1$-$C_2$ haloalkoxy (such as $OCF_3$), hydroxyl, —NR$_{10}$R$_{11}$, and $C_1$-$C_6$ alkanoyl.

In other aspects, the invention provides compounds of Formulas IIIa, IIIb, IIIc, IIId, IIIe or IIIf wherein
$R_3$ is H, halogen, $C_1$-$C_6$ alkyl, $C_1$-$C_6$ alkoxy, haloalkyl, or CN;
$R_4$ is H, halogen; $C_1$-$C_6$ alkyl; $C_1$-$C_6$ alkoxy; $C_1$-$C_6$ haloalkyl; haloalkoxy, CN, phenyloxy, —SO$_2$—($C_1$-$C_6$ alkyl), —NR$_{10}$R$_{11}$, $C_1$-$C_6$ alkanoyl, oxazolyl, pyrazolyl, thiazolyl, pyridyl, furanyl, thienyl, or phenyl; and
$R_5$ is H, $C_1$-$C_6$ alkyl, —SO$_2$—NR$_{10}$R$_{11}$, or halogen.

In other aspects, the invention provides compounds of Formulas IIIa, IIIb, IIIc, IIId, IIIe or IIIf, wherein $R_6$ and $R_7$ are independently H or methyl.

In still other aspects, the invention provides compounds of Formulas IIIa, IIIb, IIIc, IIId, IIIe or IIIf, wherein $R_3$ and $R_5$ are independently H, halo, $CF_3$, $CHF_2$ or methyl.

In still other aspects, the invention provides compounds of Formulas IIIa, IIIb, IIIc, IIId, IIIe or IIIf, wherein $R_4$, $R_6$ and $R_7$ are independently H, halo, $CF_3$, $CHF_2$ or methyl.

In other aspects, the invention provides compounds of Formulas IIIa, IIIb, IIIc, IIId, IIIe or IIIf, wherein $R_4$ is H, halogen (in one aspect, I, Br, F or Cl), $C_1$-$C_6$ alkyl optionally substituted with halogen or hydroxyl, $C_1$-$C_6$ alkoxy, $OCF_3$, or CN.

In yet still other aspects, the invention provides compounds of Formulas IIIa, IIIb, IIIc, IIId, IIIe or IIIf, wherein $R_4$ is phenyloxy, —SO$_2$—($C_1$-$C_6$ alkyl), —NR$_{10}$R$_{11}$, $C_1$-$C_6$ alkanoyl, oxazolyl, pyrazolyl, thiazolyl, pyridyl, furanyl, thienyl, or phenyl.

In still yet another aspect, the invention provides compounds of Formulas IIIa, IIIb, IIIc, IIId, IIIe or IIIf, wherein $R_4$ is —NR$_{10}$R$_{11}$.

In still yet another aspect, the invention provides compounds of Formulas IIIa, IIIb, IIIc, IIId, IIIe or IIIf, wherein $R_4$ is —NR$_{10}$R$_{11}$, and $R_3$, $R_5$, $R_6$, and $R_7$ are H.

In yet still another aspect, the invention provides compounds of Formulas IIIa, IIIb, IIIc, IIId, IIIe or IIIf, wherein $R_3$, $R_4$, $R_5$, $R_6$, and $R_7$ are H, halo, $CF_3$, $CHF_2$ or methyl.

In yet still another aspect, the invention provides compounds of Formulas IIIa, IIIb, IIIc, IIId, IIIe or IIIf, wherein $R_3$, $R_5$, $R_6$, and $R_7$ are H.

In still another aspect, the invention provides compounds of Formulas IIIa, IIIb, IIIc, IIId, IIIe or IIIf, wherein $R_4$ is chloro.

In yet still another aspect, the invention provides compounds of Formulas IIIa, IIIb, IIIc, IIId, IIIe or IIIf, wherein $R_4$ is chloro, and $R_3$, $R_5$, $R_6$, and $R_7$ are H.

In another aspect, the invention provides compounds of Formulas IIIa, IIIb, IIIc, IIId, IIIe or IIIf, wherein at least one of $R_3$, $R_4$, or $R_5$ is chloro, and $R_6$ and $R_7$ are H.

In another aspect, the invention provides compounds of Formulas IIIa, IIIb, IIIc, IIId, IIIe or IIIf, wherein $R_3$ is hydrogen, halogen, $C_1$-$C_4$ alkyl, $C_1$-$C_4$ alkoxy, $CF_3$, or CN;
$R_4$ is hydrogen, halogen, $C_1$-$C_4$ alkyl, $C_1$-$C_4$ alkoxy, $CF_3$, $OCF_3$, CN, phenyloxy, —SO$_2$—($C_1$-$C_4$ alkyl), —NR$_{10}$R$_{11}$, $C_1$-$C_4$ alkanoyl, and
$R_5$ is hydrogen, $C_1$-$C_4$ alkyl, —SO$_2$NR$_{10}$R$_{11}$ or halogen.

In still yet another aspect, the invention provides compounds of Formulas IIIa, IIIb, IIIc, IIId, IIIe or IIIf, wherein $R_4$ is halogen (in one aspect, F or Cl), $C_1$-$C_4$ alkyl, $C_1$-$C_4$ alkoxy, $CF_3$, $OCF_3$, or CN.

In another aspect, the invention provides compounds of Formulas IIIa, IIIb, IIIc, IIId, IIIe or IIIf, wherein $R_4$, $R_5$, $R_6$, and $R_7$ are hydrogen.

In another aspect, the invention provides compounds of Formulas IIIa, IIIb, IIIc, IIId, IIIe or IIIf, wherein $R_3$ is hydrogen, halogen, $C_1$-$C_4$ alkyl, $C_1$-$C_4$ alkoxy, $CF_3$, or CN;

$R_4$ is oxazolyl, pyrazolyl, thiazolyl, pyridyl, furanyl, thienyl, or phenyl; and $R_5$ is hydrogen, $C_1$-$C_4$ alkyl, —$SO_2$ $NR_{10}R_{11}$, or halogen.

In still yet another aspect, the invention provides compounds of Formulas IIIa, IIIb, IIIc, IIId, IIIe or IIIf, wherein $R_4$ is halogen (in one aspect, F or Cl), $CH_3$, $OCH_3$, $CF_3$, or $OCF_3$.

In another aspect, the invention provides compounds of Formulas IIIa, IIIb, IIIc, IIId, IIIe or IIIf, wherein $R_3$ is hydrogen, halogen, $C_1$-$C_2$ alkyl, $C_1$-$C_2$ alkoxy, $CF_3$, or CN;

$R_4$ is hydrogen, halogen, $C_1$-$C_2$ alkyl, $C_1$-$C_2$ alkoxy, $C_1$-$C_2$ haloalkyl, $C_1$-$C_2$ haloalkoxy, CN, —$NR_{10}R_{11}$, $C_2$-$C_3$ alkanoyl, oxazolyl, pyrazolyl, thiazolyl, pyridyl, furanyl, or thienyl;

$R_5$ is hydrogen, $CH_3$, or F; and $R_6$ and $R_7$ are independently hydrogen or halogen.

In still yet another aspect, the invention provides compounds of Formulas IIIa, IIIb, IIIc, IIId, IIIe or IIIf, wherein $R_4$ is $CF_3$, or $OCF_3$.

In yet another aspect, the invention provides compounds of Formulas IIIa, IIIb, IIIc, IIId, IIIe or IIIf, wherein $R_4$ and $R_5$, or $R_5$ and $R_6$ and the carbons to which they are attached form a benzo ring which is optionally substituted with optionally substituted with 1 or 2 groups that are independently halogen, hydroxyl, $C_1$-$C_4$ alkyl, $C_1$-$C_4$ alkoxy, $C_1$-$C_3$ haloalkyl, $C_1$-$C_3$ haloalkoxy, CN or $NO_2$ In still yet another aspect, the invention provides compounds of Formulas IIIa, IIIb, IIIc, IIId, IIIe or IIIf, wherein $R_4$ and $R_5$, or $R_5$ and $R_6$ and the carbons to which they are attached form a pyridyl, pyrrolyl, thienyl, furanyl, pyrrolidinyl, piperidinyl ring, each of which is optionally substituted with 1, 2, or 3 groups that are independently $C_1$-$C_4$ alkyl, $C_1$-$C_4$ alkoxy, halogen, or $C_1$-$C_4$ alkanoyl wherein the alkanoyl group is optionally substituted with up to 3 halogen atoms (such as F).

In one aspect, the invention provides compounds of Formulas IIIa, IIIb, IIIc, IIId, IIIe or IIIf, wherein $R_6$ and $R_7$ are independently hydrogen or methyl.

In one aspect, the invention provides compounds of Formulas IIIa, IIIb, IIIc, IIId, IIIe or IIIf, wherein $R_3$ and $R_5$ are independently hydrogen, halo, or methyl.

In another aspect, the invention provides compounds of Formula IV, i.e., compounds of Formula II, wherein the A-ring is $C_3$-$C_8$ cycloalkyl, which is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —$S(O)_{0-2}$—($C_1$-$C_6$ alkyl), —$NR_{10}R_{11}$, $C_1$-$C_6$ alkanoyl, $C_0$-$C_3$alkyl$CO_2R'$, pyridyl, thienyl, furanyl, pyrrolyl, pyrrolidinyl, piperidinyl, piperazinyl, phenyl, phenyl $C_1$-$C_4$ alkyl, or —$SO_2NR_{10}R_{11}$.

In yet another aspect, the invention provides compounds of Formula IVa, IVb or IVc, i.e. compounds of Formula IV wherein no carbons in the [3.2.1] ring system are replaced with an —O—, —$S(O)_{0-2}$—, or —$NR_{15}$— group, having the following structures:

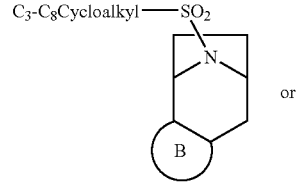

Formula IVa

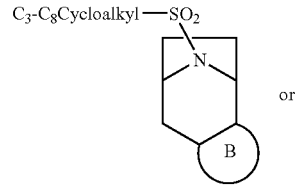

Formula IVb

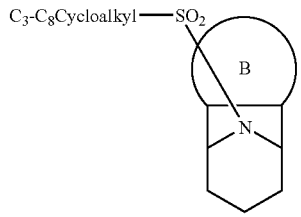

Formula IVc wherein, the B-ring is a heteroaryl or heterocycloalkyl ring, each of which is optionally substituted at a substitutable position with a group that is independently is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —$S(O)_{0-2}R'$, hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or CO—C$_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$; and the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl.

In yet another aspect, the invention provides compounds of Formula IVd, IVe or IVf, i.e. compounds of Formula IV having the following structures:

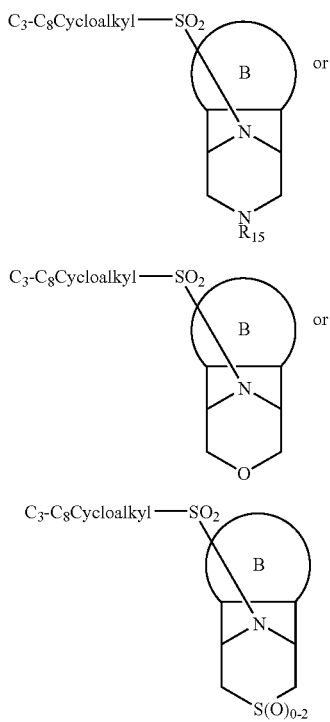

wherein, the B-ring is a heteroaryl or heterocycloalkyl ring, each of which is optionally substituted at a substitutable position with a group that is independently is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or CO—$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$;

the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, —N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl; and R$_{15}$ is H, phenyl, pyridyl, pyrimidinyl, oxazolyl, thienyl, furanyl, pyrrolyl, piperidinyl, piperazinyl, pyrrolidinyl, imidazolidinyl, indolyl, —SO$_2$R', —C(O)R'. —C(O)OR', or $C_1$-$C_6$ alkyl optionally substituted with phenyl, hydroxyl, or halogen, where the above cyclic groups are optionally substituted with 1 to 5 groups that are independently halogen, hydroxyl, $C_1$-$C_4$ alkyl, $C_1$-$C_4$ alkoxy, $C_1$-$C_4$ haloalkyl (such as CF$_3$), $C_1$-$C_4$ haloalkoxy (such as OCF$_3$), CN, amino, NH($C_1$-$C_6$ alkyl), N($C_1$-$C_6$ alkyl) ($C_1$-$C_6$ alkyl), or NO$_2$.

In some aspects, the invention provides compounds of Formula IVg, i.e., compounds according to any one of Formulas IVa, IVb, IVc, IVd, IVe or IVf wherein the B-ring is pyrazolyl, imidazolyl, pyrrolyl, triazolyl, pyrrolidinyl, pyrazolidinyl, imidazolidinyl, triazolopyrimidinyl, imidazopyrimidinyl, pyrazolopyrimidinyl, indolyl, or pyridyl, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$.

In yet another aspect, the invention provides compounds of Formula IV-1, i.e, compounds according to any one of Formulas IVa, IVb, IVc, IVd, IVe, IVf, or IVg, wherein the $C_3$-$C_8$ cycloalkyl group is cyclopropyl.

In yet another aspect, the invention provides compounds of Formula IV-2, i.e, compounds according to any one of Formulas IVa, IVb, IVc, IVd, IVe, IVf, or IVg, wherein the $C_3$-$C_8$ cycloalkyl group is cyclobutyl.

In yet another aspect, the invention provides compounds of Formula IV-3, i.e, compounds according to any one of Formulas IVa, IVb, IVc, IVd, IVe, IVf, or IVg, wherein the $C_3$-$C_8$ cycloalkyl group is cyclopentyl.

In yet another aspect, the invention provides compounds of Formula IV-4, i.e, compounds according to any one of Formulas IVa, IVb, IVc, IVd, IVe, IVf, or IVg, wherein the $C_3$-$C_8$ cycloalkyl group is cyclohexyl.

In yet another aspect, the invention provides compounds of Formula IV-5, i.e, compounds according to any one of Formulas IVa, IVb, IVc, IVd, IVe, IVf, or IVg, wherein the $C_3$-$C_8$ cycloalkyl group is cycloheptyl.

In yet another aspect, the invention provides compounds of Formula IV-6, i.e, compounds according to any one of Formulas IVa, IVb, IVc, IVd, IVe, IVf, or IVg, wherein the $C_3$-$C_8$ cycloalkyl group is cyclooctyl.

In another aspect, the invention provides compounds of Formula V, i.e., compounds of Formula II, wherein the A-ring is heteroaryl that is pyridyl, pyrimidyl, pyridazinyl, pyrazinyl, thienyl, furanyl, pyrrolyl, pyrazolyl, or imidazolyl, each of which is optionally substituted at one or more substitutable positions with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —S(O)$_{0-2}$—($C_1$-$C_6$ alkyl), —NR$_{10}$R$_{11}$, $C_1$-$C_6$ alkanoyl, $C_0$-$C_3$alkylCO$_2$R', pyridyl, thienyl, furanyl, pyrrolyl, pyrrolidinyl, piperidinyl, piperazinyl, phenyl, phenyl $C_1$-$C_4$ alkyl or —SO$_2$NR$_{10}$R$_{11}$.

In another aspect, the invention provides compounds of Formulas Va, Vb or Vc, i.e. compounds of Formula V having the following structures:

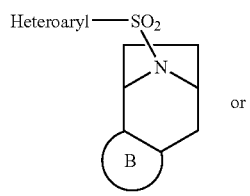

Formula Va or

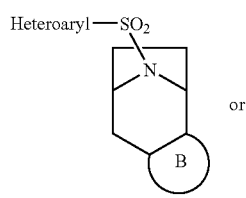

Formula Vb or

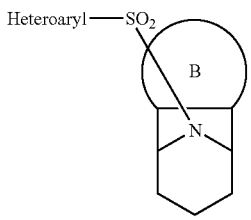

Formula Vc

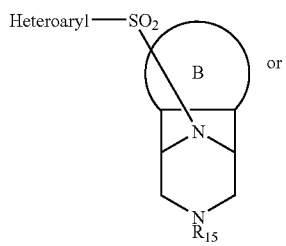

Formula Vd or

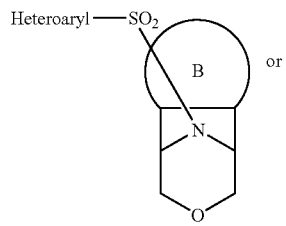

Formula Ve or

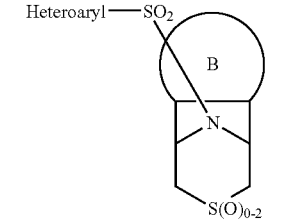

Formula Vf wherein, the B-ring is a heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R'', —NR'SO$_2$R'', —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$; and the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR'', —NR'S(O)$_2$R'', —OS(O)$_2$R'', —NR'C(O)R'', CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl.

In yet another aspect, the invention provides compounds of Formula Vd, Ve or Vf, i.e. compounds of Formula V wherein one of the carbons in the [3.2.1] ring system is replaced with an —O—, —S(O)$_{0-2}$—, or —NR$_{15}$— group, with the following structures:

wherein, the B-ring is a heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R'', —NR'SO$_2$R—, —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$;

the [3.2.1] ring system is optionally substituted with 1 1, 2, 3, or 4 groups that are independently oxo, halogen, $C_1$-$C_8$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR'', —NR'S(O)$_2$R'', —OS(O)$_2$R'', —NR'C(O)R'', CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl; and $R_{15}$ is H, phenyl, pyridyl, pyrimidinyl, oxazolyl, thienyl, furanyl, pyrrolyl, piperidinyl, piperazinyl, pyrrolidinyl, imidazolidinyl, indolyl, —SO$_2$R', —C(O)R'. —C(O)OR', or $C_1$-$C_6$ alkyl optionally substituted with phenyl, hydroxyl, or halogen, where the above cyclic groups are optionally substituted with 1 to 5 groups that are independently halogen, hydroxyl, $C_1$-$C_4$ alkyl, $C_1$-$C_4$ alkoxy, $C_1$-$C_4$ haloalkyl (such as CF$_3$), $C_1$-$C_4$ haloalkoxy (such as OCF$_3$), CN, amino, NH($C_1$-$C_6$ alkyl), N($C_1$-$C_6$ alkyl) ($C_1$-$C_6$ alkyl), or NO$_2$.

In some aspects, the invention provides compounds of Formula Vg, i.e., compounds according to any one of Formulas Va, Vb, Vc, Vd, Ve or Vf wherein the B-ring is pyrazolyl, imidazolyl, pyrrolyl, triazolyl, pyrrolidinyl, pyrazolidinyl, imidazolidinyl, triazolopyrimidinyl, imidazopyrimidinyl, pyrazolopyrimidinyl, or indolyl, or pyridyl, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$.

In still another aspect, the invention provides compounds of Formula V-1, i.e, compounds according to any one of Formulas II, Va, Vb, Vc, Vd, Ve, Vf, or Vg, wherein the heteroaryl group is pyridyl, which is optionally substituted at one or more substitutable positions with groups that are independently halogen, $C_1$-$C_6$ alkyl, $C_1$-$C_6$ alkoxy, CF$_3$, OCF$_3$, hydroxyl, CN, phenyloxy, —SO$_2$—($C_1$-$C_6$ alkyl), —NR$_{10}$R$_{11}$, $C_1$-$C_6$ alkanoyl, pyridyl, phenyl, or —SO$_2$NR$_{10}$R$_{11}$, where each R$_{10}$ and R$_{11}$ is independently H or $C_1$-$C_6$ alkyl. In some embodiments pyridyl is substituted with halogen, for example chloro.

In still another aspect, the invention provides compounds of Formula V-2, i.e, compounds according to any one of Formulas II, Va, Vb, Vc, Vd, Ve, Vf, or Vg, wherein the heteroaryl group is pyrimidyl, which is optionally substituted at one or more substitutable positions with groups that are independently halogen, $C_1$-$C_6$ alkyl, $C_1$-$C_6$ alkoxy, CF$_3$, OCF$_3$, hydroxyl, CN, phenyloxy, —SO$_2$—($C_1$-$C_6$ alkyl), —NR$_{10}$R$_{11}$, $C_1$-$C_6$ alkanoyl, pyridyl, phenyl, or —SO$_2$NR$_{10}$R$_{11}$, where each R$_{10}$ and R$_{11}$ is independently H or $C_1$-$C_6$ alkyl. In some aspects pyrimidyl is substituted with halogen, for example chloro.

In still another aspect, the invention provides compounds of Formula V-3, i.e, compounds according to any one of Formulas II, Va, Vb, Vc, Vd, Ve, Vf, or Vg, wherein the heteroaryl group is pyridazinyl, which is optionally substituted at one or more substitutable positions with groups that are independently halogen, $C_1$-$C_6$ alkyl, $C_1$-$C_6$ alkoxy, CF$_3$, OCF$_3$, hydroxyl, CN, phenyloxy, —SO$_2$—($C_1$-$C_6$ alkyl), —NR$_{10}$R$_{11}$, $C_1$-$C_6$ alkanoyl, pyridyl, phenyl, or —SO$_2$NR$_{10}$R$_{11}$, where each R$_{10}$ and R$_{11}$ is independently H or $C_1$-$C_6$ alkyl. In some aspects pyridazinyl is substituted with halogen, for example chloro.

In still another aspect, the invention provides compounds of Formula V-4, i.e, compounds according to any one of Formulas II, Va, Vb, Vc, Vd, Ve, Vf, or Vg, wherein the heteroaryl group is pyrazinyl, which is optionally substituted at one or more substitutable positions with groups that are independently halogen, $C_1$-$C_6$ alkyl, $C_1$-$C_6$ alkoxy, CF$_3$, OCF$_3$, hydroxyl, CN, phenyloxy, —SO$_2$—($C_1$-$C_6$ alkyl), —NR$_{10}$R$_{11}$, $C_1$-$C_6$ alkanoyl, pyridyl, phenyl, or —SO$_2$NR$_{10}$R$_{11}$, where each R$_{10}$ and Ran is independently H or $C_1$-$C_6$ alkyl. In some aspects pyrazinyl is substituted with halogen, for example chloro.

In still another aspect, the invention provides compounds of Formula V-5, i.e, compounds according to any one of Formulas II, Va, Vb, Vc, Vd, Ve, Vf, or Vg, wherein the heteroaryl group is thienyl, which is optionally substituted at one or more substitutable positions with groups that are independently halogen, $C_1$-$C_6$ alkyl, $C_1$-$C_6$ alkoxy, CF$_3$, OCF$_3$, hydroxyl, CN, phenyloxy, —SO$_2$—($C_1$-$C_6$ alkyl), —NR$_{10}$R$_{11}$, $C_1$-$C_6$ alkanoyl, pyridyl, phenyl, or —SO$_2$NR$_{10}$R$_{11}$, where each R$_{10}$ and R$_{11}$ is independently H or $C_1$-$C_6$ alkyl, In some exemplary compounds the thienyl is substituted with halogen, for example chloro or bromo.

In still another aspect, the invention provides compounds of Formula V-6, i.e, compounds according to any one of Formulas II, Va, Vb, Vc, Vd, Ve, Vf, or Vg, wherein the heteroaryl group is furanyl, which is optionally substituted at one or more substitutable positions with groups that are independently halogen, $C_1$-$C_6$ alkyl, $C_1$-$C_6$ alkoxy, CF$_3$, OCF$_3$, hydroxyl, CN, phenyloxy, —SO$_2$—($C_1$-$C_6$ alkyl), —NR$_{10}$R$_{11}$, $C_1$-$C_6$ alkanoyl, pyridyl, phenyl, or —SO$_2$NR$_{10}$R$_{11}$, where each R$_{10}$ and R$_{11}$ is independently H or $C_1$-$C_6$ alkyl In some aspects furanyl is substituted with halogen, for example chloro.

In another aspect, the invention provides compounds of Formula VI, i.e., compounds of Formula II, wherein the A-ring is heterocycloalkyl that is pyrrolidinyl, piperidinyl, piperazinyl, morpholinyl, thiomorpholinyl, or thiomorpholinyl-S,S-dioxide, where each of the above rings is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —S(O)$_{0-2}$—($C_1$-$C_6$ alkyl), —NR$_{10}$R$_{11}$, $C_1$-$C_6$ alkanoyl, $C_0$-$C_3$alkylCO$_2$R', pyridyl, thienyl, furanyl, pyrrolyl, pyrrolidinyl, piperidinyl, piperazinyl, phenyl, phenyl $C_1$-$C_4$ alkyl, or —SO$_2$NR$_{10}$R$_{11}$.

In another aspect, the invention provides compounds of Formulas VIa, VIb or VIc, i.e. compounds of Formula VI wherein no carbons in the [3.2.1] ring system are replaced with an —O—, —S(O)$_{0-2}$—, or —NR$_{15}$— group, having the following structures:

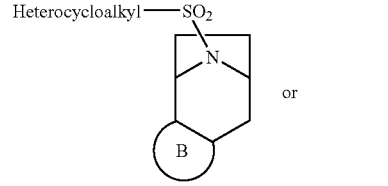

Formula Va

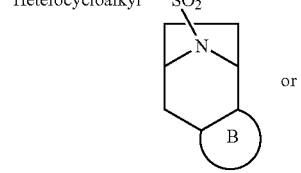

Formula Vb

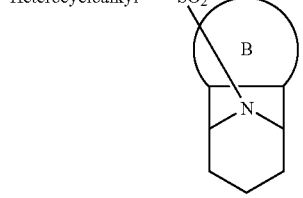

Formula Vc wherein, the B-ring is a heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$; and the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl.

In yet another aspect, the invention provides compounds of Formula VId, VIe or VIf, i.e. compounds of Formula VI wherein one of the carbons in the [3.2.1] ring system is replaced with an —O—, —S(O)$_{0-2}$—, or —NR$_{15}$— group, In another aspect, the invention provides compounds of Formulas VId, VIe or VIf, i.e. compounds of Formula V having the following structures:

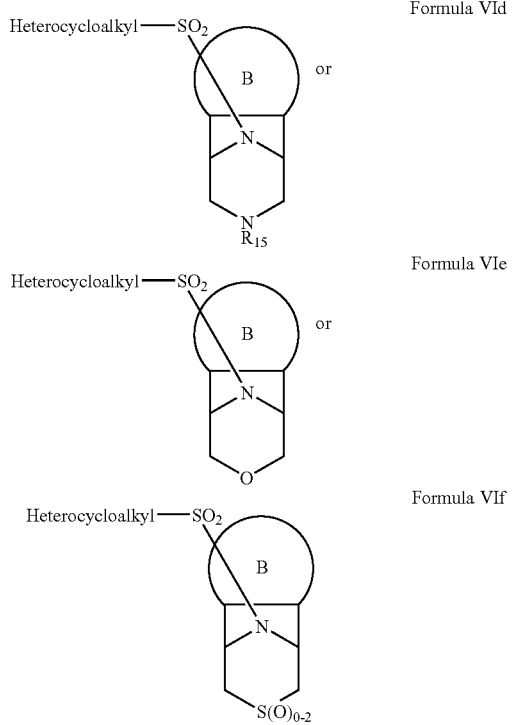

Formula VId

Formula VIe

Formula VIf wherein, the B-ring is a heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_8$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$;

the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl; and $R_{15}$ is H, phenyl, pyridyl, pyrimidinyl, oxazolyl, thienyl, furanyl, pyrrolyl, piperidinyl, piperazinyl, pyrrolidinyl, imidazolidinyl, indolyl, —SO$_2$R', —C(O)R'. —C(O)OR', or $C_1$-$C_6$ alkyl optionally substituted with phenyl, hydroxyl, or halogen, where the above cyclic groups are optionally substituted with 1 to 5 groups that are independently halogen, hydroxyl, $C_1$-$C_4$ alkyl, $C_1$-$C_4$ alkoxy, $C_1$-$C_4$ haloalkyl (such as CF$_3$), $C_1$-$C_4$ haloalkoxy (such as OCF$_3$), CN, amino, NH($C_1$-$C_6$ alkyl), N($C_1$-$C_6$ alkyl) ($C_1$-$C_6$ alkyl), or NO$_2$.

In some aspects, the invention provides compounds of Formula VIg, i.e., compounds according to any one of Formulas VIa, VIb, VIc, VId, Vie or VIf wherein the B-ring is pyrazolyl, imidazolyl, pyrrolyl, triazolyl, pyrrolidinyl, pyrazolidinyl, imidazolidinyl, triazolopyrimidinyl, imidazopyrimidinyl, pyrazolopyrimidinyl, or indolyl, or pyridyl, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$.

In another aspect, the invention provides compounds of Formula VI-1, i.e., compounds according to any one of Formulas VI, VIa, VIb, VIc, VId, VIe, VIf, or VIg, where the heterocycloalkyl group is pyrrolidinyl, which is optionally substituted at one or more substitutable positions with groups that are independently halogen, $C_1$-$C_6$ alkyl, $C_1$-$C_6$ alkoxy, CF$_3$, OCF$_3$, hydroxyl, CN, phenyloxy, —SO$_2$—($C_1$-$C_6$ alkyl), —NR$_{10}$R$_{11}$, $C_1$-$C_6$ alkanoyl, pyridyl, phenyl, or —SO$_2$NR$_{10}$R$_{11}$, where each $R_{10}$ and $R_{11}$ is independently H or $C_1$-$C_6$ alkyl.

In another aspect, the invention provides compounds of Formula VI-2, i.e., compounds according to any one of Formulas VI, VIa, VIb, VIc, VId, VIe, VIf, or VIg, where the heterocycloalkyl group is piperidinyl, which is optionally substituted at one or more substitutable positions with groups that are independently halogen, $C_1$-$C_6$ alkyl, $C_1$-$C_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$, where each R$_{10}$ and R$_{11}$ is independently H or C$_1$-C$_6$ alkyl.

In yet another aspect, the invention provides compounds of Formula VI-3, i.e., compounds according to any one of Formulas VI, VIa, VIb, VIc, VId, VIe, VIf, or VIg, where the heterocycloalkyl group is piperazinyl, which is optionally substituted at one or more substitutable positions with groups that are independently halogen, C$_1$-C$_6$ alkyl, C$_1$-C$_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$, where each R$_{10}$ and R$_{11}$ is independently H or C$_1$-C$_6$ alkyl.

In still another aspect, the invention provides compounds of Formula VI-4, i.e., compounds according to any one of Formulas VI, VIa, VIb, VIc, VId, VIe, VIf, or VIg, where the heterocycloalkyl group is morpholinyl, which is optionally substituted at one or more substitutable positions with groups that are independently halogen, C$_1$-C$_6$ alkyl, C$_1$-C$_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$, where each R$_{10}$ and R$_{11}$ is independently H or C$_1$-C$_6$ alkyl.

In another aspect, the invention provides compounds of Formula VI-5, i.e., compounds according to any one of Formulas VI, VIa, VIb, VIc, VId, VIe, VIf, or VIg, where the heterocycloalkyl group is thiomorpholinyl, which is optionally substituted at one or more substitutable positions with groups that are independently halogen, C$_1$-C$_6$ alkyl, C$_1$-C$_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$, where each R$_{10}$ and R$_{11}$ is independently H or C$_1$-C$_6$ alkyl.

In another aspect, the invention provides compounds of Formula VI-6, i.e., compounds according to any one of Formulas VI, VIa, VIb, VIc, VId, VIe, VIf, or VIg, where the heterocycloalkyl group is thiomorpholinyl-S,S-dioxide, which is optionally substituted at one or more substitutable positions with groups that are independently halogen, C$_1$-C$_6$ alkyl, C$_1$-C$_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$, where each R$_{10}$ and R$_{11}$ is independently H or C$_1$-C$_6$ alkyl.

In another aspect, the invention provides compounds of Formulas IIa or IIIb, i.e., compounds of Formula II, with the structures:

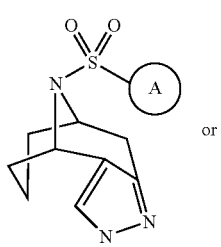

Formula IIa or

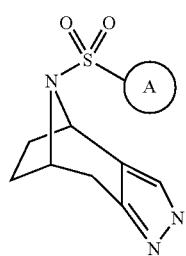

Formula IIb including stereoisomers, tautomers and mixtures of stereoisomers and/or tautomers, and/or pharmaceutical salts thereof, wherein A is aryl, cycloalkyl, heteroaryl or heterocycloalkyl, where each ring is optionally substituted at a substitutable position with halogen, C$_1$-C$_6$ alkyl, C$_2$-C$_6$ alkenyl, C$_2$-C$_6$ alkynyl, C$_1$-C$_6$ alkoxy, haloalkyl, haloalkoxy, hydroxyl, hydroxyalkyl, CN, phenyloxy, —S(O)$_{0-2}$—(C$_1$-C$_6$ alkyl), —NR$_{10}$R$_{11}$, C$_1$-C$_6$ alkanoyl, C$_0$-C$_3$alkylCO$_2$R', pyridyl, thienyl, furanyl, pyrrolyl, pyrrolidinyl, piperidinyl, piperazinyl, phenyl, phenyl C$_1$-C$_4$ alkyl, or —SO$_2$NR$_{10}$R$_{11}$;

the bridged ring including the fused pyrazol ring is optionally substituted at a substitutable position with a group that is independently C$_1$-C$_6$ alkyl, C$_3$-C$_8$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$R', hydroxy, hydroxyalkyl, halo, C$_1$-C$_2$ haloalkyl, C$_1$-C$_2$ haloalkoxy, —NR'C(O)R", —NR'SO$_2$R", —C(O)R', —C(O)OR', —(C$_1$-C$_4$ alkyl)-C(O)OR$_{13}$, —C(O)alkylOC(O)R'; —C(O)NR$_{10}$R$_{11}$, —OC(O)NR$_{10}$R$_{11}$, —NR'C(O)OR', oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, phenyloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$;

R$_{10}$ and R$_{11}$ at each occurrence are independently H or C$_1$-C$_6$ alkyl, where the alkyl is optionally substituted with an aryl, where the aryl is optionally substituted with 1 to 5 groups that are independently halogen, hydroxyl, alkyl, alkoxy, haloalkyl, haloalkoxy, CN or NO$_2$; and R$_{10}$ and R$_{11}$ together may form a 3-8 membered ring optionally including an additional heteroatom such as N, O or S; and R' is hydrogen, C$_1$-C$_6$ alkyl, haloalkyl, C$_2$-C$_6$ alkenyl or phenyl optionally substituted with 1 to 5 groups that are independently halogen, C$_1$-C$_6$ alkyl, —C(O)OR', C$_1$-C$_6$ alkoxy, haloalkyl, haloalkoxy, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, NO$_2$, or —SO$_2$NR$_{10}$R$_{11}$.

In some aspects, the invention provides compounds of Formulas IIa or IIb where the A ring is aryl, for example phenyl optionally substituted with 1 to 5 groups that are independently halogen, hydroxyl, alkyl, alkoxy, haloalkyl, haloalkoxy, CN or NO$_2$. In some exemplary compounds the ring is a phenyl ring optionally substituted with 1 to 5 groups that are halogen, such as chloro, bromo, iodo or fluoro.

In other aspects, the invention provides compounds of Formulas IIa or IIb where the A ring is heteroaryl, for example furanyl, thienyl or pyridyl, each of which is optionally substituted with 1 to 3 groups that are independently halogen, hydroxyl, alkyl, alkoxy, haloalkyl, haloalkoxy, CN or NO$_2$. In some exemplary compounds the ring is a thienyl ring optionally substituted with 1 to 2 groups that are halogen, such as chloro, or bromo.

In another aspect, the invention provides compounds of Formula VII, i.e., compounds of formula I, having the structure:

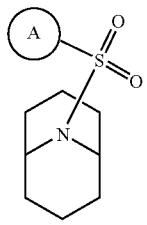

Formula VII where two adjacent carbons (not including the bridgehead carbons) in the ring system combine to form part of a fused heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', —C$_0$-C$_3$ alkyl-OH, halo, $C_1$-$C_2$ haloalkyl, $C_1$-$C_2$ haloalkoxy, —NC(O)R', —C(O)R', —C(O)OR', —C(O)alkylOC(O)R', —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$;

0 or 1 of the carbons in the [3.3.1] ring system is optionally replaced with an —O—, —S(O)$_{0-2}$—, or —NR$_{15}$— group;

the [3.3.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl;

R$_{13}$ is H or $C_1$-$C_6$ alkyl optionally substituted with aryl (such as phenyl or naphthyl, more preferably, phenyl), hydroxyl, or halogen, where the aryl is optionally substituted with 1 to 5 groups that are independently halogen, hydroxyl, alkyl, alkoxy, haloalkyl, haloalkoxy, CN or NO$_2$ R' and R" are independently of each other hydrogen, $C_1$-$C_6$ alkyl, haloalkyl, $C_2$-$C_6$ alkenyl or phenyl optionally substituted with 1 to 5 groups that are independently halogen, $C_1$-$C_6$ alkyl, —C(O)OR', $C_1$-$C_6$ alkoxy, haloalkyl (such as CF$_3$), haloalkoxy (such as OCF$_3$), hydroxyl, CN, phenyloxy, —SO$_2$—($C_1$-$C_6$ alkyl), —NR$_{10}$R$_{11}$, $C_1$-$C_6$ alkanoyl, pyridyl, phenyl, NO$_2$, or —SO$_2$NR$_{10}$R$_{11}$; and R$_{15}$ is H, phenyl, pyridyl, pyrimidinyl, oxazolyl, thiazolyl, imidazolyl, thienyl, furanyl, pyrrolyl, piperidinyl, piperazinyl, pyrrolidinyl, imidazolidinyl, indolyl, quinolinyl, —SO$_2$R', —C(O)R'. —C(O)OR', or $C_1$-$C_6$ alkyl optionally substituted with phenyl, hydroxyl, or halogen, where the above cyclic groups are optionally substituted with 1 to 5 groups that are independently halogen, hydroxyl, $C_1$-$C_6$ alkyl, $C_1$-$C_6$ alkoxy, $C_1$-$C_6$ haloalkyl (such as CF$_3$ or CH$_2$CF$_3$), $C_1$-$C_4$ haloalkoxy (such as OCF$_3$ or OCH$_2$CF$_3$), CN, amino, NH($C_1$-$C_6$ alkyl), N($C_1$-$C_6$ alkyl) ($C_1$-$C_6$ alkyl) or NO$_2$.

In another aspect, the invention provides compounds of formula VIII, i.e. compounds of formula VII, wherein the A-ring is phenyl or naphthyl (preferably phenyl) which is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —S(O)$_{0-2}$—($C_1$-$C_6$ alkyl), —NR$_{10}$R$_{11}$, $C_1$-$C_6$ alkanoyl, $C_0$-$C_3$alkylCO$_2$R', pyridyl, thienyl, furanyl, pyrrolyl, pyrrolidinyl, piperidinyl, piperazinyl, phenyl, phenyl $C_1$-$C_4$ alkyl, or —SO$_2$NR$_{10}$R$_{11}$.

In another aspect, the invention provides compounds of Formula VIIIa and VIIIb, i.e., compound of formula VIII, having the following structures:

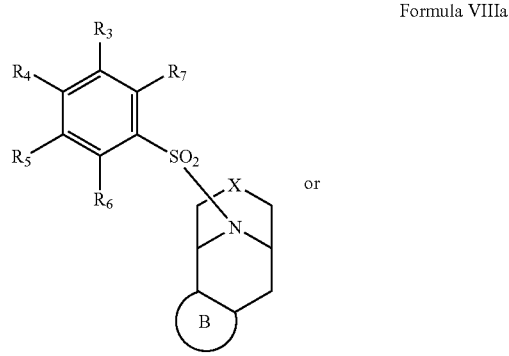

Formula VIIIa

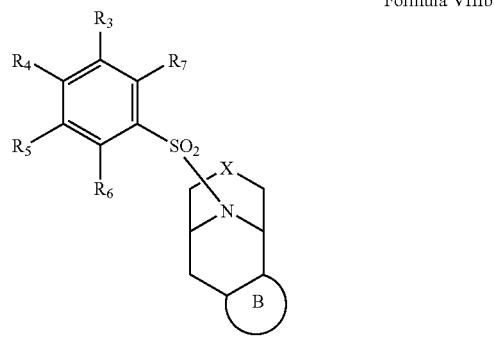

Formula VIIIb wherein,

X is —C—, —CH—, —CH$_2$—, —O—, —S(O)$_{0-2}$—, or —NR$_{15}$—, where the —C— and —CH— groups are optionally substituted with 1 or 2 groups that are independently oxo (oxo can only be a substituent on —C—), halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or —N—O—R$_{13}$;

the B-ring is a heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, phenyloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$;

the [3.3.1] ring system is optionally substituted with 1, 2, 3, or 4 groups that are independently oxo, halogen, C$_1$-C$_6$ alkyl, C$_2$-C$_6$ alkenyl, C$_1$-C$_6$ haloalkyl, C$_2$-C$_6$ alkynyl, hydroxy, hydroxyalkyl, C$_1$-C$_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR'", —NR'S(O)$_2$R", —OS(O)$_2$R", —NR'C(O)R", CN, —N—NR$_{12}$, or =N—O—R$_{13}$ and additionally, two adjacent carbons (not including the bridgehead carbons) may combine to form a cycloalkyl ring that may optionally be substituted with halogen, C$_1$-C$_6$ alkyl or haloalkyl;

R$_3$, R$_4$, R$_5$, R$_6$, R$_7$ are independently of each other H, halogen, C$_1$-C$_6$ alkyl, C$_1$-C$_6$ haloalkyl, C$_1$-C$_6$ haloalkoxy, CN, hydroxyl, C$_1$-C$_6$ alkoxy, —C$_1$-C$_3$ alkyl-OH, —C$_1$-C$_3$ alkyl-alkoxy, phenyloxy, —SO$_2$R', —NR$_{10}$R$_{11}$, C$_1$-C$_6$ alkanoyl, oxazolyl, pyrazolyl, thiazolyl, pyridyl, pyrimidinyl, imidazolyl, indolyl, furanyl, thienyl, phenyl, or phenyl C$_1$-C$_4$ alkyl, or R$_4$ and R$_5$, or R$_5$ and R$_6$ and the carbons to which they are attached form a heterocycloalkyl or a heteroaryl ring which is optionally substituted with 1, 2, 3, or 4 groups that are independently C$_1$-C$_4$ alkyl, C$_1$-C$_4$ alkoxy, halogen, or C$_1$-C$_4$ alkanoyl wherein the alkanoyl group is optionally substituted with up to 3 halogen atoms; or R$_4$ and R$_5$, or R$_5$ and R$_6$ and the carbons to which they are attached form a benzo ring which is optionally substituted with 1 to 5 groups that are independently halogen, hydroxyl, alkyl, alkoxy, haloalkyl, haloalkoxy, CN or NO$_2$;

R' and R" are independently of each other hydrogen, C$_1$-C$_6$ alkyl, haloalkyl, C$_2$-C$_6$ alkenyl or phenyl optionally substituted with 1 to 5 groups that are independently halogen, C$_1$-C$_6$ alkyl, —C(O)OR', C$_1$-C$_6$ alkoxy, haloalkyl (such as CF$_3$), haloalkoxy (such as OCF$_3$), hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, NO$_2$, or —SO$_2$NR$_{10}$R$_{11}$; and R$_{15}$ is H, phenyl, pyridyl, pyrimidinyl, oxazolyl, thienyl, furanyl, pyrrolyl, piperidinyl, piperazinyl, pyrrolidinyl, imidazolidinyl, indolyl, —SO$_2$R', —C(O)R'. —C(O)OR', or C$_1$-C$_6$ alkyl optionally substituted with phenyl, hydroxyl, or halogen, where the above cyclic groups are optionally substituted with 1 to 5 groups that are independently halogen, hydroxyl, C$_1$-C$_4$ alkyl, C$_1$-C$_4$ alkoxy, C$_1$-C$_4$ haloalkyl (such as CF$_3$), C$_1$-C$_4$ haloalkoxy (such as OCF$_3$), CN, amino, NH(C$_1$-C$_6$ alkyl), N(C$_1$-C$_6$ alkyl)(C$_1$-C$_6$ alkyl), or NO$_2$.

In some aspects, the invention provides compounds of Formula VIIIc or VIIId, i.e., compounds of formula VIII having the following structures:

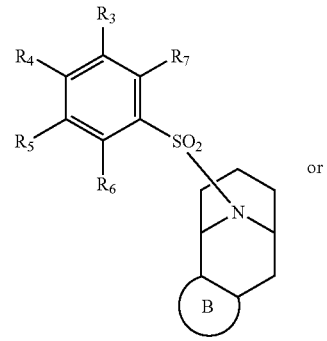

Formula VIIIc or

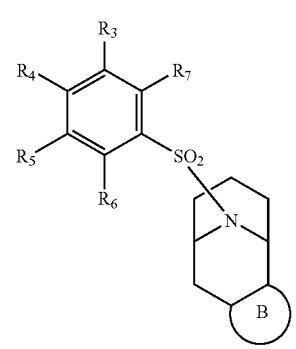

Formula VIIId

, where X is —CH$_2$— and R$_3$, R$_4$, R$_5$, R$_6$, R$_7$ and the B-ring are as defined for Formulas VIIIa and VIIIb.

In another aspect, the invention provides compounds of Formula VIIIe or VIIIf, i.e., compounds of formula VIII having the following structures:

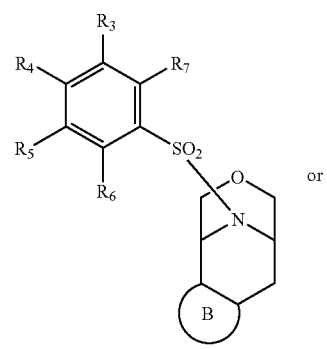

Formula VIIIe or

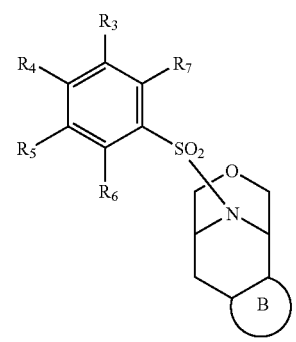

Formula VIIIf

, where X is —O—. and $R_3$, $R_4$, $R_5$, $R_6$, $R_7$ and the B-ring are as defined for Formulas VIIIa and VIIIb.

In still another aspect, the invention provides compounds of Formula VIIIg or VIIIh, i.e., compounds of formula VIII having the following structures:

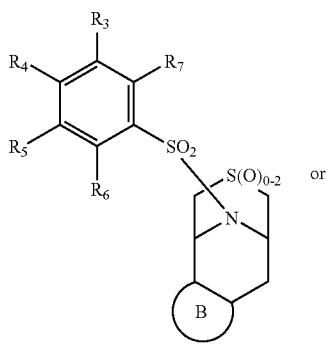

Formula VIIIg

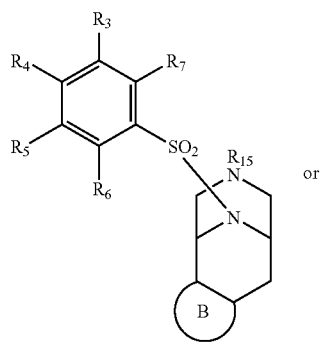

Formula VIIIh where X is —$S(O)_{0-2}$—. and $R_3$, $R_4$, $R_5$, $R_6$, $R_7$ and the B-ring are as defined for Formulas VIIIa and VIIIb.

In still another aspect, the invention provides compounds of Formula VIIIm or VIIIn, i.e., compounds of formula VIII having the following structures:

Formula VIIIm

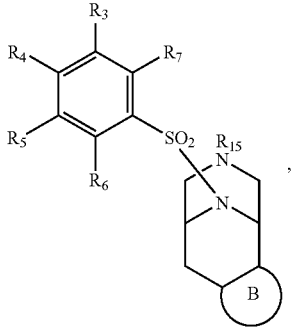

Formula VIIIn where X is —$NR_{15}$—, and $R_3$, $R_4$, $R_5$, $R_6$, $R_7$ and the B-ring are as defined for Formulas VIIIa and VIIIb.

In some aspects, the invention provides compounds of Formula VIIIo, i.e., compounds according to any one of Formulas VIII, VIIIa, VIIIb, VIIIc, VIIId, VIIIe, VIIIf, VIIIg, VIIIh, VIIIm, or VIIIn wherein the B-ring is pyrazolyl, imidazolyl, pyrrolyl, triazolyl, pyrrolidinyl, pyrazolidinyl, imidazolidinyl, triazolopyrimidinyl, imidazopyrimidinyl, pyrazolopyrimidinyl, or indolyl or pyridyl, each of which is optionally substituted at a substitutable position with a group that is independently $C_1$-$C_6$ alkyl, $C_3$-$C_8$ cycloalkyl, $C_2$-$C_6$ alkenyl, $C_2$-$C_8$ alkynyl, $C_1$-$C_6$ alkoxy, amino, $C_1$-$C_6$ alkylamino, $C_1$-$C_6$ dialkylamino, —$S(O)_{0-2}R'$, hydroxy, hydroxyalkyl, halo, $C_1$-$C_2$ haloalkyl, $C_1$-$C_2$ haloalkoxy, —NR'C(O)R'', —$NR'SO_2R''$, —C(O)R', —C(O)OR', —C(O)alkylOC(O)R'; —$C(ONR_{10}R_{11}$, oxo, CN, or $C_0$-$C_1$alkylphenyl, where the phenyl is optionally substituted with 1-5 groups independently selected from halogen, $C_1$-$C_6$ alkyl, —$CO_2R'$, $C_1$-$C_6$ alkoxy, haloalkyl, haloalkoxy, hydroxyl, CN, $NO_2$, phenyloxy, —$S(O)_{0-2}$—($C_1$-$C_6$ alkyl), —$NR_{10}R_{11}$, $C_1$-$C_6$ alkanoyl, pyridyl, phenyl, and —$SO_2NR_{10}R_{11}$.

In other aspects, the invention provides compounds according to any one of Formulas VIII, or VIIIa-VIIIo, wherein $R_3$ is H, halogen, $C_1$-$C_6$ alkyl, $C_1$-$C_6$ alkoxy, haloalkyl, or CN;

$R_4$ is H, halogen, $C_1$-$C_6$ alkyl, $C_1$-$C_6$ alkoxy, $C_1$-$C_6$ haloalkyl, haloalkoxy, CN, phenyloxy, —$SO_2$—($C_1$-$C_6$ alkyl), —$R_{10}R_{11}$, $C_1$-$C_6$ alkanoyl, oxazolyl, pyrazolyl, thiazolyl, pyridyl, furanyl, thienyl, or phenyl; and $R_{3'}$ is H, $C_1$-$C_6$ alkyl —$SO_2NR_{10}R_{11}$ or halogen.

In other aspects, the invention provides compounds according to any one of Formulas VIII, or VIIIa-VIIIo, wherein $R_6$ and $R_7$ are independently H or methyl.

In other aspects, the invention provides compounds according to any one of Formulas VIII, or VIIIa-VIIIo, wherein $R_3$ and $R_5$ are independently H, halo, or methyl.

In other aspects, the invention provides compounds according to any one of Formulas VIII, or VIIIa-VIIIo, wherein $R_4$ is H, halogen (in one aspect, I, Br, F or Cl), $C_1$-$C_6$ alkyl optionally substituted with halogen or hydroxy, $C_1$-$C_6$ alkoxy, $CF_3$, $OCF_3$, or CN.

In other aspects, the invention provides compounds according to any one of Formulas VIII, or VIIIa-VIIIo, wherein $R_4$ is phenyloxy, —$SO_2$—($C_1$-$C_6$ alkyl), —$NR_{10}R_{11}$, $C_1$-$C_6$ alkanoyl, oxazolyl, pyrazolyl, thiazolyl, pyridyl, furanyl, thienyl, or phenyl.

In other aspects, the invention provides compounds according to any one of Formulas VIII, or VIIIa-VIIIo, wherein $R_4$ is —$NR_{10}R_{11}$.

In other aspects, the invention provides compounds according to any one of Formulas VIII, or VIIIa-VIIIo, wherein $R_4$ is $-NR_{10}R_{11}$, and $R_3$, $R_5$, $R_6$, and $R_7$ are H.

In other aspects, the invention provides compounds according to any one of Formulas VIII, or VIIIa-VIIIo wherein $R_3$, $R_4$, $R_5$, $R_6$, and $R_7$ are H, halo, $CF_3$, $CHF_2$ or methyl In other aspects, the invention provides compounds according to any one of Formulas VIII, or VIIIa-VIIIo, wherein $R_3$, $R_5$', $R_6$, and $R_7$ are H.

In other aspects, the invention provides compounds according to any one of Formulas VIII, or VIIIa-VIIIo, wherein $R_4$ is chloro.

In other aspects, the invention provides compounds according to any one of Formulas VIII, or VIIIa-VIIIo, wherein $R_4$ is chloro, and $R_3$, $R_5$, $R_6$, and $R_7$ are H.

In another aspect, the invention provides compounds of Formulas VIII, or VIIIa-VIIIo, wherein at least one of $R_3$, $R_4$, or $R_5$ is chloro, and $R_6$ and $R_7$ are H.

In yet still another aspect, the invention provides compounds of Formulas VIII, or VIIIa-VIIIo, wherein $R_3$, $R_5$, $R_6$, and $R_7$ are H.

In still another aspect, the invention provides compounds of Formulas VIII, or VIIIa-VIIIo, wherein $R_4$ is chloro.

In yet still another aspect, the invention provides compounds of Formulas VIII, or VIIIa-VIIIo, wherein $R_4$ is chloro, and $R_3$, $R_5$, $R_6$, and $R_7$ are H.

In another aspect, the invention provides compounds of Formulas VIII, or VIIIa-VIIIo, wherein at least one of $R_3$, $R_4$, or $R_5$ is chloro, and $R_6$ and $R_7$ are H.

In another aspect, the invention provides compounds of Formulas VIII, or VIIIa-VIIIo, wherein $R_3$ is hydrogen, halogen, $C_1$-$C_4$ alkyl, $C_1$-$C_4$ alkoxy, $CF_3$, or CN;

$R_4$ is hydrogen, halogen, $C_1$-$C_4$ alkyl, $C_1$-$C_4$ alkoxy, $CF_3$, $OCF_3$, CN, phenyloxy, $-SO_2-(C_1$-$C_4$ alkyl), $-NR_{10}R_{11}$, $C_1$-$C_4$ alkanoyl, and $R_5$ is hydrogen, $C_1$-$C_4$ alkyl, $-SO_2NR_{10}R_{11}$ or halogen.

In still yet another aspect, the invention provides compounds of Formulas VIII, or VIIIa-VIIIo, wherein $R_4$ is halogen (in one aspect, F or Cl), $C_1$-$C_4$ alkyl, $C_1$-$C_4$ alkoxy, $CF_3$, $OCF_3$, or CN.

In another aspect, the invention provides compounds of Formulas VIII, or VIIIa-VIIIo, wherein $R_4$, $R_5$ $R_6$, and $R_7$ are hydrogen.

In another aspect, the invention provides compounds of Formulas VIII, or VIIIa-VIIIo, wherein $R_3$ is hydrogen, halogen, $C_1$-$C_4$ alkyl, $C_1$-$C_4$ alkoxy, $CF_3$, or CN;

$R_4$ is oxazolyl, pyrazolyl, thiazolyl, pyridyl, furanyl, thienyl, or phenyl; and $R_5$ is hydrogen, $C_1$-$C_4$ alkyl, $-SO_2 NR_{10}R_{11}$, or halogen.

In still yet another aspect, the invention provides compounds of Formulas VIII, or VIIIa-VIIIo, wherein $R_4$ is halogen (in one aspect, F or Cl), $CH_3$, $OCH_3$, $CF_3$, or $OCF_3$.

In another aspect, the invention provides compounds of Formulas VIII, or VIIIa-VIIIo, wherein $R_3$ is hydrogen, halogen, $C_1$-$C_2$ alkyl, $C_1$-$C_2$ alkoxy, $CF_3$, or CN;

$R_4$ is hydrogen, halogen, $C_1$-$C_2$ alkyl, $C_1$-$C_2$ alkoxy, $C_1$-$C_2$ haloalkyl, $C_1$-$C_2$ haloalkoxy, CN, $-NR_{10}R_{11}$, $C_2$-$C_3$ alkanoyl, oxazolyl, pyrazolyl, thiazolyl, pyridyl, furanyl, or thienyl;

$R_5$ is hydrogen, $CH_3$, or F; and $R_6$ and $R_7$ are independently hydrogen or halogen.

In still yet another aspect, the invention provides compounds of Formulas VIII, or VIIIa-VIIIo, wherein $R_4$ is $CF_3$, or $OCF_3$.

In yet another aspect, the invention provides compounds of Formulas VIII, or VIIIa-VIIIo, wherein $R_4$ and $R_5$, or $R_5$ and $R_6$ and the carbons to which they are attached form a benzo ring which is optionally substituted with optionally substituted with 1 or 2 groups that are independently halogen, hydroxyl, $C_1$-$C_4$ alkyl, $C_1$-$C_4$ alkoxy, $C_1$-$C_3$ haloalkyl, $C_1$-$C_3$ haloalkoxy, CN or $NO_2$.

In still yet another aspect, the invention provides compounds of Formulas VIII, or VIIIa-VIIIo, wherein $R_4$ and $R_5$, or $R_5$ and $R_6$ and the carbons to which they are attached form a pyridyl, pyrrolyl, thienyl, furanyl, pyrrolidinyl, piperidinyl ring, each of which is optionally substituted with 1, 2, or 3 groups that are independently $C_1$-$C_4$ alkyl, $C_1$-$C_4$ alkoxy, halogen, or $C_1$-$C_4$ alkanoyl wherein the alkanoyl group is optionally substituted with up to 3 halogen atoms (such as F).

In one aspect, the invention provides compounds of Formulas VIII, or VIIIa-VIIIo, wherein $R_6$ and $R_7$ are independently hydrogen or methyl.

In one aspect, the invention provides compounds of Formulas VIII, or VIIIa-VIIIo, wherein $R_3$ and $R_5$ are independently hydrogen, halo, or methyl.

In another aspect, the invention provides compounds of Formula IX, i.e., compounds of Formula VIII, wherein the A-ring is $C_3$-$C_8$ cycloalkyl, which is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, $-S(O)_{0-2}-(C_1$-$C_6$ alkyl), $-NR_{10}R_{11}$, $C_1$-$C_6$ alkanoyl, $C_0$-$C_3$alkyl$CO_2R'$, pyridyl, thienyl, furanyl, pyrrolyl, pyrrolidinyl, piperidinyl, piperazinyl, phenyl, phenyl $C_1$-$C_4$ alkyl, or $-SO_2NR_{10}R_{11}$.

In yet another aspect, the invention provides compounds of Formula IXa or IXb, i.e. compounds of Formula IX having the following structures:

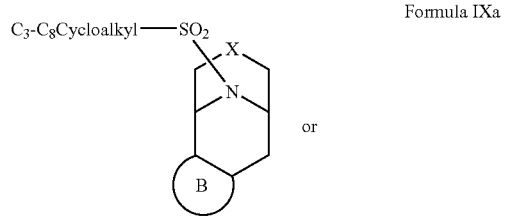

Formula IXa or

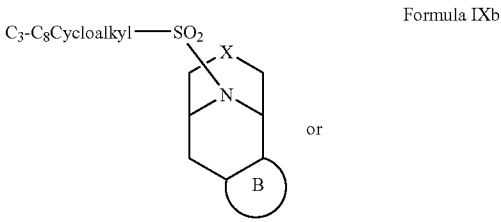

Formula IXb wherein

X is $-C-$, $-CH-$, $-CH_2-$, $-O-$, $-S(O)_{0-2}-$, or $-NR_{15}-$, where the $-C-$ and $-CH-$ groups are optionally substituted with 1 or 2 groups that are independently oxo (oxo can only be a substituent on $-C-$), halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, $-C(O)OR_{13}$, $-(C_1$-$C_4$ alkyl)-$C(O)OR_{13}$, $-CONR_{10}R_{11}$, $-OC(O)NR_{10}R_{11}$, $-NR'C(O)OR''$, $-NR'S(O)_2R''$, $-OS(O)_2R''$, $-NR'C(O)R''$, CN, $=N-NR_{12}$, or $=N-O-R_{13}$;

the B-ring is a heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, $-S(O)_{0-2}R'$, hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$;

the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl; and $R_{15}$ is H, phenyl, pyridyl, pyrimidinyl, oxazolyl, thienyl, furanyl, pyrrolyl, piperidinyl, piperazinyl, pyrrolidinyl, imidazolidinyl, indolyl, —SO$_2$R', —C(O)R'. —C(O)OR', or $C_1$-$C_6$ alkyl optionally substituted with phenyl, hydroxyl, or halogen, where the above cyclic groups are optionally substituted with 1 to 5 groups that are independently halogen, hydroxyl, $C_1$-$C_4$ alkyl, $C_1$-$C_4$ alkoxy, $C_1$-$C_4$ haloalkyl (such as CF$_3$), $C_1$-$C_4$ haloalkoxy (such as OCF$_3$), CN, amino, NH($C_1$-$C_6$ alkyl), N($C_1$-$C_6$ alkyl)($C_1$-$C_6$ alkyl), or NO$_2$.

In yet another aspect, the invention provides compounds of Formula IXa or IXb, wherein X is NR$_{15}$.

In yet another aspect, the invention provides compounds of Formula IXa or IXb, wherein X is NR$_{15}$ where $R_{15}$ is H, —SO$_2$R', —C(O)R', or $C_1$-$C_6$ alkyl, and R' is $C_1$-$C_6$ alkyl, haloalkyl, or phenyl optionally substituted with 1 to 3 groups that are independently halogen, $C_1$-$C_6$ alkyl, —C(O)OR', $C_1$-$C_6$ alkoxy, haloalkyl (such as CF$_3$), haloalkoxy (such as OCF$_3$), hydroxyl, CN, or NO$_2$.

In still another aspect, the invention provides compounds of Formula IXa or IXb, wherein X is O.

In another aspect, the invention provides compounds of Formula IXa or IXb, wherein X is —S(O)$_{0-2}$—.

In another aspect, the invention provides compounds of Formula IXa or IXb, wherein X is —C—, —CH—, —CH$_2$—, where the —C— and —CH— groups are optionally substituted with 1 or 2 groups that are independently oxo (oxo can only be a substituent on —C—), halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$.

In some aspects, the invention provides compounds of Formula IXc, i.e., compounds according to any one of Formulas IX, IXa, or IXb, wherein the B-ring is pyrazolyl, imidazolyl, pyrrolyl, triazolyl, pyrrolidinyl, pyrazolidinyl, imidazolidinyl, triazolopyrimidinyl, imidazopyrimidinyl, pyrazolopyrimidinyl, indolyl, or pyridyl, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$.

In yet still another aspect, the invention provides compounds of Formula IX-1, i.e., compounds according to any one of Formulas IXa, IXb, or IXc where the B-ring is defined as above and where the $C_3$-$C_8$ cycloalkyl group is cyclopropyl.

In yet still another aspect, the invention provides compounds of Formula IX-2, i.e., compounds according to any one of Formulas IXa, IXb, or IXc where the B-ring is defined as above and where the $C_3$-$C_8$ cycloalkyl group is cyclobutyl.

In yet still another aspect, the invention provides compounds of Formula IX-3, i.e., compounds according to any one of Formulas IXa, IXb, or IXc where the B-ring is defined as above and where the $C_3$-$C_8$ cycloalkyl group is cyclopentyl.

In yet still another aspect, the invention provides compounds of Formula IX-4, i.e., compounds according to any one of Formulas IXa, IXb, or IXc where the B-ring is defined as above and where the $C_3$-$C_8$ cycloalkyl group is cyclohexyl.

In yet still another aspect, the invention provides compounds of Formula IX-5, i.e., compounds according to any one of Formulas IXa, IXb, or IXc where the B-ring is defined as above and where the $C_3$-$C_8$ cycloalkyl group is cycloheptyl.

In yet still another aspect, the invention provides compounds of Formula IX-6, i.e., compounds according to any one of Formulas IXa, IXb, or IXc where the B-ring is defined as above and where the $C_3$-$C_8$ cycloalkyl group is cyclooctyl.

In another aspect, the invention provides compounds of Formula X, i.e., compounds of Formula VII, where the A-ring is heteroaryl that is pyridyl, pyrimidyl, pyridazinyl, pyrazinyl, thienyl, furanyl, pyrrolyl, pyrazolyl, or imidazolyl, each of which is optionally substituted at one or more substitutable positions with groups that are independently halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —S(O)$_{0-2}$—($C_1$-$C_6$ alkyl), —NR$_{10}$R$_{11}$, $C_1$-$C_6$ alkanoyl, $C_0$-$C_3$alkylCO$_2$R', pyridyl, thienyl, furanyl, pyrrolyl, pyrrolidinyl, piperidinyl, piperazinyl, phenyl, phenyl $C_1$-$C_4$ alkyl, or —SO$_2$NR$_{10}$R$_{11}$.

In another aspect, the invention provides compounds of Formula Xa or Xb, i.e., compounds of Formula X, having the following structures:

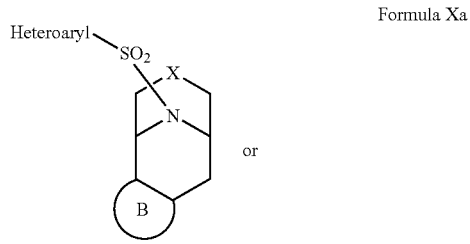

Formula Xa or

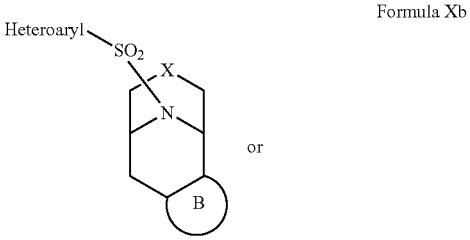

Formula Xb or wherein,

X is —C—, —CH—, —CH$_2$—, —O—, —S(O)$_{0-2}$—, or —NR$_{15}$—, where the —C— and —CH— groups are optionally substituted with 1 or 2 groups that are independently oxo (oxo can only be a substituent on —C—), halogen, C$_1$-C$_6$ alkyl, C$_2$-C$_6$ alkenyl, C$_1$-C$_6$ haloalkyl, C$_2$-C$_6$ alkynyl, hydroxy, hydroxyalkyl, C$_1$-C$_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$;

the B-ring is a heteroaryl or heterocycloalkyl ring, each of which is optionally substituted at a substitutable position with a group that is independently C$_1$-C$_6$ alkyl, C$_3$-C$_8$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$R', hydroxy, hydroxyalkyl, halo, C$_1$-C$_2$ haloalkyl, C$_1$-C$_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, phenyloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$;

the [3.3.1] ring system is optionally substituted with 1, 2, 3, or 4 groups that are independently oxo, halogen, C$_1$-C$_6$ alkyl, C$_2$-C$_6$ alkenyl, C$_1$-C$_6$ haloalkyl, C$_2$-C$_6$ alkynyl, hydroxy, hydroxyalkyl, C$_1$-C$_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, C$_1$-C$_6$ alkyl or haloalkyl; and R$_{15}$ is H, phenyl, pyridyl, pyrimidinyl, oxazolyl, thienyl, furanyl, pyrrolyl, piperidinyl, piperazinyl, pyrrolidinyl, imidazolidinyl, indolyl, —SO$_2$R', —C(O)R'. —C(O)OR', or C$_1$-C$_6$ alkyl optionally substituted with phenyl, hydroxyl, or halogen, where the above cyclic groups are optionally substituted with 1 to 5 groups that are independently halogen, hydroxyl, C$_1$-C$_4$ alkyl, C$_1$-C$_4$ alkoxy, C$_1$-C$_4$ haloalkyl (such as CF$_3$), C$_1$-C$_4$ haloalkoxy (such as OCF$_3$), CN, amino, NH(C$_1$-C$_6$ alkyl), N(C$_1$-C$_6$ alkyl) (C$_1$-C$_6$ alkyl), or NO$_2$.

In yet another aspect, the invention provides compounds of Formula Xa or Xb, wherein X is NR$_{15}$.

In yet another aspect, the invention provides compounds of Formula Xa or Xb, wherein X is NR$_{15}$ where R$_{15}$ is H, —SO$_2$R', —C(O)R', or C$_1$-C$_6$ alkyl, and R' is C$_1$-C$_6$ alkyl, haloalkyl, or phenyl optionally substituted with 1 to 3 groups that are independently halogen, C$_1$-C$_6$ alkyl, —C(O)OR', C$_1$-C$_6$ alkoxy, haloalkyl (such as CF$_3$), haloalkoxy (such as OCF$_3$), hydroxyl, CN, or NO$_2$.

In still another aspect, the invention provides compounds of Formula Xa or Xb, wherein X is O.

In another aspect, the invention provides compounds of Formula Xa or Xb, wherein X is —S(O)$_{0-2}$—.

In another aspect, the invention provides compounds of Formula Xa or Xb, wherein X is —C—, —CH—, —CH$_2$—, where the —C— and —CH— groups are optionally substituted with 1 or 2 groups that are independently oxo (oxo can only be a substituent on —C—), halogen, C$_1$-C$_6$ alkyl, C$_2$-C$_6$ alkenyl, C$_1$-C$_6$ haloalkyl, C$_2$-C$_6$ alkynyl, hydroxy, hydroxyalkyl, C$_1$-C$_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R', CN, =N—NR$_{12}$, or =N—O—R$_{13}$.

In some aspects, the invention provides compounds of Formula Xc, i.e., compounds according to any one of Formulas Xa, or Xb, wherein the B-ring is pyrazolyl, imidazolyl, pyrrolyl, triazolyl, pyrrolidinyl, pyrazolidinyl, imidazolidinyl, triazolopyrimidinyl, imidazopyrimidinyl, pyrazolopyrimidinyl, indolyl, or pyridyl, each of which is optionally substituted at a substitutable position with a group that is independently C$_1$-C$_6$ alkyl, C$_3$-C$_8$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$R', hydroxy, hydroxyalkyl, halo, C$_1$-C$_2$ haloalkyl, C$_1$-C$_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, phenyloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$.

In another aspect, the invention provides compounds of Formula X-1, i.e, compounds according to any one of Formulas Xa, Xb, or Xc, where the B-ring is as defined above and the heteroaryl group is pyridyl, which is optionally substituted at one or more substitutable positions with groups that are independently halogen, C$_1$-C$_6$ alkyl, C$_1$-C$_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$ where each R$_{10}$ and R$_{11}$ is independently H or C$_1$-C$_6$ alkyl. In some exemplary compounds the pyridyl is substituted with halogen, for example chloro.

In another aspect, the invention provides compounds of Formula X-2, i.e. compounds according to any one of Formulas Xa, Xb, or Xc, where the B-ring is as defined above and the heteroaryl group is pyrimidyl, which is optionally substituted at one or more substitutable positions with groups that are independently halogen, C$_1$-C$_6$ alkyl, C$_1$-C$_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$, where each R$_{10}$ and R$_{11}$ is independently H or C$_1$-C$_6$ alkyl.

In yet another aspect, the invention provides compounds of Formula X-3, i.e. compounds according to any one of Formulas Xa, Xb, or Xc, where the B-ring is as defined above and the heteroaryl group is pyridazinyl, which is optionally substituted at one or more substitutable positions with groups that are independently halogen, C$_1$-C$_6$ alkyl, C$_1$-C$_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$, where each R$_{10}$ and R$_{11}$ is independently H or C$_1$-C$_6$ alkyl.

In still another aspect, the invention provides compounds of Formula X-4, i.e. compounds according to any one of Formulas Xa, Xb, or Xc, where the B-ring is as defined above and the heteroaryl group is pyrazinyl, which is optionally substituted at one or more substitutable positions with groups that are independently halogen, C$_1$-C$_6$ alkyl, C$_1$-C$_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$, where each R$_{10}$ and R$_{11}$ is independently H or C$_1$-C$_6$ alkyl.

In another aspect, the invention provides compounds of Formula X-5, i.e. compounds according to any one of Formulas Xa, Xb, or Xc, where the B-ring is as defined above and the heteroaryl group is thienyl, which is optionally substituted at one or more substitutable positions with groups that are independently halogen, C$_1$-C$_6$ alkyl, C$_1$-C$_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$, where each R$_{10}$ and R$_{11}$ is independently H or C$_1$-C$_6$ alkyl. In some exemplary compounds the thienyl is substituted with halogen, for example chloro.

In yet still another aspect, the invention provides compounds of Formula X-6, i.e, compounds according to any one of Formulas Xa, Xb, or Xc, where the B-ring is as defined above and the heteroaryl group is furanyl, which is optionally substituted at one or more substitutable positions with groups that are independently halogen, C$_1$-C$_6$ alkyl, C$_1$-C$_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$, where each R$_{10}$ and R$_{11}$ is independently H or C$_1$-C$_6$ alkyl.

In another aspect, the invention provides compounds of Formula XI, i.e., compounds of Formula VII where the A-ring is heterocycloalkyl that is pyrrolidinyl, piperidinyl, piperazinyl, morpholinyl, thiomorpholinyl, or thiomorpholinyl-S,S-dioxide, where each of the above rings is optionally substituted at a substitutable position with halogen, C$_1$-C$_6$ alkyl, C$_2$-C$_6$ alkenyl, C$_2$-C$_6$ alkynyl, C$_1$-C$_6$ alkoxy, haloalkyl, haloalkoxy, hydroxyl, hydroxyalkyl, CN, phenyloxy, —S(O)$_{0-2}$—(C$_1$-C$_6$ alkyl), —NR$_{10}$R$_{11}$, C$_1$-C$_6$ alkanoyl, CO—C$_3$alkylCO$_2$R', pyridyl, thienyl, furanyl, pyrrolyl, pyrrolidinyl, piperidinyl, piperazinyl, phenyl, phenyl C$_1$-C$_4$ alkyl, or —SO$_2$NR$_{10}$R$_{11}$.

In another aspect, the invention provides compounds of Formula XIa and XIb i.e., compounds of formula XI having the following structures:

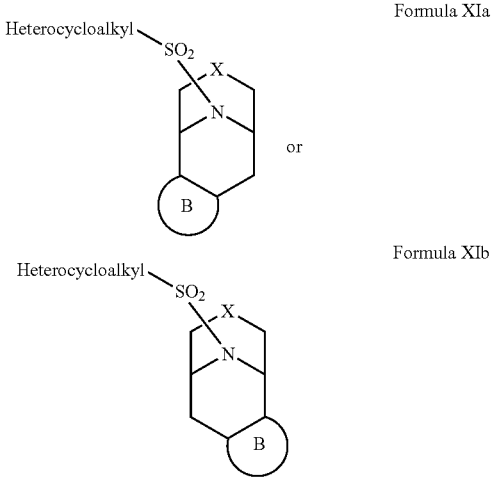

Formula XIa

Formula XIb where

X is —C—, —CH—, —CH$_2$—, —O—, —S(O)$_{0-2}$—, or —NR$_{15}$—, where the —C— and —CH— groups are substituted with 1 or 2 groups that are independently oxo (oxo can only be a substituent on —C—), halogen, C$_1$-C$_6$ alkyl, C$_2$-C$_6$ alkenyl, C$_1$-C$_6$ haloalkyl, C$_2$-C$_6$ alkynyl, hydroxy, hydroxyalkyl, C$_1$-C$_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R', —NR'C(O)R", CN, =N—NR$_{12}$, or =N—O—R$_{13}$;

the B-ring is a heteroaryl or heterocycloalkyl ring, each of which is optionally substituted at a substitutable position with a group that is independently C$_1$-C$_6$ alkyl, C$_3$-C$_3$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$R', hydroxy, hydroxyalkyl, halo, C$_1$-C$_2$ haloalkyl, C$_1$-C$_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, phenyloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$; and R$_{15}$ is H, phenyl, pyridyl, pyrimidinyl, oxazolyl, thienyl, furanyl, pyrrolyl, piperidinyl, piperazinyl, pyrrolidinyl, imidazolidinyl, indolyl, —SO$_2$R', —C(O)R'. —C(O)OR', or C$_1$-C$_6$ alkyl optionally substituted with phenyl, hydroxyl, or halogen, where the above cyclic groups are optionally substituted with 1 to 5 groups that are independently halogen, hydroxyl, C$_1$-C$_4$ alkyl, C$_1$-C$_4$ alkoxy, C$_1$-C$_4$ haloalkyl (such as CF$_3$), C$_1$-C$_4$ haloalkoxy (such as OCF$_3$), CN, amino, NH(C$_1$-C$_6$ alkyl), N(C$_1$-C$_6$ alkyl) (C$_1$-C$_6$ alkyl), or NO$_2$.

In yet another aspect, the invention provides compounds of Formula XIa or XIb, wherein X is NR$_{15}$.

In yet another aspect, the invention provides compounds of Formula XIa or XIb, wherein X is NR$_{15}$ where R$_{15}$ is H, —SO$_2$R', —C(O)R', or C$_1$-C$_6$ alkyl, and R' is C$_1$-C$_6$ alkyl, haloalkyl, or phenyl optionally substituted with 1 to 3 groups that are independently halogen, C$_1$-C$_6$ alkyl, —C(O)OR', C$_1$-C$_6$ alkoxy, haloalkyl (such as CF$_3$), haloalkoxy (such as OCF$_3$), hydroxyl, CN, or NO$_2$.

In still another aspect, the invention provides compounds of Formula XIa or XIb, wherein X is O.

In another aspect, the invention provides compounds of Formula XIa or XIb, wherein X is —S(O)$_{0-2}$—.

In another aspect, the invention provides compounds of Formula XIa or XIb, wherein X is —C—, —CH—, —CH$_2$—, where the —C— and —CH— groups are optionally substituted with 1 or 2 groups that are independently oxo (oxo can only be a substituent on —C—), halogen, C$_1$-C$_6$ alkyl, C$_2$-C$_6$ alkenyl, C$_1$-C$_6$ haloalkyl, C$_2$-C$_6$ alkynyl, hydroxy, hydroxyalkyl, C$_1$-C$_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$.

In some aspects, the invention provides compounds of Formula XIc, i.e., compounds according to any one of Formulas XIa or XIb, wherein the B-ring is pyrazolyl, imidazolyl, pyrrolyl, triazolyl, pyrrolidinyl, pyrazolidinyl, imidazolidinyl, triazolopyrimidinyl, imidazopyrimidinyl, pyrazolopyrimidinyl, or pyridyl, each of which is optionally substituted at a substitutable position with a group that is independently C$_1$-C$_6$ alkyl, C$_3$-C$_8$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$R', hydroxy, hydroxyalkyl, halo, C$_1$-C$_2$ haloalkyl, C$_1$-C$_2$ haloalkoxy, —NR'C(O)R", —NR'SO$_2$R", —C(O)R', —C(O)OR', —C(O)alkylOC(O)R'; —C(O)NR$_{10}$R$_{11}$, oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, phenyloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$.

In another aspect, the invention provides compounds of Formula XI-1, i.e., compounds according to any one of Formulas XIa, XIb, or XIc, where the heterocycloalkyl group is pyrrolidinyl, which is optionally substituted at one or more substitutable positions with groups that are independently halogen, C$_1$-C$_6$ alkyl, C$_1$-C$_6$ alkoxy, CF$_3$, OCF$_3$, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, or —SO$_2$NR$_{10}$R$_{11}$, where each R$_{10}$ and R$_{11}$ is independently H or C$_1$-C$_6$ alkyl.

In another aspect, the invention provides compounds of Formula XI-2, i.e., compounds according to any one of Formulas XIa, XIb, or XIc, where the heterocycloalkyl group is piperidinyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{10}R_{11}$, $C_1$-$C_6$ alkanoyl, pyridyl, phenyl, or —$SO_2NR_{10}R_{11}$, where each $R_{10}$ and $R_{11}$ is independently H or $C_1$-$C_6$ alkyl.

In yet another aspect, the invention provides compounds of Formula XI-3, i.e., compounds according to any one of Formulas XIa, XIb, or XIc, where the heterocycloalkyl group is piperazinyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{10}R_{11}$, $C_1$-$C_6$ alkanoyl, pyridyl, phenyl, or —$SO_2NR_{10}R_{11}$, where each $R_{10}$ and $R_{11}$ is independently H or $C_1$-$C_6$ alkyl.

In still another aspect, the invention provides compounds of Formula XI-4, i.e., compounds according to any one of Formulas XIa, XIb, or XIc, where the heterocycloalkyl group is morpholinyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{10}R_{11}$, $C_1$-$C_6$ alkanoyl, pyridyl, phenyl, or —$SO_2NR_{10}R_{11}$, where each $R_{10}$ and $R_{11}$ is independently H or $C_1$-$C_6$ alkyl.

In another aspect, the invention provides compounds of Formula XI-5, i.e., compounds according to any one of Formulas XIa, XIb, or XIc, where the heterocycloalkyl group is thiomorpholinyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{10}R_{11}$, $C_1$-$C_6$ alkanoyl, pyridyl, phenyl, or —$SO_2NR_{10}R_{11}$, where each $R_{10}$ and $R_{11}$ is independently H or $C_1$-$C_6$ alkyl.

In another aspect, the invention provides compounds of Formula XI-6, i.e., compounds according to any one of Formulas XIa, XIb, or XIc, where the heterocycloalkyl group is thiomorpholinyl-S,S-dioxide, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{10}R_{11}$, $C_1$-$C_6$ alkanoyl, pyridyl, phenyl, or —$SO_2NR_{10}R_{11}$, where each $R_{10}$ and $R_{11}$ is independently H or $C_1$-$C_6$ alkyl.

In further aspects, the invention provides compounds of Formulas IV-1 to IV-6, IVa to IVf, V-1 to V-6, Va to Vf, VI-1 to VI-6, VIa to VIf, VIIIa to VIIIg, VIIIh, VIIIm, VIIIn, IX-1 to IX-6, IXa, IXb, IXc, X-1 to X-6, Xa, Xb, Xc, XI-1 to XI-6, XIa, XIb, XIc, wherein the B-ring is pyrazolyl, imidazolyl, pyrrolyl, triazolyl, pyrrolidinyl, pyrazolidinyl, imidazolidinyl or pyridyl, each of which is optionally substituted at a substitutable position with a group that is independently $C_1$-$C_4$ alkyl, $C_3$-$C_6$ cycloalkyl, $C_2$-$C_6$ alkenyl, $C_2$-$C_6$ alkynyl, $C_1$-$C_4$ alkoxy, amino, $C_1$-$C_4$ alkylamino, $C_1$-$C_4$ dialkylamino, —$S(O)_{0-2}R'$, hydroxy, hydroxy $C_1$-$C_4$ alkyl, halo, $C_1$-$C_2$ haloalkyl (such as $CF_3$), $C_1$-$C_2$ haloalkoxy (such as $OCF_3$), —NR'C(O)R'', —NR'$SO_2$R'', —C(O)R', —C(O)OR', —C(O)alkylOC(O)R'; —C(O)$NR_{10}R_{11}$, oxo, CN, or $C_0$-$C_1$alkylphenyl, where the phenyl is optionally substituted with 1-5 groups independently selected from halogen, $C_1$-$C_4$ alkyl, —$CO_2R'$, $C_1$-$C_4$ alkoxy, $C_1$-$C_2$ haloalkyl (such as $CF_3$), $C_1$-$C_2$ haloalkoxy (such as $OCF_3$), hydroxyl, CN, $NO_2$, phenyloxy, —$S(O)_{0-2}$—($C_1$-$C_6$ alkyl), —$NR_{10}R_{11}$, $C_1$-$C_6$ alkanoyl, pyridyl, phenyl, and —$SO_2NR_{10}R_{11}$.

In some other aspects, the invention provides compounds of Formulas IV-1 to IV-6, IVa to IVf, V-1 to V-6, Va to Vf, VI-1 to VI-6, VIa to VIf, VIIIa to VIIIg, VIIIh, VIIIm, VIIIn, IX-1 to IX-6, IXa, IXb, IXc, X-1 to X-6, Xa, Xb, Xc, XI-1 to XI-6, XIa, XIb, XIc, wherein the B-ring is pyrazolyl, imidazolyl, pyrrolyl, triazolyl, pyrrolidinyl, pyrazolidinyl, imidazolidinyl or pyridyl, each of which is unsubstituted.

In some other aspects, the invention provides compounds of Formulas IV-1 to IV-6, IVa to IVf, V-1 to V-6, Va to Vf, VI-1 to VI-6, VIa to VIf, VIIIa to VIIIg, VIIIh, VIIIm, VIIIn, IX-1 to IX-6, IXa, IXb, IXc, X-1 to X-6, Xa, Xb, Xc, XI-1 to XI-6, XIa, XIb, XIc, wherein the B-ring is pyrazolyl, imidazolyl, pyrrolyl, triazolyl, pyrrolidinyl, pyrazolidinyl, imidazolidinyl or pyridyl, each of which is substituted at a substitutable position with a group that is independently $C_1$-$C_4$ alkyl, $C_3$-$C_6$ cycloalkyl, $C_2$-$C_6$ alkenyl, $C_1$-$C_4$ alkoxy, amino, $C_1$-$C_4$ alkylamino, $C_1$-$C_4$ dialkylamino, —$S(O)_{0-2}R'$, hydroxy, hydroxy $C_1$-$C_4$ alkyl, halo, $C_1$-$C_2$ haloalkyl (such as $CF_3$), $C_1$-$C_2$ haloalkoxy (such as $OCF_3$), —C(O)R', —C(O)OR', —C(O)alkylOC(O)R'; —C(O)$NR_{10}R_{11}$, oxo, CN, or $C_0$-$C_1$alkylphenyl, where the phenyl is optionally substituted with 1-3 groups independently selected from halogen, $C_1$-$C_4$ alkyl, —$CO_2R'$, $C_1$-$C_4$ alkoxy, $C_1$-$C_2$ haloalkyl (such as $CF_3$), $C_1$-$C_2$ haloalkoxy (such as $OCF_3$), hydroxyl, —$NR_{10}R_{11}$, and $C_1$-$C_6$ alkanoyl.

In some aspects, the invention provides compounds of Formulas IV-1 to IV-6, IVa to IVf, V-1 to V-6, Va to Vf, VI-1 to VI-6, VIa to VIf, VIIIa to VIIIg, VIIIh, VIIIm, VIIIn, IX-1 to IX-6, IXa, IXb, IXc, X-1 to X-6, Xa, Xb, Xc, XI-1 to XI-6, XIa, XIb, XIc, wherein the B-ring is triazolopyrimidinyl, imidazopyrimidinyl, pyrazolopyrimidinyl, or indolyl, each of which is optionally substituted at a substitutable position with a group that is independently $C_1$-$C_4$ alkyl, $C_3$-$C_6$ cycloalkyl, $C_2$-$C_6$ alkenyl, $C_2$-$C_6$ alkynyl, $C_1$-$C_4$ alkoxy, amino, $C_1$-$C_4$ alkylamino, $C_1$-$C_4$ dialkylamino, —$S(O)_{0-2}R'$, hydroxy, hydroxy $C_1$-$C_4$ alkyl, halo, $C_1$-$C_2$ haloalkyl (such as $CF_3$), $C_1$-$C_2$ haloalkoxy (such as $OCF_3$), —NR'C(O)R'', —NR'$SO_2$R'', —C(O)R', —C(O)OR', —C(O)alkylOC(O)R'; —C(O)$NR_{10}R_{11}$, oxo, CN, or $C_0$-$C_1$alkylphenyl, where the phenyl is optionally substituted with 1-5 groups independently selected from halogen, $C_1$-$C_4$ alkyl, —$CO_2R'$, $C_1$-$C_4$ alkoxy, $C_1$-$C_2$ haloalkyl (such as $CF_3$), $C_1$-$C_2$ haloalkoxy (such as $OCF_3$), hydroxyl, CN, $NO_2$, phenyloxy, —$S(O)_{0-2}$—($C_1$-$C_6$ alkyl), —$NR_{10}R_{11}$, $C_1$-$C_6$ alkanoyl, pyridyl, phenyl, and —$SO_2NR_{10}R_{11}$.

In some other aspects, the invention provides compounds of Formulas IV-1 to IV-6, IVa to IVf, V-1 to V-6, Va to Vf, VI-1 to VI-6, VIa to VIf, VIIIa to VIIIg, VIIIh, VIIIm, VIIIn, IX-1 to IX-6, IXa, IXb, IXc, X-1 to X-6, Xa, Xb, Xc, XI-1 to XI-6, XIa, XIb, XIc, wherein the B-ring is triazolopyrimidinyl, imidazopyrimidinyl, pyrazolopyrimidinyl, or indolyl, each of which is unsubstituted.

In some other aspects, the invention provides compounds of Formulas IV-1 to IV-6, IVa to IVf, V-1 to V-6, Va to Vf, VI-1 to VI-6, VIa to VIf, VIIIa to VIIIg, VIIIh, VIIIm, VIIIn, IX-1 to IX-6, IXa, IXb, IXc, X-1 to X-6, Xa, Xb, Xc, XI-1 to XI-6, XIa, XIb, XIc, wherein the B-ring is triazolopyrimidinyl, imidazopyrimidinyl, pyrazolopyrimidinyl, or indolyl, each of which is substituted at a substitutable position with a group that is independently $C_1$-$C_4$ alkyl, $C_3$-$C_6$ cycloalkyl, $C_2$-$C_6$ alkenyl, $C_1$-$C_4$ alkoxy, amino, $C_1$-$C_4$ alkylamino, $C_1$-$C_4$ dialkylamino, —$S(O)_{0-2}R'$, hydroxy, hydroxy $C_1$-$C_4$ alkyl, halo, $C_1$-$C_2$ haloalkyl (such as $CF_3$), $C_1$-$C_2$ haloalkoxy (such as $OCF_3$), —C(O)R', —C(O)OR', —C(O)alkylOC(O)R'; —C(O)$NR_{10}R_{11}$, oxo, CN, or $C_0$-$C_1$alkylphenyl, where the phenyl is optionally substituted with 1-3 groups independently selected from halogen, $C_1$-$C_4$ alkyl, —$CO_2R'$, $C_1$-$C_4$ alkoxy, $C_1$-$C_2$ haloalkyl (such as $CF_3$), $C_1$-$C_2$ haloalkoxy (such as $OCF_3$), hydroxyl, —$NR_{10}R_{11}$, and $C_1$-$C_6$ alkanoyl.

In some aspects, the invention provides compounds of formula XV, i.e., compounds according to any one of Formulas Ia to Ie, II, IIIa to IIIf, IV-1 to IV-6, IVa to IVf, V-1 to V-6, Va to Vf, VI-1 to VI-6, VIa to VIf, VIIIa to VIIIg, VIIIh, VIIIm, VIIIn, IX-1 to IX-6, IXa, IXb, IXc, X-1 to X-6, Xa, Xb, Xc, XI-1 to XI-6, XIa, XIb, XIc, where the B-ring has the formula:

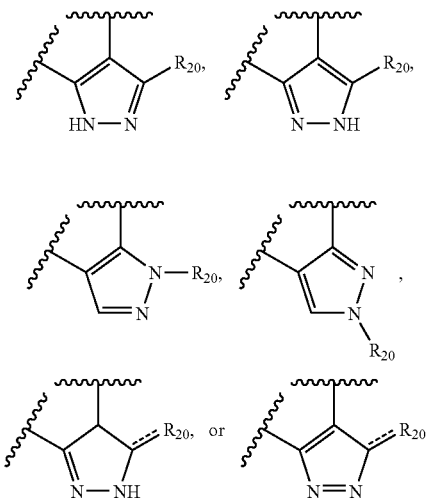

wherein $R_{20}$ is H, $C_1$-$C_6$ alkyl, $C_1$-$C_6$ alkoxy, oxo, amino, $C_1$-$C_6$ alkylamino, $C_1$-$C_6$ dialkylamino, —R'C(O)R", halo, or $CF_3$; and where the dashed bond represents an optional second bond.

In other aspects, the invention provides compounds of Formula XV, where the B-ring has the formula:

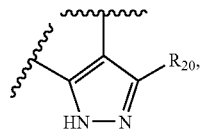

wherein $R_{20}$ is H, $C_1$-$C_6$ alkyl, $C_1$-$C_6$ alkoxy, amino, $C_1$-$C_6$ alkylamino, $C_1$-$C_6$ dialkylamino, —NR'C(O)R", halo, or $CF_3$.

In other aspects, the invention provides compounds of Formula XV, where the B-ring has the formula:

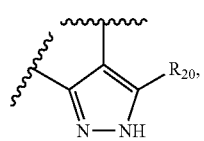

wherein $R_{20}$ is H, $C_1$-$C_6$ alkyl, $C_1$-$C_6$ alkoxy, amino, $C_1$-$C_6$ alkylamino, $C_1$-$C_6$ dialkylamino, —NR'C(O)R", halo, or $CF_3$.

In other aspects, the invention provides compounds of Formula XV, where the B-ring has the formula:

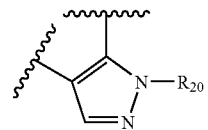

wherein $R_{20}$ is H, $C_1$-$C_6$ alkyl, $C_1$-$C_6$ alkoxy, amino, $C_1$-$C_6$ alkylamino, $C_1$-$C_6$ dialkylamino, —NR'C(O)R", halo, or $CF_3$.

In other aspects, the invention provides compounds of Formula XV, where the B-ring has the formula:

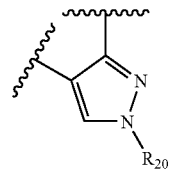

wherein $R_{20}$ is H, $C_1$-$C_6$ alkyl, $C_1$-$C_6$ alkoxy, amino, $C_1$-$C_6$ alkylamino, $C_1$-$C_6$ dialkylamino, —NR'C(O)R", halo, or $CF_3$.

In other aspects, the invention provides compounds of Formula XV, where the B-ring has the formula:

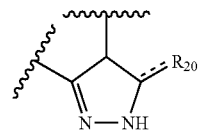

wherein $R_{20}$ is H, $C_1$-$C_6$ alkyl, $C_1$-$C_6$ alkoxy, oxo, amino, $C_1$-$C_6$ alkylamino, $C_1$-$C_6$ dialkylamino, —R'C(O)R", halo, or $CF_3$; and where the dashed bond represents an optional second bond.

In other aspects, the invention provides compounds of Formula XV, where the B-ring has the formula:

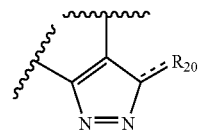

wherein $R_{20}$ is H, $C_1$-$C_6$ alkyl, $C_1$-$C_6$ alkoxy, oxo, amino, $C_1$-$C_6$ alkylamino, $C_1$-$C_6$ dialkylamino, —R'C(O)R", halo, or $CF_3$; and where the dashed bond represents an optional second bond.

In other aspects, the invention provides compounds of formula XVI, i.e., compounds according to any one of Formulas Ia to Ie, II, IIIa to IIIf, IV-1 to IV-6, IVa to IVf, V-1 to V-6, Va to Vf, VI-1 to VI-6, VIa to VIf, VIIIa to VIIIg, VIIIh, VIIIm, VIIIn, IX-1 to IX-6, IXa, IXb, IXc, X-1 to X-6, Xa, Xb, Xc, XI-1 to XI-6, XIa, XIb, XIc, where the B-ring has the formula:

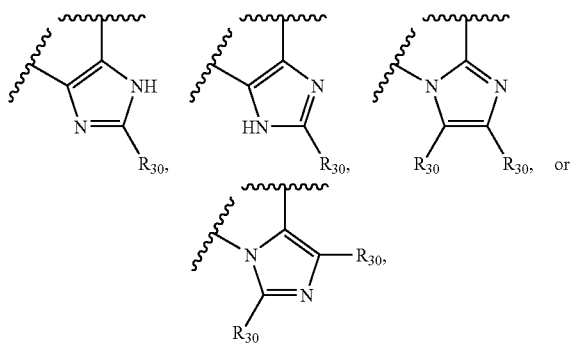

wherein R$_{30}$ is H, C$_1$-C$_4$ alkyl, C$_1$-C$_4$ alkoxy, amino, C$_1$-C$_4$ alkylamino, C$_1$-C$_4$ dialkylamino, C$_1$-C$_4$ alkythio, halo, CF$_3$, or phenyl.

In other aspects, the invention provides compounds of Formula XVI, where the B-ring has the formula:

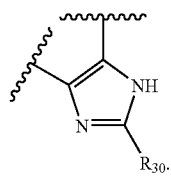

In other aspects, the invention provides compounds of Formula XVI, where the B-ring has the formula:

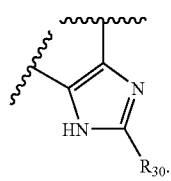

In other aspects, the invention provides compounds of Formula XVI, where the B-ring has the formula:

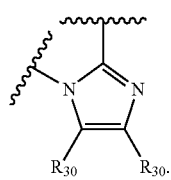

In other aspects, the invention provides compounds of Formula XVI, where the B-ring has the formula:

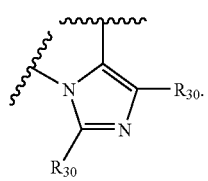

In other aspects, the invention provides compounds of formula XVII, i.e., compounds according to any one of Formulas Ia to Ie, II, IIIa to IIIf, IV-1 to IV-6, IVa to IVf, V-1 to V-6, Va to Vf, VI-1 to VI-6, VIa to VIf, VIIIa to VIIIg, VIIIh, VIIIm, VIIIn, IX-1 to IX-6, IXa, IXb, IXc, X-1 to X-6, Xa, Xb, Xc, XI-1 to XI-6, XIa, XIb, XIc, where the B-ring has the formula:

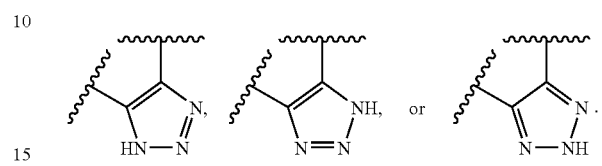

In other aspects, the invention provides compounds of Formula XVII, where the B-ring has the formula:

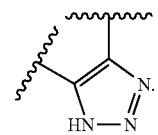

In other aspects, the invention provides compounds of Formula XVII, where the B-ring has the formula:

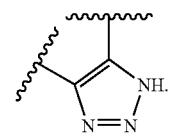

In other aspects, the invention provides compounds of Formula XVII, where the B-ring has the formula:

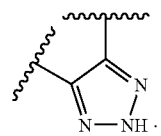

In another aspect, the invention provides compounds of Formulas VIIa or VIIb, including stereoisomers, tautomers and mixtures of stereoisomers and/or tautomers, and pharmaceutical salts thereof, with the structure:

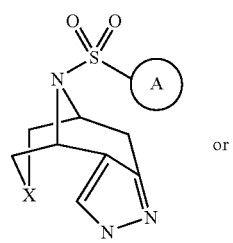

Formula VIIa or

-continued

Formula VIIb

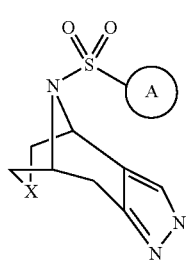

wherein

X is —C—, —CH—, —CH$_2$—, —O—, —S(O)$_{0-2}$—, or —NR$_{15}$—, where the —C— and —CH— groups are optionally substituted with 1 or 2 groups that are independently oxo (oxo can only be a substituent on —C—), halogen, C$_1$-C$_6$ alkyl, C$_2$-C$_6$ alkenyl, C$_1$-C$_6$ haloalkyl, C$_2$-C$_6$ alkynyl, hydroxy, hydroxyalkyl, C$_1$-C$_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$;

A is aryl, cycloalkyl, heteroaryl or heterocycloalkyl, where each ring is optionally substituted at a substitutable position with halogen, C$_1$-C$_6$ alkyl, C$_2$-C$_6$ alkenyl, C$_2$-C$_6$ alkynyl, C$_1$-C$_6$ alkoxy, haloalkyl, haloalkoxy, hydroxyl, hydroxyalkyl, CN, phenyloxy, —S(O)$_{0-2}$—(C$_1$-C$_6$ alkyl), —NR$_{10}$R$_{11}$, C$_1$-C$_6$ alkanoyl, C$_0$-C$_3$alkylCO$_2$R', pyridyl, thienyl, furanyl, pyrrolyl, pyrrolidinyl, piperidinyl, piperazinyl, phenyl, phenyl C$_1$-C$_4$ alkyl, or —SO$_2$NR$_{10}$R$_{11}$;

the bridged ring including the fused pyrazol ring is optionally substituted at a substitutable position with a group that is independently C$_1$-C$_6$ alkyl, C$_3$-C$_8$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$R', hydroxy, hydroxyalkyl, halo, C$_1$-C$_2$ haloalkyl, C$_1$-C$_2$ haloalkoxy, —NR'C(O)R", —NR'SO$_2$R", —C(O)R', —C(O)OR', —(C$_1$-C$_4$ alkyl)-C(O)OR$_{13}$, —C(O)alkylOC(O)R'; —C(O)NR$_{10}$R$_{11}$, —OC(O)NR$_{10}$R$_{11}$, —NR'C(O)OR", oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, phenyloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$;

R$_{10}$ and R$_{11}$ at each occurrence are independently H or C$_1$-C$_6$ alkyl, where the alkyl is optionally substituted with an aryl, where the aryl is optionally substituted with 1 to 5 groups that are independently halogen, hydroxyl, alkyl, alkoxy, haloalkyl, haloalkoxy, CN or NO$_2$; and R$_{10}$ and R$_{11}$ together may form a 3-8 membered ring optionally including an additional heteroatom such as N, O or S;

R$_{15}$ is H, phenyl, pyridyl, pyrimidinyl, oxazolyl, thienyl, furanyl, pyrrolyl, piperidinyl, piperazinyl, pyrrolidinyl, imidazolidinyl, indolyl, —SO$_2$R', —C(O)R'. —C(O)OR', or C$_1$-C$_6$ alkyl optionally substituted with phenyl, hydroxyl, or halogen, where the above cyclic groups are optionally substituted with 1 to 5 groups that are independently halogen, hydroxyl, C$_1$-C$_4$ alkyl, C$_1$-C$_4$ alkoxy, C$_1$-C$_4$ haloalkyl (such as CF$_3$), C$_1$-C$_4$ haloalkoxy (such as OCF$_3$), CN, amino, NH(C$_1$-C$_6$ alkyl), N(C$_1$-C$_6$ alkyl) (C$_1$-C$_6$ alkyl), or NO$_2$; and R' is hydrogen, C$_1$-C$_6$ alkyl, haloalkyl, C$_2$-C$_6$ alkenyl or phenyl optionally substituted with 1 to 5 groups that are independently halogen, C$_1$-C$_6$ alkyl, —C(O)OR', C$_1$-C$_6$ alkoxy, haloalkyl, haloalkoxy, hydroxyl, CN, phenyloxy, —SO$_2$—(C$_1$-C$_6$ alkyl), —NR$_{10}$R$_{11}$, C$_1$-C$_6$ alkanoyl, pyridyl, phenyl, NO$_2$, or —SO$_2$NR$_{10}$R$_{11}$;

including stereoisomers, tautomers, mixtures of stereoisomers and/or tautomers or pharmaceutically acceptable salts thereof.

In yet another aspect, the invention provides compounds of Formula VIIa or VIIb, wherein X is NR$_{15}$.

In yet another aspect, the invention provides compounds of Formula VIIa or VIIb, wherein X is NR$_{15}$ where R$_{15}$ is H, —SO$_2$R', —C(O)R', or C$_1$-C$_6$ alkyl, and R' is C$_1$-C$_6$ alkyl, haloalkyl, or phenyl optionally substituted with 1 to 3 groups that are independently halogen, C$_1$-C$_6$ alkyl, —C(O)OR', C$_1$-C$_6$ alkoxy, haloalkyl (such as CF$_3$), haloalkoxy (such as OCF$_3$), hydroxyl, CN, or NO$_2$.

In still another aspect, the invention provides compounds of Formula VIIa or VIIb, wherein X is O.

In another aspect, the invention provides compounds of Formula VIIa or VIIb, wherein X is —S(O)$_{0-2}$—.

In another aspect, the invention provides compounds of Formula VIIa or VIIb, wherein X is —C—, —CH—, —CH$_2$—, where the —C— and —CH— groups are optionally substituted with 1 or 2 groups that are independently oxo (oxo can only be a substituent on —C—), halogen, C$_1$-C$_6$ alkyl, C$_2$-C$_6$ alkenyl, C$_1$-C$_6$ haloalkyl, C$_2$-C$_6$ alkynyl, hydroxy, hydroxyalkyl, C$_1$-C$_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$.

In some aspects, the invention provides compounds of Formula VII where the A ring is aryl, for example phenyl optionally substituted with 1 to 5 groups that are independently halogen, hydroxyl, alkyl, alkoxy, haloalkyl, haloalkoxy, CN or NO$_2$. In some exemplary compounds the ring is a phenyl ring optionally substituted with 1 to 5 groups that are halogen, such as chloro, bromo, iodo or fluoro.

In other aspects, the invention provides compounds of Formula VII where the A ring is heteroaryl, for example furanyl, thienyl or pyridyl, optionally substituted with 1 to 5 groups that are independently halogen, hydroxyl, alkyl, alkoxy, haloalkyl, haloalkoxy, CN or NO$_2$. In some exemplary compounds the ring is a thienyl ring optionally substituted with 1 to 2 groups that are halogen, such as chloro, or bromo.

In still another aspect, the invention provides a composition comprising a compound or salt of Formula I and at least one pharmaceutically acceptable solvent, adjuvant, excipient, carrier, binder or disintegrant.

In still another aspect, the invention provides a method of treating Alzheimer's disease comprising administering a therapeutically effective amount of a compound or salt of Formula I to a patient in need of such treatment.

In another aspect, the compounds of the invention have minimal interaction or preferably, no interaction with Notch.

In some aspects the compounds are selected from:
12-(4-Chloro-benzenesulfonyl)-4,5,12-triaza-tricyclo [6.3.1.0$^{2,6}$]dodeca-2(6),3-diene;
12-(4-Chloro-benzenesulfonyl)-5-methyl-4,5,12-triaza-tricyclo[6.3.1.0$^{2,6}$]dodeca-2(6),3-diene;
5-tert-Butyl-12-(4-chloro-benzenesulfonyl)-4,5,12-triaza-tricyclo[6.3.1.0$^{2,6}$]dodeca-2(6),3-diene;
5-Benzyl-12-(4-chloro-benzenesulfonyl)-4,5,12-triaza-tricyclo[6.3.1.0$^{2,6}$]dodeca-2(6),3-diene;
12-(4-Chloro-benzenesulfonyl)-5-(4-isopropyl-phenyl)-4,5, 12-triaza-tricyclo[6.3.1.0$^{2,6}$]dodeca-2(6),3-diene;
12-(4-Chloro-benzenesulfonyl)-5-cyclohexyl-4,5,12-triaza-tricyclo[6.3.1.0$^{2,6}$]dodeca-2(6),3-diene;
16-(4-Chloro-benzenesulfonyl)-4,8,9,16-tetraaza-tetracyclo [10,3,1,0$^{2,10}$,0$^{5,9}$]hexadeca-2(10),3,5,7-tetraene;

16-(4-Chloro-benzenesulfonyl)-7-methyl-4,8,9,16-tetraaza-tetracyclo[10,3,1.0$^{2,10}$,0$^{5,9}$]-hexadeca-2(10),3,5,7-tetraene;
16-(4-Chloro-benzenesulfonyl)-7-hydroxy-4,8,9,16-tetraaza-tetracyclo[10,3,1.0$^{2,10}$,0$^{5,9}$]-hexadeca-2(10),3,5,7-tetraene;
16-(4-Chloro-benzenesulfonyl)-6-phenyl-4,8,9,16-tetraaza-tetracyclo[10,3,1.0$^{2,10}$,0$^{5,9}$]-hexadeca-2(10),3,5,7-tetraene;
16-(4-Chloro-benzenesulfonyl)-7-phenyl-4,8,9,1,6-tetraaza-tetracyclo[10,3,1.0$^{2,10}$,0$^{5,9}$]-hexadeca-2(10),3,5,7-tetraene;
16-(4-Chloro-benzenesulfonyl)-4,6,8,9,16-pentaaza-tetracyclo[10,3,1.0$^{2,10}$,0$^{5,9}$]hexadeca-2(10),3,5,7-tetraene;
16-(4-Chloro-benzenesulfonyl)-7-methylthio-4,6,8,9,16-pentaaza-tetracyclo-[10,3,1.0$^{2,10}$,0$^{5,9}$]hexadeca-2(10),3,5,7-tetraene;
16-(4-Chloro-benzenesulfonyl)-4,6,9,16-tetraaza-tetracyclo[10,3,1.0$^{2,10}$,0$^{5,9}$]hexadeca-2(10),3,5,7-tetraene;
12-(4-Chloro-benzenesulfonyl)-5-oxa-4,12-diaza-tricyclo[6.3.1.0$^{2,6}$]dodeca-2(6),3-diene;
13-(4-Chloro-benzenesulfonyl)-5-methyl-4,6,13-triaza-tricyclo[7.3.1.0$^{2,7}$]trideca-2(7),3,5-triene;
2-[12-(4-Chloro-benzenesulfonyl)-4,5,12-triaza-tricyclo[6.3.1.0$^{2,6}$]dodeca-2(6),3-dien-5-yl]-ethanol;
16-(4-Chloro-benzenesulfonyl)-6-acetamido-4,8,9,16-tetraaza-tetracyclo[10,3,1.0$^{2,10}$,0$^{5,9}$]-hexadeca-2(10),3,5,7-tetraene;
16-(4-Chloro-benzenesulfonyl)-7-amino-4,6,8,9,16-pentaaza-tetracyclo[10,3,1.0$^{2,10}$,0$^{5,9}$]-hexadeca-2(10),3,5,7-tetraene;
12-(4-Chloro-benzenesulfonyl)-4,5,12-triaza-tricyclo[6.3.1.0$^{2,6}$]-2(6),3-dien-3-ol;
12-(4-Chloro-benzenesulfonyl)-4-methyl-4,5,12-triaza-tricyclo[6.3.1.0$^{2,6}$]dodeca-2,5-dien-3-ol;
16-(4-Chloro-benzenesulfonyl)-5-fluoro-9,16-diaza-tetracyclo[10,3,1.0$^{2,10}$,0$^{3,8}$]hexadeca-2(10),3(8),4,6-tetraene;
12-(4-Chloro-benzenesulfonyl)-4,5,12-triaza-tricyclo[6.3.1.0$^{2,6}$]dodeca-2(6),3-diene (2 enantiomers);
11-(4-Chloro-benzenesulfonyl)-4,5,11-triaza-tricyclo[6.3.1.0$^{2,6}$]undeca-2(6),3-diene;
12-(4-Chloro-benzenesulfonyl)-3-methyl-4,5,12-triaza-tricyclo[6.3.1.0$^{2,6}$]dodeca-2(6),3-diene;
12-(4-Chloro-benzenesulfonyl)-5-methyl-3-trifluoromethyl-4,5,12-triaza-tricyclo[6.3.1.0$^{2,6}$]-dodeca-2(6),3-diene;
12-(4-Chloro-benzenesulfonyl)-3-trifluoromethyl-4,5,12-triaza-tricyclo[6.3.1.0$^{2,6}$]dodeca-2(6),3-diene;
1-[12-(4-Chloro-benzenesulfonyl)-4,5,12-triaza-tricyclo[6.3.1.0$^{2,6}$]dodeca-2,5-dien-4-yl]-ethanone;
1-[12-(4-Chloro-benzenesulfonyl)-4,5,12-triaza-tricyclo[6.3.1.0$^{2,6}$]dodeca-2,5-dien-4-yl]-2-methyl-propan-1-one;
Acetic acid 2-[12-(4-chloro-benzenesulfonyl)-4,5,12-triaza-tricyclo[6.3.1.0$^{2,6}$]dodeca-2,5-dien-4-yl]-1,1-dimethyl-2-oxo-ethyl ester;
12-(4-Chloro-benzenesulfonyl)-4,5,12-triaza-tricyclo[6.3.1.0$^{2,6}$]dodeca-2,5-diene-4-carboxylic acid allyl ester;
13-(4-Chloro-benzenesulfonyl)-4,6,13-triaza-tricyclo[7.3.1.0$^{2,7}$]trideca-2(7),3,5-trien-5-ylamine;
13-(4-Chloro-benzenesulfonyl)-4,6,13-triaza-tricyclo[7.3.1.0$^{2,7}$]trideca-2(7),3,5-triene;
12-(4-Chloro-benzenesulfonyl)-3-trifluoromethyl-4,5,12-triaza-tricyclo[6.3.1.0$^{2,6}$]dodeca-2(6),3-diene;
12-(4-Chloro-benzenesulfonyl)-3,4,5,12-tetraaza-tricyclo[6.3.1.0$^{2,6}$]dodeca-2(6),3-diene;
13-(4-Chloro-benzenesulfonyl)-5-methoxy-4,6,13-triaza-tricyclo[7.3.1.0$^{2,7}$]trideca-2(7),3,5-triene;
3-Chloro-12-(4-chloro-benzenesulfonyl)-4,5,12-triaza-tricyclo[6.3.1.0$^{2,6}$]dodeca-2(6),3-diene;
12-(4-Chloro-benzenesulfonyl)-3-methyl-4,5,12-triaza-tricyclo[6.3.1.0$^{2,6}$]dodeca-2(6),3-diene;
12-(4-Chloro-benzenesulfonyl)-3-difluoromethyl-4,5,12-triaza-tricyclo[6.3.1.0$^{2,6}$]dodeca-2(6),3-diene;
12-(4-Chloro-benzenesulfonyl)-4,5,12-triaza-tricyclo[6.3.1.0$^{2,6}$]dodeca-2(6),3-dien-3-ylamine;
12-(4-Chloro-benzenesulfonyl)-3-difluoromethyl-4,5,12-triaza-tricyclo[6.3.1.0$^{2,6}$]dodeca-2(6),3-diene;
12-(4-Chloro-benzenesulfonyl)-3-methylsulfanyl-4,5,12-triaza-tricyclo[6.3.1.0$^{2,6}$]dodeca-2(6),3-diene;
12-(4-Chloro-benzenesulfonyl)-4,5,12-triaza-tricyclo[6.3.1.0$^{2,6}$]dodeca-2(6),3-dien-7-one;
12-(4-Chloro-benzenesulfonyl)-7-methyl-4,5,12-triaza-tricyclo[6.3.1.0$^{2,6}$]dodeca-2(6),3-diene;
12-(4-Chloro-benzenesulfonyl)-10-oxa-4,5,12-triaza-tricyclo[6.3.1.0$^{2,6}$]dodeca-2(6),3-diene;
12-(4-Chloro-benzenesulfonyl)-7-ethyl-4,5,12-triaza-tricyclo[6.3.1.0$^{2,6}$]dodeca-2(6),3-diene;
12-(5-Chloro-thiophene-2-sulfonyl)-4,5,12-triaza-tricyclo[6.3.1.0$^{2,6}$]dodeca-2(6),3-diene (2 enantiomers);
12-(4-Chloro-benzenesulfonyl)-4,5,12-triaza-tricyclo[6.3.1.0$^{2,6}$]dodeca-2(6),3-dien-7-ol (2 enantiomers);
12-(4-Chloro-benzenesulfonyl)-4,5,12-triaza-tricyclo[6.3.1.0$^{2,6}$]dodeca-2(6),3-dien-3-ylamine (2 enantiomers);
N-[12-(4-Chloro-benzenesulfonyl)-4,5,12-triaza-tricyclo[6.3.1.0$^{2,6}$]dodeca-2(6),3-dien-7-yl]-acetamide (2 enantiomers);
12-(4-Chloro-benzenesulfonyl)-4,5,12-triaza-tricyclo[6.3.1.0$^{2,6}$]dodeca-2(6),3-diene-10-carboxylic acid ethyl ester;
[12-(4-Chloro-benzenesulfonyl)-4,5,12-triaza-tricyclo[6.3.1.0$^{2,6}$]dodeca-2(6),3-dien-10-yl]-methanol;
12-(4-Chloro-benzenesulfonyl)-4,5,12-triaza-tricyclo[6.3.1.0$^{2,6}$]dodeca-2(6),3-diene-10-carboxylic acid;
12-(4-Chloro-benzenesulfonyl)-4,5,10,12-tetraaza-tricyclo[6.3.1.0$^{2,6}$]dodeca-2(6),3-diene-10-carboxylic acid tert-butyl ester;
12-(4-Chloro-benzenesulfonyl)-4,5,10,12-tetraaza-tricyclo[6.3.1.0$^{2,6}$]dodeca-2(6),3-diene;
12-(4-Chloro-benzenesulfonyl)-4-amino-3-thia-5,12-diaza-tricyclo[6.3.1.0$^{2,6}$]dodeca-2(6),4-diene;
12-(4-Chloro-benzenesulfonyl)-10,10-difluoro-4,5,12-triaza-tricyclo[6.3.1.0$^{2,6}$]dodeca-2(6),3-diene;
12-(4-Chloro-benzenesulfonyl)-10-difluoromethyl-4,5,12-triaza-tricyclo[6.3.1.0$^{2,6}$]dodeca-2(6),3-diene;
12-(4-Chloro-benzenesulfonyl)-10-methoxymethyl-4,5,12-triaza-tricyclo[6.3.1.0$^{2,6}$]dodeca-2(6),3-diene;
12-(4-Chloro-benzenesulfonyl)-1-methoxycarbonyl-4,5,12-triaza-tricyclo[6.3.1.0$^{2,6}$]dodeca-2(6),3-diene;
12-(4-Chloro-benzenesulfonyl)-1-methyl-4,5,12-triaza-tricyclo[6.3.1.0$^{2,6}$]dodeca-2(6),3-diene;
12-(2-Pyridinesulfonyl)-4,5,12-triaza-tricyclo[6.3.1.0$^{2,6}$]dodeca-2(6),3-diene;
12-(3-Pyridinesulfonyl)-4,5,12-triaza-tricyclo[6.3.1.0$^{2,6}$]dodeca-2(6),3-diene;
12-(4-Pyridinesulfonyl)-4,5,12-triaza-tricyclo[6.3.1.0$^{2,6}$]dodeca-2(6),3-diene;
12-(4-Chloro-benzenesulfonyl)-7-cyano-4,5,12-triaza-tricyclo[6.3.1.0$^{2,6}$]dodeca-2(6),3-diene;
Dimethyl-carbamic acid 12-(4-Chloro-benzenesulfonyl)-4,5,12-triaza-tricyclo[6.3.1.0$^{2,6}$]dodeca-2(6),3-dien-7-yl ester;

12-(4-Chloro-benzenesulfonyl)-4,5,10,12-tetraaza-tricyclo[6.3.1.0$^{2,6}$]dodeca-2(6),3-diene-10-carboxylic acid methyl ester;

1-[12-(4-Chloro-benzenesulfonyl)-4,5,10,12-tetraaza-tricyclo[6.3.1.0$^{2,6}$]dodeca-2(6),3-diene-10-yl]-ethanone;

12-(4-Chloro-benzenesulfonyl)-4,5,12-triaza-tetracyclo[6.3.1.0$^{2,6}$.0$^{9,11}$]dodeca-2(6),3-diene;

12-(4-Chloro-benzenesulfonyl)-10-thiazol-2-yl-4,5,10,12-tetraaza-tricyclo[6.3.1.0$^{2,6}$]dodeca-2(6),3-diene;

12-(4-Chloro-benzenesulfonyl)-10,10-difluoro-4,5,12-triaza-tetracyclo[6.3.1.0$^{2,6}$.0$^{9,11}$]dodeca-2(6),3-diene;

12-(4-Chloro-benzenesulfonyl)-10-methanesulfonyl-4,5,10,12-tetraaza-tricyclo[6.3.1.0$^{2,6}$]dodeca-2(6),3-diene;

11-(4-Chloro-benzenesulfonyl)-9,9,10,10-tetrafluoro-4,5,11-triaza-tricyclo[6.2.1.0$^{2,6}$]undeca-2(6),3-diene;

12-(4-Chloro-benzenesulfonyl)-7-fluoro-4,5,12-triaza-tricyclo[6.3.1.0$^{2,6}$]dodeca-2(6),3-diene; and 12-(4-Chloro-benzenesulfonyl)-7,7-difluoro-4,5,12-triaza-tricyclo[6.3.1.0$^{2,6}$]dodeca-2(6),3-diene;

including single stereoisomers, tautomers, mixtures of stereoisomers and/or tautomers and pharmaceutical acceptable salts thereof.

In some other aspects, the compounds are selected from a group having the following exemplary structures:

Exemplary Structures

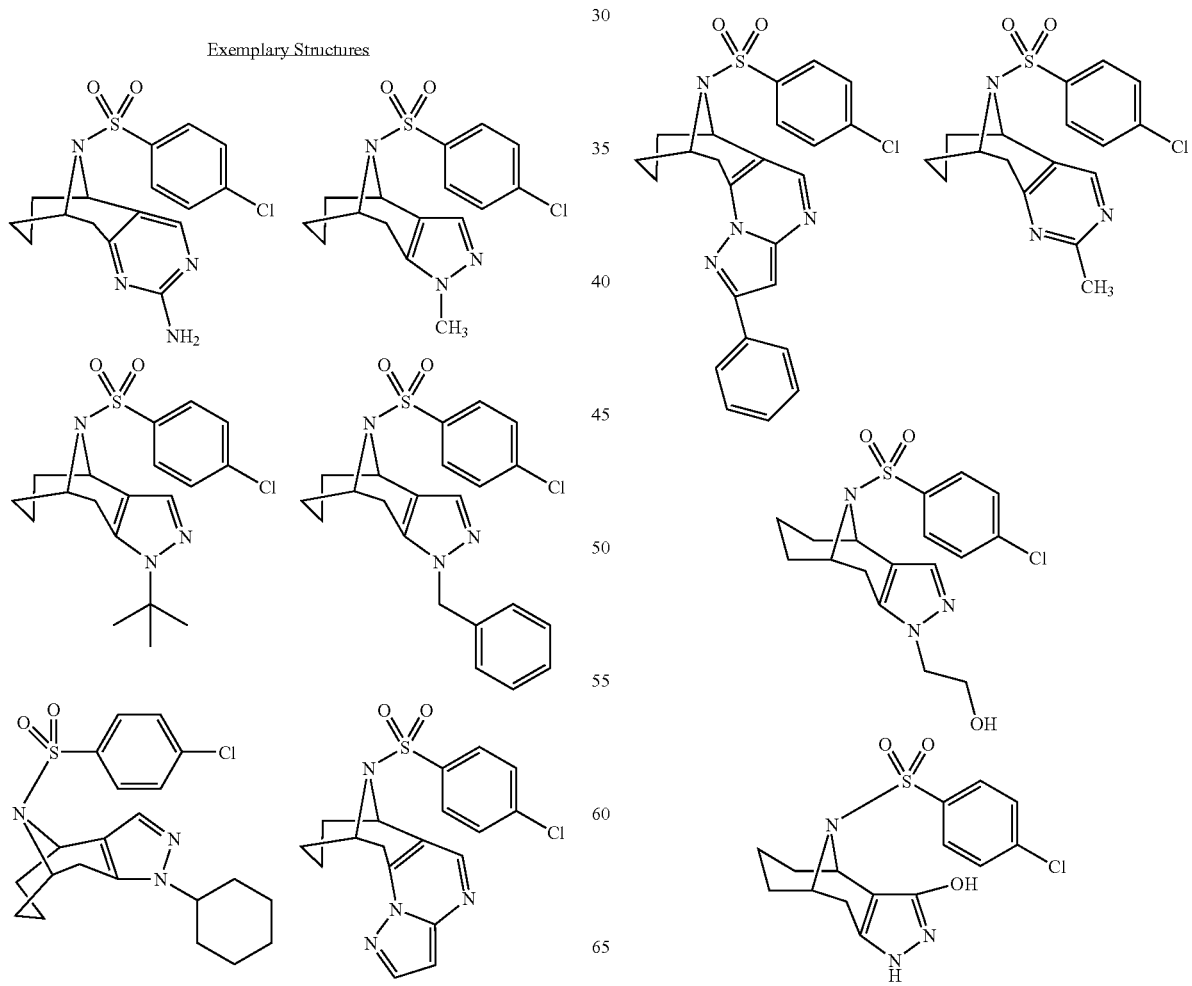

-continued
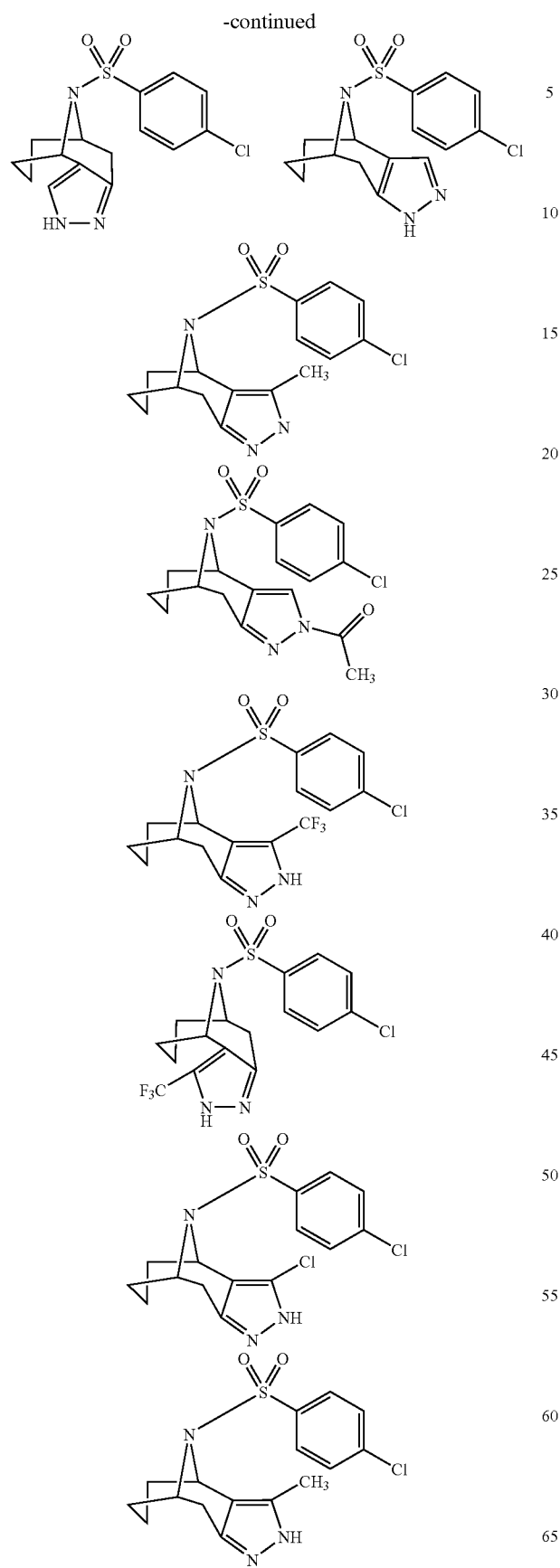
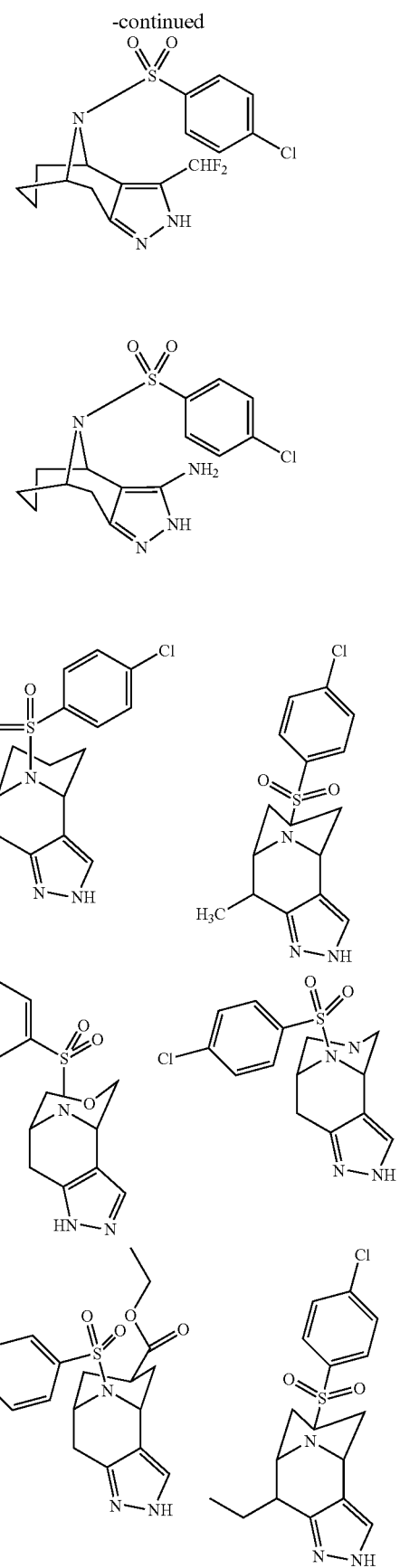

-continued
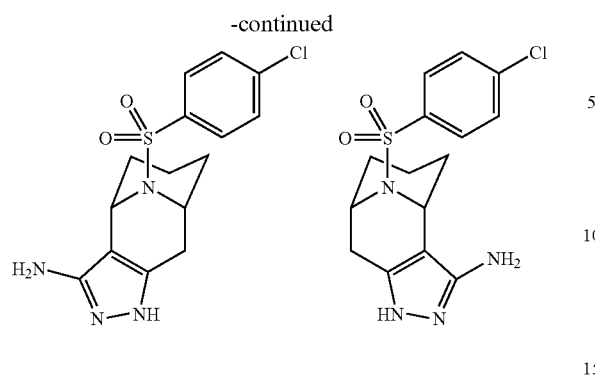
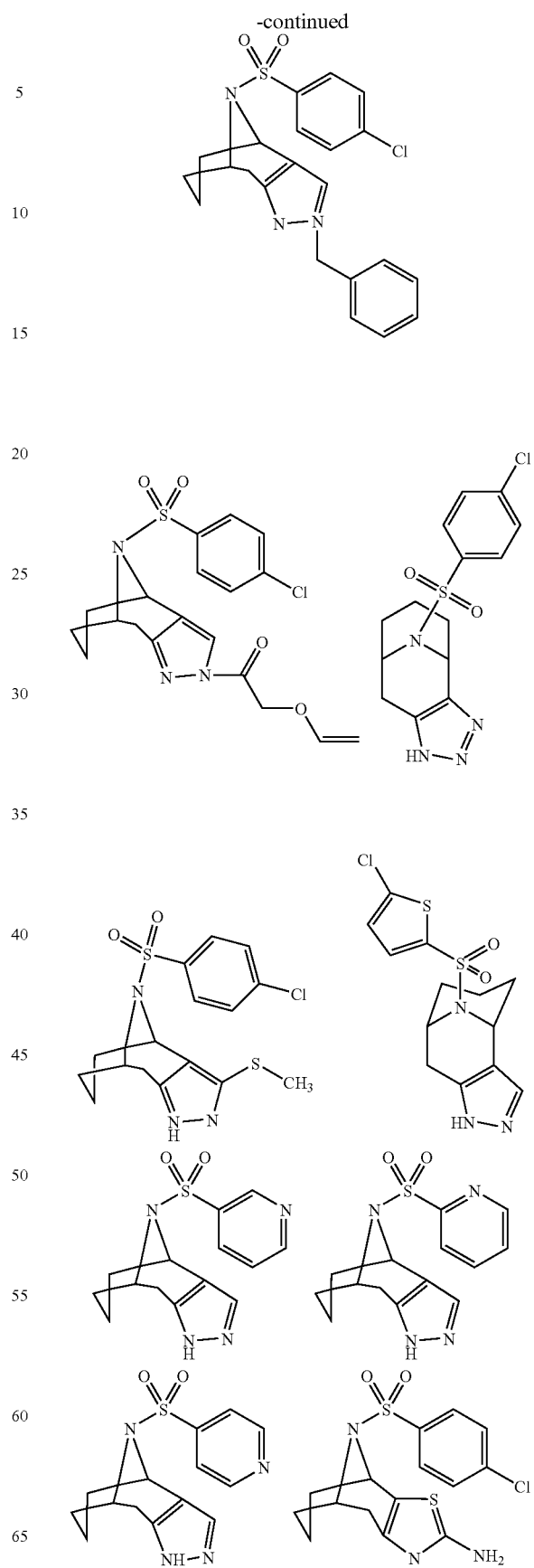

-continued

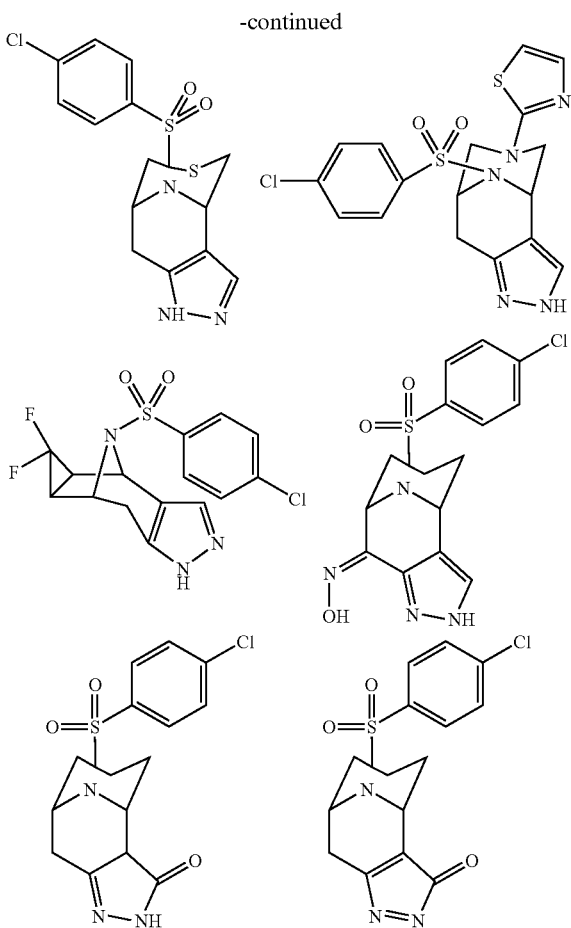

The compounds of general Formula I encompass the sulfonamido derivatives of the invention as disclosed, and/or the pharmaceutically acceptable salts, solvates, or polymorphs of such compounds. In addition, the compounds of this invention include the individual stereochemical and geometrical isomers, tautomers, and mixtures thereof, arising from the selection of substituent groups. Certain compounds of this invention may exist in isomeric forms. The invention contemplates all such stereoisomers both in pure form and in admixture, as well as racemic mixtures.

DEFINITIONS

The definitions and explanations below are for the terms as used throughout this entire document including both the specification and the claims. Throughout the specification and the appended claims, a given formula or name shall encompass all isomers thereof, such as stereoisomers, geometrical isomers, optical isomers, tautomers, and mixtures thereof where such isomers exist, as well as pharmaceutically acceptable salts and solvates thereof, such as for instance hydrates.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, 3, or 4 $R_q$ groups where the $R_q$ groups can be the same or different. It will be understood by those skilled in the art with respect to any group containing one or more substituents that such groups are not intended to introduce any substitution or substitution patterns that are sterically impractical and/or synthetically non-feasable.

APP, amyloid precursor protein, is defined as any APP polypeptide, including APP variants, mutations, and isoforms, for example, as disclosed in U.S. Pat. No. 5,766,846.

A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Pharmaceutically acceptable refers to those properties and/or substances that are acceptable to the patient from a toxicological and/or safety point of view.

A therapeutically effective amount is defined as an amount effective to reduce or lessen at least one symptom of the disease being treated or to reduce or delay onset of one or more clinical markers or symptoms of the disease.

By "alkanoyl" is meant an acyl radical Alk-C(O)—, wherein Alk is an alkyl radical as defined herein. Examples of alkanoyl include acetyl, propionyl, butyryl, isobutyryl, valeryl, isovaleryl, 2-methyl-butyryl, 2,2-dimethylpropionyl, valeryl, hexanoyl, heptanoyl, octanoyl and the like.

By "alkyl" and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent is shorter or longer than 6 carbons, it will be so indicated in the second "C" as, for example, "$C_1$-$C_{10}$" indicates a maximum of 10 carbons. The term also includes substituted alkyl groups, and refers to an alkyl group in which 1 or more hydrogen atoms is replaced by a substituent independently selected from the group: acyl, acyloxy, alkoxy, amino (wherein the amino group may be a cyclic amine), aryl, heteroaryl, heterocyclyl, carboxyl, oxo, amido, cyano, cycloalkyl, cycloalkenyl, halogen, hydroxyl, nitro, sulfamoyl, sulfanyl, sulfinyl, sulfonyl, and sulfonic acid, By "alkylene" is meant a diradical alkyl group, whereby alkyl is as defined above.

By "aryloxy" is meant the group —O-aryl, where aryl is as defined herein. More preferably the aryl portion of the aryloxy group is phenyl or naphthyl, still more preferably, phenyl.

By "arylalkyl" is meant the group -alkyl-aryl, wherein alkyl and aryl are defined herein.

By the term "halogen" in the present invention is meant fluorine, bromine, chlorine, and/or iodine.

By "alkenyl" and "$C_2$-$C_6$ alkenyl" is meant straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like. The term also includes substituted alkenyl groups, and refers to an alkenyl group in which 1 or more hydrogen atoms is replaced by a substituent independently selected from the group: acyl, acyloxy, alkoxy, amino (wherein the amino group may be a cyclic amine), aryl, heteroaryl, heterocyclyl, carboxyl, oxo, amido, cyano, cycloalkyl, cycloalkenyl, halogen, hydroxyl, nitro, sulfamoyl, sulfanyl, sulfinyl, sulfonyl, and sulfonic acid.

By "alkynyl" refers to a monoradical branched or unbranched, unsaturated or polyunsaturated hydrocarbon chain, having from about 2 to 20 carbon atoms, for example 2 to 10 carbon atoms and comprising at least one triple bond, and preferably 1 to 3. The term also includes substituted alkynyl groups, and refers to an alkynyl group in which 1 or more hydrogen atoms is replaced by a substituent independently selected from the group: acyl, acyloxy, alkoxy, amino (wherein the amino group may be a cyclic amine), aryl, heterocyclyl, heteroaryl, carboxyl, oxo, amido, cyano, cycloalkyl, cycloalkenyl, halogen, hydroxyl, nitro, sulfamoyl, sulfanyl, sulfinyl, sulfonyl, and sulfonic acid.

By "cycloalkyl" is meant saturated carbocyclic radicals having three to twelve carbon atoms. The cycloalkyl can be monocyclic, a polycyclic fused system, or a bi or polycyclic bridged system, such as adamantyl or bicyclo[2.2.1]heptyl. Examples of such radicals include cyclopropyl, cyclobutyl, cyclopentyl and cyclohexyl. Preferred cycloalkyl groups are cyclopentyl, cyclohexyl, and cycloheptyl. The cycloalkyl groups herein are unsubstituted or, substituted in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "aryl" is meant an aromatic carbocyclic group having a single ring (e.g., phenyl) or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, fluorenyl, tetralinyl or 6,7,8,9-tetrahydro-5H-benzo[a]cycloheptenyl. The aryl groups herein are unsubstituted or substituted in one or more substitutable positions with various groups. For example, such aryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "oxo" is meant the group =O.

By "halogen" in the present invention=is meant fluorine, bromine, chlorine, and/or iodine.

By "haloalkyl" is meant an alkyl radical having the meaning as defined above wherein one or more hydrogens are replaced by a halogen. Examples of such haloalkyls include chloromethyl, 1-bromoethyl, fluoromethyl, difluoromethyl, trifluoromethyl, 1,1,1-trifluoroethyl and the like.

By "heteroaryl" is mean at least one or more aromatic ring systems of 5-, 6-, or 7-membered rings which includes fused ring systems of 9-11 atoms containing at least one and up to four heteroatoms selected from nitrogen, oxygen, or sulfur. Preferred heteroaryl groups of the present invention include pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridyl, benzotetrahydrofuranyl, benzotetrahydrothienyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or substituted in one or more substitutable positions with various groups. For example, such heteroaryl groups may be optionally substituted with, for example, $C_1$-$C_6$ alkyl, $C_1$-$C_6$ alkoxy, halogen, hydroxy, cyano, nitro, amino, mono($C_1$-$C_6$) alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "heterocycle", "heterocycloalkyl" or "heterocyclyl" is meant one or more carbocyclic ring systems of 4-, 5-, 6-, or 7-membered rings which includes fused ring systems of 9-11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazolyl, dihydropyridyl, dihydropyrimidinyl, dihydrofuryl, dihydropyranyl, tetrahydrothienyl S-oxide, tetrahydrothienyl S,S-dioxide and homothiomorpholinyl S-oxide. The heterocycle groups herein are unsubstituted or substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino ($C_1$-$C_6$)alkyl or oxo.

Most compounds were named using Autonom 2000 4.01.305, which is available from Beilstein Information Systems, Inc, Englewood, Colo., or ChemDraw v.10.0, (available from Cambridgesoft at 100 Cambridge Park Drive, Cambridge, Mass. 02140). Alternatively, the names were generated based on the IUPAC rules.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of Formula I.

The invention also encompasses the acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I.

The term "acid prodrug group" denotes a moiety that is converted in vivo into an active carboxylic acid compound of formula I. Such prodrug groups are generally known in the art and include ester forming groups, to form an ester prodrug, such as benzyloxy, di($C_1$-$C_6$)alkylaminoethyloxy, acetoxymethyl, pivaloyloxymethyl, phthalidoyl, ethoxycarbonyloxyethyl, 5-methyl-2-oxo-1,3-dioxol-4-yl methyl, and ($C_1$-$C_6$) alkoxy optionally substituted by N-morpholino and amide-forming groups such as di($C_1$-$C_6$)alkylamino. Preferred prodrug groups include $C_1$-$C_6$ alkoxy forming an ester, and $O^-M^+$ where $M^+$ represents a cation to form a salt of the acid. Preferred cations include sodium, potassium, and ammonium. Other cations include magnesium and calcium. Further preferred prodrug groups include $O^=M^{++}$ where $M^{++}$ is a divalent cation such as magnesium or calcium.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The invention also encompasses the prodrugs of the compounds of Formula I. Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvates, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

Formulations suitable for inhalation or insufflation include solutions and suspensions in pharmaceutically acceptable aqueous or organic solvents, or mixtures thereof, and powders. The liquid or solid compositions may contain suitable pharmaceutically acceptable excipients as describe above. The compositions may be administered by oral or nasal respiratory route for local or systemic effect. Compositions may be nebulized by use of inert gases or vaporized, and breathed directly from the nebulizing/vaporizing device or the nebulizing device may be attached to a facemask tent or intermittent positive pressure-breathing machine.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

The disclosures in this document of all articles and references, including patents, are incorporated herein by reference in their entirety.

The invention is illustrated further by the following examples, which are not to be construed as limiting the invention in scope or spirit to the specific procedures described in them.

The starting materials and various intermediates may be obtained from commercial sources, prepared from commercially available compounds, and/or prepared using known synthetic methods.

General Synthetic Procedures

Reagents and solvents obtained from commercial suppliers were used without further purification unless otherwise stated. Thin layer chromatography was performed on precoated 0.25 mm silica gel plates (E. Merck, silica gel 60, $F_{254}$). Visualization was achieved using UV illumination or staining with phosphomolybdic acid, ninhydrin or other common staining reagents. Flash chromatography was performed using either a Biotage Flash 40 system and prepacked silica gel columns or hand packed columns (E. Merck silica gel 60, 230-400 mesh). Preparatory HPLC was performed on a Varian Prepstar high performance liquid chromatograph. $^1$H NMR spectra were recorded on either a Varian Gemini 300 MHz spectrometer or a Bruker Avance 300 MHz spectrometer. Chemical shifts are reported in ppm (δ) and were calibrated using the undeuterated solvent resonance as internal standard. Mass spectra were recorded on an Agilent series 1100 mass spectrometer connected to an Agilent series 1100 HPLC.

Exemplary HPLC Procedures

High Pressure Liquid Chromatography (HPLC) procedures employed the following methods.

Method 1: A 20% [B]: 80% [A] to 70% [B]: 30% [A] gradient in 1.75 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection at 35° C.

Method 2: An isocratic gradient employing 10-20% EtOH or isopropanol in hexane on a Chiralcel OD or Chiralcel OJ 2 cm×25 cm column, 220 nm detection at rt.

The compounds of the invention can be prepared using methods known in the art of organic synthesis. For example, the compounds of the invention, as well as all intermediates, can be synthesized by known processes using either solution or solid phase techniques, as shown below. Representative procedures for preparing compounds of the invention are outlined in the following schemes.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Second Edition, Wiley, New York, 1991, and references cited therein.

Scheme 1

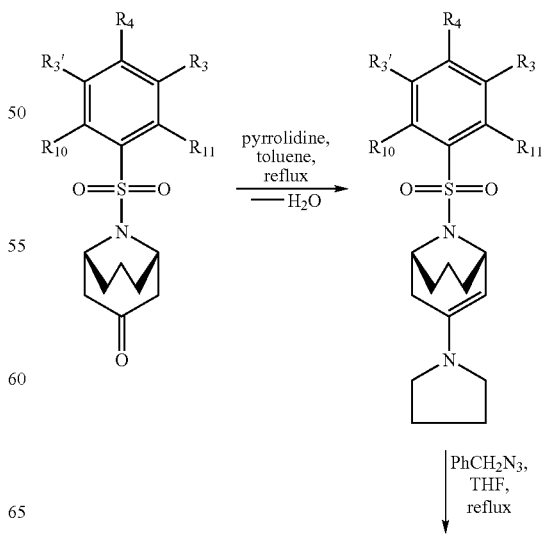

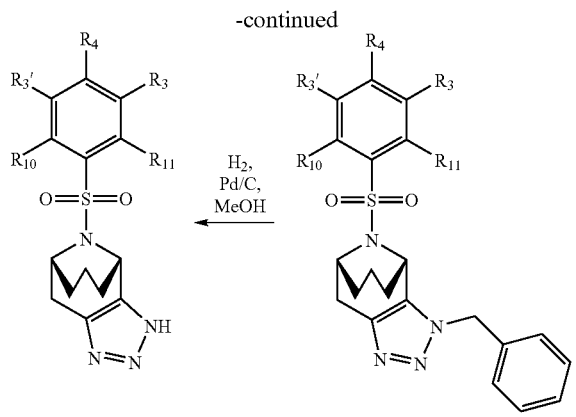

In Scheme 1, $R_{10}$, $R_{3'}$, $R_4$, $R_3$, and $R_{11}$ are as defined in formula 1, and the ketone is converted to the enamine by refluxing the ketone, an equivalent of acid (such as 4-toluenesulfonic acid) and an equivalent of a base capable of forming an enamine, such as pyrrolidine, in a solvent, such as toluene or a higher boiling hydrocarbon solvent, while removing water using a Dean Stark trap or other dehydrating means. Following complete reaction as evidenced by NMR of an aliquot, the enamine is isolated by washing the toluene based reaction mixture with aqueous $NaHCO_3$, and then with sat. NaCl. After drying, the solvent is removed to afford a product suitable for immediate use in the next reaction.

The enamine is converted to the triazole by refluxing the enamine and an equivalent of an azide, such as benzyl azide which is illustrated above, (other azides, such as $C_1$-$C_6$ alkyl azides or substituted benzyl azides [with groups such as OMe, halo or Me, for example], may also be used), in tetrahydrofuran or a higher boiling ethereal solvent. Following complete reaction as evidenced by TLC, the triazole is isolated by diluting the THF based reaction mixture with EtOAc, followed by washing with 0.5 M citric acid, then with sat. NaCl, and then the reaction mixture is dried and filtered. Evaporation of the solvent affords a product, which is purified by flash chromatography. If desired, The triazole compound then has the benzyl group removed by stirring with catalytic Pd/C and excess ammonium formate in methanol or another higher alcohol. Following complete reaction as evidenced by TLC, the de-benzylated triazole is isolated after filtering and concentrating the reaction mixture. If desired, the triazole is purified using column chromatography or preparative HPLC. The triazole may then be further manipulated (converted into an amide, alkylated, sulfonylated, etc.) using methods known in the art.

Scheme 2

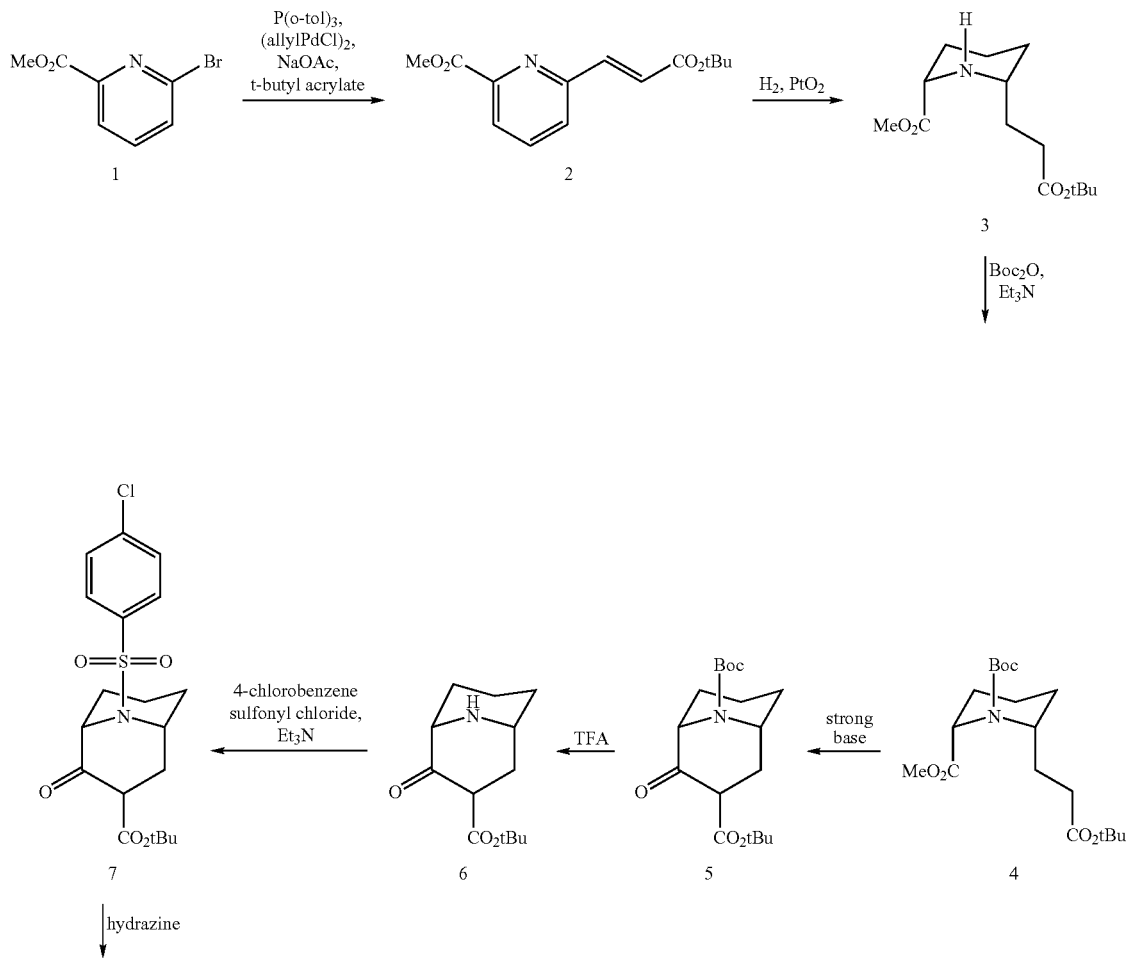

-continued

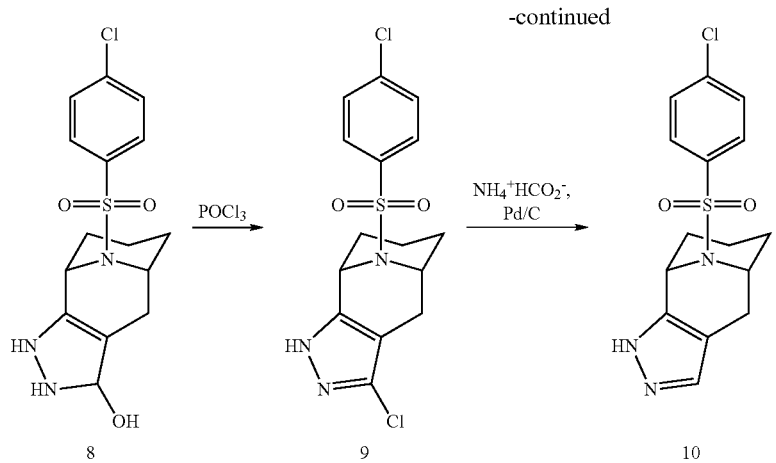

6-(2-tert-Butoxycarbonyl-vinyl)-pyridine-2-carboxylic acid methyl ester (2)

Methyl 6-bromo-2-pyridinecarboxylate (1) (5.0 g, 23.1 mmol), sodium acetate (5.7 g, 3.0 eq), tris-O-tolylphosphine (0.7 g, 2.3 mmol), allylpalladium chloride dimer (0.34 g, 0.93 mmol) and tert-butyl acrylate (3.6 g, 1.2 eq) are mixed in toluene (25 ml), and the resulting slurry is heated under a nitrogen atmosphere at 110° C. for approximately 12-16 hours. After cooling to ambient temperature, the precipitate is removed by filtration, and rinsed with ethyl acetate. The filtrate is washed with 1 M aqueous citric acid, water, and brine, and then dried with $MgSO_4$ and filtered. The solvent is removed, and the resulting yellow solid is crystallized from EtOAc/hexane to give the pure product as a yellow solid. MS: m/z ($EI^+$) 264.1.

6-(2-tert-Butoxycarbonyl-ethyl)-piperidine-2-carboxylic acid methyl ester (3)

Compound 2 (1.0 g) is dissolved in glacial acetic acid (10 ml) and $PtO_2$ (100 mg) is added. Hydrogenation is carried out in Parr shaker at 55 psi for 3 days. The catalyst is removed by filtration through Celite, and the solvent is evaporated to give the desired product as a yellow oil. $^1$H NMR ($CD_3OD$) δ 3.73 (s, 3H), 3.40-3.33 (m, 1H), 2.61-2.52 (m, 1H), 2.34-2.29 (m, 2H), 2.03-1.99 (m, 1H), 1.93-1.88 (m, 1H), 1.76-1.68 (m, 3H), 1.50-1.33 (m, 11H), 1.11-1.02 (m, 1H).

6-(2-tert-Butoxycarbonyl-ethyl)-piperidine-1,2-dicarboxylic acid 1-tert-butyl ester 2-methyl ester (4)

Compound 3 (970 mg) is dissolved in methylene chloride (10 ml). Triethylamine (0.81 ml) and $(Boc)_2O$ (640 mg) are then added. The resulting mixture is stirred at room temperature overnight. The mixture is diluted with additional methylene chloride (50 ml) and washed with sat. $NaHCO_3$ (twice) and brine (once). After treatment with $MgSO_4$ and filtering, the solvent is removed via rotavapor to give the desired product as a pale yellow oil. $^1$H NMR ($CD_3OD$) δ 4.85 (bs, 1H), 4.24 (bs, 1H), 3.76 (s, 3H), 2.36-2.31 (m, 4H), 1.86-1.50 (m, 24H).

Of course, when compound 3 is converted into compound 4, other protecting groups, such as Cbz, or benzyl can be used.

Compound 4 is converted into compound 5 by treatment with a strong base in an organic solvent, thereby promoting a Dieckman cyclization. Suitable strong bases include sodium ethoxide, potassium tert-butoxide, and lithium diisopropyl amide, KHMDS, and the like. Suitable organic solvents include ethanol, THF, DMF, and the like. Isolation of the product is accomplished by neutralization of the strong base, followed by an extractive workup. Purification of compound 5 is accomplished by recrystallization, flash chromatography, or preparative HPLC.

Compound 5 is converted to the trifluoroacetate salt of compound 6 by treatment with neat trifluoroacetic acid, followed by evaporation of the excess acid and any solvent that is present.

The trifluoroacetate salt of compound 6 is converted to compound 7 by treatment with a sulfonyl chloride, such as 4-chlorobenzenesulfonyl chloride (which is illustrated above) and triethylamine in dichloromethane. Compound 7 is isolated by diluting the reaction mixture with EtOAc, followed by washing the resulting organic phase with mild aqueous acid and saturated aqueous NaCl, followed by treatment with a drying agent, filtering and evaporation of the solvent. Purification of compound 7 is accomplished by recrystallization, flash chromatography, or preparative HPLC.

Compound 7 is converted into compound 8 by treatment with excess hydrazine in ethanol or a higher boiling alcohol, and refluxing the mixture. Compound 8 is isolated by evaporating the excess hydrazine and alcohol solvent. Purification of compound 8 is accomplished by recrystallization, flash chromatography, or preparative HPLC.

Compound 8 is converted into compound 9 by heating in the presence of phosphorus oxychloride, which can be used as the solvent. Excess phosphorus oxychloride is removed by evaporation, and then compound 9 is isolated by dissolution in ethyl acetate and then washing with a mildly alkaline aqueous solution. Compound 9 is purified using methods known in the art, or it is used in the following reaction without purification.

Compound 9 is converted into compound 10 by stirring in the presence of catalytic Pd/C and excess ammonium formate while dissolved in methanol. Following complete conversion of compound 9, compound 10 is isolated by removal of the Pd/C catalyst by filtration, and removal of the excess ammonium formate and methanol solvent by evaporation. Purification of compound 11 is accomplished by recrystallization, flash chromatography, or preparative HPLC.

Certain compounds of this invention are prepared from other compounds of this invention via known reactions and functional group transformations. Examples of such transformations are ester hydrolysis, amide formation, and reductive alkylation; with examples of these are described in the preparations below. Starting materials are obtained from commercial sources or prepared by known methods as described in the examples below.

Compounds included in this invention are exemplified by the following examples, which should not be construed as limiting the scope of this disclosure. Analogous structures and alternative synthetic routes within the scope of the invention will be apparent to those skilled in the art.

Preparation of Some Intermediates:

Preparation 1

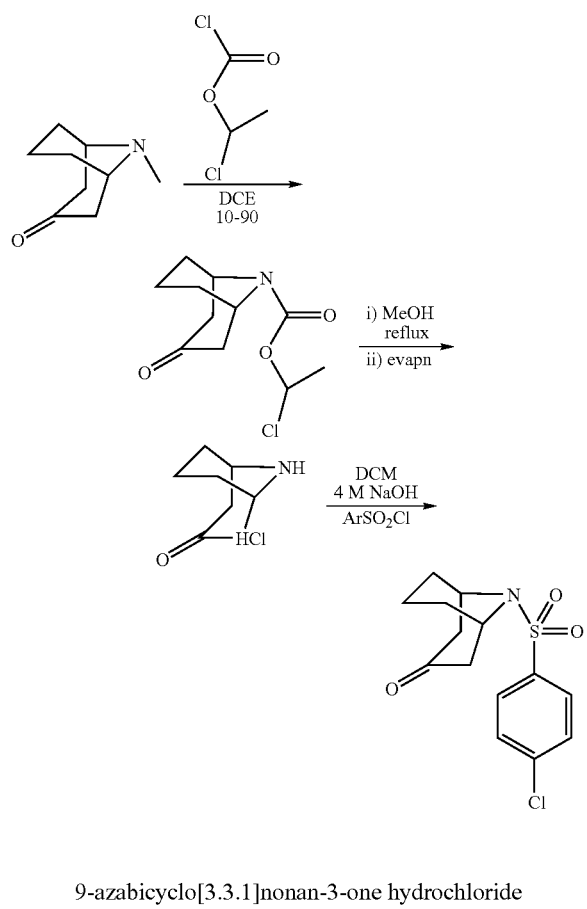

9-azabicyclo[3.3.1]nonan-3-one hydrochloride

The pseudo-pelletierine (3.35 g, 21.9 mmol) was dissolved in 1,2-dichloroethane (18 mL) and 1-chloroethyl chloroformate (4.7 g, 33 mmol) is added all at once with good stirring. After stirring 30 min at RT, the stirred mixture is heated in a 90° C. bath for 3 h and evaporated under a stream of nitrogen. The residue is taken up in dry MeOH (25 mL) and lowly heated to reflux for 2 h and evaporated under a stream of nitrogen. The solids are taken up in additional dry MeOH and heated in a 90° C. bath and evaporated again to yield 3.8 g the hydrochloride salt. MS (ES) m/e 140.0 (M+H)$^+$.

The amine hydrochloride (2.98 g, 16.9 mmol) was dissolved in dichloromethane (20 mL) and 4 M aq NaOH (11 mL). The 4-chlorobenzenesulfonyl chloride (5.07 g, 24 mmol) is added all at once to the reaction mixture with good stirring. After stirring at RT for 16 h, N,N-diethyl-ethylene-diamine (1.39 g, 12 mmol) is added and stirred for 1 h. The reaction mixture was diluted with dichloromethane and acidified to pH 4 using aq NaHSO$_4$. The aqueous phase was separated and extracted once with dichloromethane. The combined organic phases were washed with 5% NaHSO$_4$ (three times), water, brine, and then dried (Na$_2$SO$_4$) and evaporated to yield 5.03 g of the product upon evaporation. Further purification was optionally performed by applying the product in dichloromethane to a silica gel column and elution (0-10% EtOAc in dichloromethane) to yield the purified product upon evaporation. MS (ES) m/e 314.0 (M+H)$^+$.

The following compounds were prepared essentially according to the procedures described above.

9-(4-iodophenylsulfonyl)-9-azabicyclo[3.3.1]nonan-3-one: MS (ES) m/e 406.0 (M+H)$^+$.

8-(4-chlorophenylsulfonyl)-8-azabicyclo[3.2.1]octan-3-one: MS (ES) m/e 300.0 (M+H)$^+$.

8-(4-bromophenylsulfonyl)-8-azabicyclo[3.2.1]octan-3-one: MS (ES) m/e 344.0 (M+H)$^+$.

8-(4-iodophenylsulfonyl)-8-azabicyclo[3.2.1]octan-3-one: MS (ES) m/e 391.0 (M+H)$^+$.

tert-butyl 3-oxo-9-azabicyclo[3.3.1]nonane-9-carboxylate: MS (ES) m/e 262.0 (M+Na)$^+$.

Preparation 2

2-bromo-9-(4-chlorophenylsulfonyl)-9-azabicyclo[3.3.1]nonan-3-one and 2-amino-9-(4-chlorophenylsulfonyl)-9-azabicyclo[3.3.1]nonan-3-one

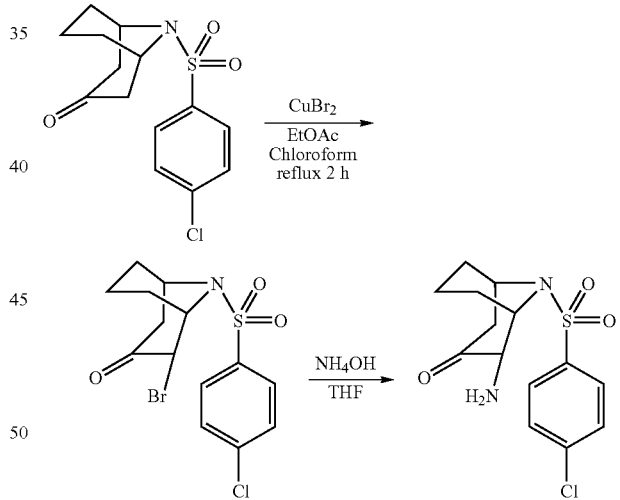

To a solution of the ketone (9-[(4-chlorophenyl)sulfonyl]-9-azabicyclo[3.3.1]nonan-3-one, 31 mg, 0.10 mmol) dissolved in ethyl acetate (0.8 mL) and chloroform (0.4 mL) was added cupric bromide (34.6 mg, 0.12 mmol). The reaction mixture was stirred in a 85° C. bath for 4 h, whereupon LC-MS showed nearly complete consumption of the ketone. After cooling to RT, the reaction mixture was diluted with dichloromethane, filtered, and washed with 10% NaHSO$_3$, water, brine, and then dried (Na$_2$SO$_4$) passed through silica gel and evaporated to yield the crude 2-bromo-9-(4-chlorophenylsulfonyl)-9-azabicyclo[3.3.1]nonan-3-one. MS (ES) m/e 392.0 (M+H)$^+$.

The bromo-ketone (25 mg) dissolved in THF (2 mL) was added ammonium hydroxide (2 mL), and the reaction mixture was capped stirred in an 85° C. bath for 4 h. After cooling to RT, the reaction mixture was evaporated, diluted with dichloromethane, and washed with water, brine, and then dried ($Na_2SO_4$) and evaporated to yield 2-amino-9-(4-chlorophenylsulfonyl)-9-azabicyclo[3.3.1]nonan-3-one. MS (ES) m/e 329.0 (M+H)+.

The following compound was prepared essentially according to the procedure described above.

tert-butyl 2-bromo-3-oxo-9-azabicyclo[3.3.1]nonane-9-carboxylate; MS (ES) m/e 392.0 (M+H)+.

Preparation 3

2-acetyl-9-(4-chlorophenylsulfonyl)-9-azabicyclo[3.3.1]nonan-3-one

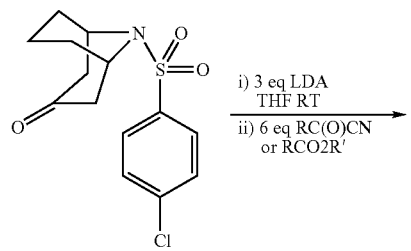

i) 3 eq LDA
   THF RT
ii) 6 eq RC(O)CN
    or RCO2R'

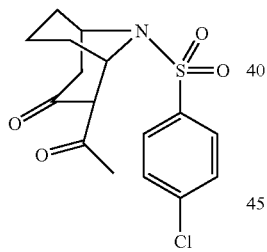

The ketone (9-[(4-chlorophenyl)sulfonyl]-9-azabicyclo[3.3.1]nonan-3-one, 94 mg, 0.30 mmol) under nitrogen was dissolved in THF (1.5 mL), and with good stirring at room temperature, lithium diisopropylamide (1.0 M in cyclohexane/THF, 1.0 mL, 1.0 mmol) was added all at once by syringe. After stirring for 15 min, pyruvonitrile (140 mg, 2.0 mmol) was added all at once to the reaction mixture and stirred vigorously for 30 min at RT and for 24 h in a 60° C. bath. The reaction mixture was partially evaporated under a stream of nitrogen while being warmed in a 70° C. bath. The black residue was dissolved with water and dichloromethane and acidified with aq $NaHSO_4$. The organic phase was separated and combined with one additional dichloromethane extraction of the aq phase. The organic phase was washed with 0.1 M NaOH (3×), and the basic washes were combined and acidified to pH 1-2 using aq $NaHSO_4$. The acidic phase was extracted with dichloromethane (3×), and the combined dichloromethane extracts were washed with brine (2×), and then dried ($Na_2SO_4$) and evaporated to yield the brown solid product. MS (ES) m/e 356.0 (M+H)+.

Example 1

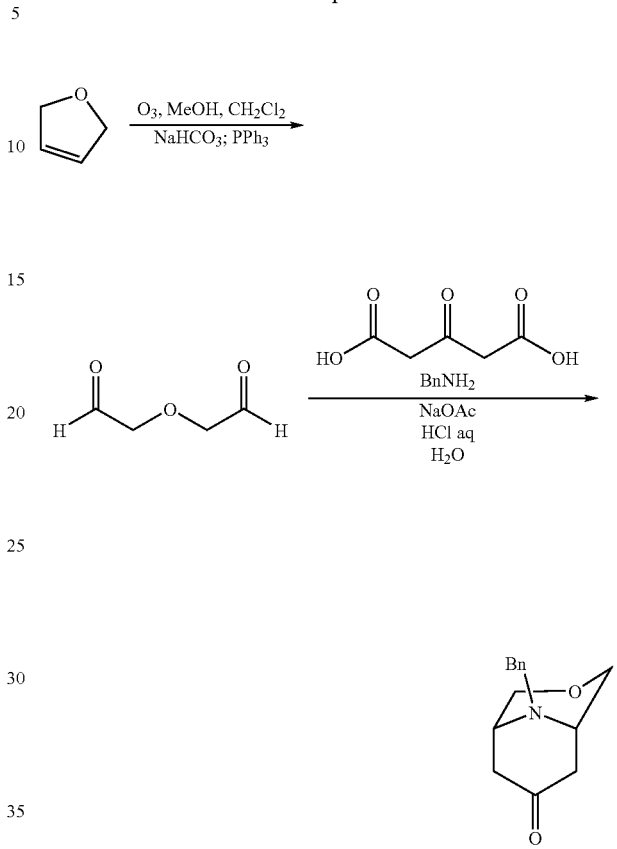

9-Benzyl-3-oxa-9-aza-bicyclo[3.3.1]nonan-7-one.

To a stirring mixture of 2,5-dihydrofuran (3.5 g, 49.9 mmol) in $CH_2Cl_2$/MeOH (10:1) at −78° C. was added $NaHCO_3$ (3.5 g). An excess of ozone was bubbled into this mixture for 45 min. The resulting mixture was then purged with a stream of $N_2$ for 10 min at −78° C. To this reaction mixture was added $PPh_3$ (6.6 g, 25 mmol). The reaction mixture was slowly warmed up to room temperature over 48 h. The reaction mixture was filtered to remove solid $NaHCO_3$ and then concentrated to half of its original volume under reduced pressure. To this crude mixture was added water (10 mL). Acetone-1,3-dicarboxylic acid (3.65 g, 25.0 mmol) and sodium acetate (2.2 g, 26.25 mmol) were added to the crude aldehyde in $H_2O$. Benzylamine (2.68 g, 25.0 mmol) was dissolved in aqueous HCl (3 N, 16 mL) and was subsequently added to the stirring solution of the dialdehyde and the dicarboxylic acid over a 15 min period. The reaction mixture was stirred for 3 days at room temperature after which the pH was adjusted to 8 by the addition of potassium carbonate. The resulting solution was extracted with EtOAc (4×50 mL), the organic extracts dried ($MgSO_4$), filtered, and concentrated under vacuum. The resulting residue was purified by silica gel chromatography to give 3.3 g of 9-benzyl-3-oxa-9-aza-bicyclo[3.3.1]nonan-7-one as a yellowish solid. Retention time (min)=0.352 and 0.243, Method [1], MS (ESI) 232.2 (M+H); $^1$H-NMR (300 MHz, $CDCl_3$) δ 7.49-7.27 (m, 5H), 3.91 (s, 2H), 3.84 (d, J=10.44 Hz, 2H), 3.71 (d, J=10.44 Hz, 2H), 3.15 (d, J=5.5 Hz, 2H), 2.74 (dd, J=15.94, 6.05 Hz, 2H), 2.32 (d, J=15.4 Hz, 2H).

Example 2

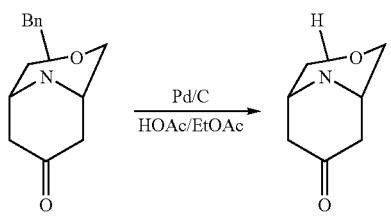

3-Oxa-9-aza-bicyclo[3.3.1]nonan-7-one.

To a stirring mixture of 9-benzyl-3-oxa-9-aza-bicyclo [3.3.1]nonan-7-one (1.1 g, 4.76 mmol) in EtOAc/HOAc (6 mL, 1:1, v/v) was added palladium on carbon (250 mg). The resulting mixture was stirred at room temperature under an atmosphere of hydrogen for 2 days. The suspension was filtered through Celite and the filtrate was concentrated under vacuum to give a quantitative yield of 3-oxa-9-aza-bicyclo [3.3.1]nonan-7-one as a yellow oil. This crude mixture was converted to the corresponding hydrochloric salt by the addition of HCl (3 mL, 1N aqueous HCl). The mixture was concentrated under reduced pressure and this process was repeated twice. Retention time (min)=0.231, Method [1], MS (ESI) 142.2 (M+H).

Example 3

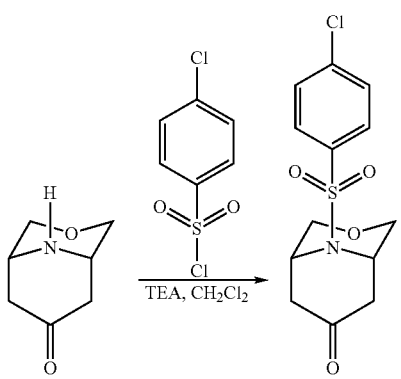

9-(4-Chloro-benzenesulfonyl)-3-oxa-9-aza-bicyclo [3.3.1]nonan-7-one.

To a stirring mixture of 3-oxa-9-aza-bicyclo[3.3.1]nonan-7-one (408 mg, 2.3 mmol) in dichloromethane (8 mL) was added Et₃N (1.2 mL, 9.2 mmol) and 4-chlorobenzenesulfonyl chloride (582 mg, 2.76 mmol). The reaction mixture was stirred at room temperature for 2 h. The reaction mixture was diluted with dichloromethane (50 mL) and washed with a saturated aqueous NaHCO₃ solution (15 mL). The aqueous phase was separated and extracted twice with EtOAc (2×25 mL). The combined organic phases were then dried (Na₂SO₄), filtered, concentrated under vacuum, and the residue was purified on a silica gel column (eluant hexane/ EtOAc, 50/50 to 100) to give 510 mg (70%) of 9-(4-chloro-benzenesulfonyl)-3-oxa-9-aza-bicyclo[3.3.1]nonan-7-one as a white solid; Retention time (min)=1.687 min, Method [1], MS (ESI) 316.1 (M+H); $^1$H-NMR (300 MHz, CDCl₃) δ 7.84-7.81 (m, 2H), 7.56-7.51 (m, 2H), 4.28-4.27 (m, 2H), 3.76 (d, J=12.1 Hz, 2H), 3.61 (d, J=11.5 Hz, 2H), 2.65 (dd, J=15.93, 5.49 Hz, 2H), 2.46 (d, J=15.93 Hz, 2H); $^{13}$C-NMR (75 MHz, CDCl₃) δ 204.3, 140.1, 139.1, 130.1, 128.7, 71.7, 51.7, 44.4 ppm.

Example 4

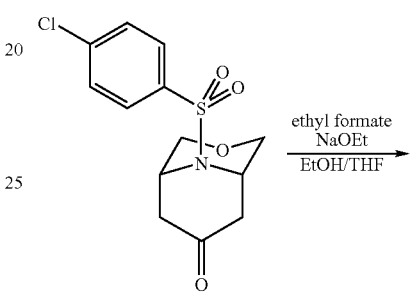

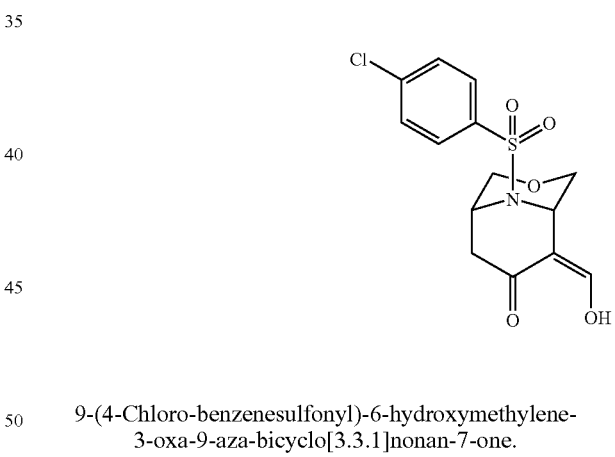

9-(4-Chloro-benzenesulfonyl)-6-hydroxymethylene-3-oxa-9-aza-bicyclo[3.3.1]nonan-7-one.

To a stirring mixture of 9-(4-chloro-benzenesulfonyl)-3-oxa-9-aza-bicyclo[3.3.1]nonan-7-one (170 mg, 0.54 mmol) in THF/ethanol (3 mL, 1/1, v/v) was added ethyl formate (400 mg, 5.4 mmol) followed by sodium ethoxide (0.61 mL of 21% solution in ethanol). The resulting mixture was heated to 60° C. for 30 minutes after which the solution was cooled to room temperature and quenched by the addition of a saturated aqueous NH₄Cl solution (10 mL). The resulting mixture was extracted with EtOAc (2×20 mL) and the combined organic phases were dried (Na₂SO₄), filtered and concentrated under vacuum to yield 9-(4-chloro-benzenesulfonyl)-2-hydroxymethylene-9-aza-bicyclo[3.3.1]nonan-3-one as a yellow solid. This crude product was directly taken to the next reaction without any further purification. Retention time (min)=1.651 min, Method [1], MS (ESI) 344.0 (M+H).

Example 5

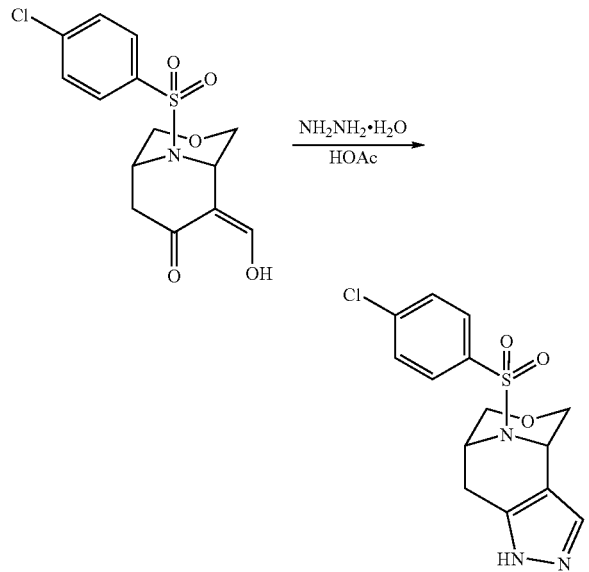

12-(4-Chloro-benzenesulfonyl)-10-oxa-4,5,12-triaza-tricyclo[6.3.1.0²,⁶]dodeca-2(6),3-diene To a solution of 9-(4-chloro-benzenesulfonyl)-2-hydroxymethylene-3-oxa-9-aza-bicyclo[3.3.1]nonan-3-one in glacial acetic acid (0.2 mL) followed by hydrazine monohydrate (0.5 mL). The reaction mixture was stirred at 100° C. for 1 h after which the solution was cooled to room temperature and quenched by the addition of a saturated aqueous NaHCO₃ solution (until pH>7). The resulting solution was extracted with EtOAc (3×20 mL), the organic extracts were combined, dried (Na₂SO₄), filtered, concentrated and purified by silica gel column chromatography (Elution with 50% EtOAc/hex, 80% EtOAc/hex, 100% EtOAc, and 5% MeOH/EtOAc) and preparative HPLC to give 12-(4-chloro-benzenesulfonyl)-10-oxa-4,5,12-triaza-tricyclo[6.3.1.0²,⁶]dodeca-2(6),3-diene as a white solid. Retention time (min)=1.299 min, Method 1, MS (ESI) 340.0 (M+H); ¹H-NMR (300 MHz, CDCl₃) δ 7.65-7.63 (m, 2H), 7.53 (s, 1H), 7.39-7.30 (m, 2H), 5.1 (s, 1H), 4.26 (d, J=7.14 Hz, 1H), 3.90 (ddd, J=5.0, 2.2, 2.2 Hz, 4H), 3.67 (dd, J=11.0, 1.65 Hz, 1H), 3.01 (dd, J=17.58, 7.14 Hz, 1H), 2.82 (d, J=17.58 Hz, 1H); ¹³C-NMR (75 MHz, CDCl₃) δ 143.3, 140.3, 137.8, 129.7, 128.8, 126.9, 116.2, 77.4, 73.4, 48.3, 48.2, 24.5 ppm.

Example 6

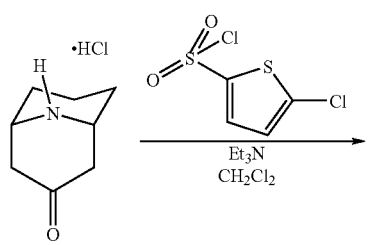

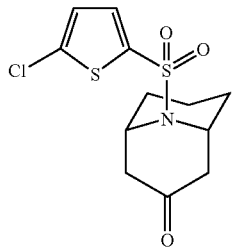

9-(5-Chloro-thiophene-2-sulfonyl)-9-aza-bicyclo[3.3.1]nonan-3-one.

To a stirring mixture of 9-aza-bicyclo[3.3.1]nonan-3-one. HCl (440 mg, 2.5 mmol) in dichloromethane (10 mL) was added Et₃N (1.4 mL, 10 mmol) and 5-chlorothiophene-2-sulfonyl chloride (700 mg, 3.22 mmol). The reaction mixture was stirred at room temperature for 2 h. The reaction mixture was diluted with dichloromethane (50 mL) and washed with a saturated aqueous NaHCO₃ solution (15 mL). The aqueous phase was separated and extracted twice with EtOAc (2×25 mL). The combined organic phases were then dried (Na₂SO₄), filtered, concentrated under vacuum and the residue was purified on a silica gel column (eluant hexane/EtOAc, 50/50 to 100) to give 9-(5-chloro-thiophene-2-sulfonyl)-9-aza-bicyclo[3.3.1]nonan-3-one as a white solid. Retention time (min)=2.048 min, Method [1], MS (ESI) 320.0 (M+H).

Example 7

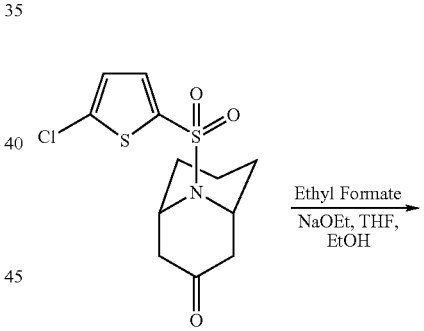

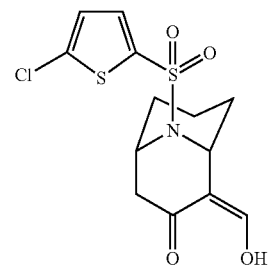

9-(5-Chloro-thiophene-2-sulfonyl)-2-hydroxymethylene-9-aza bicyclo[3.3.1]nonan-3-one.

To a stirring mixture of 9-(5-chloro-thiophene-2-sulfonyl)-9-aza-bicyclo[3.3.1]nonan-3-one (160 mg, 0.50 mmol) in THF/ethanol (3 mL, 1/1, v/v) was added ethyl formate (500 mg, 6.76 mmol) followed by sodium ethoxide (0.56 mL of 21% solution in ethanol). The resulting mixture was heated to 60° C. for 30 minutes after which the solution was cooled to room temperature and quenched by the addition of a saturated aqueous NH₄Cl solution (10 mL). The resulting mixture was extracted with EtOAc (2×20 mL) and the combined organic phases were dried (Na₂SO₄), filtered and concentrated under vacuum to yield 9-(5-chloro-thiophene-2-sulfonyl)-2-hydroxymethylene-9-aza-bicyclo[3.3.1]nonan-3-one as a white solid. This crude product was directly taken to the next reaction without any further purification. Retention time (min)= 1.985 min, Method [1], MS (ESI) 348.0 (M+H).

Example 8

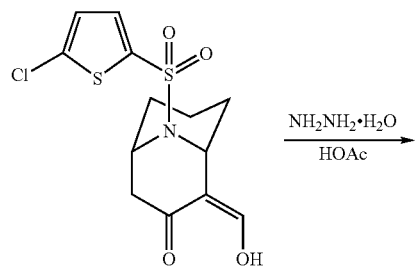

12-(5-Chloro-thiophene-2-sulfonyl)-4,5,12-triaza-tricyclo[6.3.1.0²,⁶]dodeca-2(6),3-diene To a solution of 9-(5-chloro-thiophene-2-sulfonyl)-2-hydroxymethylene-9-aza-bicyclo[3.3.1]nonan-3-one crude mixture in glacial acetic acid (3 mL) followed by hydrazine monohydrate (1 mL). The reaction mixture was stirred at 100° C. for 1 h after which the solution was cooled to room temperature and quenched by the addition of saturated NaHCO₃ solution (until pH>7). The resulting solution was extracted with EtOAc (3×20 mL), the organic extracts were combined, dried (Na₂SO₄), filtered, concentrated and purified by silica gel column chromatography (Elution with 50% EtOAc/hex, 80% EtOAc/hex, 100% EtOAc, and 5% MeOH/EtOAc) and preparative HPLC to give 12-(5-chloro-thiophene-2-sulfonyl)-4,5,12-triaza-tricyclo[6.3.1.0²,⁶]dodeca-2(6),3-diene as a white solid. Retention time (min)= 1.649 min, Method 1, MS (ESI) 344.0 (M+H); ¹H-NMR (300 MHz, CDCl₃) δ 7.47 (s, 1H), 7.25 (s, 1H), 7.22 (d, J=4.4 Hz, 1H), 5.28 (b s, 1H), 4.56 (t, J=6.04 Hz, 1H), 3.11 (dd, J=17.58, 7.69 Hz, 1H), 2.66 (d, J=17.58 Hz, 1H), 2.09-1.92 (m, 2H), 1.74-1.57 (m, 3H), 1.44-1.29 (m, 1H); ¹³C-NMR (75 MHz, CDCl₃) δ 143.4, 139.2, 137.7, 131.8, 127.4, 127.0, 117.0, 48.0, 47.9, 32.3, 31.7, 25.4, 15.3 ppm.

Example 9

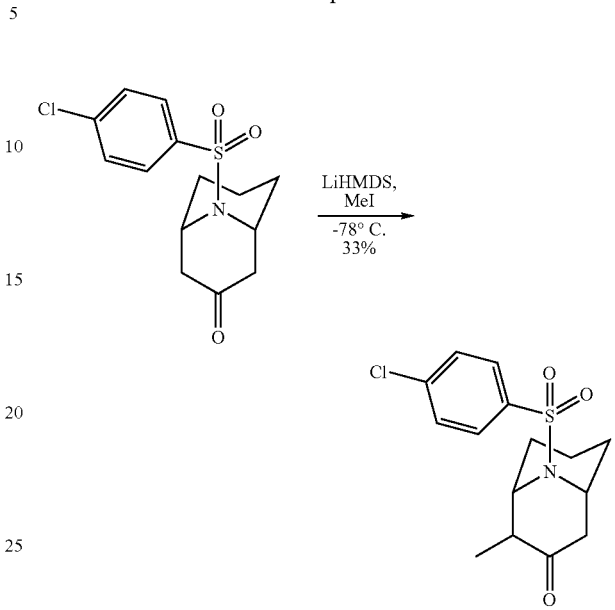

9-(4-Chloro-benzenesulfonyl)-2-methyl-9-aza-bicyclo[3.3.1]nonan-3-one.

To a stirring mixture of 9-(4-chloro-benzenesulfonyl)-9-aza-bicyclo[3.3.1]nonan-3-one (550 mg, 1.75 mmol) in THF (2 mL) at −78° C. was added LiHMDS in THF (2.62 mL, 1.0 M in THF, 2.62 mmol) dropwise over 15 min. The resulting mixture was allowed to stir at −78° C. for 30 min before the addition of MeI (1.24 g, 8.75 mmol). The reaction mixture was stirred at −78° C. for 2.5 h before it was allowed to warm up to room temperature for 15 min. The reaction mixture was quenched by the addition of a saturated aqueous NH₄Cl solution (25 mL) and EtOAc (25 mL). The layers were separated and the aqueous layer was extracted with EtOAc (2×25 mL). The combined organic layers were washed with brine, dried over MgSO₄, filtered, and concentrated under reduced pressure. The crude mixture was purified via silica gel chromatography to give 9-(4-chloro-benzenesulfonyl)-2-methyl-9-aza-bicyclo[3.3.1]nonan-3-one as a white solid. Retention time (min) 2.13 min, Method [1], MS (ESI) 350 (M+Na).

Example 10

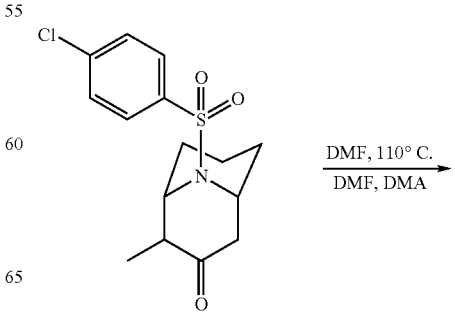

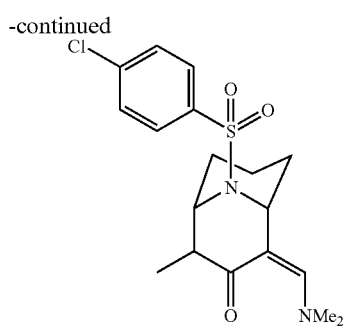

9-(4-Chloro-benzenesulfonyl)-2-dimethylaminomethylene-4-methyl-9-aza-bicyclo[3.3.1]nonan-3-one.

To a stirring mixture of 9-(4-chloro-benzenesulfonyl)-2-methyl-9-aza-bicyclo[3.3.1]nonan-3-one (500 mg, 1.52 mmol) in DMF (1 mL) was added N,N-dimethylformamide dimethyl acetal (1 mL). The resulting mixture was heated to 110° C. for 2 h after which the reaction mixture was concentrated under reduced pressure to give the desired product as a brown oil. This crude product was directly taken to the next reaction without any further purification. Retention time (min)=2.2 min, Method [1], MS (ESI) 356 (M−NMe$_2$+OH+H).

Example 11

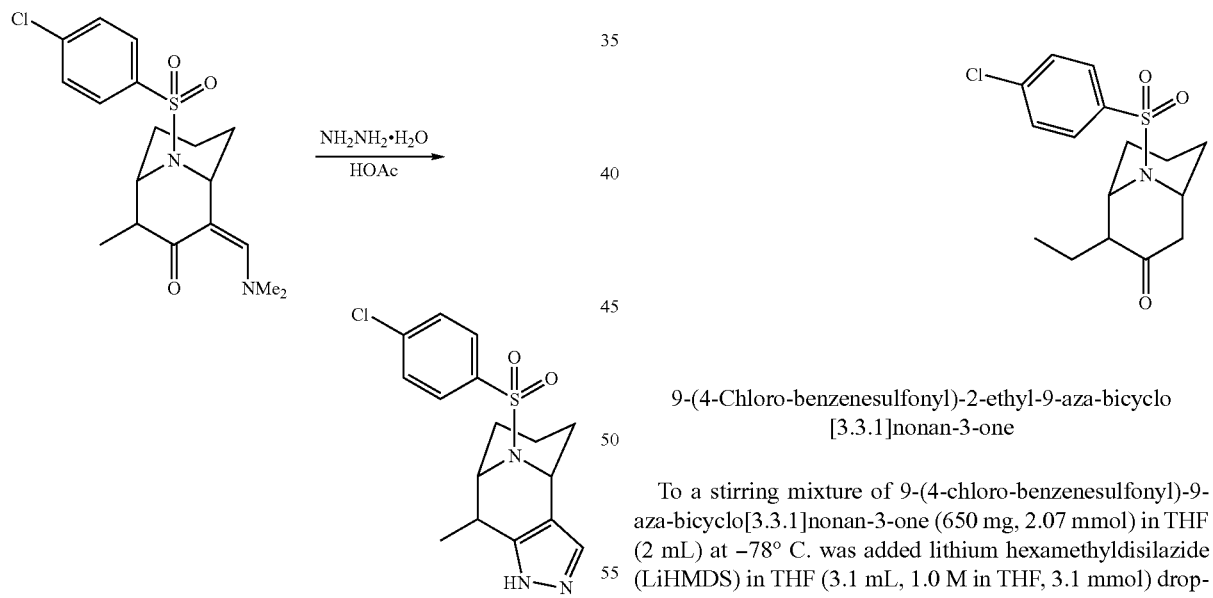

12-(4-Chloro-benzenesulfonyl)-7-methyl-4,5,12-triaza-tricyclo[6.3.1.0$^{2,6}$]dodeca-2(6),3-diene To a solution of 9-(4-chloro-benzenesulfonyl)-2-dimethylaminomethylene-4-methyl-9-aza-bicyclo[3.3.1]nonan-3-one crude mixture in glacial acetic acid (1 mL) followed by hydrazine monohydrate (0.5 mL). The reaction mixture was stirred at 100° C. for 1 h after which the solution was cooled to room temperature and quenched by the addition of a saturated aqueous NaHCO$_3$ solution (until pH>7). The resulting solution was extracted with EtOAc (3×20 mL), the organic extracts were combined, dried (Na$_2$SO$_4$), filtered, concentrated and purified by silica gel column chromatography and preparative HPLC to give 12-(4-chloro-benzenesulfonyl)-7-methyl-4,5,12-triaza-tricyclo[6.3.1.0$^{2-6}$]dodeca-2(6),3-diene as a white solid. Retention time (min)=1.72, Method [1], MS (ESI) 352.0 (M+H); $^1$H-NMR (300 MHz, CDCl$_3$) δ 7.81-7.78 (m, 2H), 7.47-7.43 (m, 2H), 7.27 (s, 1H), 5.2 (b s, 1H), 4.09 (d, J=4.94 Hz, 1H), 2.89 (q, J=7.14 Hz, 1H), 1.82-1.60 (m, 3H), 1.42-1.34 (m, 3H), 1.19 (d, J=7.14 Hz, 3H); $^{13}$C-NMR (75 MHz, CDCl$_3$) δ 149.9, 140.7, 139.0, 129.6, 128.7, 126.4, 115.6, 55.83, 48.6, 34.1, 31.1, 30.9, 21.8, 15.6 ppm.

Example 12

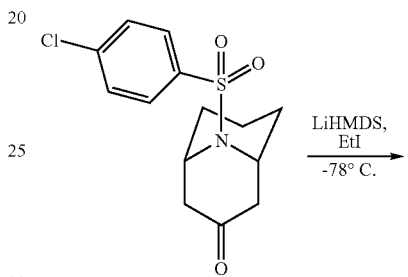

9-(4-Chloro-benzenesulfonyl)-2-ethyl-9-aza-bicyclo[3.3.1]nonan-3-one

To a stirring mixture of 9-(4-chloro-benzenesulfonyl)-9-aza-bicyclo[3.3.1]nonan-3-one (650 mg, 2.07 mmol) in THF (2 mL) at −78° C. was added lithium hexamethyldisilazide (LiHMDS) in THF (3.1 mL, 1.0 M in THF, 3.1 mmol) dropwise over 15 min. The resulting mixture was allowed to stir at −78° C. for 30 min before the addition of EtI (650 mg, 8.75 mmol). The reaction mixture was stirred at −78° C. for 2.5 h before it was allowed to warm up to room temperature for 15 min. The reaction mixture was quenched with a saturated aqueous NH$_4$Cl solution and EtOAc (25 mL, 1:1, v/v). The layers were separated and the aqueous layer was extracted with EtOAc (2×25 mL). The combined organic layers were washed with brine, dried over MgSO$_4$, filtered, and concentrated under reduced pressure. The crude mixture was purified via silica gel chromatography to give 9-(4-chloro-benzenesulfonyl)-2-ethyl-9-aza-bicyclo[3.3.1]nonan-3-one as a white solid. Retention time (min)=2.295, Method [1], MS (ESI) 342 (M+H).

Example 13

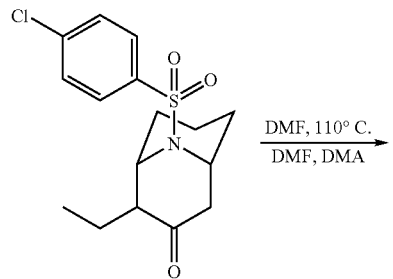

9-(4-Chloro-benzenesulfonyl)-2-dimethylaminomethylene-4-ethyl-9-aza-bicyclo[3.3.1]nonan-3-one.

To a stirring mixture of 9-(4-chloro-benzenesulfonyl)-2-ethyl-9-aza-bicyclo[3.3.1]nonan-3-one (180 mg, 0.52 mmol) in DMF (1 mL) was added N,N-dimethylformamide dimethyl acetal (1 mL). The resulting mixture was heated to 110° C. for 2 h after which the reaction mixture was concentrated under reduced pressure to give the desired product as a brown oil. This crude product was directly taken to the next reaction without any further purification. Retention time (min)=2.365 min, Method [1], MS (ESI) 370 (M-NMe$_2$+OH+H).

Example 14

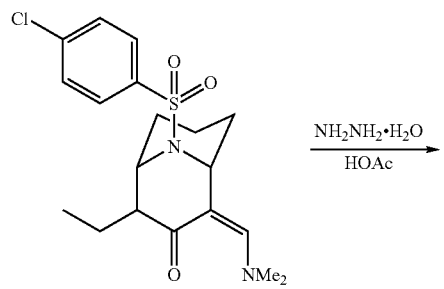

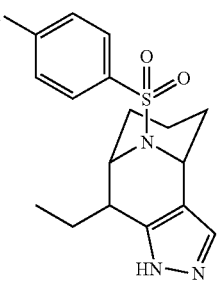

12-(4-Chloro-benzenesulfonyl)-7-ethyl-4,5,12-triaza-tricyclo[6.3.1.0$^{2,6}$]dodeca-(6),3-diene To a solution of 9-(4-chloro-benzenesulfonyl)-2-dimethylaminomethylene-4-ethyl-9-aza-bicyclo[3.3.1]nonan-3-one crude mixture in glacial acetic acid (1 mL) followed by hydrazine monohydrate (0.5 mL). The reaction mixture was stirred at 100° C. for 1 h after which the solution was cooled to room temperature and quenched by the addition of a saturated aqueous NaHCO$_3$ solution (until pH>7). The resulting solution was extracted with EtOAc (3×20 mL), the organic extracts were combined, dried (Na$_2$SO$_4$), filtered, concentrated and purified by silica gel column chromatography and preparative HPLC to give 12-(4-chloro-benzenesulfonyl)-7-ethyl-4,5,12-triaza-tricyclo[6.3.1.0$^{2,6}$]dodeca-2(6),3-diene as a white solid. Retention time (min)=1.896, Method [1], MS (ESI) 366.1 (M+H); $^1$H-NMR (300 MHz, CDCl$_3$) δ 7.81-7.78 (m, 2H), 7.47-7.43 (m, 2H), 7.25 (s, 1H), 5.15 (b s, 1H), 4.27 (d, J=4.95 Hz, 1H), 2.56 (dd, J=9.34, 5.49 Hz, 1H), 2.10-1.22 (m, 8H), 1.02 (t, J=7.14 Hz, 3H) (major diastereomer); $^1$H-NMR (300 MHz, CDCl$_3$) δ 7.68-7.66 (m, 2H), 7.35-7.32 (m, 2H), 7.22 (s, 1H), 5.28 (b s, 1H), 4.31 (d, J=5.5 Hz, 1H), 2.80-2.73 (m, 1H), 2.05-1.21 (m, 8H), 1.06 (t, J=7.69 Hz, 3H) (minor diastereomer).

Example 15

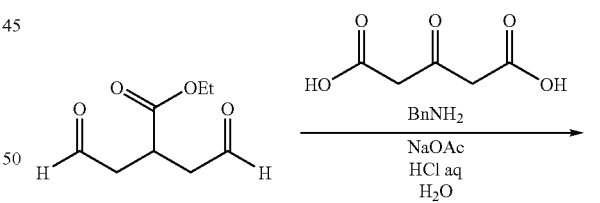

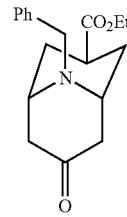

9-Benzyl-7-oxo-9-aza-bicyclo[3.3.1]nonane-3-carboxylic acid ethyl ester.

Acetone-1,3-dicarboxylic acid (8.81 g, 60.36 mmol) and sodium acetate (5.04 g, 61.5 mmol) were added to a solution of 4-oxo-2-(2-oxo-ethyl)-butyric acid ethyl ester (European Patent EP 0330788A1) (10.3 g, 60.36 mmol) in H$_2$O (75 mL). Benzylamine (6.59 mL, 60.36 mmol) was dissolved in aqueous HCl (3 N, 41 mL) and was subsequently added to the stirring solution of the dialdehyde and the dicarboxylic acid over a 15 minute period. The reaction mixture was stirred for 3 days at room temperature after which the pH was adjusted to 8 by the addition of potassium carbonate. The resulting solution was extracted with methylene chloride (4×50 mL), the organic extracts dried (Na$_2$SO$_4$), filtered and concentrated under vacuum. The resulting residue was purified by silica gel chromatography, (eluant hexane/EtOAc 9/1 to 1/1, v/v) to give 7.43 g (40%) of 9-benzyl-7-oxo-9-aza-bicyclo[3.3.1]nonane-3-carboxylic acid ethyl ester as a brown oil. Retention time (min)=0.963, method [1], MS (ESI) 302.2 (M+H); $^1$H NMR (300 MHz, CDCl$_3$) δ 7.43-7.10 (m, 5H), 4.10 (q, J=7.1 Hz, 2H), 3.91 (s, 2H), 3.41-3.38 (m, 2H), 2.74 (dd, J=16.5, 6.6 Hz, 2H), 2.61-2.48 (m, 1H), 2.30 (d, J=16.5 Hz, 2H), 2.08 (dt, J=3.8 Hz, J=13.2 Hz, 2H), 1.81-1.72 (m, 2H), 1.22 (t, J=7.1 Hz, 3H).

Example 16

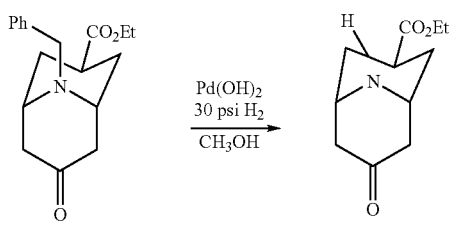

7-Oxo-9-aza-bicyclo[3.3.1]nonane-3-carboxylic acid ethyl ester.

9-Benzyl-7-oxo-9-aza-bicyclo[3.3.1]nonane-3-carboxylic acid ethyl ester (11.1 g, 36.8 mmol) was dissolved in methanol (30 mL) and added to a suspension of palladium hydroxide (1 g) in methanol (10 mL) in a Parr bottle. The Parr bottle was filled with hydrogen (30 psi) and evacuated three times. The Parr bottle was refilled with hydrogen (30 psi) and shook for 12 h. The suspension was filtered through Celite and concentrated under vacuum to give 7.81 g (quantitative yield) of 7-oxo-9-aza-bicyclo[3.3.1]nonane-3-carboxylic acid ethyl ester as a yellow oil. Retention time (min)=0.369, method [1], MS (ESI) 212.1 (M+H).

Example 17

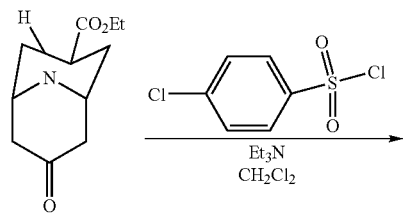

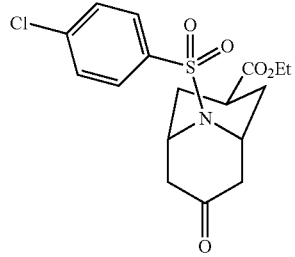

9-(4-Chloro-benzenesulfonyl)-7-oxo-9-aza-bicyclo[3.3.1]nonane-3-carboxylic acid ethyl ester 7-Oxo-9-aza-bicyclo[3.3.1]nonane-3-carboxylic acid ethyl ester (5.91 g, 27.9 mmol) was dissolved in methylene chloride (60 mL). Et$_3$N (7.76 mL, 55.9 mmol) and 4-chlorobenzenesulfonyl chloride (7.08 g, 33.6 mmol) were added and the reaction mixture was stirred at room temperature for 2 h. The reaction mixture was diluted with methylene chloride (50 mL) and washed with saturated NaHCO$_3$ (50 mL). The aqueous phase was separated and extracted once with methylene chloride (50 mL). The combined organic phases were then dried (Na$_2$SO$_4$), filtered, concentrated under vacuum and the residue was purified on a silica gel column (eluant hexane/EtOAc, 9/1 to 1/1) to give 9.52 g (88%) of 9-(4-chloro-benzenesulfonyl)-7-oxo-9-aza-bicyclo[3.3.1]nonane-3-carboxylic acid ethyl ester. Retention time (min)= 2.100, method [1], MS (ESI) 408.1 (M+Na); $^1$H NMR (300 MHz, CDCl$_3$) δ 7.81 (d, J=8.2 Hz, 2H), 7.51 (d, J=8.2 Hz, 2H), 4.61-4.57 (m, 2H), 4.09 (q, J=7.1 Hz, 2H), 2.80 (dd, J=17.0, 7.1 Hz, 2H), 2.67-2.51 (m, 1H), 2.41 (d, J=16.4 Hz, 2H), 1.99-1.90 (m, 2H), 1.80 (dt, J=13.2, 4.4 Hz, 2H), 1.20 (t, J=7.1 Hz, 3H).

Example 18

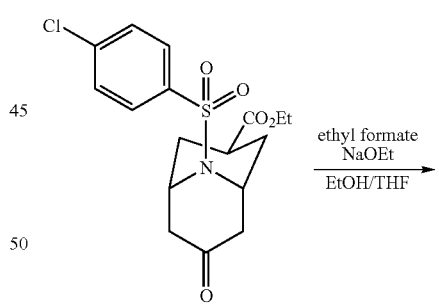

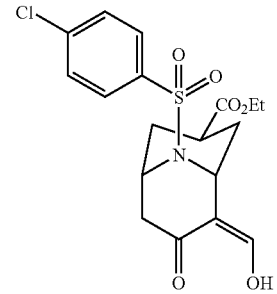

9-(4-Chloro-benzenesulfonyl)-6-hydroxymethylene-7-oxo-9-aza-bicyclo[3.3.1]nonane-3-carboxylic acid ethyl ester.

9-(4-Chloro-benzenesulfonyl)-7-oxo-9-aza-bicyclo[3.3.1]nonane-3-carboxylic acid ethyl ester (2.49 g, 6.45 mmol) was dissolved in THF/ethanol (14 mL, 1/1, v/v). Ethyl formate (5.19 mL, 64.53 mmol) was added followed by sodium ethoxide (6.2 mL of 21% solution in ethanol). The resulting mixture was heated to 60° C. for 30 minutes after which the solution was cooled to room temperature and quenched by the addition of saturated aqueous NH$_4$Cl (10 mL). The resulting mixture was extracted with EtOAc (2×20 mL) and the combined organic phases were dried (Na$_2$SO$_4$), filtered and concentrated under vacuum to yield 2.51 g (94%) of 9-(4-chloro-benzenesulfonyl)-6-hydroxymethylene-7-oxo-9-aza-bicyclo[3.3.1]nonane-3-carboxylic acid ethyl ester as a yellow oil. Retention time (min)=2.017, method [1], MS (ESI) 414.0 (M+H).

Example 19

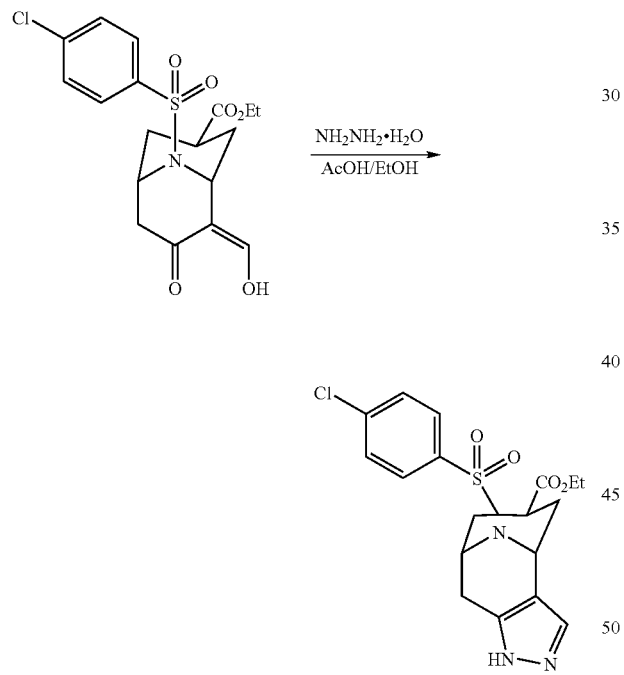

12-(4-Chloro-benzenesulfonyl)-4,5,12-triaza-tricyclo[6.3.1.0$^{2,6}$]dodeca-2(6),3-diene-10-carboxylic acid ethyl ester To a solution of 9-(4-chloro-benzenesulfonyl)-6-hydroxymethylene-7-oxo-9-aza-bicyclo[3.3.1]nonane-3-carboxylic acid ethyl ester (2.48 g, 5.99 mmol) in ethanol (10 mL) was added glacial acetic acid (0.2 mL) followed by hydrazine monohydrate (2.9 mL, 59.9 mmol). The reaction mixture was stirred at room temperature for 1 h after which saturated NaHCO$_3$ (10 mL) was added. The resulting solution was extracted with EtOAc (3×20 mL), the organic extracts were combined, dried (Na$_2$SO$_4$), filtered, concentrated and purified by silica gel column chromatography (eluant hexane/EtOAc, 9/1 to 1/1) and preparative HPLC to give 12-(4-chloro-benzenesulfonyl)-4,5,12-triaza-tricyclo[6.3.1.0$^{2,6}$]dodeca-2(6),3-diene-10-carboxylic acid ethyl ester as a white solid. Retention time (min)=1.739, method [1], MS (ESI) 410.1 (M+H); $^1$H NMR (300 MHz, CDCl$_3$) δ 7.66 (d, J=8.2 Hz, 2H), 7.51 (s, 1H), 7.38 (d, J=8.2 Hz, 2H), 5.37 (bs, 1H), 4.61-4.55 (m, 1H), 4.09 (q, J=7.1 Hz, 2H), 3.04 (dd, J=17.6, 7.1 Hz, 1H), 2.67 (d, J=17.6 Hz, 1H), 2.48-2.31 (m, 1H), 2.11-1.91 (m, 4H), 1.20 (t, J=7.1 Hz, 3H).

Example 20

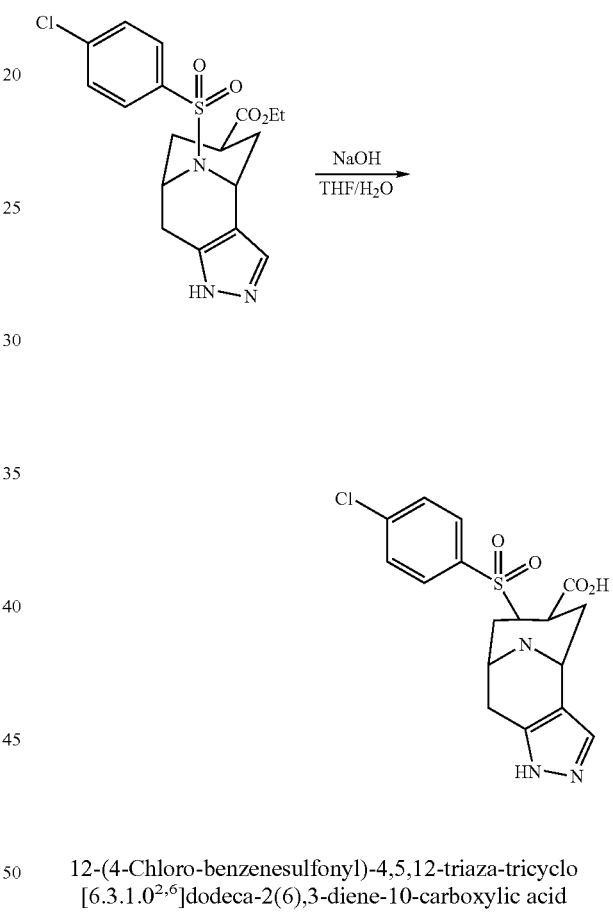

12-(4-Chloro-benzenesulfonyl)-4,5,12-triaza-tricyclo[6.3.1.0$^{2,6}$]dodeca-2(6),3-diene-10-carboxylic acid Sodium hydroxide (0.5 mL, 3 N solution) was added to a solution 12-(4-chloro-benzenesulfonyl)-4,5,12-triaza-tricyclo[6.3.1.0$^{2,6}$]dodeca-2(6),3-diene-10-carboxylic acid ethyl ester (321 mg, 0.783 mmol) in THF (2 mL). The resulting mixture was stirred at room temperature for 4 h. The reaction mixture was extracted with EtOAc (2×5 mL) and the combined organic phases were dried (Na$_2$SO$_4$), filtered, concentrated and purified by preparative HPLC to give 12-(4-chloro-benzenesulfonyl)-4,5,12-triaza-tricyclo[6.3.1.0$^{2,6}$]dodeca-2(6),3-diene-10-carboxylic acid as a white solid. Retention time (min)=1.316, method [1], MS (ESI) 382.0 (M+H); $^1$H NMR (300 MHz, CDCl$_3$) δ 7.56 (d, J=8.7 Hz, 2H), 7.30-7.22

(m, 3H), 5.30-5.25 (m, 1H), 4.54-4.45 (m, 1H), 2.80 (dd, J=17.0, J=7.7 Hz, 1H), 2.50 (d, J=17.0 Hz, 1H), 2.42-2.30 (m, 1H), 2.24-1.85 (m, 4H).

Example 21

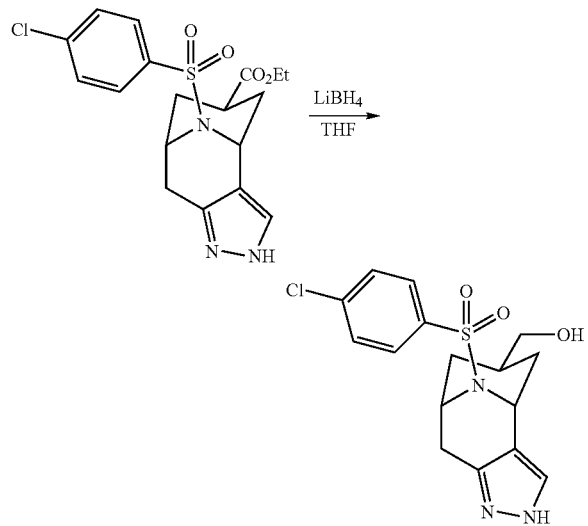

[12-(4-Chloro-benzenesulfonyl)-4,5,12-triaza-tricyclo[6.3.1.0²,⁶]dodeca-2,5-dien-10-yl]-methanol Lithium borohydride (17 mg, 0.80 mmol) was added to a solution of 12-(4-chloro-benzenesulfonyl)-4,5,12-triaza-tricyclo[6.3.1.0²,⁶]dodeca-2(6),3-diene-10-carboxylic acid ethyl ester (328 mg, 0.80 mmol) in THF (3 mL). The resulting solution was stirred at room temperature for 18 h then heated to 60° C. for 2 h. The reaction was quenched by the addition of water (5 mL) and the resulting mixture was extracted with EtOAc (3×5 mL). The combined organic phases were dried (Na₂SO₄), filtered, concentrated and purified by silica gel column chromatography (eluant hexane/EtOAc, 9/1 to 1/1) and preparative HPLC to give [12-(4-chloro-benzenesulfonyl)-4,5,12-triaza-tricyclo[6.3.1.0²,⁶]dodeca-2,5-dien-10-yl]-methanol as a white solid. Retention time (min)=1.242, method [1], MS (ESI) 368.0 (M+H); ¹H NMR (300 MHz, CDCl₃) δ 7.73 (d, J=8.2 Hz, 2H), 7.58 (s, 1H), 7.38 (d, J=8.2 Hz, 2H), 5.33 (s, 1H), 4.48 (d, J=7.1 Hz, 1H), 3.41 (d, J=2.7 Hz, 2H), 3.08 (dd, J=17.6, 7.7 Hz, 1H), 2.62 (d, J=17.6 Hz, 1H), 1.81-1.54 (m, 5H).

Example 22

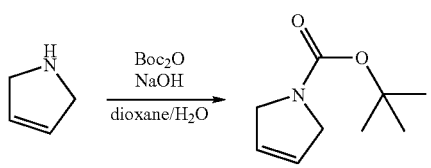

2,5-Dihydro-pyrrole-1-carboxylic acid tert-butyl ester 2,5-Dihydro-1H-pyrrole (8 g, 115.7 mmol) was dissolved in dioxane (150 mL). A solution of NaOH (6.9 g, 173.6 mmol) in H₂O (150 mL) was added followed by di-tert-butyl dicarbonate (37.8 g, 173.6 mmol). The reaction mixture was stirred at room temperature for 12 h and subsequently concentrated to approximately 30 mL under vacuum. The resulting solution was extracted with methylene chloride (3×50 mL) and the combined organic phases were dried (Na₂SO₄), filtered and concentrated under vacuum to afford 18.7 g (96%) of 2,5-dihydro-pyrrole-1-carboxylic acid tert-butyl ester as a yellow oil. Retention time (min)=1.872, method [1], MS (ESI) 114.1 (M-tBu+2H); ¹H NMR (300 MHz, CDCl₃) δ 5.81-5.69 (m, 2H), 4.19-4.05 (m, 4H), 1.45 (s, 9H).

Example 23

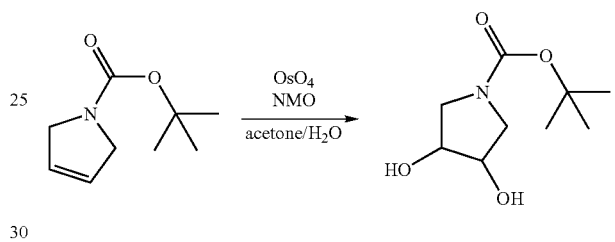

3,4-Dihydroxy-pyrrolidine-1-carboxylic acid tert-butyl ester

Osmium tetroxide (4.46 mL of a 4% aqueous solution) was added to a solution of N-Methylmorpholine-N-Oxide (NMO) in water (50 mL) and acetone (24 mL). The resulting solution was allowed to stir for 30 minutes after which a solution of 2,5-dihydro-pyrrole-1-carboxylic acid tert-butyl ester (19.8 g, 117.0 mmol) in acetone (24 mL) was added over 2 h. The reaction mixture was allowed to stir for 20 h after which sodium bisulfite (5 g) was added in one portion. The suspension was stirred for 15 minutes and subsequently filtered and concentrated under vacuum to remove the acetone. The aqueous solution was adjusted to pH 2 by the addition of sulfuric acid and was subsequently extracted with EtOAc (3×50 mL). The combined organic phases were dried (Na₂SO₄), filtered, and concentrated under vacuum to give 24.8 g (quantitative) of 3,4-dihydroxy-pyrrolidine-1-carboxylic acid tert-butyl ester as a yellow oil. Retention time (min)=0.792, method [1], MS (ESI) 226.1 (M+Na); ¹H NMR (300 MHz, CDCl₃) δ 4.21-4.15 (m, 2H), 3.61-3.55 (m, 2H), 3.41-3.34 (m, 2H), 1.42 (s, 9H).

Example 24

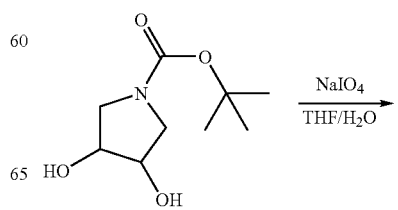

-continued

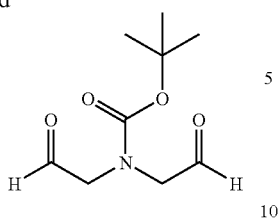

Bis-(2-oxo-ethyl)-carbamic acid tert-butyl ester

Sodium periodate (20.31 g, 94.96 mmol) in H₂O (118 mL) was added to a cooled solution of 3,4-dihydroxy-pyrrolidine-1-carboxylic acid tert-butyl ester (19.3 g, 94.6 mmol) in THF (158 mL) over a 30 minute period. The resulting white suspension was allowed to stir at room temperature for 3 h. The suspension was filtered and the filtrate concentrated under vacuum to remove the THF. The resulting aqueous solution was used directly in the next reaction.

Example 25

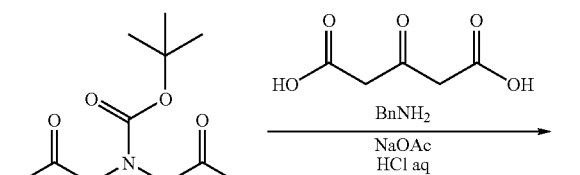

9-Benzyl-7-oxo-3,9-diaza-bicyclo[3.3.1]nonane-3-carboxylic acid tert-butyl ester Acetone-1,3-dicarboxylic acid (13.8 g, 94.96 mmol) and sodium acetate (7.94 g, 96.8 mmol) were added to a solution of bis-(2-oxo-ethyl)-carbamic acid tert-butyl ester (19.1 g, 94.96 mmol) in H₂O (118 mL). Benzylamine (10.3 mL, 94.96 mmol) was dissolved in aqueous HCl (3 N, 63 mL) and was subsequently added to the stirring solution of the dialdehyde and the dicarboxylic acid over a 15 minute period. The reaction mixture was stirred for 3 days at room temperature after which the pH was adjusted to 8 by the addition of potassium carbonate. The resulting solution was extracted with methylene chloride (4×70 mL), the organic extracts dried (Na₂SO₄), filtered and concentrated under vacuum. The resulting residue was purified by silica gel chromatography, (eluant hexane/EtOAc 9/1 to 1/1, v/v), to give 15.1 g (48%) of 9-benzyl-7-oxo-3,9-diaza-bicyclo[3.3.1]nonane-3-carboxylic acid tert-butyl ester as a brown oil. Retention time (min)=1.195, method [1], MS (ESI) 331.2 (M+H); ¹H NMR (300 MHz, CDCl₃) δ 7.43-7.15 (m, 5H), 4.00-3.81 (m, 4H), 3.21 (bs, 2H), 3.20-2.98 (m, 2H), 2.62 (dd, J=15.9 Hz, 5.5 Hz, 2H), 2.28-2.17 (m, 2H), 1.42 (s, 9H).

Example 26

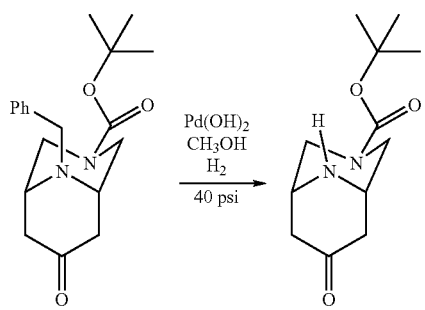

7-Oxo-3,9-diaza-bicyclo[3.3.1]nonane-3-carboxylic acid tert-butyl ester.

9-Benzyl-7-oxo-3,9-diaza-bicyclo[3.3.1]nonane-3-carboxylic acid tert-butyl ester (16.6 g, 50.5 mmol) was dissolved in methanol (40 mL) and added to a suspension of palladium hydroxide (1 g) in methanol (10 mL) in a Parr bottle. The Parr bottle was filled with hydrogen (40 psi) and evacuated three times. The Parr bottle was refilled with hydrogen (40 psi) and shook for 48 h. The suspension was filtered through Celite and concentrated under vacuum to give 12.1 g (quantitative yield) of 7-oxo-3,9-diaza-bicyclo[3.3.1]nonane-3-carboxylic acid tert-butyl ester as a yellow oil. Retention time (min)=0.531, method [1], MS(ESI) 481.3 (2M+H).

Example 27

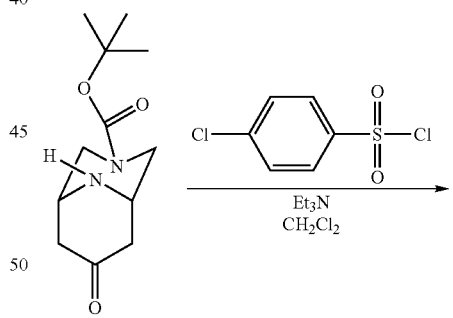

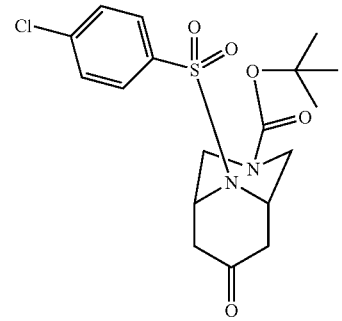

9-(4-Chloro-benzenesulfonyl)-7-oxo-3,9-diaza-bicyclo[3.3.1]nonane-3-carboxylic acid tert-butyl ester 7-Oxo-3,9-diaza-bicyclo[3.3.1]nonane-3-carboxylic acid tert-butyl ester (11.7 g, 48.6 mmol) was dissolved in methylene chloride (100 mL). Et$_3$N (13.5 mL, 97.3 mmol) and 4-chlorobenzenesulfonyl chloride (12.3 g, 58.4 mmol) were added and the reaction mixture was stirred at room temperature for 5 h. The reaction mixture was diluted with methylene chloride (50 mL) and washed with saturated NaHCO$_3$ (50 mL). The aqueous phase was separated and extracted once with methylene chloride (50 mL). The combined organic phases were then dried (Na$_2$SO$_4$), filtered, concentrated under vacuum and the residue was purified on a silica gel column (eluant hexane/EtOAc, 20/1 to 1/1) to give 16.6 g (82%) of 9-(4-chloro-benzenesulfonyl)-7-oxo-3,9-diaza-bicyclo[3.3.1]nonane-3-carboxylic acid tert-butyl ester as a yellow oil. Retention time (min)=2.164, method [1], MS (ESI) 437.0 (M+Na); $^1$H NMR (300 MHz, CDCl$_3$) δ 7.81 (d, J=8.8 Hz, 2H), 7.51 (d, J=8.8 Hz, 2H), 4.40 (d, J=4.4 Hz, 2H), 4.18-3.95 (m, 2H), 2.95-2.81 (m, 2H), 2.59 (dd, J=15.9, 6.0 Hz, 2H), 2.38 (d, J=15.9 Hz, 2H), 1.40 (s, 9H).

Example 28

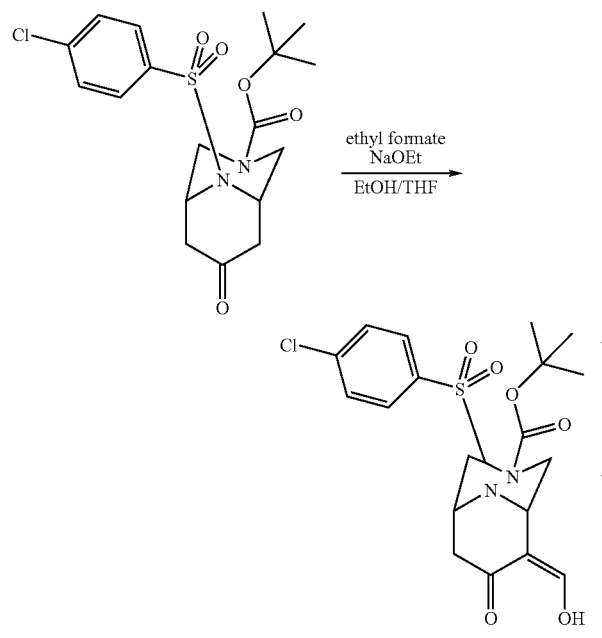

9-(4-Chloro-benzenesulfonyl)-6-hydroxymethylene-7-oxo-3,9-diaza-bicyclo[3.3.1]nonane-3-carboxylic acid tert-butyl ester.

9-(4-Chloro-benzenesulfonyl)-7-oxo-3,9-diaza-bicyclo[3.3.1]nonane-3-carboxylic acid tert-butyl ester (5.08 g, 12.2 mmol) was dissolved in THF/ethanol (40 mL, 1/1, v/v). Ethyl formate (9.84 mL, 122.4 mmol) was added followed by sodium ethoxide (12 mL of 21% solution in ethanol). The resulting mixture was stirred at room temperature for 30 minutes then heated to 60° C. for 30 minutes after which the solution was cooled back to room temperature and quenched by the addition of saturated aqueous NH$_4$Cl (10 mL). The resulting mixture was extracted with EtOAc (3×20 mL) and the combined organic phases were dried (Na$_2$SO$_4$), filtered and concentrated under vacuum to yield 5.43 g (quantitative) of 9-(4-chloro-benzenesulfonyl)-6-hydroxymethylene-7-oxo-3,9-diaza-bicyclo[3.3.1]nonane-3-carboxylic acid tert-butyl ester as a yellow oil. Retention time (min)=2.114, method [1], MS (ESI) 465.0 (M+Na).

Example 29

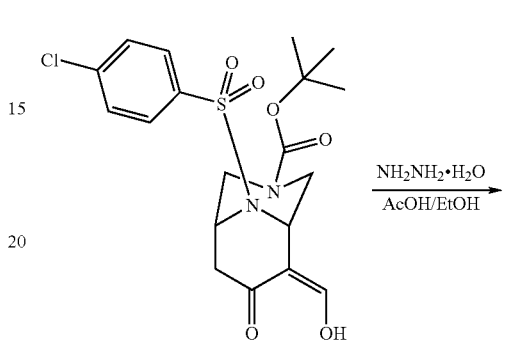

12-(4-Chloro-benzenesulfonyl)-4,5,10,12-tetraazatricyclo[6.3.1.0$^{2,6}$]dodeca-2(6),3-diene-10-carboxylic acid tert-butyl ester To a solution of 9-(4-chloro-benzenesulfonyl)-6-hydroxymethylene-7-oxo-3,9-diaza-bicyclo[3.3.1]nonane-3-carboxylic acid tert-butyl ester (4.91 g, 11.1 mmol) in ethanol (20 mL) was added glacial acetic acid (0.5 mL) followed by hydrazine monohydrate (5.39 mL, 111.1 mmol). The reaction mixture was stirred at room temperature for 1 h after which saturated NaHCO$_3$ (10 mL) was added. The resulting solution was extracted with EtOAc (3×20 mL), the organic extracts were combined, dried (Na$_2$SO$_4$), filtered, concentrated and purified by silica gel column chromatography (eluant hexane/EtOAc, 9/1 to 2/8) and preparative HPLC to give 12-(4-chloro-benzenesulfonyl)-4,5,10,12-tetraaza-tricyclo[6.3.1.0$^{2,6}$]dodeca-2(6),3-diene-10-carboxylic acid tert-butyl ester as a white solid. Retention time (min)=1.794, method [1], MS (ESI) 439.1 (M+H); $^1$H NMR (300 MHz, CDCl$_3$) δ 7.60 (d, J=8.2 Hz, 2H), 7.40 (s, 1H), 7.32 (d, J=8.2 Hz, 2H), 5.39 (s, 1H), 4.31 (s, 1H), 4.15-4.00 (m, 1H), 3.90 (d, J=12.1 Hz, 1H), 3.39-3.10 (m, 2H), 2.75-2.60 (m, 2H), 1.20-1.07 (m, 9H).

Example 30

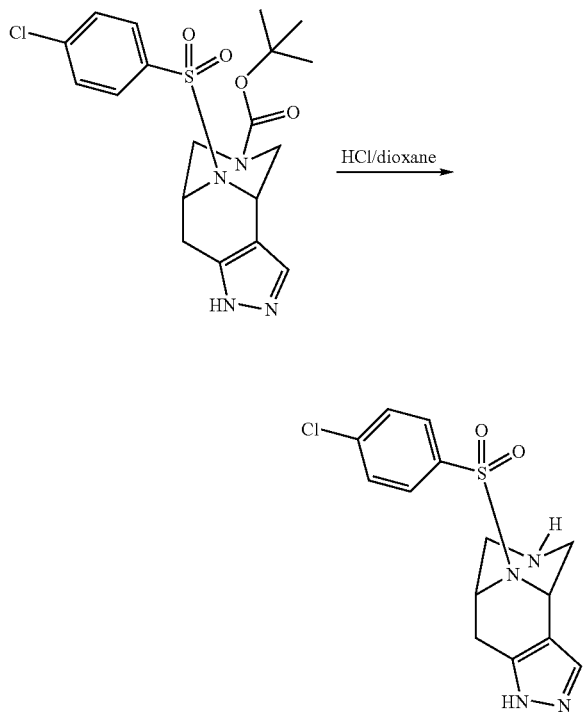

12-(4-Chloro-benzenesulfonyl)-4,5,10,12-tetraaza-tricyclo[6.3.1.0²,⁶]dodeca-2(6),3-diene 12-(4-Chloro-benzenesulfonyl)-4,5,10,12-tetraaza-tricyclo[6.3.1.0²,⁶]dodeca-2(6),3-diene-10-carboxylic acid tert-butyl ester (207 mg, 0.471 mmol) was covered with HCl in dioxane (4 N, 2 mL). The reaction mixture was stirred at room temperature for 2 h after which it was concentrated under vacuum and purified by preparative HPLC to give 12-(4-chloro-benzenesulfonyl)-4,5,10,12-tetraaza-tricyclo [6.3.1.0²,⁶]dodeca-2(6),3-diene as a white solid. Retention time (min)=1.125, method [1], MS (ESI) 339.1 (M+H); $^1$H NMR (300 MHz, CDCl$_3$) δ 7.59 (d, J=8.2 Hz, 2H), 7.30-7.25 (m, 3H), 5.09 (s, 1H), 4.35-4.14 (m, 1H), 3.25-3.18 (m, 2H), 2.98 (d, J=13.7 Hz, 1H), 2.77 (dd, J=17.0, 7.1 Hz, 2H), 2.55 (d, J=17.0 Hz, 1H)

Example 31

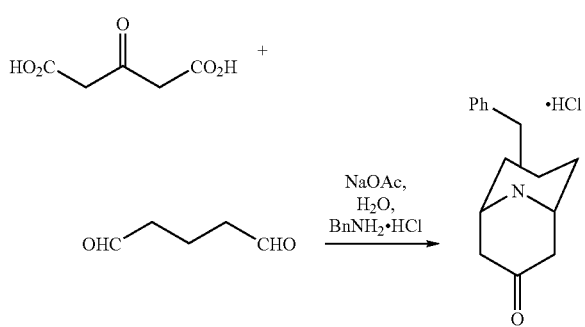

9-Benzyl-9-azabicyclo[3.3.1]nonan-3-one hydrochloride.

A two-liter, 2-neck flask, an overhead stirrer and an addition funnel were used. Glutaraldehyde (100 mL, 50% aq. solution) was placed in the flask. Water (63 mL) was added. 36.5 grams of 1,3-acetonedicarboxylic acid were added. Some bubbling was observed. NaOAc (14.25 g) was added and the mixture was stirred vigorously. A solution of benzylamine hydrochloride (35.6 g) in 112 mL of water was placed in the addition funnel. Alternatively it may be advantageous to dissolve the benzylamine hydrochloride in 80 mL of water and 30 mL of 0.12 N aqueous HCl, instead of 112 mL of H$_2$O. The amine solution was added to the reaction mixture portionwise. Foaming and bubbling was observed. A dark yellow, sticky solid formed. The reaction mixture was allowed to stir overnight. Methylene chloride (500 mL) was added, followed by K$_2$CO$_3$ which was added until the pH~8. The layers were separated and the aqueous layer was extracted with CH$_2$Cl$_2$ (500 mL). The combined organic layers were passed through 300 mL of basic alumina and dried over MgSO$_4$. The solution was then passed through 1.2 L of silica gel. The silica gel was washed with 300 mL of CH$_2$Cl$_2$ after which the silica gel was eluted with 2000 mL of 5% MeOH in CH$_2$Cl$_2$. The combined organic layers were concentrated by rotary evaporation to afford 26.9 g (47% yield) of 9-benzyl-9-azabicyclo [3.3.1]nonan-3-one as a pale yellow solid. The pale yellow solid was dissolved in THF and 4 N HCl in dioxane was added to obtain the hydrochloride salt as a white precipitate. NB. This is a modification of a procedure found in: G. Gonzalez Trigo, *Anales de Quimica*, 1979, 782-783.

Example 32

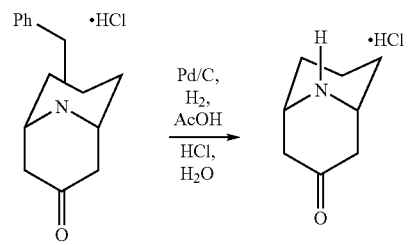

9-Azabicyclo[3.3.1]nonan-3-one hydrochloride.

9-benzyl-9-azabicyclo[3.3.1]nonan-3-one hydrochloride (38.8 g) was dissolved in 450 mL of glacial acetic acid. 13.5 Grams of 10% Pd/C (Degussa catalyst E101—containing 50% water) was added. After the appropriate evacuation & purge cycles, the mixture was agitated under 62 psi of H$_2$ at rt overnight. TLC (3% MeOH in CH$_2$Cl$_2$ on silica gel) indicated that the reaction was complete. The reaction mixture was filtered through Celite and concentrated by rotary evaporation under vacuum. The product was redissolved in 0.12 N HCl (250 mL) and the solution was concentrated in vacuo. This was repeated once more with 0.12 N HCl (250 mL). The product was then dissolved in 1 N HCl and concentrated to dryness under vacuum. A sticky brown solid was obtained. The material was recrystallized once from isopropanol and once from EtOH to give 9-azabicyclo[3.3.1]nonan-3-one

Example 33

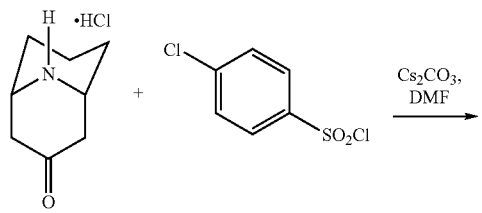

9-(4-Chlorophenylsulfonyl)-9-azabicyclo[3.3.1]nonan-3-one.

20.9 g of 9-azabicyclo[3.3.1]nonan-3-one hydrochloride was dissolved in 600 mL of DMF. 89.0 g of $Cs_2CO_3$ followed by 29 g of 4-chlorobenzenesulfonyl chloride was added and the reaction mixture was stirred overnight at rt. After an additional day of stirring, the reaction mixture was poured into 1.4 L of vigorously stirring EtOAc. The mixture was stirred for 2 h and allowed to stand at rt overnight. The mixture was filtered to remove undissolved solids and the filtrate was washed with $H_2O$ (2 L×3) and brine (2 L). The organic layer was dried over $MgSO_4$, filtered and the solvent was removed by rotary evaporation. A granular, tan solid was produced. Trituration with methanol dissolved a tan impurity to afford 9-(4-chlorophenylsulfonyl)-9-azabicyclo[3.3.1]nonan-3-one as a white crystalline solid (25.9 g, 69% yield).

Example 34

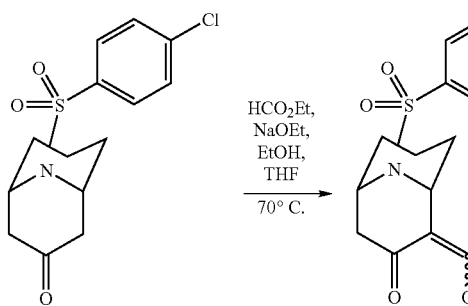

9-(4-Chlorophenylsulfonyl)-2-(hydroxymethylene)-9-azabicyclo[3.3.1]nonan-3-one A solution of 0.27 g (0.9 mmol) of 9-(4-chlorophenylsulfonyl)-9-azabicyclo[3.3.1]nonan-3-one in 2.0 mL of THF was stirred at rt and 0.70 mL (8.7 mmol) of ethyl formate was added followed by 1.0 mL of EtOH and 0.78 mL of a 21 wt % solution of NaOEt in EtOH. The reaction mixture was stirred at 70° C. for 1 h. The reaction mixture was concentrated by rotary evaporation, quenched with sat. aq. $NH_4Cl$ and extracted with $CHCl_3$. The organic layer was dried over $MgSO_4$, filtered and concentrated to afford 0.25 g (86%) of 9-(4-chlorophenylsulfonyl)-2-(hydroxymethylene)-9-azabicyclo[3.3.1]nonan-3-one as an orange solid. $^1$H NMR (300 MHz, $CDCl_3$) δ 14.11 (s, 1H), 8.24 (s, 1H), 7.73 (d, J=8.6 Hz, 2H), 7.45 (d, J=8.6 Hz, 2H), 4.85 (s, 1H), 4.32 (m, 1H), 2.58 (dd, J=19.8, 7.7 Hz, 1H), 2.17 (d, J=19.8 Hz, 1H), 2.00-1.76 (m, 2H), 1.61 (m, 5H).

Example 35

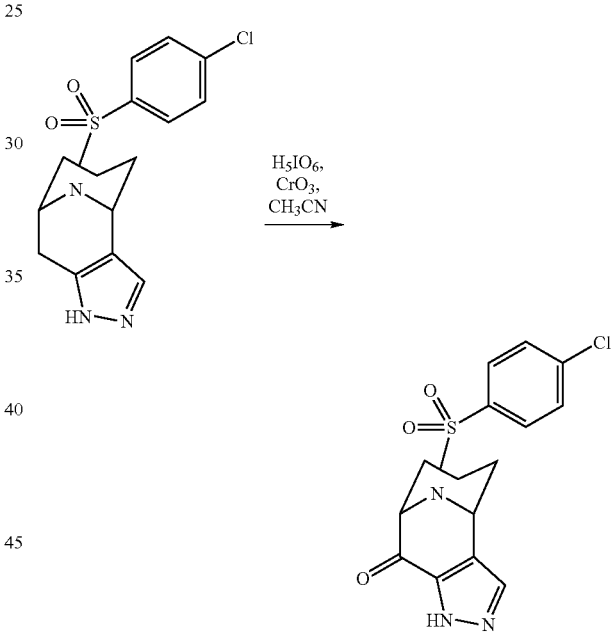

12-(4-Chloro-benzenesulfonyl)-4,5,12-triaza-tricyclo[6.3.1.0$^{2,6}$]dodeca-2(6),3-dien-7-one To a solution of $H_5IO_6$ (1.86 g, 8.15 mmol) in $CH_3CN$ (15 mL) was added $CrO_3$ (22.2 mg, 0.22 mmol) followed by 12-(4-chloro-benzenesulfonyl)-4,5,12-triaza-tricyclo[6.3.1.02,6]dodeca-2(6),3-diene (500 mg, 1.48 mmol). After two hours the heterogeneous reaction was filtered and the filtrate concentrated. The residue was taken-up in EtOAc and washed with water (3×25 mL), 5% $NaHSO_3$ (2×25 mL), brine (1×20 mL), dried over $MgSO_4$, filtered and concentrated to give an oil. The crude product was purified by preparative TLC eluting with 1:1 hexanes/EtOAc to give 12-(4-chlorobenzenesulfonyl)-4,5,12-triaza-tricyclo[6.3.1.0$^{2,6}$]dodeca-2(6),3-dien-7-one (285 mg, 55%) as a white solid.

Separation of the racemate using Method 2 gave 2 enantiomers MS (ES) m/e 352.0. (M+H):

Enantiomer A: $^1$H-NMR (CDCl$_3$) δ 7.62 (s, 1H), 7.51 (d, J=8.4 Hz, 2H), 7.22, (d, J=8.8 Hz, 2H), 5.46 (app. s, 1H), 4.49-4.47 (m, 1H), 2.21-1.90 (m, 4H), 1.71-1.57 (m, 2H), 1.39-1.22 (m, 1H) and Enantiomer B: $^1$H-NMR (CDCl$_3$) δ7.48-7.45 (m, 3H), 7.23 (d, J=8.8 Hz, 2H), 5.43 (app. s, 1H), 4.47-4.46 (m, 1H), 2.23-1.91 (m, 3H), 1.71-1.60 (m, 2H), 1.39-1.28 (m, 1H).

Example 36

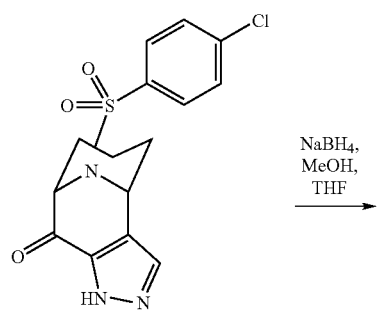

12-(4-Chloro-benzenesulfonyl)-4,5,12-triaza-tricyclo[6.3.1.0$^{2,6}$]dodeca-2(6),3-dien-7-ol To a solution of 12-(4-chloro-benzenesulfonyl)-4,5,12-triaza-tricyclo[6.3.1.0$^{2,6}$]dodeca-2(6),3-dien-7-one (58 mg, 0.16 mmol) in 2:1 MeOH/THF (3 mL) was added NaBH$_4$ (12 mg, 0.33 mmol) in portions. After sixteen hours the reaction was quenched with half saturated KHSO$_4$ and then diluted with EtOAc and water. The separated organic phase was washed with water (10 mL), brine (10 mL), dried over MgSO$_4$, filtered and concentrated to yield 12-(4-chlorobenzenesulfonyl)-4,5,12-triaza-tricyclo[6.3.1.0$^{2,6}$]dodeca-2(6),3-dien-7-ol (44 mg, 76%) as a white fluffy solid. MS (ES) m/e 354.0. (M+H)

1H-NMR (DMSO-d6) δ 7.77 (d, J=8.2 Hz, 2H), 7.59 (d, J=8.8 Hz, 2H), 7.33 (br s, 1H), 5.13 (app s, 1H), 4.62-4.59 (m, 1H), 4.17-4.12 (m, 1H), 2.12-2.08 (m, 1H), 1.80-1.60 (m, 1H), 1.51-1.32 (m, 4H)

Example 37

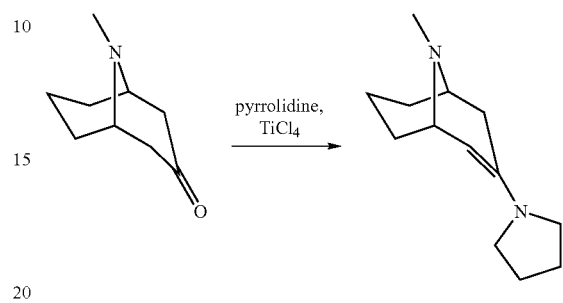

9-Methyl-3-(pyrrolidin-1-yl)-9-azabicyclo[3.3.1]non-3-ene.

To pseudo-pelletierine (1.5 g, 9.8 mmol) in toluene (75 mL) was added pyrrolidine (4.9 mL, 58.75 mmol). TiCl$_4$ (0.66 mL, 6.0 mmol) in toluene (10 mL) was then added to the mixture at −5° C. The reaction mixture was left to warm up to rt and stirred for 2 days. The mixture was filtered and the filtrate was concentrated to a residue and toluene (100 mL) was added and the mixture was filtered again. The filtrate was concentrated to a residue to afford the product (2.0 g, 100%) as yellow oil.

Example 38

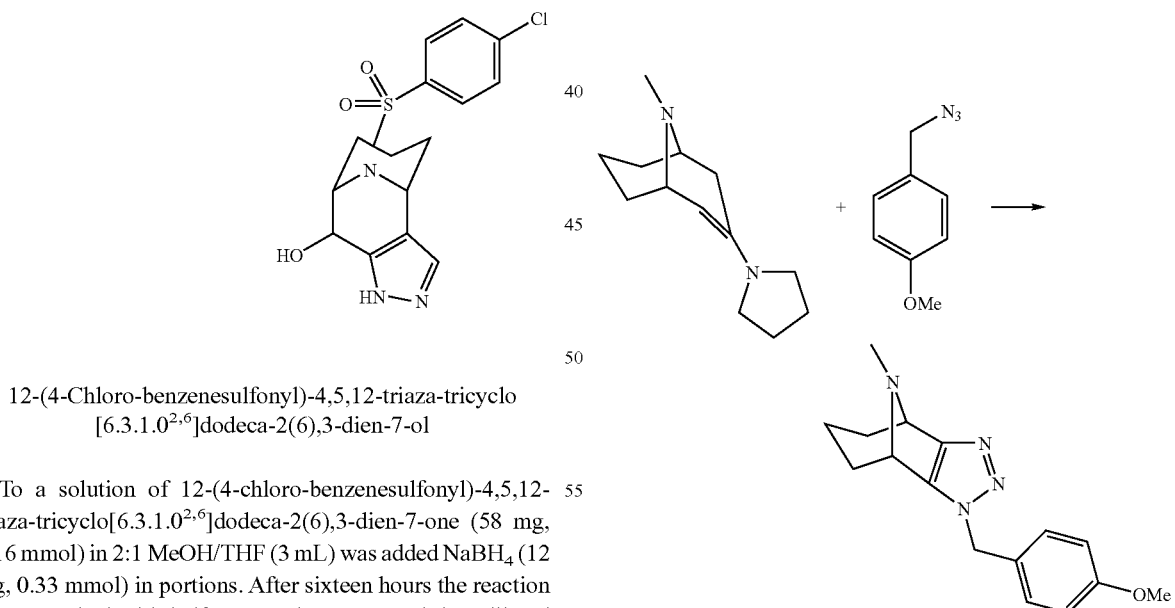

12-Methyl-5-(4-methoxybenzyl)-3,4,5,12-tetraaza-tricyclo[6.3.1.0$^{2,6}$]dodeca-2(6),3-diene A mixture of 9-methyl-3-(pyrrolidin-1-yl)-9-azabicyclo[3.3.1]non-3-ene (1.2 g, 5.9 mmol) and 4-methoxybenzylazide (0.96 g, 5.9 mmol) was heated at 50° C. for 2 days. The crude mixture was purified by prep HPLC to afford the product (1.0 g, 3.4 mmol, 57% yield) as yellow oil.

Example 39

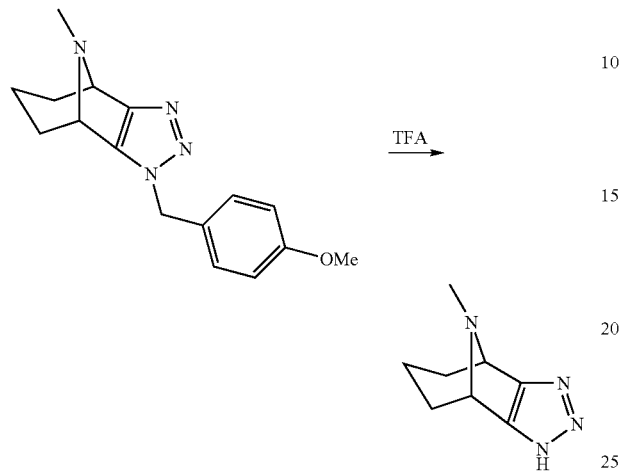

12-Methyl-3,4,5,12-tetraaza-tricyclo[6.3.1.0²,⁶]dodeca-2(6),3-diene.

12-Methyl-5-(4-methoxybenzyl)-3,4,5,12-tetraaza-tricyclo[6.3.1.0²,⁶]dodeca-2(6),3-diene (0.5 g, 1.7 mmol) in trifluoroacetic acid (TFA) (6 mL) was heated at 65° C. overnight. The solvent was removed and the residue was purified by prep HPLC to afford the product (200 mg, 1.1 mmol, 65% yield) as yellow oil.

Example 40

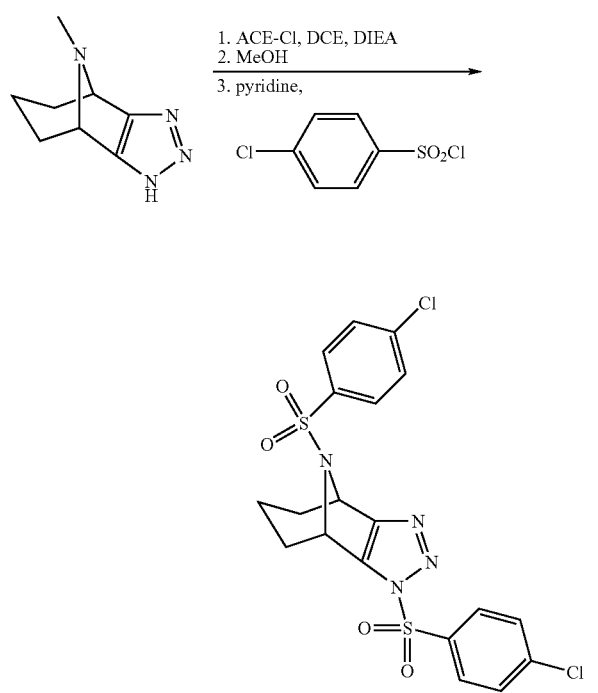

12,5-bis(4-Chloro-benzenesulfonyl)-3,4,5,12-tetraaza-tricyclo[6.3.1.0²,⁶]dodeca-2(6),3-diene To 12-methyl-3,4,5,12-tetraaza-tricyclo[6.3.1.02,6] dodeca-2(6),3-diene (80 mg, 0.45 mmol) in 1,2-dichloroethane (DCE) (0.5 mL) was added N,N-diisopropylethylamine (DIEA) (83 µL, 0.48 mmol) followed by 1-chloroethyl chloroformate (ACE-Cl) (0.12 ml, 1.1 mmol). The mixture was stirred at rt for 30 min then it was heated at 90° C. overnight. The solvent was removed by evaporation and MeOH (2 mL) was added. The mixture was heated at reflux overnight. The solvent was removed. The residue was dissolved in pyridine (2 mL) and the 4-chlorobenzenesulfonyl chloride (285 mg, 1.35 mmol) was added at rt. The reaction was stirred at rt overnight. The pyridine was removed under vacuum. The residue was partitioned between EtOAc/H₂O. The organic layer was washed with H₂O and brine. It was dried and concentrated and purified by prep TLC to afford the product (15 mg, 0.029 mmol, 6.5% yield) as a mixture of regioisomers.

Example 50

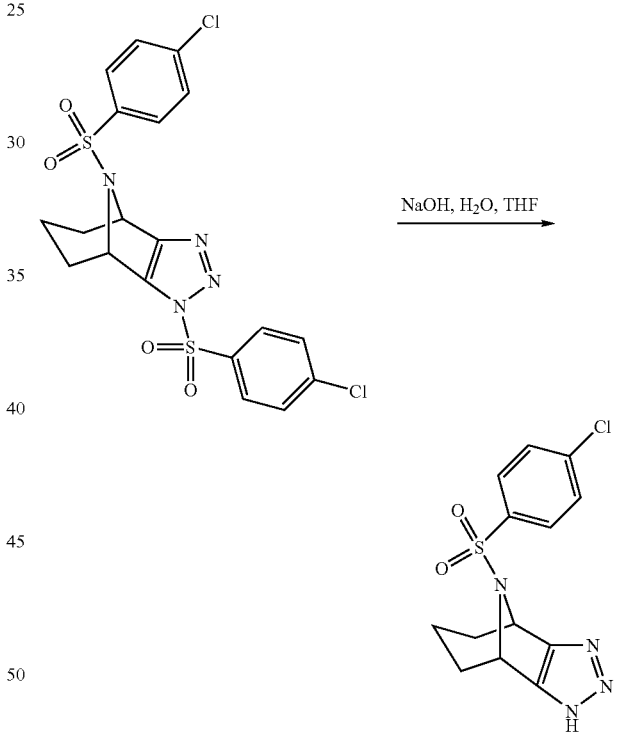

12-(4-Chloro-benzenesulfonyl)-3,4,5,12-tetraaza-tricyclo[6.3.1.0²,⁶]dodeca-2(6),3-diene To 12,5-bis(4-chloro-benzenesulfonyl)-3,4,5,12-tetraaza-tricyclo[6.3.1.02,6]dodeca-2(6),3-diene (15 mg, 0.029 mmol) in THF (200 µL) was added H₂O (100 µM) followed by 1M NaOH solution in H₂O (100 µL). The mixture was heated at 75° C. for 3 hr. The mixture was partitioned between EtOAc/H₂O. The organic layer was washed with brine, dried and concentrated. The residue was purified by prep TLC to 12-(4-Chloro-benzenesulfonyl)-3,4,5,12-tetraaza-tricyclo [6.3.1.0²,⁶]dodeca-2(6),3-diene (5.3 mg, 0.016 mmol, 54% yield). MS (ES) m/e 339.0 (M+H)

$^1$H-NMR (CDCl$_3$) δ 7.62 (d, J=8.7 Hz, 2H), 7.31 (d, J=8.7 Hz, 2H), 5.41 (m, 1H), 4.58 (bt, J=5.4 Hz, 1H), 2.89 (dd, J=17.1 Hz, 7.6 Hz, 1H), 59 (d, J=17.1 Hz, 1H), 2.00 (m, 2H), 1.75 (m, 2H), 1.56 (m, 1H), 1.26 (m, 1H)

Example 51

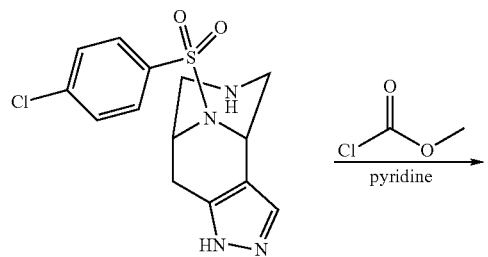

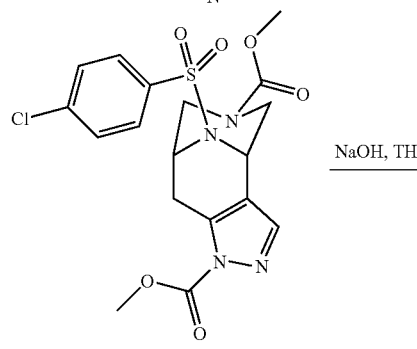

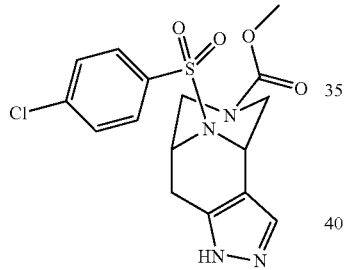

12-(4-Chloro-benzenesulfonyl)-4,5,10,12-tetraaza-tricyclo[6.3.1.0$^{2,6}$]dodeca-2(6),3-diene-10-carboxylic acid methyl ester 12-(4-Chloro-benzenesulfonyl)-4,5,10,12-tetraaza-tricyclo[6.3.1.0$^{2,6}$]dodeca-2(6),3-diene (204 mg, 0.602 mmol) was dissolved in pyridine (1 mL) and cooled to 0° C. Methyl chloroformate (0.139 mL, 1.80 mmol) was added over 15 minutes and the resulting solution was stirred at room temperature for 2 h. The reaction mixture was diluted with methylene chloride (10 mL), washed with aqueous HCl (5 mL, 1 N) and aqueous NaHCO$_3$ (5 mL), dried (Na$_2$SO$_4$), filtered and concentrated under vacuum to give 275 mg of 12-(4-chloro-benzenesulfonyl)-4,5,10,12-tetraaza-tricyclo[6.3.1.0$^{2,6}$]dodeca-2(6),3-diene-5,10-dicarboxylic acid dimethyl ester as a brown oil. Retention time (min)=1.704, method [1], MS (ESI) 455.1 (M+H).

Aqueous sodium hydroxide (3 N, 0.39 mL, 1.18 mmol) was added to a stirring solution of 12-(4-chloro-benzenesulfonyl)-4,5,10,12-tetraaza-tricyclo[6.3.1.0$^{2,6}$]dodeca-2(6),3-diene-5,10-dicarboxylic acid dimethyl ester (270 mg, 0.594 mmol) in THF (1 mL). The reaction mixture was stirred for 3 h at room temperature and subsequently diluted with methylene chloride (10 mL) and water (5 mL). The phases were separated and the aqueous layer was extracted with methylene chloride (2×5 mL). The organic extracts were combined, dried (Na$_2$SO$_4$), filtered, concentrated and purified by preparative HPLC to give 12-(4-chloro-benzenesulfonyl)-4,5,10,12-tetraaza-tricyclo[6.3.1.0$^{2,6}$]dodeca-2(6),3-diene-10-carboxylic acid methyl ester as a white solid. Retention time (min)=1.435, method [1], MS(ESI) 397.13 (M+H); $^1$H NMR (300 MHz, CDCl$_3$) δ 7.60 (d, J=8.2 Hz, 2H), 7.50 (s, 1H), 7.35 (d, J=8.2 Hz, 2H), 5.21 (s, 1H), 4.41 (s, 1H), 4.19-4.01 (m, 1H), 3.90 (d, J=13.2 Hz, 1H), 3.60-3.40 (m, 3H), 3.35-3.14 (m, 2H), 2.85-2.80 (m, 1H), 2.71 (d, J=17.6 Hz, 1H).

Example 52

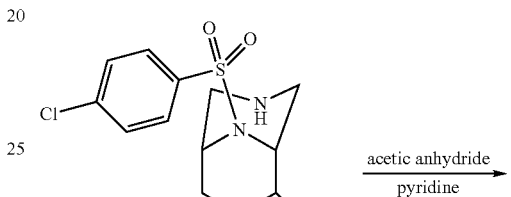

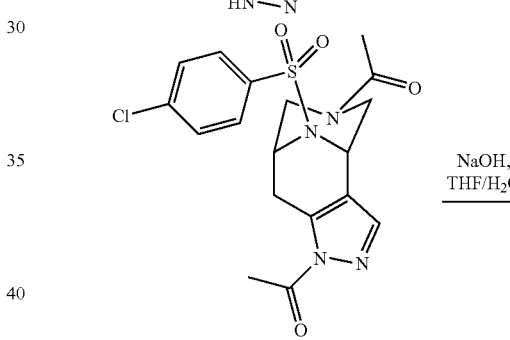

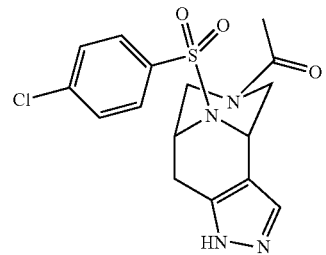

1-[12-(4-Chloro-benzenesulfonyl)-4,5,10,12-tetraaza-tricyclo[6.3.1.0$^{2,6}$]dodeca-2(6),3-dien-10-yl]-ethanone Acetic anhydride (0.5 mL) was added to a solution of 12-(4-chloro-benzenesulfonyl)-4,5,10,12-tetraaza-tricyclo[6.3.1.0$^{2,6}$]dodeca-2(6),3-diene (210 mg, 0.619 mmol) in pyridine (0.5 mL) over 15 minutes and the resulting solution was stirred at room temperature for 1 h. The reaction mixture was diluted with methylene chloride (10 mL), washed with aqueous HCl (5 mL, 1 N) and aqueous NaHCO$_3$ (5 mL), dried (Na$_2$SO$_4$), filtered and concentrated under vacuum to give 250 mg of 1-[5-acetyl-12-(4-chloro-benzenesulfonyl)-4,5,10,12-tetraaza-tricyclo[6.3.1.0²,⁶]dodeca-2(6),3-dien-10-yl]-ethanone as a brown oil. Retention time (min)=1.587, method [1], MS (ESI) 423.1 (M+H).

Aqueous sodium hydroxide (3 N, 0.56 mL, 1.70 mmol) was added to a stirring solution of 1-[5-acetyl-12-(4-chloro-benzenesulfonyl)-4,5,10,12-tetraaza-tricyclo[6.3.1.0²,⁶]dodeca-2(6),3-dien-10-yl]-ethanone (240 mg, 0.567 mmol) in THF (2 mL). The reaction mixture was stirred for 3 h at room temperature and subsequently diluted with ethyl acetate (10 mL) and water (5 mL). The phases were separated and the aqueous layer was extracted with ethyl acetate (2×5 mL). The organic extracts were combined, dried (Na$_2$SO$_4$), filtered, concentrated and purified by preparative HPLC to give 1-[12-(4-chloro-benzenesulfonyl)-4,5,10,12-tetraaza-tricyclo[6.3.1.0²,⁶]dodeca-2(6),3-dien-10-yl]-ethanone as a white solid. Retention time (min)=1.242, method [1], MS (ESI) 381.0 (M+H); $^1$H NMR (300 MHz, CDCl$_3$) (rotamers) δ 7.68-7.58 (m, 2H), 7.44 and 7.41 (2×s, 1H), 7.38-7.30 (m, 2H), 5.32-5.20 (m, 1H), 4.78 and 4.55 (2×d, J=13.2 Hz, 1H), 4.48-4.35 (m, 1H), 3.90-3.54 (m, 2H), 3.08-2.62 (m, 3H), 2.00 and 1.61 (2×s, 3H).

Example 53

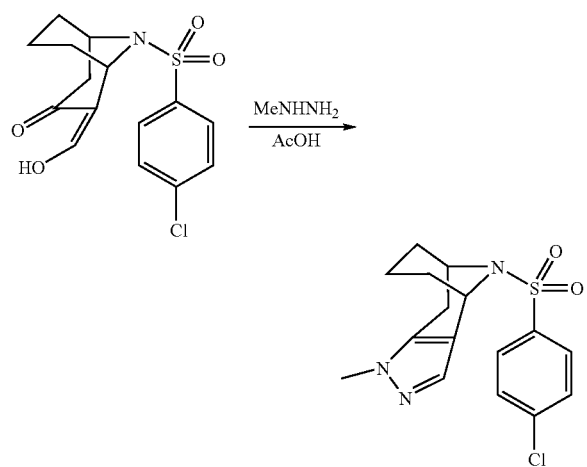

12-(4-Chloro-benzenesulfonyl)-5-methyl-4,5,12-triaza-tricyclo[6.3.1.0²,⁶]dodeca-2(6),3-diene To a suspension of the enol-ketone (9-[(4-chlorophenyl)sulfonyl]-2-(hydroxymethylene)-9-azabicyclo[3.3.1]nonan-3-one, 34 mg, 0.10 mmol) and glacial acetic acid (0.8 mL) in a vial was added the methylhydrazine (0.2 mL) with good stirring. The vial was capped and the reaction mixture was stirred evenly and heated to 100° C. Upon complete consumption of the enol-ketone (0.2-18 h, LC-MS), the reaction mixture was evaporated under a stream of nitrogen while being warmed in a 90° C. bath. The brown residue was dissolved with dichloromethane and water. The organic phase was washed with 5% aq NaHSO$_4$ (3×), 5% aq NaHCO$_3$ (2×), and brine (2×), dried (Na$_2$SO$_4$), applied to a silica gel column and eluted (0-8% MeOH in dichloromethane) to yield the product upon evaporation. MS (ES) m/e 352.0 (M+H)$^+$.

Example 54

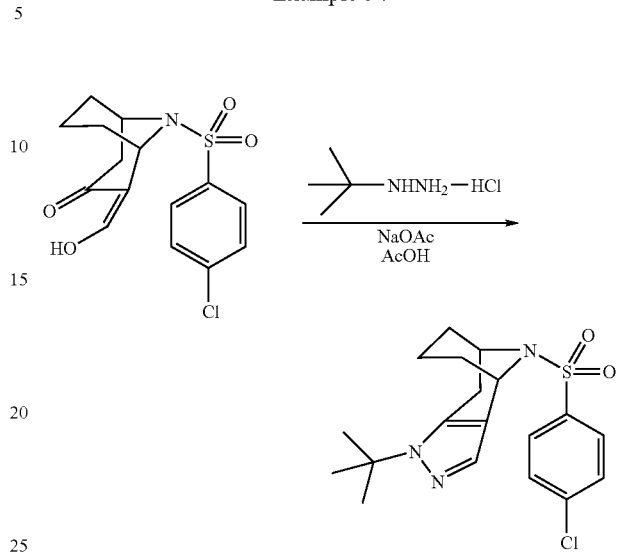

5-tert-Butyl-12-(4-chloro-benzenesulfonyl)-4,5,12-triaza-tricyclo[6.3.1.0²,⁶]dodeca-2(6),3-diene To a suspension of the enol-ketone (9-[(4-chlorophenyl)sulfonyl]-2-(hydroxymethylene)-9-azabicyclo[3.3.1]nonan-3-one, 34 mg, 0.10 mmol), sodium acetate (41 mg, 0.5 mmol) and glacial acetic acid (0.8 mL) in a vial was added the tert-butylhydrazine hydrochloride (31 mg, 0.25 mmol) with good stirring. The vial was capped and the reaction mixture was stirred evenly and heated to 100° C. Upon complete consumption of the enol-ketone (2-18 h, LC-MS), the reaction mixture was evaporated under a stream of nitrogen while being warmed in a 90° C. bath. The brown residue was dissolved with dichloromethane and water. The organic phase was washed with 5% NaHSO$_4$ (3×), 5% NaHCO3 (2×), and brine (2×), dried (Na$_2$SO$_4$), applied to a silica gel column and eluted (0-10% EtOAc in dichloromethane) to yield the product upon evaporation. MS (ES) m/e 306.0 (M+H)$^+$.

$^1$H NMR (CDCl3) δ 7.55 (dt, J=8.8, 2.5 Hz, 2H), 7.22 (dt, J=8.8, 2.5 Hz, 2H), 7.13 (s, 1H), 5.20 (br s, 1H), 4.42-4.35 (m, 1H), 2.69 (dd, J=17.1, 7.5 Hz, 1H), 2.46 (d, J=17.1 Hz, 1H), 2.05-1.85 (m, 2H), 1.70-1.30 (m, 4H), 1.36 (s, 9H).

Example 55

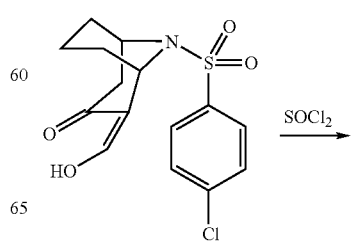

107

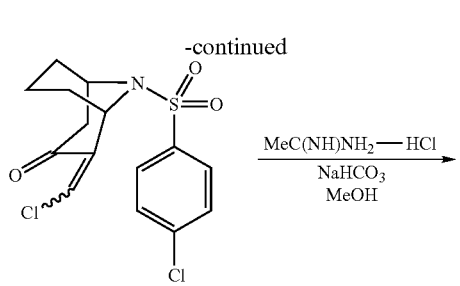

-continued 13-(4-Chloro-benzenesulfonyl)-5-methyl-4,6,13-triaza-tricyclo[7.3.1.0²,⁷]trideca-2(7),3,5-triene The enol-ketone (34 mg, 0.10 mmol) in excess thionyl chloride (2.5 mL) in a vial was heated in a 75° C. bath with good stirring for 1 h. While being warmed in a 75° C. bath, the reaction mixture was evaporated under a stream of nitrogen, an additional 1 mL of thionyl chloride was added and evaporated, and finally an additional 1 mL of chloroform was added and evaporated. The amber residue was dissolved with dichloromethane and applied to a silica gel column and eluted (0-10% EtOAc in dichloromethane) to yield the chloroalkene product upon evaporation.

To the chloroalkene was added dry NaHCO$_3$ (34 mg, 0.4 mmol) and acetamidine hydrochloride (24 mg, 0.25 mmol) and methanol (0.6 mL). The reaction mixture was stirred evenly and heated in a capped vial to 90° C. Upon complete consumption of the chloroalkene (22 h, LC-MS), the reaction mixture was evaporated under a stream of nitrogen while being warmed in a 80° C. bath. The brown residue was dissolved with dichloromethane and water. The organic phase was separated and washed with 5% NaHSO$_4$ (3×), 5% NaHCO$_3$ (2×), and brine (2×), dried (Na$_2$SO$_4$), filtered, applied to a silica gel column and eluted (0-10% EtOAc in dichloromethane) to yield the product upon evaporation. MS (ES) m/e 364.0 (M+H)$^+$.

$^1$H NMR (CDCl$_3$) δ 8.26 (s, 1H), 7.62 (d, J=8.8 Hz, 2H), 7.31 (d, J=8.8 Hz, 2H), 5.12 (br s, 1H), 4.50 (br s, 1H), 3.00 (dd, J=19.6, 8.0 Hz, 1H), 2.63 (s, 3H), 2.62 (d, J=19.0 Hz, 1H), 2.13-1.87 (m, 2H), 1.76-1.52 (m, 2H), 1.38-1.18 (m, 2H).

Example 56

Step 1: Diethyl 3-oxo-9-azabicyclo[3.3.1]nonane-2,4-dicarboxylate

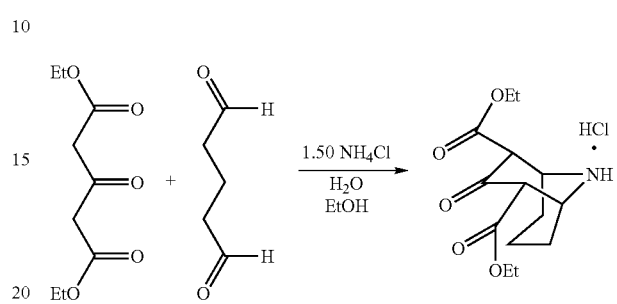

The diethylacetone-1,3-dicarboxylate (60.62 g, 300 mmol) was dissolved in ethanol (100 mL) and water (50 mL), and 50% aq glutaraldehyde (63.32 g, 315 mmol) was added all at once with good stirring. The reaction mixture was placed in a 48-50° C. bath and stirred while a 35° C. aq ammonium chloride solution (24.0 g, 0.460 mmol; 80 mL water) was added over 20 min. After stirring 2 h in the 50° C. bath the starting materials had been predominantly consumed (LC-MS), so the reaction mixture was evaporated under a stream of nitrogen while being warmed in a 90° C. bath to yield a slurry of the hydrochloride salt (~230 cc). MS (ES) m/e 284.0 (M+H)$^+$.

Step 2: Diethyl 9-(4-chlorophenylsulfonyl)-3-oxo-9-azabicyclo[3.3.1]nonane-2,4-dicarboxylate

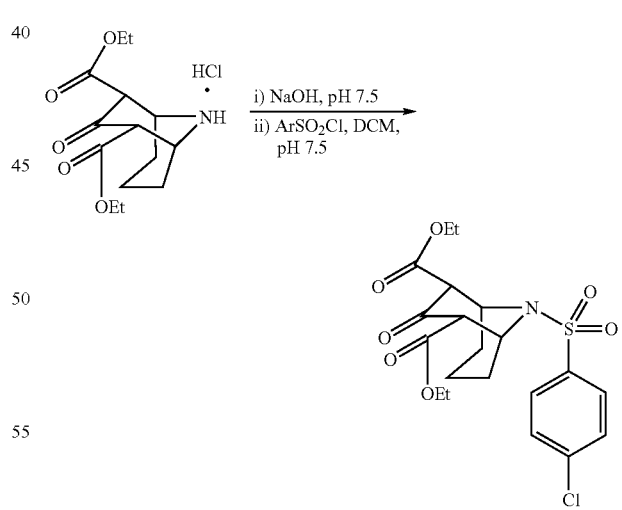

The slurry of amine hydrochloride from Method 11 (using glutaraldehyde; ~300 mmol) was suspended in dichloromethane (150 mL) and 4 M aq NaOH (120 mL). To the well-stirred reaction mixture was added 4-chlorobenzenesulfonyl chloride (73.14 g, 346.5 mmol) in dichloromethane (70 mL) over 10 min. After stirring at RT for 1 h, an additional 20 mL 4M NaOH and 10 mL satd aq NaHCO$_3$ were added to maintain the reaction mixture pH between pH 5.5-8.5. After stirring at RT for 2 h, N,N-diethyl-ethylenediamine (13.9 g, 120 mmol) is added dropwise and stirred for 1 h. The reaction mixture was acidified to pH 6 using aq NaHSO$_4$. The aqueous phase was separated and extracted once with dichloromethane. The combined organic phases were washed with 5% NaHSO$_4$ (three times), water, brine, and then dried (Na$_2$SO$_4$) and evaporated to yield 129 g (94% yield overall from diethyl acetonedicarboxylate) of the enol-diester product as a semisolid after applying full vacuum (18 h, 50° C. bath). MS (ES) m/e 458.0 (M+H)$^+$.

Step 3: Ethyl 9-(4-chlorophenylsulfonyl)-3-oxo-9-azabicyclo[3.3.1]nonane-2-carboxylate

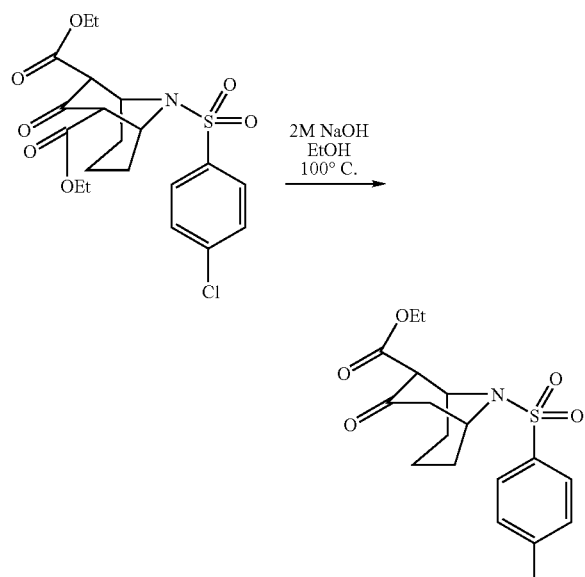

The ketodiester (14.0 g, 30.58 mmol) was dissolved in warm ethanol (20 mL) and 2.0 M aq NaOH (38.3 mL, 76.5 mmol). The reaction mixture was stirred in a 100° C. bath for 2 h, where LC-MS showed consumption of the diester. After cooling to RT, concentrated aq NaHSO$_4$ was added cautiously (CO$_2$ evolution) with stirring until the reaction mixture was acidified to pH 1-2, and stirred an additional 30 min in a 50° C. bath. The reaction mixture was then extracted with dichloromethane (3×), and the combined organic phases were washed with 5% NaHCO$_3$ (2×), water, brine, and then dried (Na$_2$SO$_4$) and evaporated to yield 9.75 g (83% yield) of the product which crystallized on standing. MS (ES) m/e 386.0 (M+H)$^+$.

Step 4: 12-(4-Chloro-benzenesulfonyl)-4,5,12-triaza-tricyclo[6.3.1.0$^{2,6}$]-2(6),3-dien-3-ol

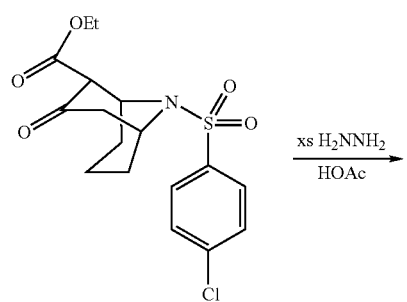

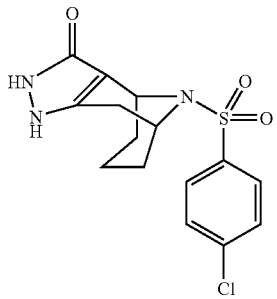

To a suspension of the ketoester (39 mg, 0.10 mmol) and glacial acetic acid (1 mL) in a vial was added the hydrazine hydrate (0.4 mL) with good stirring. The vial was capped and the reaction mixture was stirred evenly and heated to 120° C. Upon complete consumption of the ketoester (18-48 h, LC-MS), the reaction mixture was evaporated under a stream of nitrogen while being warmed in a 90° C. bath. The brown residue was dissolved with dichloromethane/isopropanol (4:1) and water. The organic phase was washed with water, 1% aq NaHSO$_4$, 1% aq NaHCO$_3$ (2×), and brine (2×), dried (Na$_2$SO$_4$), and evaporated to yield the product as a tan solid. MS (ES) m/e 354.0 (M+H)$^+$.

Similarly the following compound was prepared following the procedure above:

12-(4-Chloro-benzenesulfonyl)-5-methyl-4,5,12-triaza-tricyclo[6.3.1.0$^{2,6}$]-2(6),3-dien-3-ol; MS (ES) m/e 368.0 (M+H)$^+$. was prepared following the procedure above Example 57

2-[12-(4-Chloro-benzenesulfonyl)-4,5,12-triaza-tricyclo[6.3.1.0$^{2,6}$]dodeca-2(6),3-dien-5-yl]-ethanol Prepared as described in Example 5 using hydroxyethylhydrazine and 9-(4-chlorophenylsulfonyl)-2-(hydroxymethylene)-9-azabicyclo[3.3.1]nonan-3-one which was prepared as described in Example 34.

$^1$H NMR (CDCl$_3$) δ 7.62 (d, J=8.6 Hz, 2H, minor), 7.58 (d, J=8.6 Hz, 2H, major), 7.28 (d, J=8.6 Hz, 2H, major), 7.24 (d, J=8.6 Hz, 2H, minor), 5.23 (br s, 1H, major), 5.18 (br s, 1H, minor), 4.46 (t, J=5.8 Hz, 1H, major), 4.44 (t, J=5.8 Hz, 1H, minor) 4.10 (m, 2H, minor) 3.92-3.70 (m, 6H, mixture) 2.80 (dd, J=17.2, 8.0 Hz, 1H, minor), 2.56 (dd, J=17.2, 8.0 Hz, 1H, major), 2.47 (d, J=17.2 Hz, 1H, minor), 2.04-1.87 (m, 4H, mixture), 1.75-1.36 (m, 8H, mixture); MS (ES) m/e 382.0 (M+H)$^+$.

Example 58

12-(4-Chloro-benzenesulfonyl)-4,5,12-triaza-tricyclo[6.3.1.0$^{2,6}$]dodeca-2(6),3-diene Prepared as described in Example 5 using 9-(4-chlorophenylsulfonyl)-2-(hydroxymethylene)-9-azabicyclo[3.3.1]nonan-3-one which was prepared as described in Example 34.

$^1$H-NMR (CDC$_{13}$) δ 7.60 (d, J=8.7 Hz, 2H), 7.27 (d, J=8.7 Hz, 2H), 7.23 (s, 1H), 5.26 (s, 1H), 4.44 (m, 1H), 2.75 (dd, J=17.1, 7.5 Hz, 1H), 2.47 (d, J=17.1 Hz, 1H), 2.03-1.86 (m, 2H), 1.67-1.33 (m, 4H); MS (ES) nm/e 338.0 (M+H)$^+$.

Example 59

16-(4-Chloro-benzenesulfonyl)-4,8,9,16-tetraaza-tetracyclo[10,3,1,0$^{2,10}$,0$^{5,9}$]-hexadeca-2(10),3,5,7-tetraene Prepared as described in Example 5 using 9-(4-chlorophenylsulfonyl)-2-(hydroxymethylene)-9-azabicyclo[3.3.1]nonan-3-one which was prepared as described in Example 34 and 3-aminopyrazole.

$^1$H NMR (CDCl$_3$) δ 8.21 (s, 1H), 8.08 (d, J=2.3 Hz, 1H), 7.61 (d, J=8.6 Hz, 2H), 7.20 (d, J=8.6 Hz, 2H), 6.70 (d, J=2.3 Hz, 1H), 5.26 (m, 1H), 4.66 (m, 1H), 3.29 (dd, J=19.9, 7.7 Hz, 1H), 2.90 (d, J=19.9 Hz, 1H), 2.19-1.93 (m, 2H), 1.77 (m, 2H), 1.60 (m, 1H), 1.43 (m, 1H). MS (ES) m/e 389.0 (M+H)$^+$.

Example 60

16-(4-Chloro-benzenesulfonyl)-7-methyl-4,8,9,16-tetraaza-tetracyclo-[10,3,1,0$^{2,10}$,0$^{5,9}$]hexadeca-2(10),3,5,7-tetraene; MS (ES) m/e 403.0 (M+H)$^+$.

Prepared as described in Example 5 using 9-(4-chlorophenylsulfonyl)-2-(hydroxymethylene)-9-azabicyclo[3.3.1]nonan-3-one which was prepared as described in Example 34 and 3-amino-5-methylpyrazole.

$^1$H NMR (CDCl$_3$) δ 8.13 (s, 1H), 7.58 (dt, J=8.7, 2.3 Hz, 2H), 7.19 (dt, J=8.7, 2.3 Hz, 2H), 6.47 (s, 1H), 5.23 (br s, 1H), 4.66-4.58 (m, 1H), 3.21 (dd, J=19.6, 7.7 Hz, 1H), 2.84 (d, J=19.6 Hz, 1H), 2.50 (s, 3H), 2.20-1.90 (m, 2H), 1.80-1.70 (m, 2H)

Example 61

16-(4-Chloro-benzenesulfonyl)-7-hydroxy-4,8,9,16-tetraaza-tetracyclo[10,3,1,0$^{2,10}$,0$^{5,9}$]-hexadeca-2(10),3,5,7-tetraene; MS (ES) m/e 405.0 (M+H)$^+$.

Example 62

16-(4-Chloro-benzenesulfonyl)-6-phenyl-4,8,9,16-tetraaza-tetracyclo-[10,3,1,0$^{2,10}$,0$^{5,9}$]-hexadeca-2(10),3,5,7-tetraene; MS (ES) m/e 465.0 (M+H)$^+$.

Prepared as described in Example 5 using 9-(4-chlorophenylsulfonyl)-2-(hydroxymethylene)-9-azabicyclo[3.3.1]nonan-3-one which was prepared as described in Example 34 and 3-amino-4-phenylpyrazole $^1$H-NMR (CDCl$_3$) δ 8.38 (s, 1H), 8.28 (s, 1H), 8.00 (m, 2H), 7.63 (m, 2H), 7.47 (dd(app. t), J=7.7 Hz, 2H), 7.31 (m, 1H), 7.21 (d, J=8.8 hz, 2H), 5.28 (m, 1H), 4.68 (m, 1H), 3.30 (dd, J=20.0, 8.0 Hz, 1H), 2.92 (d, J=20.0 Hz, 1H), 2.15 (m, 1H), 2.01 (m, 1H), 1.79 (m, 2H), 1.65 (m, 1H), 1.46 (m, 1H).

Example 63

16-(4-Chloro-benzenesulfonyl)-7-phenyl-4,8,9,16-tetraaza-tetracyclo-[10,3,1,0$^{2,10}$,0$^{5,9}$]-hexadeca-2(10),3,5,7-tetraene; MS (ES) m/e 465.0 (M+H)$^+$.

Prepared as described in Example 5 using 9-(4-chlorophenylsulfonyl)-2-(hydroxymethylene)-9-azabicyclo[3.3.1]nonan-3-one which was prepared as described in Example 34 and 3-amino-5-phenylpyrazole.

$^1$H NMR (CDCl$_3$) δ 8.18 (s, 1H), 7.97 (m, 2H), 7.67 (d, J=8.6 Hz, 2H), 7.50-7.38 (m, 3H), 7.23 (d, J=8.6 Hz, 2H), 6.97 (s, 1H), 5.25 (s, 1H), 4.67 (m, 1H), 3.36 (dd, J=19.9, 7.8 Hz, 1H), 3.00 (d, J=19.9 Hz, 1H), 2.20-1.95 (m, 2H), 1.78 (m, 2H), 1.65 (m, 1H), 1.47 (m, 1H).

Example 64

12-(4-Chloro-benzenesulfonyl)-5-(4-isopropyl-phenyl)-4,5,12-triaza-tricyclo[6.3.1.0$^{2,6}$]dodeca-2(6),3-diene; MS (ES) m/e 456.0 (M+H)$^+$.

Prepared as described in Example 5 using 4-isopropylphenylhydrazine and 9-(4-chlorophenylsulfonyl)-2-(hydroxymethylene)-9-azabicyclo[3.3.1]nonan-3-one which was prepared as described in Example 34.

$^1$H NMR (CDCl$_3$) δ 7.60 (dt, J=8.7, 2.3 Hz, 2H), 7.39 (s, 1H), 7.31-7.24 (m, 4H), 7.09 (dt, J=8.7, 2.3 Hz, 2H), 5.31 (t, J=2.8 Hz, 1H), 4.45 (t, J=5.7 Hz, 1H), 2.96 (sept, J=6.9 Hz, 1H), 2.66 (dd, J=17.2, 7.5 Hz, 1H), 2.40 (d, J=17.2 Hz, 1H), 2.12-1.90 (m, 2H), 1.73-1.38 (m, 4H), 1.28 (d, J=6.9 Hz, 6H).

Example 65

5-tert-Butyl-12-(4-chloro-benzenesulfonyl)-4,5,12-triaza-tricyclo[6.3.1.0$^{2,6}$]dodeca-2(6),3-diene; MS (ES) m/e 394.0 (M+H)$^+$.

Prepared as described in Example 5 using tert-butyl hydrazine and 9-(4-chlorophenylsulfonyl)-2-(hydroxymethylene)-9-azabicyclo[3.3.1]nonan-3-one which was prepared as described in Example 34.

$^1$H NMR (CDCl$_{13}$) δ 7.55 (dt, J=8.8, 2.5 Hz, 2H), 7.22 (dt, J=8.8, 2.5 Hz, 2H), 7.13 (s, 1H), 5.20 (br s, 1H), 4.42-4.35 (m, 1H), 2.69 (dd, J=17.1, 7.5 Hz, 1H), 2.46 (d, J=17.1 Hz, 1H), 2.05-1.85 (m, 2H), 1.70-1.30 (m, 4H), 1.36 (s, 9H).

Example 66

12-(4-Chloro-benzenesulfonyl)-5-cyclohexyl-4,5,12-triaza-tricyclo[6.3.1.0$^{2,6}$]dodeca-2(6),3-diene; MS (ES) m/e 420.0 (M+H)$^+$.

Prepared as described in Example 5 using cyclohexylhydrazine and 9-(4-chlorophenylsulfonyl)-2-(hydroxymethylene)-9-azabicyclo[3.3.1]nonan-3-one which was prepared as described in Example 34.

Example 67

5-Benzyl-12-(4-chloro-benzenesulfonyl)-4,5,12-triaza-tricyclo[6.3.1.0$^{2,6}$]dodeca-2(6),3-diene; MS (ES) m/e 428.0 (M+H)$^+$.

Prepared as described in Example 5 using benzylhydrazine and 9-(4-chlorophenylsulfonyl)-2-(hydroxymethylene)-9-azabicyclo[3.3.1]nonan-3-one which was prepared as described in Example 34.

$^1$H NMR (CDCl$_3$) (mixture of regioisomers) δ 7.88-7.81 (m, 1H, minor), 7.59-7.50 (m, 2H), 7.49-7.43 (m, 1H, major), 7.43-7.11 (m, 5H), 7.02-6.91 (m, 1H), 5.25-5.17 (m, 1H), 5.15 (AB q, J=15.6 Hz, dn=21.2 Hz, 2H, minor), 5.01 (AB q, J=15.6 Hz, dn=21.2 Hz, 2H, major), 4.49-4.36 (m, 1H), 2.73 (dd, J=17.1, 7.8 Hz, 1H, minor), 2.47 (dd, J=17.1, 7.8 Hz, 1H, major), 2.17 (d, J=17.1 Hz, 1H, major), 2.06-1.82 (m, 2H), 1.72-1.42 (m, 2H), 1.40-1.20 (m, 2H).

Example 68

12-(4-Chloro-benzenesulfonyl)-5-methyl-4,5,12-triaza-tricyclo[6.3.1.0$^{2,6}$]dodeca-2(6),3-diene MS (ES) m/e 416.0 (M+H)$^+$.

Prepared as described in Example 5 using methyl hydrazine and 9-(4-chlorophenylsulfonyl)-2-(hydroxymethylene)-9-azabicyclo[3.3.1]nonan-3-one which was prepared as described in Example 34.

Example 69

16-(4-Chloro-benzenesulfonyl)-4,6,8,9,16-pentaaza-tetracyclo[10,3,1,0$^{2,10}$,0$^{5,9}$]hexadeca-2(10),3,5,7-tetraene MS (ES) m/e 390.0 (M+H)$^+$.

Prepared as described in Example 5 using 9-(4-chlorophenylsulfonyl)-2-(hydroxymethylene)-9-azabicyclo[3.3.1]nonan-3-one which was prepared as described in Example 34 and 3-amino-1,2,4-triazole $^1$H NMR (CDCl$_3$) δ 8.55 (s, 1H), 8.48 (s, 1H), 7.65 (d, J=8.8 Hz, 2H), 7.30 (d, J=8.8 Hz, 2H), 5.35 (m, 1H), 4.66 (m, 1H), 3.39 (dd, J=20.0, 8.0 Hz, 1H), 2.98 (d, J=20.0 Hz, 1H), 2.20-1.92 (m, 2H), 1.78 (m, 2H), 1.66 (m, 1H), 1.34 (m, 1H).

Example 70

16-(4-Chloro-benzenesulfonyl)-7-methylthio-4,6,8,9,16-pentaaza-tetracyclo-[10,3,1,0$^{2,10}$,0$^{5,9}$]hexadeca-2(10),3,5,7-tetraene MS (ES) m/e 436.0 (M+H)$^+$.

Prepared as described in Example 5 using 9-(4-chlorophenylsulfonyl)-2-(hydroxymethylene)-9-azabicyclo[3.3.1]nonan-3-one which was prepared as described in Example 34 and 3-amino-5-methylthio-1,2,4-triazole.

$^1$H NMR (CDCl$_3$) δ 8.42 (s, 1H), 7.65 (d, J=8.6 Hz, 2H), 7.31 (d, J=8.6 Hz, 2H), 5.30 (s, 1H), 4.62 (m, 1H), 3.32 (dd, J=20.0, 7.7 Hz, 1H), 2.92 (d, J=20.0 Hz, 1H), 2.72 (s, 3H), 2.17-1.91 (m, 2H), 1.75 (m, 2H), 1.62 (m, 1H), 1.33 (m, 1H).

Example 71

16-(4-Chloro-benzenesulfonyl)-4,6,9,16-tetraaza-tetracyclo[10,3,1,0$^{2,10}$,0$^{5,9}$]hexadeca-2(10),3,5,7-tetraene MS (ES) m/e 389.0 (M+H)

Prepared as described in Example 5 using 9-(4-chlorophenylsulfonyl)-2-(hydroxymethylene)-9-azabicyclo[3.3.1]nonan-3-one which was prepared as described in Example 34 and 2-aminoimidazole sulfate.

$^1$H NMR (300 MHz, CDCl$_3$) δ 8.31 (s, 1H), 7.86 (d, J=1.3 Hz, 2H), 7.64 (d, J=8.5 Hz, 2H), 7.28 (d, J=8.5 Hz, 2H), 7.23 (d, J=1.3 Hz, 2H), 5.26 (bs, 1H), 4.63 (bs, 2H), 3.1 (dd, J=18.6, 7.7 Hz, 1H), 2.95 (d, J=21.6 Hz, 1H), 2.03 (m, 2H), 1.65 (m, 2H), 1.36 (m, 2H).

Example 72

12-(4-Chloro-benzenesulfonyl)-5-oxa-4,12-diaza-tricyclo[6.3.1.0$^{2,6}$]dodeca-2(6),3-diene MS (ES) m/e 339.0 (M+H)

Prepared as described in Example 5 using hydroxyamine hydrochloride and 9-(4-chlorophenylsulfonyl)-2-(hydroxymethylene)-9-azabicyclo[3.3.1]nonan-3-one which was prepared as described in Example 34.

Example 73

16-(4-Chloro-benzenesulfonyl)-6-acetamido-4,8,9,16-tetraaza-tetracyclo-[10,3,1,0$^{2,10}$,0$^{5,9}$]hexadeca-2(10),3,5,7-tetraene MS (ES) m/e 432.0 (M+H)

Prepared as described in Example 5 using 9-(4-chlorophenylsulfonyl)-2-(hydroxymethylene)-9-azabicyclo[3.3.1]nonan-3-one which was prepared as described in Example 34 and 3-amino-4-pyrazolecarboxamide hemisulfate salt.

$^1$H NMR (300 MHz, CDCl$_3$) δ 8.65 (s, 1H), 8.34 (s, 1H), 7.64 (d, J=8.7 Hz, 2H), 7.29 (d, J=8.7 Hz, 2H), 5.62 (bs, 1H), 5.29 (bs, 1H), 4.64 (bs, 1H), 3.39 (dd, J=20.1, 7.9 Hz, 1H), 3.03 (d, J=20.1 Hz, 1H), 2.16 (m, 2H), 1.93 (m, 2H), 1.35 (m, 2H).

Example 74

16-(4-Chloro-benzenesulfonyl)-7-amino-4,6,8,9,16-pentaaza-tetracyclo-[10,3,1,0$^{2,10}$,0$^{5,9}$]hexadeca-2(10),3,5,7-tetraene MS (ES) m/e 405.0 (M+H)

Prepared as described in Example 5 using 9-(4-chlorophenylsulfonyl)-2-(hydroxymethylene)-9-azabicyclo[3.3.1]nonan-3-one which was prepared as described in Example 34 and 3,5-diamino-1,2,4-triazole.

$^1$H NMR (300 MHz, CDCl$_3$) δ 8.26 (s, 1H), 7.62 (d, J=8.7 Hz, 2H), 7.30 (d, J=8.7 Hz, 2H), 5.26 (bs, 1H), 4.70 (bs, 2H), 4.60 (bs, 1H), 3.19 (dd, J=19.6, 8.0 Hz, 1H), 2.81 (d, J=19.7 Hz, 1H), 2.10 (m, 2H), 1.94 (m, 2H), 1.32 (m, 2H).

Example 75

12-(4-Chloro-benzenesulfonyl)-4,5,12-triaza-tricyclo[6.3.1.0$^{2,6}$]-2(6),3-dien-3-ol MS (ES) m/e 354.0 (M+H)

Prepared as described in Example using methyl 9-(4-chlorophenylsulfonyl)-3-oxo-9-azabicyclo[3.3.1]nonane-2-carboxylate, which was prepared as described in Example 12 using dimethyl carbonate and 9-(4-chlorophenylsulfonyl)-9-azabicyclo[3.3.1]nonan-3-one. See also: Bonjoch, Josep; Linares, Ana; Guardia, Manel; Bosch, Joan. Heterocycles 1987, 26(8), 2165-74.

Example 76

12-(4-Chloro-benzenesulfonyl)-4-methyl-4,5,12-triaza-tricyclo[6.3.1.0$^{2,6}$]dodeca-2,5-dien-3-ol MS (ES) m/e 368.0 (M+H)

Prepared as described in Example using methylhydrazine and methyl 9-(4-chlorophenylsulfonyl)-3-oxo-9-azabicyclo[3.3.1]nonane-2-carboxylate, which was prepared as described in Example 12 using dimethyl carbonate and 9-(4-chlorophenylsulfonyl)-9-azabicyclo[3.3.1]nonan-3-one. See also: Bonjoch, Josep; Linares, Ana; Guardia, Manel; Bosch, Joan. Heterocycles 1987, 26(8), 2165-74.

¹H NMR (300 MHz, CDCl₃) δ 7.80 (d, J=8.5 Hz, 2H), 7.50 (d, J=8.5 Hz, 2H), 4.62 (bs, 1H), 3.34 (s, 3H), 2.94 (dd, J=14.6, 6.0 Hz, 1H), 2.68 (d, J=14.8 Hz, 1H), 2.16 (m, 2H), 1.69 (m, 2H), 1.42 (m, 2H).

Example 77

16-(4-Chloro-benzenesulfonyl)-5-fluoro-9,16-diaza-tetracyclo[10,3,1,0$^{2,10}$,0$^{3,8}$]hexadeca-2(10),3(8),4,6-tetraene MS (ES) m/e 405.0 (M+H)

Prepared as similarly described in: Mewshaw, Richard E.; Silverman, Lisa S.; Mathew, Rose M.; Kaiser, Carl; Sherrill, Ronald G.; Cheng, Menyan; Tiffany, Carol W.; Karbon, E. William; Bailey, Michael A.; et al. J. Med. Chem. 1993, 36(10), 1488-95.

Example 78

12-(4-Chloro-benzenesulfonyl)-4,5,12-triaza-tricyclo[6.3.1.0$^{2,6}$]dodeca-2(6),3-diene MS (ES) m/e 338.0 (M+H) chiral single isomers Prepared as described in Example 5 using 9-(4-chlorophenylsulfonyl)-2-(hydroxymethylene)-9-azabicyclo[3.3.1]nonan-3-one, which was prepared as described in Example 34, followed by separation of the chiral isomers using HPLC Method 2.

¹H-NMR (CDCl₃) δ 7.60 (d, J=8.7 Hz, 2H), 7.27 (d, J=8.7 Hz, 2H), 7.23 (s, 1H), 5.26 (s, 1H), 4.44 (m, 1H), 2.75 (dd, J=17.1, 7.5 Hz, 1H), 2.47 (d, J=17.1 Hz, 1H), 2.03-1.86 (m, 2H), 1.67-1.33 (m, 4H).

Example 79

11-(4-Chloro-benzenesulfonyl)-4,5,1-triaza-tricyclo[6.3.1.0$^{2,6}$]undeca-2(6),3 diene MS (ES) m/e 324.0 (M+H)

Prepared as described in Example 5 using 8-(4-chlorophenylsulfonyl)-2-(hydroxymethylene)-8-azabicyclo[3.2.1]octan-3-one, which was prepared as described in Example 34 using 8-(4-chlorophenylsulfonyl)-8-azabicyclo[3.2.1]octan-3-one, which was prepared as described in Example 33 using 8-azabicyclo[3.2.1]octan-3-one.

Example 80

12-(4-Chloro-benzenesulfonyl)-3-methyl-4,5,12-triaza-tricyclo[6.3.1.0$^{2,6}$]dodeca-2(6),3-diene MS (ES) m/e 352.0 (M+H)

Prepared as described in Example 5 using 9-(4-chlorophenylsulfonyl)-2-(1-hydroxyethylidene)-9-azabicyclo[3.3.1]nonan-3-one which was prepared as described in Example 34 using acetonitrile and lithium diisopropylamine. See also: Ferrer, Leticia Oliveira; Margaretha, Paul. Chemical Communications 2001, (5), 481-482.

Example 81

12-(4-Chloro-benzenesulfonyl)-5-methyl-3-trifluoromethyl-4,5,12-triaza-tricyclo[6.3.1.0$^{2,6}$]dodeca-2(6),3-diene MS (ES) m/e 420.0 (M+H)

Prepared as described in Example 5 using methylhydrazine and 9-(4-chlorophenylsulfonyl)-2-(1-hydroxyethylidene)-9-azabicyclo[3.3.1]nonan-3-one which was prepared as described in Example 34 using ethyl trifluoroacetate and lithium diisopropylamine. See also: Ferrer, Leticia Oliveira; Margaretha, Paul. Chemical Communications 2001, (5), 481-482.

¹H NMR (300 MHz, CDCl₃) δ 7.58 (d, J=8.6 Hz, 2H), 7.29 (d, J=8.6 Hz, 2H), 5.29 (bs, 1H), 4.51 (t, J=5.4 Hz, 1H), 3.50 (s, 3H), 2.60 (dd, J=16.9, 7.6 Hz, 1H), 2.30 (d, J=16.9 Hz, 1H), 1.97 (m, 2H), 1.66 (m, 2H), 1.30 (m, 2H).

Example 82

12-(4-Chloro-benzenesulfonyl)-3-trifluoromethyl-4,5,12-triaza-tricyclo-[6.3.1.0$^{2,6}$]dodeca-2(6),3-diene MS (ES) m/e 406.0 (M+H).

Prepared as described in Example 5 using 9-(4-chlorophenylsulfonyl)-2-(1-hydroxyethylidene)-9-azabicyclo[3.3.1]nonan-3-one which was prepared as described in Example 34 using ethyl trifluoroacetate and lithium diisopropylamine.

¹H NMR (CDCl₃) δ 7.60 (d, J=8.8 Hz, 2H), 7.29 (d, J=8.8 Hz, 2H), 5.33 (br s, 1H), 4.53 (t, J=5.8 Hz, 1H), 2.77 (dd, J=17.1, 7.5 Hz, 1H), 2.44 (d, J=17.1 Hz, 1H), 2.07-1.90 (m, 2H), 1.80-1.40 (m, 2H), 1.40-1.20 (m, 2H)

Example 83

1-[12-(4-Chloro-benzenesulfonyl)-4,5,12-triaza-tricyclo[6.3.1.0$^{2,6}$]dodeca-2,5-dien-4-yl]-ethanone MS (ES) m/e 380.0 (M+H).

Prepared by acylation of 12-(4-chloro-benzenesulfonyl)-4,5,12-triaza-tricyclo[6.3.1.02,6]dodeca-2(6),3-diene using acetyl chloride.

¹H NMR (CDCl₃) δ 7.89 (s, 1H), 7.65 (d, J=8.8 Hz, 2H), 7.33 (d, J=8.8 Hz, 2H), 5.23 (br s, 1H), 4.51 (t, J=6.4 Hz, 1H), 2.89 (dd, J=18.0, 7.9 Hz, 1H), 2.60 (s, 3H), 2.55 (d, J=18.0 Hz, 1H), 2.07-1.90 (m, 2H), 1.80-1.40 (m, 2H), 1.40-1.20 (m, 2H).

Example 84

1-[12-(4-Chloro-benzenesulfonyl)-4,5,12-triaza-tricyclo[6.3.1.0$^{2,6}$]dodeca-2,5-dien-4-yl]-2-methyl-propan-1-one MS (ES) m/e 408.0 (M+H).

Prepared by acylation of 12-(4-chloro-benzenesulfonyl)-4,5,12-triaza-tricyclo[6.3.1.0$^{2,6}$]-dodeca-2(6),3-diene using isobutyryl chloride.

¹H NMR (CDCl₃) δ 7.86 (s, 1H), 7.62 (d, J=8.7 Hz, 2H), 7.28 (d, J=8.7 Hz, 2H), 5.23 (m, 1H), 4.51 (s, 1H), 3.67 (hept., J=3.5 Hz, 1), 2.84 (dd, J=17.8, 8.2 Hz, 1H), 2.52 (d, J=17.8 Hz, 1H), 1.96 (m, 2H), 1.71-1.51 (m, 2H), 1.38 (m, 1H), 1.24 (d, J=4.4 Hz, 3H), 1.22 (d, J=4.4 Hz, 3H), 1.19 (m, 1H).

Example 85

Acetic acid 2-[12-(4-chloro-benzenesulfonyl)-4,5,12-triaza-tricyclo[6.3.1.0$^{2,6}$]dodeca-2,5-dien-4-yl]-1,1-dimethyl-2-oxo-ethyl ester Prepared by acylation of 12-(4-chloro-benzenesulfonyl)-4,5,12-triaza-tricyclo[6.3.1.0$^{2,6}$]dodeca-2(6),3-diene using 2-acetoxyisobutyryl chloride.

¹H NMR (CDCl₃) δ 7.92 (s, 1H), 7.59 (d, J=8.7 Hz, 2HH), 7.29 (d, J=8.7 Hz, 2H), 5.28 (m, 1H), 4.49 (m, 1H), 2.69 (dd, J=18.0 Hz, 1H), 2.45 (d, J=18.0 Hz, 1H), 2.06 (s, 3H), 1.97 (m, 2H), 1.95 (s, 3H), 1.71-1.51 (m, 2H), 1.58 (s, 3H), 1.40-1.24 (m, 1H).

Example 86

12-(4-Chloro-benzenesulfonyl)-4,5,12-triaza-tricyclo[6.3.1.0$^{2,6}$]dodeca-2,5-diene-4-carboxylic acid allyl ester MS (ES) m/e 422.0 (M+H).

Prepared by acylation of 12-(4-chloro-benzenesulfonyl)-4,5,12-triaza-tricyclo[6.3.1.02,6]dodeca-2(6),3-diene using allylchloroformate $^1$H NMR (CDCl$_3$) δ 7.79 (s, 1H), 7.63 (d, J=8.8 Hz, 2H), 7.32 (d, J=8.8 Hz, 2H), 6.03 (m, 1H), 4.79 (dd, J=17.2, 1.5 Hz, 1H), 5.36 (dd, J=10.4, 1.1 Hz, 1H), 5.23 (m, 1H), 4.90 (dt, J=6.1, 1.1 Hz, 2H), 4.48 (m, 1H), 2.89 (dd, J=17.4, 8.0 Hz, 1H), 2.59 (d, J=17.4 Hz, 1H), 1.94 (m, 2H), 1.69-1.51 (m, 3H), 1.36 (m, 1H).

Example 87

13-(4-Chloro-benzenesulfonyl)-4,6,13-triaza-tricyclo[7.3.1.0$^{2,7}$]trideca-2(7),3,5-trien-5-ylamine MS (ES) m/e 365.0 (M+H).

Prepared as described in Example 5 using 9-(4-chlorophenylsulfonyl)-2-(hydroxymethylene)-9-azabicyclo[3.3.1]nonan-3-one which was prepared as described in Example 34 and guanidine hydrochloride. See also: Hasan, Mashooda; Rashid, Naghmana; Khan, Khalid Mohammed; Snatzke, Guenther; Duddeck, Helmut; Voelter, Wolfgang Liebigs Annalen 1995, (5), 889-96.

$^1$H NMR (CDCl$_3$) δ7.93 (s, 1H), 7.64 (d, J=8.8 Hz, 2H), 7.34 (d, J=8.8 Hz, 2H), 5.03 (br s, 1H), 4.87 (br s, 2H), 4.44 (br s, 1H), 2.81 (dd, J=19.0, 8.2 Hz, 1H), 2.44 (d, J=19.0 Hz, 1H), 2.13-1.87 (m, 2H), 1.76-1.52 (m, 2H), 1.38-1.18 (m, 2H).

Example 88

13-(4-Chloro-benzenesulfonyl)-4,6,13-triaza-tricyclo[7.3.1.0$^{2,7}$]trideca-2(7),3,5-triene MS (ES) m/e 350.0 (M+H).

Prepared as described in Example 5 using 9-(4-chlorophenylsulfonyl)-2-(hydroxymethylene)-9-azabicyclo[3.3.1]nonan-3-one which was prepared as described in Example 34 and formamidine acetate. See also: Hajos, Gyorgy; Snatzke, Guenther Liebigs Annalen der Chemie 1989, (1), 31-3.

Example 89

12-(4-Chloro-benzenesulfonyl)-3-trifluoromethyl-4,5,12-triaza-tricyclo-[6.3.1.0$^{2,6}$]dodeca-2(6),3-diene MS (ES) m/e 406.0 (M+H) single separate enantiomers Prepared as described in Example 5 using 9-(4-chlorophenylsulfonyl)-2-(1-hydroxyethylidene)-9-azabicyclo[3.3.1]nonan-3-one, which was prepared as described in Example 34 using ethyl trifluoroacetate and lithium diisopropylamine, followed by separation using HPLC Method 2 gave 2 separate single enantiomers.

Example 90

13-(4-Chloro-benzenesulfonyl)-5-methoxy-4,6,13-triaza-tricyclo[7.3.1.0$^{2,7}$]trideca-2(7),3,5-triene MS (ES) m/e 380.2 (M+H)

Prepared as described in Example 5 using 9-(4-chlorophenylsulfonyl)-2-(hydroxymethylene)-9-azabicyclo[3.3.1]nonan-3-one which was prepared as described in Example 34 and O-methylisourea hemisulfate.

Example 91

3-Chloro-12-(4-chloro-benzenesulfonyl)-4,5,12-triaza-tricyclo[6.3.1.0$^{2,6}$]dodeca-2(6),3-diene MS (ES) m/e 372. (M+H)

Prepared by chlorination of 12-(4-chloro-benzenesulfonyl)-4,5,12-triaza-tricyclo[6.3.1.02,6]dodeca-2(6),3-diene using N-chlorosuccinimide.

Example 92

12-(4-Chloro-benzenesulfonyl)-3-methyl-4,5,12-triaza-tricyclo[6.3.1.0$^{2,6}$]dodeca-2(6),3-diene MS (ES) m/e 352. (M+H) single separate enantiomers Prepared as described in Example 5 using 9-(4-chlorophenylsulfonyl)-2-(1-hydroxyethylidene)-9-azabicyclo[3.3.1]nonan-3-one, which was prepared as described in Example 34 using acetonitrile and lithium diisopropylamine, followed by separation using HPLC Method 2 gave 2 enantiomers:

Enantiomer A: $^1$H NMR (CDCl$_3$) δ 7.61 (d, J=8.8 Hz, 2H), 7.30 (d, J=8.8 Hz, 2H), 5.16 (br s, 1H), 4.45 (t, J=5.8 Hz, 1H), 2.75 (dd, J=17.1, 7.5 Hz, 1H), 2.45 (d, J=17.1 Hz, 1H), 2.20 (s, 3H), 2.07-1.90 (m, 2H), 1.80-1.40 (m, 2H), 1.40-1.20 (m, 2H) and Enantiomer B: $^1$H NMR (CDCl$_3$) δ7.58 (d, J=8.8 Hz, 2H), 7.28 (d, J=8.8 Hz, 2H), 5.13 (br s, 1H), 4.42 (t, J=5.8 Hz, 1H), 2.71 (dd, J=17.0, 7.5 Hz, 1H), 2.42 (d, J=17.0 Hz, 1H), 2.18 (s, 3H), 2.02-1.84 (m, 2H), 1.68-1.58 (m, 1H), 1.57-1.28 (m, 3H).

Example 93

12-(4-Chloro-benzenesulfonyl)-3-difluoromethyl-4,5,12-triaza-tricyclo[6.3.1.0$^{2,6}$]dodeca-2(6),3-diene MS (ES) m/e 388.0. (M+H)

Prepared as described in Example 5 using 9-(4-chlorophenylsulfonyl)-2-(1-hydroxyethylidene)-9-azabicyclo[3.3.1]nonan-3-one, which was prepared as described in Example 34 using ethyl trifluoroacetate and lithium diisopropylamine.

$^1$H-NMR (CDCl$_3$) δ 7.62 (d, J=8.4 Hz, 2H), 7.28 (s, 1H), 7.28 (d, J=8.4 Hz, 2H), 5.41 (s, 1H), 4.51 (m, 1H), 2.74 (dd, J=17.4, 7.7 Hz, 1H), 2.43 (d, J=17.4 Hz, 1H), 2.05-1.92 (m, 2H), 1.78-1.64 (m, 2H), 1.56 (m, 1H), 1.40-1.25 (m, 1H).

Example 94

12-(4-Chloro-benzenesulfonyl)-4,5,12-triaza-tricyclo[6.3.1.0$^{2,6}$]dodeca-2(6),3 dien-3-ylamine MS (ES) m/e 353.0. (M+H)

Prepared as described in Example 5 using 9-(4-chlorophenylsulfonyl)-3-oxo-9-azabicyclo[3.3.1]nonane-2-carbonitrile, which was prepared as described in Example 9 using p-toluenesulfonylcyanide instead of methyl iodide.

$^1$H-NMR (CDCl$_3$) δ 7.61 (d, J=8.7 Hz, 2H), 7.30 (d, J=8.7 Hz, 2H), 5.10 (m, 1H), 4.36 (m, 1H), 3.59 (bs, 2H), 2.59 (dd, J=17.1, 7.3 Hz, 1H), 2.30 (d, J=17.1 Hz, 1H), 1.96-1.83 (m, 2H), 1.59 (m, 2H), 1.47 (m, 2H).

Example 95

12-(4-Chloro-benzenesulfonyl)-3-difluoromethyl-4,5,12-triaza-tricyclo[6.3.1.0$^{2,6}$]dodeca-2(6),3-diene MS (ES) m/e 388.0. (M+H) 2 separate single enantiomers Prepared as described in Example 5 using 9-(4-chlorophenylsulfonyl)-2-(1-hydroxyethylidene)-9-azabicyclo[3.3.1]nonan-3-one, which was prepared as described in Example 34 using ethyl difluoroacetate and lithium diisopropylamine, followed by separation using HPLC Method 2 gave 2 separate single enantiomers.

Enantiomer A: $^1$H NMR (CDCl$_3$) δ 7.75 (d, J=8.6 Hz, 2H), 7.45 (d, J=8.6 Hz, 2H), 6.06 (t, J=53.5 Hz, 1H), 5.22 (br s, 1H), 4.42-4.38 (m, 1H), 2.58 (dd, J=19.9, 8.0 Hz, 1H), 2.26 (d, J=19.9 Hz, 1H), 2.00-1.78 (m, 2H), 1.78-1.44 (m, 4H) and Enantiomer B: 1H NMR (CDCl3) δ 7.61 (d, J=8.6 Hz, 2H), 7.27 (d, J=8.6 Hz, 2H), 6.66 (t, J=54.6 Hz, 1H), 5.40 (br s, 1H), 4.50 (t, J=5.4 Hz, 1H), 2.72 (dd, J=17.2, 7.6 Hz, 1H), 2.42 (d, J=17.2 Hz, 1H), 2.05-1.90 (m, 2H), 1.78-1.60 (m, 2H), 1.60-1.45 (m, 1H), 1.31 (qt, J=13.7, 4.2 Hz, 1H).

Example 96

12-(4-Chloro-benzenesulfonyl)-3-methylsulfanyl-4,5,12-triaza-tricyclo[6.3.1.0$^{2,6}$]dodeca-2(6),3-diene MS (ES) m/e 383.9. (M+H).

Prepared as described in Example 5 using 2-(bis(methylthio)methylene)-9-(4-chlorophenylsulfonyl)-9-azabicyclo[3.3.1]nonan-3-one which was prepared by the method of Patra, Pranab K.; Suresh, J. R.; Ila, H.; Junjappa, H. Tetrahedron 1998, 54(34), 10167-10178.

$^1$H NMR (CDCl$_3$) δ 7.62 (d, J=8.8 Hz, 2H), 7.29 (d, J=8.8 Hz, 2H), 5.17 (br s, 1H), 4.47 (t, J=5.5 Hz, 1H), 2.80 (dd, J=16.9, 7.4 Hz, 1H), 2.46 (d, J=16.9 Hz, 1H), 2.43 (s, 3H), 2.02-1.85 (m, 2H), 1.63 (br t, J=10.9 Hz, 2H), 1.58-1.44 (m, 1H), 1.36 (qt, J=13.6, 4.2 Hz, 1H).

Example 97

12-(4-Chloro-benzenesulfonyl)-4,5,12-triaza-tricyclo[6.3.1.0$^{2,6}$]dodeca-2(6),3-dien-3-ylamine MS (ES) m/e 353.0. (M+H) separate single enantiomers.

Prepared as described in Example 5 using 9-(4-chlorophenylsulfonyl)-3-oxo-9-azabicyclo[3.3.1]nonane-2-carbonitrile, which was prepared as described in Example 9 using p-toluenesulfonylcyanide instead of methyl iodide, followed by separation using HPLC Method 2 gave 2 separate enantiomers.

Enantiomer A: $^1$H-NMR (CDCl$_3$) δ 7.61 (d, J=8.7 Hz, 2H), 7.30 (d, J=8.7 Hz, 2H), 5.10 (m, 1H), 4.36 (m, 1H), 3.59 (bs, 2H), 2.59 (dd, J=17.1, 7.3 Hz, 1H), 2.30 (d, J=17.1 Hz, 1H), 1.96-1.83 (m, 2H), 1.59 (m, 2H), 1.47 (m, 2H) and Enantiomer B: $^1$H-NMR (CDCl$_3$) δ 7.61 (d, J=8.7 Hz, 2H), 7.30 (d, J=8.7 Hz, 2H), 5.10 (m, 1H), 4.36 (m, 1H), 3.59 (bs, 2H), 2.59 (dd, J=17.1, 7.3 Hz, 1H), 2.30 (d, J=17.1 Hz, 1H), 1.96-1.83 (m, 2H), 1.59 (m, 2H), 1.47 (m, 2H).

Example 98

N-[12-(4-Chloro-benzenesulfonyl)-4,5,12-triaza-tricyclo[6.3.1.0$^{2,6}$]dodeca-2(6),3-dien-7-yl]-acetamide MS (ES) m/e 353.0. (M+H).

Obtained as a byproduct of the preparation of 12-(4-Chloro-benzenesulfonyl)-4,5,12-triaza-tricyclo[6.3.1.0$^{2,6}$] dodeca-2(6),3-dien-3-ylamine and isolated by separation using HPLC Method 2 giving 2 separate enantiomers:

Enantiomer A: $^1$H-NMR (CD$_3$OD) δ 7.73 (d, J=9.1 Hz, 2H), 7.32 (d, J=9.1 Hz, 2H), 5.40 (m, 1H), 4.43 (m, 1H), 2.55 (dd, J=17.3, 7.7 Hz, 1H), 2.36 (d, J=17.3 Hz, 1H), 2.15 (s, 3H), 1.88 (m, 2H), 1.70 (m, 2H), 1.53-1.29 (m, 2H) and Enantiomer B: $^1$H-NMR (CD$_3$OD) δ 7.73 (d, J=9.1 Hz, 2H), 7.32 (d, J=9.1 Hz, 2H), 5.40 (m, 1H), 4.43 (m, 1H), 2.55 (dd, J=17.3, 7.7 Hz, 1H), 2.36 (d, J=17.3 Hz, 1H), 2.15 (s, 3H), 1.88 (m, 2H), 1.70 (m, 2H), 1.53-1.29 (m, 2H).

Notch Signaling Assay for Selective Inhibitors of Gamma Secretase.

A convergence of evidence indicates that the gamma secretase complex, comprised of the presenilin subunits, mediates the intra-membrane cleavage of Amyloid precursor protein (APP), and the Notch family of proteins (De Strooper, B., P. Saftig, K. Craessaerts, H. Vanderstichele, G. Guhde, W. Annaert, K. Von Figura and F. Van Leuven (1998). "Deficiency of presenilin-1 inhibits the normal cleavage of amyloid precursor protein." Nature 391(6665): 387-90; De Strooper, B., W. Annaert, P. Cupers, P. Saftig, K. Craessaerts, J. S. Mumm, E. H. Schroeter, V. Schrijvers, M. S. Wolfe, W. J. Ray et al. (1999). "A presenilin-1-dependent gamma-secretase-like protease mediates release of Notch intracellular domain." Nature 398(6727): 518-22; Mumm, J. S., E. H. Schroeter, M. T. Saxena, A. Griesemer, X. Tian, D. J. Pan, W. J. Ray and R. Kopan (2000). "A ligand-induced extracellular cleavage regulates gamma-secretase-like proteolytic activation of Notch1." Mol Cell 5(2): 197-206; Zhang, Z., P. Nadeau, W. Song, D. Donoviel, M. Yuan, A. Bernstein and B. A. Yankner (2000). "Presenilins are required for gamma-secretase cleavage of beta-APP and transmembrane cleavage of Notch-1." Nat Cell Biot 2(7): 463-5). Cleavage of APP by gamma secretase leads to beta-amyloid synthesis. Cleavage of Notch1 by gamma secretase results in release of the Notch intracellular domain (NICD), which translocates to the nucleus and activates gene expression (Jarriault, S., C. Brou, F. Logeat, E. H. Schroeter, R. Kopan and A. Israel (1995). "Signalling downstream of activated mammalian Notch." Nature 377(6547): 355-8; Kopan, R., E. H. Schroeter, H. Weintraub and J. S. Nye (1996). "Signal transduction by activated Notch: importance of proteolytic processing and its regulation by the extracellular domain." Proc Natl Acad Sci USA 93(4): 1683-8; Schroeter, E. H., J. A. Kisslinger and R. Kopan (1998). "Notch-1 signalling requires ligand-induced proteolytic release of intracellular domain." Nature 393(6683): 382-6). In particular, Notch signaling activates transcription of the mammalian homolog of the Drosophila transcription factor hairy-enhancer of split (Hes). Transcriptional activation of Hes1 is mediated by de-repression of CBF1/RBPJk upon binding by NICD in the nucleus. These facts have been exploited to develop a reporter gene assay for Notch Signaling Hsieh, J. J., T. Henkel, P. Salmon, E. Robey, M. G. Peterson and S. D. Hayward (1996). "Truncated mammalian Notch1 activates CBF1/RBPJk-repressed genes by a mechanism resembling that of Epstein-Barr virus EBNA2." Mol Cell Biol 16(3): 952-9; Lu, F. M. and S. E. Lux (1996). "Constitutively active human Notch1 binds to the transcription factor CBF1 and stimulates transcription through a promoter containing a CBF1-responsive element." *Proc Natl Acad Sci USA* 93(11): 5663-7).

Gamma secretase inhibitors have been observed to block NICD formation, and inhibit Notch signaling (De Strooper, B., W. Annaert, P. Cupers, P. Saftig, K. Craessaerts, J. S. Mumm, E. H. Schroeter, V. Schrijvers, M. S. Wolfe, W. J. Ray et al. (1999). "A presenilin-1-dependent gamma-secretase-like protease mediates release of Notch intracellular domain." *Nature* 398(6727): 518-22). Due to the importance of Notch signaling in cell fate determination, and tissue differentiation during both development and in the adult, inhibition of Notch signaling by gamma secretase inhibitors is postulated to be a limiting factor in their therapeutic utility. In order to identify selective gamma secretase inhibitors, we have employed a reporter gene based Notch signaling assay using a constitutively active rat Notch1 construct (ZEDN1) provided by Dr Gerry Weinmaster, who is at the University of California at Los Angeles (UCLA) as described in Shawber, C., D. Nofziger, J. J. Hsieh, C. Lindsell, O. Bogler, D. Hayward and G. Weinmaster (1996). "Notch signaling inhibits muscle cell differentiation through a CBF1-independent pathway." *Development* 122(12): 3765-73 in combination with the CBF1 repressible Luciferase reporter gene 4xwtCBF1 Luc (Hsieh, J. J., T. Henkel, P. Salmon, E. Robey, M. G. Peterson and S. D. Hayward (1996). "Truncated mammalian Notch1 activates CBF1/RBPJk-repressed genes by a mechanism resembling that of Epstein-Barr virus EBNA2." *Mol Cell Biol* 16(3): 952-9).

When 4xwtCBF1 Luciferase is co-transfected with NotchδE (ZEDN1), gamma-secretase cleavage of NotchδE releases the Notch intracellular domain (NICD), which translocates to the nucleus and de-represses CBF1 mediated transcriptional repression, leading to transcription of the Luciferase reporter gene. Luciferase activity is easily assayed in cell extracts using commercially available kits. The activity of the reporter gene is directly correlated with gamma secretase cleavage of NotchδE, and as such, a reduction in Luciferase activity provides a convenient measure of inhibition of gamma secretase cleavage of NotchδE. A comparison of the $IC_{50}$ values of compounds for inhibition of Notch signaling versus inhibition of beta-amyloid production in 293sw cells is employed to guide in the selection of compounds that have the desired property of potent inhibition of beta-amyloid synthesis with minimal inhibition of Notch Signaling.

Biological Example

Gamma-Secretase Assay

The gamma-secretase APP enzyme assay was designed to measure the specific proteolytic cleavage of an APP substrate (MBP-C125 Swe fusion protein) at the Aβ40 site. The assay used a partially purified extract of IMR-32 cell membranes as the gamma-secretase enzyme preparation and a recombinant fusion protein containing the C-terminal 125 amino acids of the Swedish variant of the APP (MBP-C125swe) as the substrate. This assay involved two steps beginning with the enzymatic reaction generating a cleavage product that was captured with an immobilized antibody specific for the neo-epitope Aβ40 site. The captured cleavage product was then detected in a sandwich ELISA assay with a biotinylated reporter antibody that is specific to Aβ (17-28). Streptavidin-linked alkaline phosphatase was then added that would generate a fluorescent signal proportional to the amount of cleavage product. This assay was used to discover small molecule inhibitors of gamma-secretase.

Materials and Methods:

Briefly, a 149 mg/ml solution of BIGCHAP detergent was made with water at 42° C. and then rotated for 30 minutes at the same temperature. This warmed solution of BigCHAPS (N,N-Bis(3-D-gluconamidopropyl)cholamide) detergent was used to dissolve Brain Extract Type-V (lipid containing a minimum of 40% phosphatidylethanolamine) from Sigma (St. Louis, Mo.) to a concentration of 8 mg/ml. This solution containing BigCHAPS and lipid at 8 mg/ml is then diluted to 0.53 mg/ml lipid with a pre-warmed solution of Hepes and sodium chloride. This final solution containing Hepes buffer, sodium chloride, BigCHAPS detergent and lipid is used to create working solutions of both gamma-secretase (25 Units) and the MBP-C125 substrate (0.05 mg/ml).

Gamma-secretase was then added to a 96-well micro-titre plate and then incubated with various concentrations of inhibitor for 30 minutes at 37° C. MBPC125 substrate was then added to initiate the reaction that would run for two hours at 37° C. The reaction was quenched with the addition of SDS to a final concentration of 0.1% and then 100 μl of the reaction mixture was transferred to a capture ELISA plate and incubated overnight at 4° C. Detection of the cleavage product was performed using a standard sandwich ELISA assay and quantified using a six point standard curve.

Results

The following compounds when tested as described above exhibited inhibition with an $IC_{50}$ in a range of 500 nM-250 nM (A), in a range of 250 nM-100 nM (B), or of less than 100 nM (C).

| Compound Name | γAPP |
|---|---|
| 12-(4-Chloro-benzenesulfonyl)-4,5,12-triaza-tricyclo[6.3.1.0$^{2,6}$]dodeca-2(6),3-diene; | C |
| 12-(4-Chloro-benzenesulfonyl)-5-methyl-4,5,12-triaza-tricyclo[6.3.1.0$^{2,6}$]dodeca-2(6),3-diene; | A |
| 12-(4-Chloro-benzenesulfonyl)-5-cyclohexyl-4,5,12-triaza-tricyclo[6.3.1.0$^{2,6}$]dodeca-2(6),3-diene; | A |
| 16-(4-Chloro-benzenesulfonyl)-6-phenyl-4,8,9,16-tetraaza-tetracyclo[10,3,1,0$^{2,10}$,0$^{5,9}$]-hexadeca-2(10),3,5,7-tetraene; | B |
| 16-(4-Chloro-benzenesulfonyl)-7-phenyl-4,8,9,16-tetraaza-tetracyclo[10,3,1,0$^{2,10}$,0$^{5,9}$]-hexadeca-2(10),3,5,7-tetraene; | A |
| 12-(4-Chloro-benzenesulfonyl)-4,5,12-triaza-tricyclo[6.3.1.0$^{2,6}$]dodeca-2(6),3-diene; | C |
| 11-(4-Chloro-benzenesulfonyl)-4,5,11-triaza-tricyclo[6.3.1.0$^{2,6}$]undeca-2(6),3-diene; | C |
| 12-(4-Chloro-benzenesulfonyl)-3-methyl-4,5,12-triaza-tricyclo[6.3.1.0$^{2,6}$]dodeca-2(6),3-diene; | C |
| 12-(4-Chloro-benzenesulfonyl)-3-trifluoromethyl-4,5,12-triaza-tricyclo[6.3.1.0$^{2,6}$]dodeca-2(6),3-diene; | C |
| 1-[12-(4-Chloro-benzenesulfonyl)-4,5,12-triaza-tricyclo[6.3.1.0$^{2,6}$]dodeca-2,5-dien-4-yl]-ethanone; | C |
| 1-[12-(4-Chloro-benzenesulfonyl)-4,5,12-triaza-tricyclo[6.3.1.0$^{2,6}$]dodeca-2,5-dien-4-yl]-2-methyl-propan-1-one; | C |
| Acetic acid 2-[12-(4-chloro-benzenesulfonyl)-4,5,12-triaza-tricyclo[6.3.1.0$^{2,6}$]dodeca-2,5-dien-4-yl]-1,1-dimethyl-2-oxo-ethyl ester; | C |
| 12-(4-Chloro-benzenesulfonyl)-4,5,12-triaza-tricyclo[6.3.1.0$^{2,6}$]dodeca-2,5-diene-4-carboxylic acid allyl ester; | A |
| 13-(4-Chloro-benzenesulfonyl)-4,6,13-triaza-tricyclo[7.3.1.0$^{2,7}$]trideca-2(7),3,5-trien-5-ylamine; | B |

-continued

| Compound Name | γAPP |
|---|---|
| 2-(4-Chloro-benzenesulfonyl)-3-trifluoromethyl-4,5,12-triaza-tricyclo[6.3.1.0$^{2,6}$]dodeca-2(6),3-diene; | B |
| 3-Chloro-12-(4-chloro-benzenesulfonyl)-4,5,12-triaza-tricyclo[6.3.1.0$^{2,6}$]dodeca-2(6),3-diene; | A |
| 12-(4-Chloro-benzenesulfonyl)-3-methyl-4,5,12-triaza-tricyclo[6.3.1.0$^{2,6}$]dodeca-2(6),3-diene; | C |
| 12-(4-Chloro-benzenesulfonyl)-3-difluoromethyl-4,5,12-triaza-tricyclo[6.3.1.0$^{2,6}$]dodeca-2(6),3-diene; | C |
| 12-(4-Chloro-benzenesulfonyl)-4,5,12-triaza-tricyclo[6.3.1.0$^{2,6}$]dodeca-2(6),3-dien-3-ylamine; | C |
| 12-(4-Chloro-benzenesulfonyl)-3-difluoromethyl-4,5,12-triaza-tricyclo[6.3.1.0$^{2,6}$]dodeca-2(6),3-diene; | C |
| 12-(4-Chloro-benzenesulfonyl)-4,5,12-triaza-tricyclo[6.3.1.0$^{2,6}$]dodeca-2(6),3-dien-7-one; | A |
| 12-(4-Chloro-benzenesulfonyl)-7-methyl-4,5,12-triaza-tricyclo[6.3.1.0$^{2,6}$]dodeca-2(6),3-diene; | C |
| 12-(4-Chloro-benzenesulfonyl)-10-oxa-4,5,12-triaza-tricyclo[6.3.1.0$^{2,6}$]dodeca-2(6),3-diene; | B |
| 12-(4-Chloro-benzenesulfonyl)-7-ethyl-4,5,12-triaza-tricyclo[6.3.1.0$^{2,6}$]dodeca-2(6),3-diene; | C |
| 12-(5-Chloro-thiophene-2-sulfonyl)-4,5,12-triaza-tricyclo[6.3.1.0$^{2,6}$]dodeca-2(6),3-diene; | C |
| 12-(4-Chloro-benzenesulfonyl)-4,5,12-triaza-tricyclo[6.3.1.0$^{2,6}$]dodeca-2(6),3-dien-7-ol; | C |
| 12-(4-Chloro-benzenesulfonyl)-4,5,12-triaza-tricyclo[6.3.1.0$^{2,6}$]dodeca-2(6),3-dien-3-ylamine; | C |
| N-[12-(4-Chloro-benzenesulfonyl)-4,5,12-triaza-tricyclo[6.3.1.0$^{2,6}$]dodeca-2(6),3-dien-7-yl]-acetamide; | C |
| 12-(4-Chloro-benzenesulfonyl)-4,5,12-triaza-tricyclo[6.3.1.0$^{2,6}$]dodeca-2(6),3-diene-10-carboxylic acid ethyl ester; and | C |

The invention and the manner and process of making and using it, are now described in such full, clear, concise and exact terms as to enable any person skilled in the art to which it pertains, to make and use the same. It is to be understood that the foregoing describes preferred aspects of the invention and that modifications may be made therein without departing from the spirit or scope of the invention as set forth in the claims. To particularly point out and distinctly claim the subject matter regarded as invention, the following claims conclude this specification.

What is claimed is:

1. A compound of the formula:

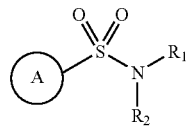

stereoisomers, tautomers, mixtures of stereoisomers and/or tautomers or pharmaceutically acceptable salts thereof,
wherein,
the A-ring is aryl, cycloalkyl, heteroaryl or heterocycloalkyl, where each ring is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, aryloxy, —S(O)$_{0-2}$—($C_1$-$C_6$ alkyl), —NR$_{10}$R$_{11}$, $C_1$-$C_6$ alkanoyl, $C_0$-$C_3$alkylCO$_2$R', heteroaryl, heterocycloalkyl, aryl, arylalkyl, or —SO$_2$NR$_{10}$R$_{11}$;

$R_1$ and $R_2$ combine to form a [3.2.1] ring system, where the nitrogen is attached to the two bridgehead carbons, where 0 or 1 of the carbons in the ring system is optionally replaced with an —O—, —S(O)$_{0-2}$—, or —NR$_{15}$— group, and where the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —(C$_1$-$C_4$ alkyl)-C(O)OR$_{13}$, —CONR$_{10}$R$_{11}$, —OC(O)NR$_{10}$R$_{11}$, —NR'C(O)OR'', —NR'S(O)$_2$R'', —OS(O)$_2$R'', —NR'C(O)R'', CN, =N—NR$_{12}$, or =N—O—R$_{13}$;

two adjacent carbons (not including the bridgehead carbons) in the [3.2.1] ring system combine to form part of a fused heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$ R', hydroxy, hydroxyalkyl, halo, $C_1$-$C_2$ haloalkyl, $C_1$-$C_2$ haloalkoxy, —NR'C(O)R'', —NR'SO$_2$R'', —C(O)R', —C(O)OR', —C(O)alkylOC(O)R', —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, aryloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$, and additionally, two adjacent carbons in the [3.2.1] ring system (not including the bridgehead carbons) may combine with one or more —C—, —CH—, and/or —CH$_2$— groups to form a cycloalkyl ring that may optionally be substituted with one or more groups that are independently halogen, $C_1$-$C_6$ alkyl or haloalkyl;

$R_{10}$ and $R_{11}$ at each occurrence are independently H or $C_1$-$C_6$ alkyl, where the alkyl is optionally substituted with an aryl, where the aryl is optionally substituted with 1 to 5 groups that are independently halogen, hydroxyl, alkyl, alkoxy, haloalkyl, haloalkoxy, CN or NO$_2$; and $R_{10}$ and $R_{11}$ together may form a 3-8 membered ring optionally including an additional heteroatom such as N, O or S;

$R_{12}$ is H, $C_1$-$C_6$ alkyl or —SO$_2$-aryl, where the aryl is optionally substituted with 1 to 5 groups that are independently halogen, hydroxyl, alkyl, alkoxy, haloalkyl, haloalkoxy, CN or NO$_2$;

$R_{13}$ is H or $C_1$-$C_6$ alkyl optionally substituted with aryl, hydroxyl, or halogen, where the aryl is optionally substituted with 1 to 5 groups that are independently halogen, hydroxyl, alkyl, alkoxy, haloalkyl, haloalkoxy, CN or NO$_2$;

$R_{15}$ is H, aryl, heteroaryl, heterocycloalkyl, SO$_2$R', —C(O)R', —C(O)OR', or $C_1$-$C_6$ alkyl optionally substituted with aryl, hydroxyl, or halogen, where the aryl groups are optionally substituted with 1 to 5 groups that are independently halogen, hydroxyl, alkyl, alkoxy, haloalkyl, haloalkoxy, CN, amino, NH($C_1$-$C_6$ alkyl), N($C_1$-$C_6$ alkyl)($C_1$-$C_6$ alkyl) or NO$_2$, and R' and R" at each occurrence are independently hydrogen, $C_1$-$C_6$ alkyl, haloalkyl, $C_2$-$C_6$ alkenyl or phenyl optionally substituted with 1 to 5 groups that are independently halogen, $C_1$-$C_6$ alkyl, —C(O)OR', $C_1$-$C_6$ alkoxy, haloalkyl, haloalkoxy, hydroxyl, CN, aryloxy, —SO$_2$—($C_1$-$C_6$ alkyl), —NR$_{10}$R$_{11}$, $C_1$-$C_{06}$ alkanoyl, pyridyl, phenyl, NO$_2$, or —SO$_2$NR$_{10}$R$_{11}$.

2. A compound or pharmaceutically acceptable salt according to claim 1, wherein the A-ring is phenyl, $C_3$-$C_8$ cycloalkyl, heteroaryl that is pyridyl, pyrimidyl, pyridazinyl, pyrazinyl, thienyl, furanyl, pyrrolyl, pyrazolyl, or imidazolyl, or heterocycloalkyl that is pyrrolidinyl, piperidinyl, piperazinyl, morpholinyl, thiomorpholinyl, or thiomorpholinyl-S,S-dioxide, where each of the above rings is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, aryloxy, —S(O)$_{0-2}$—($C_1$-$C_6$ alkyl), —NR$_{10}$R$_{11}$, $C_1$-$C_6$ alkanoyl, —C$_0$-C$_3$alkylC(O)OR', pyridyl, thienyl, furanyl, pyrrolyl, pyrrolidinyl, piperidinyl, piperazinyl, phenyl, phenyl $C_1$-$C_4$ alkyl, or —SO$_2$—NR$_{10}$R$_{11}$.

3. A compound or pharmaceutically acceptable salt according to claim 2 of the formula

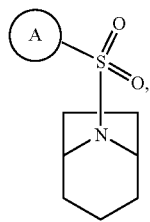

wherein, two adjacent carbons (not including the bridgehead carbons) in the [3.2.1] ring system combine to form part of a fused heteroaryl or heterocycloalkyl ring, each of which is optionally substituted at a substitutable position with $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R', —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, aryloxy, —S(O)$_{0-2}$—($C_1$-$C_6$ alkyl), —NR$_{10}$R$_{11}$, $C_1$-$C_6$ alkanoyl, pyridyl, phenyl, and —SONR$_{10}$R$_{11}$, and additionally, two adjacent carbons (not including the bridgehead carbons) may form a cycloalkyl ring that may optionally be substituted with halogen, $C_1$-$C_6$ alkyl or haloalkyl;

0 or 1 of the carbons in the [3.2.1] ring system is optionally replaced with an —O—, —S(O)$_{0-2}$—, or —NR$_{15}$— group;

the [3.2.1] ring is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$; and R$_{15}$ is H, phenyl, pyridyl, pyrimidinyl, oxazolyl, thienyl, furanyl, pyrrolyl, piperidinyl, piperazinyl, pyrrolidinyl, imidazolidinyl, indolyl, —SO$_2$R', —C(O)R', —C(O)OR', or $C_1$-$C_6$ alkyl optionally substituted with phenyl, hydroxyl, or halogen, where the above cyclic groups are optionally substituted with 1 to 5 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN, amino, NH($C_1$-$C_6$ alkyl), N($C_1$-$C_6$ alkyl)($C_1$-$C_6$ alkyl), or NO$_2$.

4. A compound or pharmaceutically acceptable salt according to claim 3, where the A-ring is phenyl, which is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, aryloxy, —S(O)$_{0-2}$—($C_1$-$C_6$ alkyl), —NR$_{10}$R$_{11}$, $C_1$-$C_6$ alkanoyl, —C$_0$-C$_3$alkylC(O)OR', pyridyl, thienyl, furanyl, pyrrolyl, pyrrolidinyl, piperidinyl, piperazinyl, phenyl, phenyl $C_1$-$C_4$ alkyl, or —SO$_2$NR$_{10}$R$_{11}$.

5. A compound or pharmaceutically acceptable salt according to claim 4, where 0 of the carbons in the [3.2.1] ring system is replaced with an —O—, —S(O)$_{0-2}$—, or —NR$_{15}$— group.

6. A compound or pharmaceutically acceptable salt according to claim 5, of the formula:

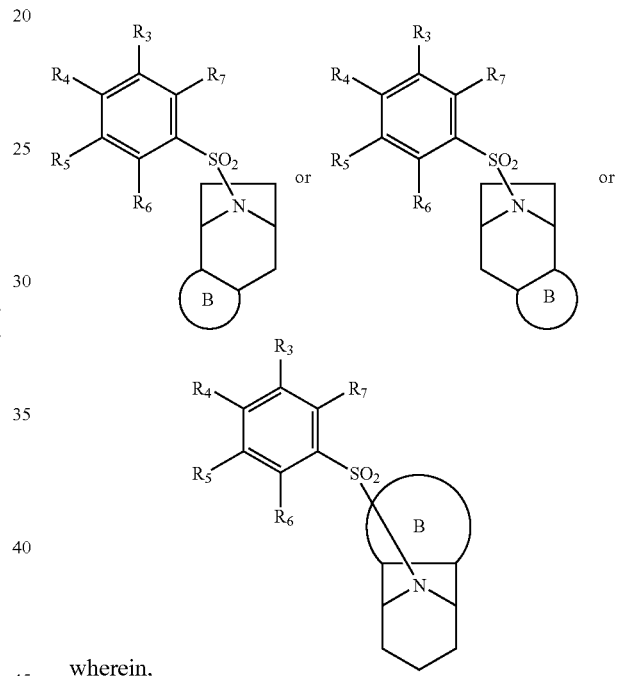

wherein, the B-ring is a heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R', —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, aryloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$—NR$_{10}$R$_{11}$;

the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$, and additionally, two adjacent carbons (not including the bridgehead carbons) may combine to form a cycloalkyl ring that may optionally be substituted with halogen, C$_1$-C$_6$ alkyl or haloalkyl;

R$_3$, R$_4$, R$_5$, R$_6$, R$_7$ are independently of each other H, halogen, C$_1$-C$_6$ alkyl, C$_1$-C$_6$ haloalkyl, C$_1$-C$_6$ haloalkoxy, CN, hydroxyl, C$_1$-C$_6$ alkoxy, —C$_1$-C$_3$ alkyl-OH, —C$_1$-C$_3$ alkyl-alkoxy, aryloxy, —SO$_2$R', —NR$_{10}$R$_{11}$, C$_1$-C$_6$ alkanoyl, heteroaryl, aryl, or arylalkyl, or R$_4$ and R$_5$, or R$_5$ and R$_6$ and the carbons to which they are attached form a heterocycloalkyl or a heteroaryl ring which is optionally substituted with 1, 2, 3, or 4 groups that are independently C$_1$-C$_4$ alkyl, C$_1$-C$_4$ alkoxy, halogen, or C$_1$-C$_4$ alkanoyl wherein the alkanoyl group is optionally substituted with up to 3 halogen atoms; or R$_4$ and R$_5$, or R$_5$ and R$_6$ and the carbons to which they are attached form a benzo ring which is optionally substituted with optionally substituted with 1 to 5 groups that are independently halogen, hydroxyl, alkyl, alkoxy, haloalkyl, haloalkoxy, CN or NO$_2$; and R' and R" are independently of each other hydrogen, C$_1$-C$_6$ alkyl, haloalkyl, C$_2$-C$_6$ alkenyl or phenyl optionally substituted with 1 to 5 groups that are independently halogen, C$_1$-C$_6$ alkyl, —C(O)OR', C$_1$-C$_6$ alkoxy, haloalkyl, haloalkoxy, hydroxyl, CN, aryloxy, —SO$_2$—(C$_1$-C$_6$ alkyl), —NR$_{10}$R$_{11}$, C$_1$-C$_6$ alkanoyl, pyridyl, phenyl, NO$_2$, or —SO$_2$NR$_{10}$R$_{11}$.

7. A compound or pharmaceutically acceptable salt according to claim 6, wherein the B-ring is pyrazolyl, imidazolyl, pyrrolyl, triazolyl, pyrrolidinyl, pyrazolidinyl, imidazolidinyl, triazolopyrimidinyl, imidazopyrimidinyl, pyrazolopyrimidinyl, indolyl or pyridyl, each of which is optionally substituted at a substitutable position with a group that is independently C$_1$-C$_6$ alkyl, C$_3$-C$_8$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$R', hydroxy, hydroxyalkyl, halo, C$_1$-C$_2$ haloalkyl, C$_1$-C$_2$ haloalkoxy, —NR'C(O)R", —NR'SO$_2$R", —C(O)R', —C(O)OR', —C(O)alkylOC(O)R', —C(O)NR$_{10}$R$_{11}$, oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, aryloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$.

8. A compound or pharmaceutically acceptable salt according to claim 6, wherein the B-ring has the formula:

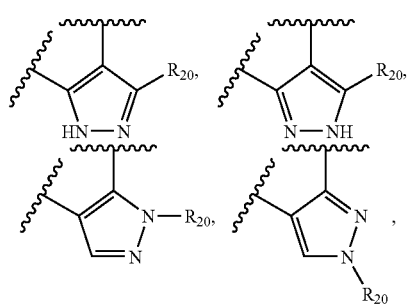

-continued

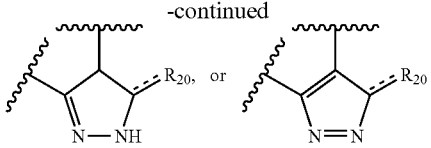

R$_{20}$ is H, C$_1$-C$_6$ alkyl, C$_1$-C$_6$ alkoxy, oxo, amino, C$_1$-C$_6$ alkylamino, C$_1$-C$_6$ dialkylamino, —R'C(O)R", halo, or CF$_3$; and where the dashed bond represents an optional second bond.

9. A compound or pharmaceutically acceptable salt according to claim 8, wherein R$_3$, R$_4$, R$_5$, R$_6$, and R$_7$ are independently of each other H, halo, CF$_3$, CHF$_2$ or methyl.

10. A compound or pharmaceutically acceptable salt according to claim 3, of the formula:

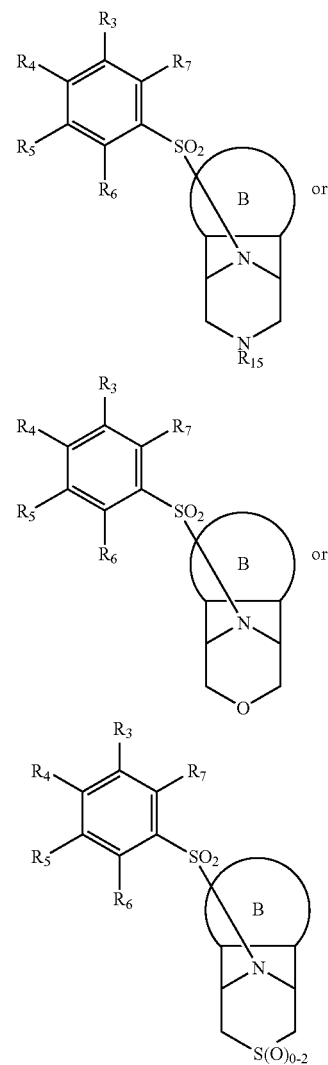

wherein, the B-ring is a heteroaryl or heterocycloalkyl ring, each of which is optionally substituted at a substitutable position with a group that is independently C$_1$-C$_6$ alkyl, C$_3$-C$_8$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$ R', hydroxy, hydroxyalkyl, halo, C$_1$-C$_2$ haloalkyl, C$_1$-C$_2$ haloalkoxy, —NR'C(O)R", —NR'SO$_2$R", —C(O)R', —C(O)OR', —C(O)alkylOC(O)R', —C(O)NR$_{10}$R$_{11}$, oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, aryloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$;

the [3.2.1] ring system is optionally substituted with 1, 2, 3, or 4 groups that are independently oxo, halogen, C$_1$-C$_6$ alkyl, C$_2$-C$_6$ alkenyl, C$_1$-C$_6$ haloalkyl, C$_2$-C$_6$ alkynyl, hydroxy, hydroxyalkyl, C$_1$-C$_6$ alkoxy, haloalkoxy, —C(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, C$_1$-C$_6$ alkyl or haloalkyl;

R$_3$, R$_4$, R$_5$, R$_6$, R$_7$ are independently of each other H, halogen, C$_1$-C$_6$ alkyl, C$_1$-C$_6$ haloalkyl, C$_1$-C$_6$ haloalkoxy, CN, hydroxyl, C$_1$-C$_6$ alkoxy, —C$_1$-C$_3$ alkyl-OH, —C$_1$-C$_3$ alkyl-alkoxy, aryloxy, —SO$_2$R', —NR$_{10}$R$_{11}$, C$_1$-C$_6$ alkanoyl, heteroaryl, aryl, or arylalkyl, or R$_4$ and R$_5$, or R$_5$ and R$_6$ and the carbons to which they are attached form a heterocycloalkyl or a heteroaryl ring which is optionally substituted with 1, 2, 3, or 4 groups that are independently C$_1$-C$_4$ alkyl, C$_1$-C$_4$ alkoxy, halogen, or C$_1$-C$_4$ alkanoyl wherein the alkanoyl group is optionally substituted with up to 3 halogen atoms; or R$_4$ and R$_5$, or R$_5$ and R$_6$ and the carbons to which they are attached form a benzo ring which is optionally substituted with 1 to 5 groups that are independently halogen, hydroxyl, alkyl, alkoxy, haloalkyl, haloalkoxy, CN or NO$_2$;

R' and R" are independently of each other hydrogen, C$_1$-C$_6$ alkyl, haloalkyl, C$_2$-C$_6$ alkenyl or phenyl optionally substituted with 1 to 5 groups that are independently halogen, C$_1$-C$_6$ alkyl, —C(O)OR', C$_1$-C$_6$ alkoxy, haloalkyl, haloalkoxy, hydroxyl, CN, aryloxy, —SO$_2$—(C$_1$-C$_6$ alkyl), —NR$_{10}$R$_{11}$, C$_1$-C$_6$ alkanoyl, pyridyl, phenyl, NO$_2$, or —SO$_2$NR$_{10}$R$_{11}$; and R$_{15}$ is H, phenyl, pyridyl, pyrimidinyl, oxazolyl, thienyl, furanyl, pyrrolyl, piperidinyl, piperazinyl, pyrrolidinyl, imidazolidinyl, indolyl, —SO$_2$R', —C(O)R'. —C(O)OR', or C$_1$-C$_6$ alkyl optionally substituted with phenyl, hydroxyl, or halogen, where the above cyclic groups are optionally substituted with 1 to 5 groups that are independently halogen, hydroxyl, C$_1$-C$_4$ alkyl, C$_1$-C$_4$ alkoxy, C$_1$-C$_4$ haloalkyl, C$_1$-C$_4$ haloalkoxy, CN, amino, NH(C$_1$-C$_6$ alkyl), N(C$_1$-C$_6$ alkyl) (C$_1$-C$_6$ alkyl), or NO$_2$.

11. A compound or pharmaceutically acceptable salt according to claim 10, wherein the B-ring is pyrazolyl, imidazolyl, pyrrolyl, triazolyl, pyrrolidinyl, pyrazolidinyl, imidazolidinyl, triazolopyrimidinyl, imidazopyrimidinyl, pyrazolopyrimidinyl, indolyl or pyridyl, each of which is optionally substituted at a substitutable position with a group that is independently C$_1$-C$_6$ alkyl, C$_3$-C$_8$ cycloalkyl, C$_2$-C$_6$ alkenyl, C$_2$-C$_6$ alkynyl, C$_1$-C$_6$ alkoxy, amino, C$_1$-C$_6$ alkylamino, C$_1$-C$_6$ dialkylamino, —S(O)$_{0-2}$R', hydroxy, hydroxyalkyl, halo, C$_1$-C$_2$ haloalkyl, C$_1$-C$_2$ haloalkoxy, —NR$_{10}$(O)R", —NR'SO$_2$R", —C(O)R', —C(O)OR', —C(O)alkylOC(O)R', —C(O)NR$_{10}$R$_{11}$, oxo, CN, or C$_0$-C$_1$alkylphenyl, where the phenyl is optionally substituted with 1-5 groups independently selected from halogen, C$_1$-C$_6$ alkyl, —CO$_2$R', C$_1$-C$_6$ alkoxy, haloalkyl, haloalkoxy, hydroxyl, CN, NO$_2$, aryloxy, —S(O)$_{0-2}$—(C$_1$-C$_6$ alkyl), —NR$_{10}$R$_{11}$, C$_1$-C$_6$ alkanoyl, pyridyl, phenyl, and —SO$_2$NR$_{10}$R$_{11}$.

12. A compound or pharmaceutically acceptable salt according to claim 10, wherein the B-ring has the formula:

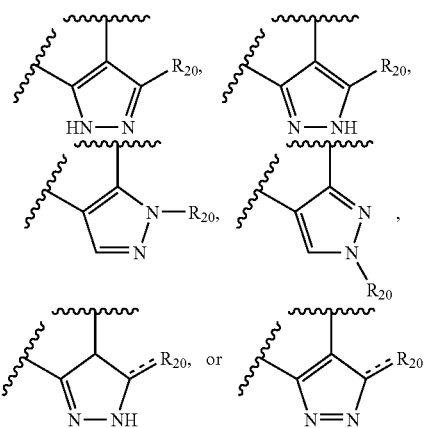

R$_{20}$ is H, C$_1$-C$_6$ alkyl, C$_1$-C$_6$ alkoxy, oxo, amino, C$_1$-C$_6$ alkylamino, C$_1$-C$_6$ dialkylamino, —R'C(O)R", halo, or CF$_3$; and where the dashed bond represents an optional second bond.

13. A compound or pharmaceutically acceptable salt according to claim 12, wherein R$_3$, R$_4$, R$_5$, R$_6$, and R$_7$ are independently of each other H, halo, CF$_3$, CHF$_2$ or methyl.

14. A compound or pharmaceutically acceptable salt according to claim 3, where the A-ring is C$_3$-C$_8$ cycloalkyl, which is optionally substituted at a substitutable position with halogen, C$_1$-C$_6$ alkyl, C$_2$-C$_6$ alkenyl, C$_2$-C$_6$ alkynyl, C$_1$-C$_6$ alkoxy, haloalkyl, haloalkoxy, hydroxyl, hydroxyalkyl, CN, aryloxy, —S(O)$_{0-2}$—(C$_1$-C$_6$ alkyl), —NR$_{10}$R$_{11}$, C$_1$-C$_6$ alkanoyl, C$_0$-C$_3$alkylCO$_2$R', pyridyl, thienyl, furanyl, pyrrolyl, pyrrolidinyl, piperidinyl, piperazinyl, phenyl, phenyl C$_1$-C$_4$ alkyl, or —SO$_2$NR$_{10}$R$_{11}$; and the [3.2.1] ring system is optionally substituted with 1, 2, 3, or 4 groups that are independently oxo, halogen, C$_1$-C$_6$ alkyl, C$_2$-C$_6$ alkenyl, C$_1$-C$_6$ haloalkyl, C$_2$-C$_6$ alkynyl, hydroxy, hydroxyalkyl, C$_1$-C$_6$ alkoxy, haloalkoxy, —O(O)OR$_{13}$, —(C$_1$-C$_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, C$_1$-C$_6$ alkyl or haloalkyl.

15. A compound or pharmaceutically acceptable salt according to claim 3, where the A-ring is heteroaryl that is pyridyl, pyrimidyl, pyridazinyl, pyrazinyl, thienyl, furanyl, pyrrolyl, pyrazolyl, or imidazolyl, each of which is optionally substituted at one or more substitutable positions with groups that are independently halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, aryloxy, —S(O)$_{0-2}$—($C_1$-$C_6$ alkyl), —NR$_{10}$R$_{11}$, $C_1$-$C_6$ alkanoyl, $C_0$-$C_3$alkylCO$_2$R', pyridyl, thienyl, furanyl, pyrrolyl, pyrrolidinyl, piperidinyl, piperazinyl, phenyl, phenyl $C_1$-$C_4$ alkyl, or —SO$_2$NR$_{10}$R$_{11}$; and the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl.

16. A compound or pharmaceutically acceptable salt according to claim 15, wherein the A ring is, thienyl, furanyl, or pyridyl, each of which is optionally substituted at one or more substitutable positions with groups that are independently halogen, $C_1$-$C_6$ alkyl, $C_1$-$C_6$ alkoxy, haloalkyl, haloalkoxy, hydroxyl, CN, aryloxy, —SO$_2$—($C_1$-$C_6$ alkyl), —NR$_{10}$R$_{11}$, $C_1$-$C_6$ alkanoyl, pyridyl, phenyl, or —SO$_2$NR$_{10}$R$_{11}$, where each R$_{10}$ and R$_{11}$ is independently H or $C_1$-$C_6$ alkyl.

17. A compound or pharmaceutically acceptable salt according to claim 3, where the A-ring is heterocycloalkyl that is pyrrolidinyl, piperidinyl, piperazinyl, morpholinyl, thiomorpholinyl, or thiomorpholinyl-S,S-dioxide, where each of the above rings is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, aryloxy, —S(O)$_{0-2}$—($C_1$-$C_6$ alkyl), —NR$_{10}$R$_{11}$, $C_1$-$C_6$ alkanoyl, $C_0$-$C_3$alkylCO$_2$R', pyridyl, thienyl, furanyl, pyrrolyl, pyrrolidinyl, piperidinyl, piperazinyl, phenyl, phenyl $C_1$-$C_4$ alkyl, or —SO$_2$NR$_{10}$R$_{11}$; and the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR$_{10}$(O)R", CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl.

18. A compound or pharmaceutically acceptable salt of formula:

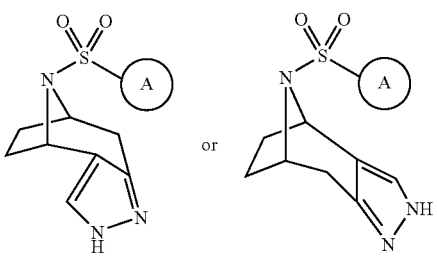

wherein

A is aryl, cycloalkyl, heteroaryl or heterocycloalkyl, where each ring is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, aryloxy, —S(O)$_{0-2}$—($C_1$-$C_6$ alkyl), —NR$_{10}$R$_{11}$, $C_1$-$C_6$ alkanoyl, $C_0$-$C_3$alkylCO$_2$R', pyridyl, thienyl, furanyl, pyrrolyl, pyrrolidinyl, piperidinyl, piperazinyl, phenyl, phenyl $C_1$-$C_4$ alkyl, or —SO$_2$NR$_{10}$R$_{11}$;

the bridged ring including the fused pyrazol ring is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —($C_1$-$C_4$ alkyl)-C(O)OR$_{13}$, —C(O)alkylOC(O)R', —C(O)NR$_{10}$R$_{11}$, —OC(O)NR$_{10}$R$_{11}$, —NR'C(O)OR', oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, aryloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$;

R$_{10}$ and R$_{11}$ at each occurrence are independently H or $C_1$-$C_6$ alkyl, where the alkyl is optionally substituted with an aryl, where the aryl is optionally substituted with 1 to 5 groups that are independently halogen, hydroxyl, alkyl, alkoxy, haloalkyl, haloalkoxy, CN or NO$_2$; or R$_{10}$ and R$_{11}$ together may form a 3-8 membered ring optionally including an additional heteroatom such as N, O or S; and R' is hydrogen, $C_1$-$C_6$ alkyl, haloalkyl, $C_2$-$C_6$ alkenyl or phenyl optionally substituted with 1 to 5 groups that are independently halogen, $C_1$-$C_6$ alkyl, —C(O)OR, $C_1$-$C_6$ alkoxy, haloalkyl, haloalkoxy, hydroxyl, CN, aryloxy, —SO$_2$—($C_1$-$C_6$ alkyl), —NR$_{10}$R$_{11}$, $C_1$-$C_6$ alkanoyl, pyridyl, phenyl, NO$_2$, or —SO$_2$NR$_{10}$R$_{11}$;

including stereoisomers, tautomers, mixtures of stereoisomers and/or tautomers or pharmaceutically acceptable salts thereof.

19. A compound that is selected from:
11-(4-Chloro-benzenesulfonyl)-9,9,10,10-tetrafluoro-4,5,11-triaza-tricyclo[6.2.1.0$^{2,6}$]undeca-2(6),3-diene;
and pharmaceutically acceptable salts thereof.

20. A method of treating Alzheimer's disease comprising administering a therapeutically effective amount of a compound or salt of claim 1 to a patient with Alzheimer's disease in need of such treatment.

21. A composition comprising a compound or salt of claim 1 and at least one pharmaceutically acceptable solvent, adjuvant, excipient, carrier, binder or disintegrant.

22. A compound or pharmaceutically acceptable salt according to claim 3, of the formula:

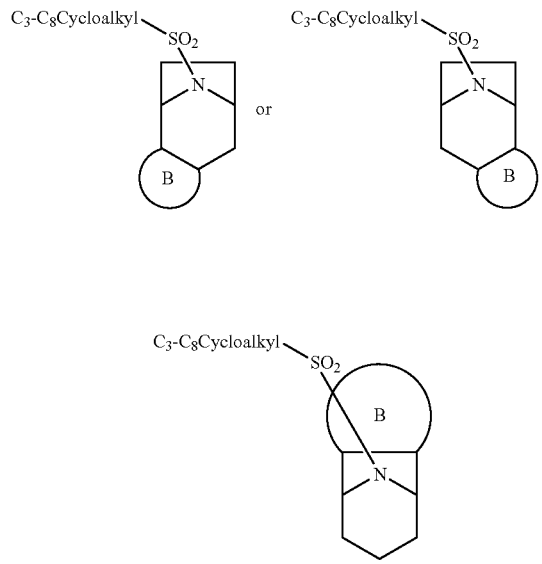

wherein, the B-ring is a heteroaryl or heterocycloalkyl ring, each of which is optionally substituted at a substitutable position with a group that is independently is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R', —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$; and the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl.

23. A compound or pharmaceutically acceptable salt according to claim 22, wherein the $C_3$-$C_8$ cycloalkyl group is cyclopropyl, cyclobutyl, cyclopentyl, cyclohexyl, cycloheptyl, or cyclooctyl.

24. A compound or pharmaceutically acceptable salt according to claim 3, of the formula:

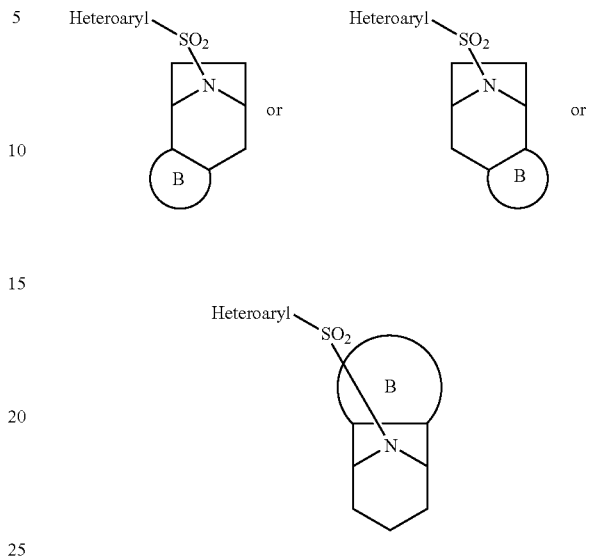

wherein the B-ring is a heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R', —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$; and the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR$_{10}$(O)R", CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl.

25. A compound or pharmaceutically acceptable salt according to claim 24, wherein the heteroaryl group is pyridyl, pyrimidyl, pyridazinyl, pyrazinyl, thienyl, or furanyl, each of which is optionally substituted at one or more substitutable positions with groups that are independently halogen, $C_1$-$C_6$ alkyl, $C_1$-$C_6$ alkoxy, CF$_3$, OCF$_3$, hydroxyl, CN, phenyloxy, —SO$_2$—($C_1$-$C_6$alkyl), —NR$_{10}$R$_{11}$, $C_1$-$C_6$ alkanoyl, pyridyl, phenyl, or —SO$_2$NR$_{10}$R$_{11}$, where each R$_{10}$ and R$_{11}$ is independently H or $C_1$-$C_6$ alkyl.

26. A compound or pharmaceutically acceptable salt according to claim 3, of the formula:

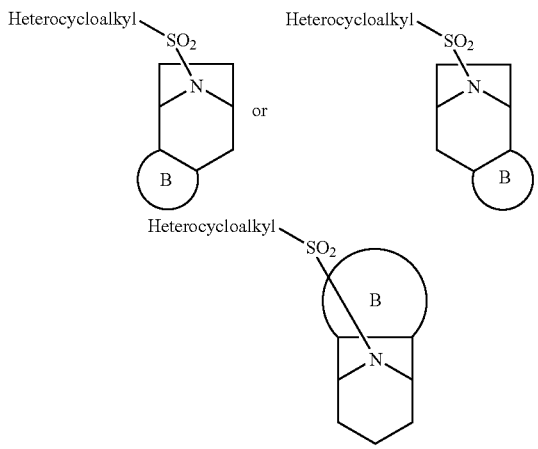

wherein the B-ring is a heteroaryl or heterocycloalkyl ring, each of which is optionally substituted at a substitutable position with a group that is independently $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R', hydroxy, hydroxyalkyl, halo, $C_1$-$C_2$ haloalkyl, $C_1$-$C_2$ haloalkoxy, —NR'C(O)R", —NR'SO$_2$R", —C(O)R', —C(O)OR', —C(O)alkylOC(O)R', —C(O)NR$_{10}$R$_{11}$, oxo, CN, or $C_0$-$C_1$alkylphenyl, where the phenyl is optionally substituted with 1-5 groups independently selected from halogen, $C_1$-$C_6$ alkyl, —CO$_2$R', $C_1$-$C_6$ alkoxy, haloalkyl, haloalkoxy, hydroxyl, CN, NO$_2$, phenyloxy, —S(O)$_{0-2}$—($C_1$-$C_6$ alkyl), —NR$_{10}$R$_{11}$, $C_1$-$C_6$ alkanoyl, pyridyl, phenyl, and —SO$_2$NR$_{10}$R$_{11}$; and the [3.2.1] ring system is optionally substituted with 1, 2, 3, or 4 groups that are independently oxo, halogen, $C_1$-$C_6$ alkyl, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —O(O)OR$_{13}$, —($C_1$-$C_4$ alkyl)-C(O)OR$_{13}$, —CONR$_{10}$R$_{11}$, —OC(O)NR$_{10}$R$_{11}$, —NR'C(O)OR", —NR'S(O)$_2$R", —OS(O)$_2$R", —NR'C(O)R", CN, =N—NR$_{12}$, or =N—O—R$_{13}$ and additionally, two adjacent carbons (not including the bridgehead carbons) may combine to form a cycloalkyl ring that may optionally be substituted with halogen, $C_1$-$C_6$ alkyl or haloalkyl.

27. A compound or pharmaceutically acceptable salt according to claim 26, wherein the heterocycloalkyl group is pyrrolidinyl, piperidinyl, piperazinyl, morpholinyl, thiomorpholinyl, or thiomorpholinyl-S,S-dioxide, each of which is optionally substituted at one or more substitutable positions with groups that are independently halogen, $C_1$-$C_6$ alkyl, $C_1$-$C_6$ alkoxy, CF$_3$, OCF$_3$, hydroxyl, CN, phenyloxy, —SO$_2$—($C_1$-$C_6$ alkyl), —NR$_{10}$R$_{11}$, $C_1$-$C_6$ alkanoyl, pyridyl, phenyl, or —SO$_2$NR$_{10}$R$_{11}$, where each R$_{10}$ and R$_{11}$ is independently H or $C_1$-$C_6$ alkyl.

* * * * *